(12) United States Patent
Mukherjee et al.

(10) Patent No.: US 12,378,568 B2
(45) Date of Patent: Aug. 5, 2025

(54) GREEN ALGAL BESTROPHIN BICARBONATE TRANSPORTERS

(71) Applicants: Board of Supervisors of Louisiana State University and Agricultural and Mechanical College, Baton Rouge, LA (US); University of York, York (GB)

(72) Inventors: Ananya Mukherjee, Baton Rouge, LA (US); James V. Moroney, Baton Rouge, LA (US); Chun Sing Lau, York (GB); Luke C. M. Mackinder, York (GB)

(73) Assignees: Board Of Supervisors of Louisiana State University and Agricultural and Mechanical College, Baton Rouge, LA (US); University of York, York (GB)

( * ) Notice: Subject to any disclaimer, the term of this patent is extended or adjusted under 35 U.S.C. 154(b) by 0 days.

(21) Appl. No.: 17/259,537

(22) PCT Filed: Jul. 12, 2019

(86) PCT No.: PCT/US2019/041584
§ 371 (c)(1),
(2) Date: Jan. 11, 2021

(87) PCT Pub. No.: WO2020/014600
PCT Pub. Date: Jan. 16, 2020

(65) Prior Publication Data
US 2021/0238623 A1 Aug. 5, 2021

Related U.S. Application Data

(60) Provisional application No. 62/769,214, filed on Nov. 19, 2018, provisional application No. 62/697,840, filed on Jul. 13, 2018.

(51) Int. Cl.
*C12N 15/82* (2006.01)
(52) U.S. Cl.
CPC ..... *C12N 15/8261* (2013.01); *C12N 15/8269* (2013.01)
(58) Field of Classification Search
None
See application file for complete search history.

(56) References Cited

U.S. PATENT DOCUMENTS

| | | |
|---|---|---|
| 4,407,956 A | 10/1983 | Howell |
| 4,536,475 A | 8/1985 | Anderson |
| 4,683,195 A | 7/1987 | Mullis et al. |
| 4,683,202 A | 7/1987 | Mullis |
| 4,684,611 A | 8/1987 | Schilperoort et al. |
| 4,800,159 A | 1/1989 | Mullis et al. |
| 5,679,558 A | 10/1997 | Gobel et al. |
| 6,140,553 A | 10/2000 | D'Halluin |
| 10,982,226 B2 | 4/2021 | Moroney et al. |
| 2005/0049212 A1 | 3/2005 | Steuernagel et al. |
| 2013/0007916 A1 | 1/2013 | Spalding |
| 2015/0299676 A1 | 10/2015 | Walsh et al. |
| 2019/0177741 A1 | 6/2019 | Moroney et al. |
| 2021/0189415 A1 | 6/2021 | Moroney et al. |

FOREIGN PATENT DOCUMENTS

| | | |
|---|---|---|
| CN | 107105626 A | 8/2017 |
| EP | 67553 A2 | 12/1982 |
| EP | 116718 B2 | 8/1984 |
| EP | 223247 A2 | 11/1986 |
| EP | 242246 B1 | 10/1987 |
| EP | 270356 B1 | 6/1988 |
| EP | 270822 A1 | 6/1988 |
| WO | WO-1984002913 A1 | 8/1984 |
| WO | WO-1985001856 A1 | 5/1985 |
| WO | WO-1992009696 A1 | 6/1992 |
| WO | WO-1996006932 A1 | 3/1996 |
| WO | WO-1997048819 A1 | 12/1997 |
| WO | WO-2000042207 A2 | 7/2000 |
| WO | WO-2000071733 A1 | 11/2000 |
| WO | WO-2009062190 A2 | 5/2009 |
| WO | WO-2015103074 A1 | 7/2015 |
| WO | WO2016/014720 A1 * | 1/2016 |
| WO | WO 2016/014720 A2 * | 1/2016 |
| WO | WO-2016087314 A2 | 6/2016 |
| WO | WO2016/087314 * | 9/2016 |

OTHER PUBLICATIONS

Written Opinion for application PCT/US19/415 (2019).*
Ill & Preiss (1998) Biochem Biophys Res Commun 244(2):573-77.*
Metting, Jr. (1996) J Ind Microbiol 17: 477-89.*
Guo et al. (2004) Proc Natl Acad Sci USA 101:9205-10, 9209.*
You (2004) Med Res Rev 24:782-74.*
Barr (Feb. 22, 2018) Memo.*
Hill & Preiss (1998) Biochem Biophys Res Commun 244(2):573-77.*
Guo et al. (2004) Proc Natl Acad Sci USA 101:9205-10.*
You (2004) Med Res Rev 24:(6):767-74.*
Zhang (2003) Curr Opin Plant Biol 6:430-40.*
Whisstock & Lesk (2003) Q Rev Biophys. 36(3):307-40.*
Brueggeman et al. (2012) Plant Cell 24:1860-75.*
Zhang et al. (2014) Plant Cell 26(4): 1398-1409.*
Sage & Coleman (2001) Trends Plant Sci 6(1):18-23.*
Kondou et al. (2009) Plant J 57(5):883-894.*
Altschul et al., (1990). "Basic local alignment search tool," J. Mol. Biol., 215:403-410.

(Continued)

*Primary Examiner* — Russell T Boggs
(74) *Attorney, Agent, or Firm* — Morrison & Foerster LLP

(57) ABSTRACT

Aspects of the present disclosure relate to genetically modified plants and/or algae with increased carbon use efficiency as a result of an increased ability for bicarbonate to cross membranes within plant cells. Other aspects of the present disclosure relate to methods of making such plants and/or algae as well as cultivating these genetically modified plants to increase carbon use efficiency and/or growing these genetically modified algae to increase carbon use efficiency.

13 Claims, 33 Drawing Sheets
(17 of 33 Drawing Sheet(s) Filed in Color)
Specification includes a Sequence Listing.

(56) References Cited

OTHER PUBLICATIONS

Altschul et al., (1997). "Gapped BLAST and PSI-BLAST: a new generation of protein database search programs," Nucleic Acids Res., 25:3389-3402.
Amoroso et al., (1998). "Uptake of HCO3- and CO2 in Cells and Chloroplasts from the Microalgae *Chlamydomonas reinhardtii* and *Dunaliella tertiolecta*," Plant Physiol, 116:193-201.
An et al., (1996). "Strong, constitutive expression of the *Arabidopsis* ACT2/ACT8 actin subclass in vegetative tissues," Plant J., 10(1);107-121.
Atkinson et al., (2015). "Introducing an algal carbon-concentrating mechanism into higher plants: location and incorporation of key components," Plant Biotechnol J, 14:1302-1315.
Benkert et al., (2008). "QMEAN: A comprehensive scoring function for model quality assessment," Proteins, 71(1):261-277.
Borkhsenious et at., (1998). "The Intracellular Localization of Ribulose-1,5-Bisphosphate Carboxylase/Oxygenase in Chlamydomonas reinhardtii," Plant Physiol, 116:1585-1591.
Christensen et al, (1992). "*Maize polyubiquitin* genes: structure, thermal perturbation of expression and transcript splicing, and promoter activity following transfer to protoplasts by electroporation," Plant Mol. Biol. 18: 675-689.
Christou et al., (1990). "Soybean genetic engineering—commercial production of transgenic plants," Trends Biotech, 8:145-151.
Datta et al., (1990). "Genetically Engineered Fertile Indica-Rice Recovered from Protoplasts," Bio/Technology, 8:736 740.
De Pater et al., (1992). "The promoter of the rice gene GOS2 is active in various different monocot tissues and binds rice nuclear factor ASF-1," The Plant Journal, 2:837-844.
Depicker et al., (1982). "Nopaline synthase: Transcript mapping and DNA sequence," J. Molec Appl Gen, 1:561-573.
Dickson et al., (2014). "Structure and insights into the function of a Ca2+-activated Cl-channel," Nature, 516(7530):213-218, 30 pages.
Duan et al., (2016). "A bestrophin-like protein modulates the proton motive force across the thylakoid membrane in *Arabidopsis*," Journal of Integrative Plant Biology, 58:848-858.
Duanmu et al., (2009). "Knockdown of limiting-CO2—induced gene HLA3 decreases HCO3-transport and photosynthetic Ci affinity in Chlamydomonas reinhardtii," PNAS, 106:5990-5995.
Engel et al., (2015). "Native architecture of the Chlamydomonas chloroplast revealed by in situ cryo-electron tomography," Elife, 13:04889, 29 pages.
Franck et al., (1980). "Nucleotide sequence of cauliflower mosaic virus DNA," Cell, 21:285-294.
Fromm et al., (1990). "Inheritance and Expression of Chimeric Genes in the Progeny of Transgenic Maize Plants," Bio/Technology, 8:833-839.
Fukuzawa et al., (2001). "Ccm1, a regulatory gene controlling the induction of a carbon-concentrating mechanism in Chlamydomonas reinhardtii by sensing CO2 availability," PNAS, 98(9):5347-5352.
Gao et al., (2015). "Expression activation and functional analysis of HLA3, a putative inorganic carbon transporter in Chlamydomonas reinhardtii," Plant Journal, 82:1-11.
Gardner et al., (1981). "The complete nucleotide sequence of an infectious clone of cauliflower mosaic virus by M13mp7 shotgun sequencing," Nucleic Acids Res, 9:2871-2888.
Gielen et al., (1984). "The complete nucleotide sequence of the TL-DNA of the Agrobacterium tumefaciens plasmid pTiAch5," EMBO J, 3:835-846.
Giordano et al., (2005). "CO2 concentrating mechanisms in algae: mechanisms, environmental modulation, and evolution," Ann Rev Plant Bio, 56:99-131.
Goodstein et al., (2012). "Phytozome: a comparative platform for green plant genomics," Nucleic Acids Res, 40:D1178-1186.
Gordon-Kamm et al., (1990). "Transformation of Maize Cells and Regeneration of Fertile Transgenic Plants," The Plant Cell, 2:603-618.
Gutknecht et al., (1977). "Diffusion of carbon dioxide through lipid bilayer membranes: effects of carbonic anhydrase, bicarbonate, and unstirred layers," J. Gen. Physic., 69:779-794.
Henikoff et al., (1992). "Amino acid substitution matrices from protein blocks," PNAS USA, 89:10915-10919.
Hinchee et al., (1988). "Production of Transgenic Soybean Plants Using Agrobacterium-Mediated DNA Transfer," Bio/Technology, 6:915-922.
Hull et al., (1978). "Structure of the Cauliflower Mosaic Virus Genome. II. Variation in DNA Structure and Sequence Between Isolates," Virology, 86:482-493.
Jin et al., (2016). "Structural insights into the LCIB protein family reveals a new group of β-carbonic anhydrases," PNAS, 113:14716-14721.
Jungnick et al., (2014). "The carbon concentrating mechanism in Chlamydomonas reinhardtii: finding the missing pieces," Photosynth Res., 121:159-173.
Karlin et al., (1990). "Methods for assessing the statistical significance of molecular sequence features by using general scoring schemes," Proc. Natl. Acad. Sci. USA, 87:2264-2268.
Karlin et al., (1993). "Applications and statistics for multiple high-scoring segments in molecular sequences," Proc. Natl. Acad. Sci. USA, 90:5873-5877.
Kearse et al., (2012). "Geneious Basic: An integrated and extendable desktop software platform for the organization and analysis of sequence data," Bioinformatics, 28(12):1647-1649.
Kuchitsu et al., (1988). "Changes of Starch Localization within the Chloroplast Induced by Changes in CO2 Concentration during Growth of Chlamydomonas reinhardtii: Independent Regulation of Pyrenoid Starch and Stroma Starch," Plant Cell Phys, 29:1269-1278.
Kumar et al., (1994). "MEGA: Molecular Evolutionary Genetics Analysis software for microcomputers," Comput Appl Biosci., 10(2):189-191.
Last et al., (1991). "pEmu: an improved promoter for gene expression in cereal cells," Theor Genet, 81:581-588.
Le et al., (2008). "An Improved General Amino Acid Replacement Matrix," Molecular Biology and Evolution, 25(7):1307-1320.
Ma et al., (2011). "Identification of a Novel Gene, CIA6, Required for Normal Pyrenoid Formation in Chlamydomonas reinhardtii," Plant Physiol, 156:884-896.
Machingura et al., (2017). "Identification and characterization of a solute carrier, CIA8, involved in inorganic carbon acclimation in Chlamydomonas reinhardtii," J Exp Bot., 68(14):3879-3890.
Mackinder et al., (2017). "A Spatial Interactome Reveals the Protein Organization of the Algal CO 2-Concentrating Mechanism," Cell, 171:133-147.
Mackinder, (2018). "The Chlamydomonas CO2-concentrating mechanism and its potential for engineering photosynthesis in plants," New Phytologist, 217: 54-61.
Marchand et al., (2018). "Ion and Metabolite Transport in the Chloroplast of Algae: Lessons from Land Plants," Cell and Molecular Life Sciences, 75(12):2153-2176.
Mariscal et al., (2006). "Differential Regulation of the Chlamydomonas Nar1 Gene Family by Carbon and Nitrogen," Protist, 157:421-433.
Merchant et al., (2007). "Genbank Acession No. CM008977.1: Hypothetical Protein CHLRE_16g662600v5 [Chlamydomonas reinhardtii]," Available online at <https://www.ncbtnlm.nih.gov/protein/PNW71636>, 2 pages.
Mitra et al., (2005). "The three carbonic anhydrase families of Chlamydomonas reinhardtii," Can J Bot, 83:780-795.
Molnar et al., (2009). "Highly specific gene silencing by artificial microRNAs in the unicellular alga *Chlamydomonas reinhardtii*," Plant J., 58(1):165-174.
Moroney et al., (1985). "Effect of Carbonic Anhydrase Inhibitors on Inorganic Carbon Accumulation by Chlamydomonas reinhardtii," Plant Physiol., 79(1):177-183.
Moroney et al., (2007). "Proposed carbon dioxide concentrating mechanism in Chlamydomonas reinhardtii," Eukaryotic Cell, 6:1251-1259.
Morth et al., (2011). "A structural overview of the plasma membrane Na+, K+-ATPase and H+-ATPase ion pumps," Nat Rev Mol Cell Biol, 12:60-70.

(56) References Cited

OTHER PUBLICATIONS

Mukherjee et al. (2019). "Thylakoid Localized Bestrophin-Like Proteins are Essential for the CO2 Concentrating Mechanism of Chlamydomonas Reinhardtii," PNAS USA, 116(34):16915-16920.
Pathirana et al., (1997). "Analyses of phosphoenolpyruvate carboxylase gene structure and expression in alfalfa," Plant J, 12:293-304.
Pootakhama et al., (2010). "Identification and Regulation of Plasma Membrane Sulfate Transporters in Chlamydomonas," Plant Physiol, 153:1653-1668.
Qu et al., (2006). "The Anion-Selective Pore of the Bestrophins, a Family of Chloride Channels Associated with Retinal Degeneration," J Neurosci, 26(20):5411-5419.
Qu et al., (2008). "Bestrophin Cl—channels are highly permeable to HCO3—," Am J Physiol Cell Physiol, 294:C1371-C1377.
Rawat et al., (1996). "Chlamydomonas reinhardtii mutants without ribulose-1,5-bisphosphate carboxylase-oxygenase lack a detectable pyrenoid," Planta, 198:263-270.
Saiki et al., (1985). "Enzymatic amplification of beta-globin genomic sequences and restriction site analysis for diagnosis of sickle cell anemia," Science, 230:1350-1354.
Schunmann et al., (2003). "A suite of novel promoters and terminators for plant biotechnology. II. The pPLEX series for use in monocots," Functional Plant Biology, 30(4):453-460.
Shimamoto et al., (1989). "Fertile transgenic rice plants regenerated from transformed protoplasts," Nature, 338:274-276.
Shirtiogawara et al., (1998). "High-Efficiency Transformation of Chlamydomonas reinhardtii by Electroporation," Genetics, 148(4):1821-1828.
Sueoka, (1960). "Mitotic Replication of Deoxyribonucleic Acid in Chlamydomonas Reinhardi," PNAS, 46:83-91.
Sulterneyer et al., (1988). "Photosynthesis and apparent affinity for dissolved inorganic carbon by cells and chloroplasts of Chlamydomonas reinhardtii grown at high and low CO2 concentrations," Planta, 176:256-260.
Thompson et al., (1994). "CLUSTAL W: improving the sensitivity of progressive multiple sequence alignment through sequence weighting, position-specific gap penalties and weight matrix choice," Nucleic Acids Res, 22(22):4673-4680.
Velten et al., (1984). "Isolation of a dual plant promoter fragment from the Ti plasmid of Agrobacterium tumefaciens," EMBO J, 3:2723-2730.
Velten et al., (1985). "Selection-expression plasmid vectors for use in genetic transformation of higher plants," Nucleic Acids Res, 13:6981-6998.
Verdaguer et al., (1998). "Functional organization of the cassava vein mosaic virus (CsVMV) promoter," Plant Mol Biol, 37:1055-1067.
Wang et al., (1997). "Improved Vectors for Agrobacterium Tumefaciens-Mediated Transformation of Monocot Plants," Acta Hort., 461:401-408.
Wang et al., (2014). "Acclimation to Very Low CO2: Contribution of Limiting CO2 Inducible Proteins, LCIB and LCIA, to Inorganic Carbon Uptake in Chlamydomonas reinhardtii," Plant Physiol, 166:2040-2050.
Xiang et al., (2001). "The Cia5 gene controls formation of the carbon concentrating mechanism in Chlamydomonas reinhardtii," PNAS, 98(9):5341-5346.
Yang et al., (2014). "Catalytically active Au—O(OH)x-species stabilized by alkali ions on zeolites and mesoporous oxides," Science, 346(6216):1498-1501.
Zhang et al., (1996). "Induction of a Pea Cell-Wall Invertase Gene by Wounding and Its Localized Expression in Phloem," Plant Physiol, 112:1111-1117.
Zhang et al., (2014). "High-Throughput Genotyping of Green Algal Mutants Reveals Random Distribution of Mutagenic Insertion Sites and Endonucleolytic Cleavage of Transforming DNA," Plant Cell, 26(4):1398-1409.
Badger, (1985). "Photosynthetic oxygen exchange," Ann Rev of Plant Physiol., 36:27-53.
Blaby et al., (2014). "The Chlamydomonas genome project: a decade on," Trends Plant Sci, 19:672-680, 18 pages.
Deikman et al., (1992). "Organization of Ripening and Ethylene Regulatory Regions in a Fruit-Specific Promoter from Tomato (Lycopersicon esculentum)," Plant Physiol., 100:2013-2017.
Extended European Search Report received for European Patent Application No. 17816042 dated Mar. 5, 2020, 2 pages.
Fischer et al., (2001). "The flanking regions of PsaD drive efficient gene expression in the nucleus of the green alga Chlamydomonas reinhardtii," Mol Genet Genomics, 265:888-894. Abstract Only.
Fraley et al., (1983). "Expression of bacterial genes in plant cells," PNAS USA, 80:4803-4807.
Fromm et al., (1985). "Expression of genes transferred into monocot and dicot plant cells by electroporation," PNAS USA, 82:5824-5828.
Frommer et al., (2002). "Plant biology: Ping-pong with boron," Nature, 420:282-283.
Fuhrmann et al., (1999). "A synthetic gene coding for the green fluorescent protein (GFP) is a versatile reporter in Chlamydomonas reinhardtii," Plant J., 19:353-361.
Furumoto et al., (2011). "A plastidial sodium-dependent pyruvate transporter," Nature, 476:472-4745, 6 pages.
GenBank, (2010). "Chlamydomonas reinhardtii strain CC-503 cw92 mt+CHLREscaffold_22, whole genome shotgun sequence, Accession: NW_001843666.1," available online at <https://www.ncbi.nlm.nih.gov/nuccore/159473002?sat=46&satkey=%2079717354>, 4 pages.
GeneCopoeia, (2001). "OmicsLink Expression-Ready ORF Collection. OmicsLink Expression-Ready ORF cDNA Collection," available online at <https://www.genecopoeia.com/product/orf/orf-clone/>, 3 pages.
Gigolashvili et al., (2009). "The plastidic bile acid transporter 5 is required for the biosynthesis of methionine-derived glucosinolates in Arabidopsis thaliana," The Plant Cell, 21:1813-1829.
Hanschen et al., (2016). "The Gonium Pectoral Genome Demonstrates Co-Option of Cell Cycle Regulation During the Evolution of Multicellularity," Nature Communications, 7:11370, 10 pages.
Horsch et al., (1984). "Inheritance of Functional Foreign Genes in Plants," Science, 233:496-498.
Huang et al., (1997). "The Arabidopsis ACT11 actin gene is strongly expressed in tissues of the emerging inflorescence, pollen, and developing ovules," Plant Mol. Biol., 33:125-139.
Im et al., (2002). "Identification and regulation of high light-induced genes in Chlamydomonas reinhardtii," Plant J., 30:301-313.
International Search Report and Written Opinion received for International Patent Application No. PCT/US2017/038278 mailed on Sep. 22, 2017, 10 pages.
Kelley et al., (2015). "The Phyre2 web portal for protein modeling, prediction and analysis," Nat Protocols, 10(16):845-858.
Khoudi et al., (1997). "An alfalfa rubisco small subunit homologue shares cis-acting elements with the regulatory sequences of the RbcS-3A gene from pea," Gene, 197:343-351.
Klee et al., (1987). "Agrobacterium-Mediated Plant Transformation and its Further Applications to Plant Biology," Ann. Rev. Plant Phys., 38:467-486.
Klein et al., (1987). "High-velocity microprojectiles for delivering nucleic acids into living cells," Nature, 327:70-73.
Lucas, (1975). "Photosynthetic Fixation of 14Carbon by internodal cells of Chara corallina," J Exp Bot, 26:331-346.
Manjunath et al., (1997). "Molecular characterization and promoter analysis of the maize cytosolic glyceraldehyde 3-phosphate dehydrogenase gene family and its expression during anoxia," Plant Mol. Biol., 33:97-112.
Martinez et al., (1989). "Structure, evolution and anaerobic regulation of a nuclear gene encoding cytosolic glyceraldehyde-3-phosphate dehydrogenase from maize," J. Mol. Biol., 208:551-565.
Merchant et al., (2007). "The Chlamydomonas Genome Reveals the Evolution of Key Animal and Plant Functions," Science, 318:245-252, 18 pages.
Moroney et al., (1986). "Complementation analysis of the inorganic carbon concentrating mechanism of Chlamydomonas reinhardtii," Mol Gen, 204:199-203.

(56) References Cited

OTHER PUBLICATIONS

Moses, (1987). "Appendix. Gene Transfer Methods Applicable to Agricultural Organisms," NCBI, 24 pages.
Mus et al., (2007). "Anaerobic acclimation in Chlamydomonas reinhardtii: Anoxic gene expression, hydrogenase induction, and metabolic pathways," J Biol Chem, 282:25475-25486.
Nakajima et al., (2013) "SLC4 family transporters in a marine diatom directly pump bicarbonate from seawater," PNAS USA, 110:1767-1772.
Needelman et al., (1970). "A general method applicable to the search for similarities in the amino acid sequence of two proteins," J. Mol. Biol., 48:443-453.
Office Action received for Japanese Patent Application No. 2018-566529 mailed Jul. 2, 2021, 11 pages.
Parker et al., (2013). "The Divergence, Actions, Roles, and Relatives of Sodium-Coupled Bicarbonate Transporters," Physiol Rev, 93:803-959.
Paszkowski et al., (1984). "Direct gene transfer to plants," EMBO J., 3(12):2717-2722.
Price et al., (2004). "Identification of a SulP-type bicarbonate transporter in marine cyanobacteria," PNAS USA, 101:18228-18233.
Price et al., (2011). "The cyanobacterial bicarbonate transporter BicA: its physiological role and the implications of structural similarities with human SLC26 transporters," Biochem Cell Biol, 89(2):178-188.
Price et al., (2013). "The cyanobacterial CCM as a source of genes for improving photosynthetic CO2 fixation in crop species," Journal of Experimental Botany, 64(3):753-768.
Pusckin et al., (2006). "SLC4 base (HCO3- , CO3 2-) transporters: classification, function, structure, genetic diseases, and knockout models," Am J Physiol Renal Physiol, 290:F580-599.
Raven, (1997). "Putting the C in phycology," Euro J Phycology, 32:319-333.
Romero et al., (2013). "The SLC4 family of bicarbonate (HCO3-) transporters," Mol Aspects Med, 34(2-3):159-182, 45 pages.
Romero, (2005). "Molecular pathophysiology of SLC4 bicarbonate transporters," Curr Opin Nephrol Hypertens, 14:495-501.
Sizova et al., (2001). "A Streptomyces rimosus aphVIII gene coding for a new type phosphotransferase provides stable antibiotic resistance to Chlamydomonas reinhardtii," Gene, 277:221-229.
Solocombe et al., (1994). "Temporal and Tissue-Specific Regulation of a *Brassica napus* Stearoyl-Acyl Carrier Protein Desaturase Gene," Plant Physiol., 104:1167-1176.
Takano et al., (2002). "*Arabidopsis* boron transporter for xylem loading," Nature, 420:337-340.
UGI Genome Portal, (2009). "BLAST comparison of SEQ ID No. 1," available online at <http://genome.jgi.doe.gov/Chlre4/Chlre4.home.html>, 12 pages.
UniProt/GeneSeq, (2007). "Chlamydomonas reinhardtii (Chlamydomonas smithii). Accession: A8IZY3," available online at <https://rest.uniprot.org/uniprotkb/A8IZY3.txt?version=23>, 2 pages.
Unknown author, (published Jan. 1, 2011). "Sequence Matches BQ812175," 5 pages.
Wang et al., (2011). "Carbon dioxide concentrating mechanism in Chlamydomonas reinhardtii: inorganic carbon transport and CO2 recapture," Photosynth Res, 109:115-122.

Weising et al. (1988). "Foreign Genes In Plants: Transfer, Structure, Expression, And Applications," Ann. Rev. Genet., 22:421-477.
Zhang et al., (1998). "An Arabidopsis MADS Box Gene That Controls Nutrient-Induced Changes in Root Architecture," Science, 279(5349):407-409.
Zhao et al., (2001). "Expression and characterization of the anion transporter homologue YNL275w in *Saccharomyces cerevisiae*," Am J Physiol Cell Physiol, 281:C33-C45.
Zhong et al., (1996). "The circadian clock gates expression of two *Arabidopsis catalase* genes to distinct and opposite circadian phases," Mol. Gen. Genet., 251:196-203.
Adler et al., (2023). "The role of BST4 in the pyrenoid of Chlamydomonas reinhardtii," bioRvix, 2023.06.15.545204, 66 pages.
Badger et al., (1994). "Measurement of CO2 and HCO3—fluxes in cyanobacteria and microalgae during steady-state photosynthesis," Physiologia Plant, 90:529-536.
Benson et al., (1993). "GenBank," Nucleic Acids Res, 21(13):2963-2965.
Ishiura, (1986). "Gene Cloning from Animal Cells," Seibutsu-Butsuri (Biophysics), 26(6):268-281, 14 pages. Abstract Translation Only.
Moroney et al., (1987). "Evidence for Inorganic Carbon Transport by Intact Chloroplasts of Chlamydomonas reinhardtii," Plant Physiol, 83:460-463.
Moroney et al., (1989). "Isolation and Characterization of a Mutant of Chlamydomonas reinhardtii Deficient in the CO2 Concentrating Mechanism," Plant Physiol, 89(3):897-903.
Moroney et al., (2011). "The carbonic anhydrase isoforms of Chlamydomonas reinhardtii: intracellular location, expression, and physiological roles," Photosynth Res, 109:133-149.
Ohnishi et al., (2010). "Expression of a Low CO2—Inducible Protein, LCI1, Increases Inorganic Carbon Uptake in the Green Alga *Chlamydomonas reinhardtii*," Plant Cell, 22:3105-3117.
Pathirana et al., (1997). "Analyses of phosphoenolpyruvate carboxylase gene structure and expression in alfalfa nodules," Plant J, 12:293-304.
Taylor et al., (2012). "Proton channels in algae: reasons to be excited," Trends Plant Sci, 17:675-684.
Yamano et al., (2010). "Light and Low-CO2-Dependent LCIB-LCIC Complex Localization in the Chloroplast Supports the Carbon-Concentrating Mechanism in Chlamydomonas reinhardtii," Plant Cell Physiol, 51:1453-1468.
Yamano et al., (2015). "Characterization of cooperative bicarbonate uptake into chloroplast stroma in the green alga *Chlamydomonas reinhardtii*," PNAS, 112:7315-7320.
Zhang et al., (1991). "Analysis of rice Act1 5' region activity in transgenic rice plants," The Plant Cell, 3:1155-1165.
Prejean, (2017). "Characterizing Two Bestrophin Mutants of Chlamydomonas reinhardtii, Undergraduate Honors Thesis," Louisiana State University & Agricultural and Mechanical College, 43 pages.
Adler et al., (2024). "Bestrophin-like protein 4 is involved in photosynthetic acclimation to light fluctuations in Chlamydomonas," Plant Physiol, 196(4):2374-2394.
Rottet et al., (2024). "Engineering the cyanobacterial ATP-driven BCT1 bicarbonate transporter for functional targeting to C3 plant chloroplasts," J Exp Bot, 75(16):4926-4943.

* cited by examiner

```
BST1   MQMQANRSSLRASPVRGLGARPLLRALPAG-RVARLNVSAQAKDPNAPIQSNPLGT--LS
BST2   --MQCLSSRPVAMGRAGSSALPRLPLRAGRVCHLGVRCQAANKDPNAPIQSNPLGSFSSQ
BST3   ------MQVSKVPSSASARCLPRLPVRTSRVCQLSVRCQAANKDPNAPIQSNPLGSFSSQ
                      *  *              *   ************

BST1   SQSGQVATLPRSEEARKYFRTVYDFPQWQKHRSSYRFAERLFQLSQSHILQNALPAISWV
BST2   --LQNQPTLPRSEEARKYFRTVYDFPQWQTHRNQYRLMKRLFSIPQSHVIQNALPSIMWV
BST3   NSSGAVVTAPRNEDARKYFRTVYDFPQWQKHRSQSRLVRRLFTIPQSHVIQNALPSIMWV
         **  *  **  ************** **     *   ***    *  ***** *  **

BST1   TLVATLVASYGYSYDQHMLPDVFPSISPNASCTAFISNTSVALSLLLVFRTNSSYGRNDE
BST2   AFTSTCVAAYMYGYDQHMLPEGFPTLAPNAACSAFISNTSVALSLLLVFRTNSSYGRNDE
BST3   TFTSTCVAAYMYGYDLHILPEGFPTLAPNAACSAFISNTSVALSLLLVFRTNSSYGRNDE
         * **  *  *  ** *  **  **  ***  ***  ************************

BST1   ARKMWGGLLNRSRDIMRQGATCFPDDQVEAKKALARWTVAFSRALRIHFQPEVTIESELQ
BST2   ARKMWGGLLNRSRDIMRQGATCFPDDQVEAKKALARWVVAFSRALRIHFQPEVTIESELK
BST3   ARKMWGGLLNRSRDIMRQGATCFPDDQVEAKKALARWTVAFARALRIHFQPEVTIESELQ
       ************************************      ***      *******************

BST1   NILTPAELQMLAKSQHRPVRAIHAISQIIQSVPMSSIHQQQMSNNLTFFHDVLGGCERLL
BST2   NILTPAELQMLAKSQHRPVRAIHAISQIIQSVPMSSIHQQQMSNNLTFFHDVLGGCERLL
BST3   NILTPAELQMLAKSQHRPVRAIHAISQIIQSVRMSSIHQQQMSNNLTFFHDVLGGCERLL
       *******************************  ***************************

BST1   RAPIPVSYTRHTARFLFAWLTLLPFALYPTTGWGVVPVCTGIAAVLCGIEEIGVQCEEPF
BST2   RAPIPVSYTRHTARFLFAWLTLLPFALYGSCGVSVIPVCSGIAAVLCGIEEIGVQCEEPF
BST3   RAPIPVSYTRHTARFLFAWLTLLPFALYGSCGVSVIPVCTGIAAVLCGIEEIGVQCEEPF
       ****************************    *   ***   *****************

BST1   GILPLDVICNRIQADVMATLKDDADTKTILAEAGLISLIPSATSATPVASAEPVLVSARP
BST2   GILPLDVICNRIQADVMATLKDDADTKTILAEAGLISLRANSAMAVENALPDLDSINAAA
BST3   GILPLDVICNRIQADVMATLKDDADTKTVLAEAGLISLIPSMSLPPTEHASPSDPVTAAA
       ****************************  *******    *     *           *

BST1   SAAPAPNNGLQVRVAMGGERK*---------------------
BST2   PNGNGSHNGNGAAVPVSVSAGASGNGMNVRISPR*---------
BST3   AAALAAANGNGAASHSNGNGSKPVSTQVPPPVLAPVTVSSSGSMNVRISPR*
            **
```

FIG. 1C

GREEN ALGAL BESTROPHIN BICARBONATE TRANSPORTERS

CROSS-REFERENCE TO RELATED APPLICATIONS

This application is a national stage application under 35 U.S.C. § 371 of International Application No. PCT/US2019/041584, filed Jul. 12, 2019, which claims the benefit of U.S. Provisional Application No. 62/769,214, filed Nov. 19, 2018, and U.S. Provisional Application No. 62/697,840, filed Jul. 13, 2018, which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 794542000100SEQLIST.TXT, date recorded: Dec. 26, 2020, size: 461 KB).

TECHNICAL FIELD

The present disclosure relates to genetically modified plants. In particular, the present disclosure relates to genetically modified plants containing green algal bestrophin bicarbonate transporters that preferably provide increased carbon use efficiency.

BACKGROUND

Green algae and other photosynthetic aquatic organisms are often exposed to low and fluctuating $CO_2$ conditions in the natural environment. There are a variety of factors that can reduce $CO_2$ availability for these organisms, including slow diffusion of gases in water, slow interconversion of the two inorganic carbon (Ci) forms carbon dioxide ($CO_2$) and bicarbonate ($HCO_3^-$), and pH changes. As a result of the changeable natural environment, most aquatic photosynthetic organisms have evolved a carbon dioxide concentrating mechanism (CCM) that is inducible under limiting $CO_2$ conditions. The CCM allows aquatic photosynthetic organisms such as green algae to effectively concentrate Ci for fixation by Rubisco (Giordano et al., Ann Rev Plant Bio 56:99-131, 2005). The current CCM model for the green alga *Chlamydomonas reinhardtii* (Jungnick et al., Photosynth Res 121:159-173, 2014; Wang and Spalding, Plant Physiol 166:2040-2050, 2014) includes bicarbonate transporters on the plasma membrane and chloroplast envelope as key components of the CCM allowing the movement of Ci, particularly $HCO_3^-$, through the membranes. Carbonic anhydrase enzymes that interconvert $CO_2$ and $HCO_3^-$ are a further important component of the CCM model (Mitra et al., Can J Bot 83:780-795, 2005; Moroney et al., Photosynth Res 109:133-149, 2011).

In *C. reinhardtii*, a compartment called the pyrenoid is located at the base of the chloroplast. The pyrenoid is the location where Rubisco is sequestered under limiting $CO_2$ conditions (Kuchitsu et al., Plant Cell Phys 29:1269-1278, 1988; Rawat et al., Planta 198:263-270, 1996; Borkhsenious et al., Plant Physiol 116:1585-1591, 1998). An extensive network of thylakoid tubules and mini-tubules is associated with the pyrenoid (Engel et al., Elife 13:04889, 2015), presumably to provide a pathway for $HCO_3^-$ to enter into the pyrenoid. The thylakoid carbonic anhydrase CAH3 is found in these tubules and it is hypothesized that CAH3 converts $HCO_3^-$ to $CO_2$ for fixation within the lumen (Moroney and Ynalvez, Eukaryotic Cell 6:1251-1259, 2007).

*C. reinhardtii* cells grown under high $CO_2$ conditions (5% v/V) exhibit a low affinity for Ci. When high $CO_2$ acclimated cells are exposed to lower $CO_2$ conditions (e.g., ambient 0.04% to low <0.01% v/v), induction of high affinity Ci transporters has been reported. While $CO_2$ will readily diffuse across membranes in the cell (Gutknecht et al., J. Gen. Physiol 69:779-794, 1977), numerous studies have since established the need for an active transport system to facilitate the movement of Ci (particularly $HCO_3^-$) to the location where fixation by Rubisco can occur in cells grown under low $CO_2$ conditions (Moroney et al., Plant Physiol 83:460-463, 1987; Sultemeyer et al., Planta 176:256-260, 1988; Badger et al., Physiologia Plant 90:529-536, 1994; Ohnishi et al., Plant Cell 22:3105-3117, 2010). In addition, molecular and physiological studies have also confirmed the occurrence of multiple forms of Ci transporters on the plasma membrane and chloroplast envelope of cells (Amoroso et al., Plant Physiol 116:193-201, 1998; Duanmu et al., PNAS 106:5990-5995, 2009; Atkinson et al., Plant Biotechnol J 5:12497, 2015; Gao et al., Plant 82:1-11, 2015; Yamano et al., PNAS 112:7315-7320, 2015).

In cyanobacteria that live in marine environments, $HCO_3^-$ transport at the plasma membrane is often coupled to the high external $Na^+$ ion concentration of saltwater. In the freshwater environments where *C. reinhardtii* is found, transport is thought to be $H^+$-coupled since $Na^+$ concentration is relatively low (Morth et al., Nat Rev Mol Cell Biol 12:60-70, 2011; Taylor et al., Trends Plant Sci 17:675-684, 2012). Consequently, genomic studies with *C. reinhardtii* and *Volvox carteri* have revealed the presence of both $H^+$- and $Na^+$-coupled transporters for sulphate and phosphate (Pootakbam et al., Plant Physiol 153:1653-1668, 2010). It is not yet clear whether this type of ion coupling is also important for bicarbonate uptake To date, two high affinity bicarbonate transport proteins and one low affinity bicarbonate transport protein in *C. reinhardtii* have been characterized and are known to be functional under low $CO_2$ conditions. The first high affinity transporter, High Light Activated protein 3 (HLA3), is an ATP-binding cassette (ABC)-type transporter of the Multi-Drug Resistance protein family, and is localized to the plasma membrane (Im and Grossman, 2002). The Hla3 transcript is induced by both high light and low $CO_2$ conditions and is controlled by the CCM 'master regulator' encoded by the Cia5 gene. Duanmu et al. (2009) showed a significant reduction in Ci affinity and Ci uptake in HLA3 RNAi knockdown mutants, supporting the role of this protein in HCOs transport. The second high affinity transporter, Low Carbon Inducible protein 1 (LCI1), is a relatively small protein. LCI1 is strongly upregulated in cells grown under low $CO_2$ conditions, and it has been localized to the plasma membrane (Ohnishi et al., Plant Cell 22:3105-3117, 2010). In addition, overexpression of the LCI1 protein in the Lcr1 (*Chlamydomonas* strain lacking a MYB-transcription factor) background resulted in increased Ci uptake. Thus, HLA3 and LCI1 are both thought to be Ci transporters located on the plasma membrane.

The third transporter, NAR1.2 (also known as LCIA), is a chloroplast envelope protein of the Formate/Nitrite transporter family. Although the NAR1.2 protein has lower affinity for bicarbonate (as revealed in the $K_{1/2}$ value which falls in the mM range), expressing NAR1.2 in *Xenopus laevis* oocytes resulted in increased $HCO_3^-$ uptake (Mariscal et al., Protist 157:421-433, 2006; Atkinson et al., Plant Biotechnol J 5:12497, 2015). NAR1.2 has been shown to be localized to the chloroplast envelope, and is believed to be involved in Ci uptake, but the molecular mechanism for this remains unclear (Yamano et al., PNAS 112:7315-7320, 2015). Experimental results indicate that NAR1.2 and HLA3 proteins have a cooperative role within the CCM (Yamano et al., PNAS 112:7315-7320, 2015). Under very low $CO_2$ conditions, NAR1.2 has been shown to act in conjunction with Low-$CO_2$ Inducible protein B (LCIB). These results suggested a model in which LCIB is involved in $CO_2$ uptake and recapture of $CO_2$ that leaks from the pyrenoid, while NAR1.2 is involved in the $HCO_3^-$ uptake and transport pathway (Wang and Spalding, Plant Physiol 166:2040-2050, 2014).

In addition to the proteins likely involved in the CCM that are described above, roles for multiple other proteins have been suggested. For example, the two soluble proteins LCIB and LCIC form a complex that has been observed to closely associate with the pyrenoid when cells are acclimated to very low $CO_2$ (Yamano et al., Plant Cell Physiol 51:1453-1468, 2010), but it is not yet certain what the role of this complex might be (Jin et al., PNAS 113:14716-14721, 2016). Another example is provided by CCP1 and CCP2, which are other putative Ci transporters that have been shown to be localized to mitochondria (Atkinson et al., Plant Biotechnol J 5:12497, 2015). This localization suggests that mitochondria may be important in CCM function, but it is not clear yet what the mechanisms of this might be or what role mitochondria could play.

Bestrophins are a family of membrane proteins that exhibit Cl-channel activity and also function as regulators of voltage-gated $Ca^{2+}$ channels. Human and mouse bestrophins have been found to have high permeability and conductance to $HCO_3^-$ (Qu and Hartzell, Am J Physiol Cell Physiol 294: C1371-C1377, 2008). However, it has been shown that amino acids in phototrophic bestrophin proteins show high diversity compared with their counterparts in mammals using protein alignment and phylogenetic tree analyses. For example, the residues forming the $Ca^{2+}$ sensing apparatus in animal bestrophin are not conserved in the bestrophin-like proteins in *Arabidopsis* (AtBest1 and AtBest2), suggesting that $Ca^{2+}$ is not required for AtBest channel activation in the chloroplast. Therefore during evolution, bestrophin proteins in phototrophs may have acquired different electrophysiological properties from those in mammals (Duan et al. Journal of Integrative Plant Biology 58:848-858, 2016). In *C. reinhardtii*, LCI11 and Cre 16.g662600 have been suggested as putative bestrophins, and Cre16.g663400 is proposed to be a bestrophin-like protein (Mackinder et al., Cell 171:133-147, 2017), but these have not been further characterized.

Current data only unambiguously support the necessity of five proteins for the inorganic carbon (Ci) influx in *C. reinhardtii*, including HLA3, LCI1, LCIA, CAH3, and LCIB (Mackinder, New Phytologist 217:54-61, 2018). As described above, these proteins are localized to the plasma membrane and the chloroplast envelope. The current model of the *C. reinhardtii* CCM suggests that at least one additional transporter or channel in the chloroplast thylakoid membrane is required to maintain a flux of $HCO_3^-$ from the stroma to CAH3 in the lumen (Mackinder New Phytologist 217:54-61, 2018). Moreover, identifying functional bicarbonate transport proteins remains an important goal. Current research has identified many possible bicarbonate transport proteins, but only a few of these have promising experimental results, and there is little mechanistic data available.

BRIEF SUMMARY

In order to meet these needs, the present disclosure is directed to green algal bestrophin polypeptides that act as bicarbonate transport proteins. Certain aspects of the present disclosure relate to a genetically altered plant or part thereof containing one or more genetic alterations that increase or provide the ability for bicarbonate to cross a membrane from a plant cell cytoplasm into a stroma of at least a portion of the chloroplasts of the plant. In some aspects, the present disclosure relates to a genetically altered plant or part thereof containing one or more genetic alterations that increase or provide the ability for bicarbonate to cross a membrane from a stroma into a lumen of at least a portion of the chloroplasts of the plant. In some embodiments, the gain of the bicarbonate membrane crossing ability is the result of the expression of at least one green algal bestrophin polypeptide. In some embodiments, the green algal bestrophin polypeptide is selected from the group of SEQ ID NO:1, SEQ ID NO:2, or SEQ ID NO:3. In some embodiments, the increase or provision of the ability for bicarbonate to cross a membrane is the result of expression of a polypeptide selected from the group of a first polypeptide with at least 70% sequence identity, at least 75% sequence identity, at least 80% sequence identity, at least 85% sequence identity, at least 90% sequence identity, or at least 95% sequence identity to SEQ ID NO:1, a second polypeptide with at least 70% sequence identity, at least 75% sequence identity, at least 80% sequence identity, at least 85% sequence identity, at least 90% sequence identity, or at least 95% sequence identity to SEQ ID NO:2, a third polypeptide with at least 70% sequence identity, at least 75% sequence identity, at least 80% sequence identity, at least 85% sequence identity, at least 90% sequence identity, or at least 95% sequence identity to SEQ ID NO:3, or any combination thereof. In some embodiments, the increase or provision of the ability for bicarbonate to cross a membrane is the result of expression of a polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments, the increase or provision of the ability for bicarbonate to cross a membrane is the result of expression of a polypeptide selected from the group of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. In some embodiments, the polypeptide is localized to a chloroplast envelope or a thylakoid membrane of at least one chloroplast within a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with increased carbon use efficiency containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with increased water use efficiency containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with increased nitrogen use efficiency containing at least one modified nucleic acid sequence with at least one coding sequence of a green algal bestropbin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with reduced photoinhibition containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some embodiments of any of the above embodiments the modified nucleic acid sequence is stably integrated into the nuclear genome of the plant. In some embodiments of any of the above embodiments, the at least one modified nucleic acid sequence additionally contains a second nucleic acid sequence encoding a signal peptide sequence or targeting sequence operably linked to the at least one coding sequence of a green algal bestrophin polypeptide, where expression of the signal peptide sequence or targeting sequence results in localization of the bestrophin polypeptide to a chloroplast envelope or chloroplast thylakoid membrane of at least one chloroplast of a plant cell.

In some embodiments of any of the above embodiments, the increased carbon use efficiency, increased water use efficiency, increased nitrogen use efficiency, or reduced photoinhibition is the result of expression of a polypeptide selected from the group of a first polypeptide with at least 70% sequence identity, at least 75% sequence identity, at least 80% sequence identity, at least 85% sequence identity, at least 90% sequence identity, or at least 95% sequence identity to SEQ ID NO:1, a second polypeptide with at least 70% sequence identity, at least 75% sequence identity, at least 80% sequence identity, at least 85% sequence identity, at least 90% sequence identity, or at least 95% sequence identity to SEQ ID NO:2, a third polypeptide with at least 70% sequence identity, at least 75% sequence identity, at least 80% sequence identity, at least 85% sequence identity, at least 90% sequence identity, or at least 95% sequence identity to SEQ ID NO:3, or any combination thereof. In some embodiments of any of the above embodiments, the increased carbon use efficiency, increased water use efficiency, increased nitrogen use efficiency, or reduced photoinhibition is the result of expression of a polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments of any of the above embodiments, the increase or provision of the ability for bicarbonate to cross a membrane is the result of expression of a polypeptide selected from the group of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63.

In some embodiments of any of the above embodiments, the plant is cowpea (i.e., black-eyed pea, *Vigna unguiculata*), soybean (i.e., soya bean, *Glycine max*), cassava (i.e., manioc, *Manihot esculenta*), rice (i.e., *Oryza sativa, Oryza glaberrima, Zizania* spp.), wheat (i.e., common wheat, spelt, durum, *Triticum aestivum, Triticum spelta, Triticum durum, Triticum* spp.), barley (i.e., *Hordeum vulgare*), rye (i.e., *Secale cereale*), oat (i.e., *Avena sativa*), potato (i.e., *Solanum tuberosum*), tomato (i.e., *Solanum lycopersicum*), or another C3 crop plant. In some embodiments, the plant is tobacco (i.e., *Nicotiana tabacum, Nicotiana edwardsonii, Nicotiana plumbagnifolia, Nicotiana longiflora*) or *Arabidopsis* (i.e., rockcress, thale cress, *Arabidopsis thaliana*). In some embodiments of any of the above embodiments, the plant is not corn (i.e., maize, *Zea mays*), sorghum (i.e., durra, great millet, milo, *Sorghum bicolor*), sugarcane (i.e., sugar cane, *Saccharum officinarum*), millet (i.e., finger millet, common millet, pearl millet, foxtail millet, *Eleusine coracana, Panicum miliaceum, Pennisetum glaucum, Setaria italica*), switchgrass (i.e., tall panic grass, thatchgrass, *Panicum virganum*), or another C4 crop plant.

In some embodiments, the plant part of any of the above embodiments is a leaf, a stem, a root, a flower, a seed, a fruit, a cell, or a portion thereof. In some embodiments, the plant part is a fruit. In some embodiments, the plant part is a grain, a kernel, a bean, or a tuber.

In some aspects, the present disclosure relates to a pollen grain or an ovule of any of the above embodiments.

In some aspects, the present disclosure relates to a protoplast produced from any of the above embodiments.

In some aspects, the present disclosure relates to a tissue culture produced from protoplasts or cells of any of the above embodiments, where the cells or protoplasts are produced from one of the plant parts in the group of leaf, anther, pistil, stem, petiole, root, root tip, fruit, seed, flower, cotyledon, hypocotyl, embryo, or meristematic cell.

In some aspects, the present disclosure relates to a genetically altered seed containing one or more genetic alterations that increase or provide the ability for bicarbonate to cross a membrane. In some embodiments, the seed produces a plant with the ability for bicarbonate to cross a membrane from a plant cell cytoplasm into a stroma of at least a portion of the chloroplasts of the plant. In some embodiments, the seed produces a plant with the ability for bicarbonate to cross a membrane from a stroma into a lumen of at least a portion of the chloroplasts of the plant. In some embodiments, the plant expresses at least one green algal bestrophin polypeptide. In some embodiments, the green algal bestrophin polypeptide is selected from the group of SEQ ID NO:1, SEQ ID NO:2, SEQ ID NO:3, or any combination thereof. In some embodiments, the plant expresses at least one polypeptide selected from the group of a first polypeptide with at least 70% sequence identity, at least 75% sequence identity, at least 80% sequence identity, at least 85% sequence identity, at least 90% sequence identity, or at least 95% sequence identity to SEQ ID NO:1, a second polypeptide with at least 70% sequence identity, at least 75% sequence identity, at least 80% sequence identity, at least 85% sequence identity, at least 90% sequence identity, or at least 95% sequence identity to SEQ ID NO:2, a third polypeptide with at least 70% sequence identity, at least 75% sequence identity, at least 80% sequence identity, at least 85% sequence identity, at least 90% sequence identity, or at least 95% sequence identity to SEQ ID NO:3, or any combination thereof. In some embodiments, the plant expresses at least one polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments, the plant expresses a polypeptide selected from the group of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. In some embodiments, the polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant. In some embodiments, the plant is cowpea, soybean, cassava, rice, soy, wheat, or other C3 crop plants. In some embodiments, the plant is not corn, sorghum, or other C4 crop plants.

In some embodiments of any of the above embodiments, the expression of endogenous carbonic anhydrases is modulated. In some embodiments, modulated expression may be increased expression, reduced expression, expression at a different location, or any combination thereof.

Certain aspects of the present disclosure relate to a method of producing a plant with increased carbon use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing carbon use efficiency of the plant.

In some aspects, the present disclosure relates to a method of producing a plant with increased water use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing water use efficiency of the plant.

In some aspects, the present disclosure relates to a method of producing a plant with increased nitrogen use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing nitrogen use efficiency of the plant.

In some aspects, the present disclosure relates to a method of producing a plant with reduced photoinhibition, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby reducing photoinhibition of the plant.

In some aspects, the present disclosure relates to a method of producing a plant with increased growth or productivity, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing growth or productivity of the plant.

In some embodiments of any of the above methods, the expression of endogenous carbonic anhydrases is modulated. In some embodiments, modulated expression may be increased expression, reduced expression, expression at a different location, or any combination thereof.

In some aspects, the present disclosure relates to a method of cultivating a plant with increased carbon use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases carbon use efficiency as compared to a plant grown under the same conditions that lacks the one or more genetic alterations.

In some aspects, the present disclosure relates to a method of cultivating a plant with increased water use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases water use efficiency as compared to a plant grown under the same conditions that lacks the one or more genetic alterations.

In some aspects, the present disclosure relates to a method of cultivating a plant with increased nitrogen use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases nitrogen use efficiency as compared to a plant grown under the same conditions that lacks the one or more genetic alterations.

In some aspects, the present disclosure relates to a method of cultivating a plant with reduced photoinhibition, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane reduces photoinhibition as compared to a plant grown under the same conditions that lacks the one or more genetic alterations.

In some aspects, the present disclosure relates to a method of cultivating a plant with increased growth or productivity, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases growth or productivity as compared to a plant grown under the same conditions that lacks the one or more genetic alterations.

In some aspects, the present disclosure relates to a method of cultivating a plant with increased carbon use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases carbon use efficiency as compared to a plant grown under the same conditions that lacks the one or more genetic alterations.

In some aspects, the present disclosure relates to a method of cultivating a plant with increased water use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases water use efficiency as compared to a plant grown under the same conditions that lacks the one or more genetic alterations.

In some aspects, the present disclosure relates to a method of cultivating a plant with increased nitrogen use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases nitrogen use efficiency as compared to a plant grown under the same conditions that lacks the one or more genetic alterations.

In some aspects, the present disclosure relates to a method of cultivating a plant with reduced photoinhibition, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane reduces photoinhibition as compared to a plant grown under the same conditions that lacks the one or more genetic alterations.

In some aspects, the present disclosure relates to a method of cultivating a plant with increased growth or productivity, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases growth or productivity as compared to a plant grown under the same conditions that lacks the one or more genetic alterations.

In some embodiments of any of the above methods, the seed, tissue culture, or protoplast has one or more genetic alterations that modulate the expression of endogenous carbonic anhydrases. In some embodiments, modulated expression may be increased expression, reduced expression, expression at a different location, or any combination thereof.

In some embodiments of any of the above methods, the increase or provision of the ability for bicarbonate to cross a membrane is the result of the expression of at least one polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments of any of the above methods, the increase or provision of the ability for bicarbonate to cross a membrane is the result of the expression of at least one polypeptide from selected from the group of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. In some embodiments of any of the above methods, the plant is cowpea, soybean, cassava, rice, soy, wheat, or other C3 crop plants. In some embodiments of any of the above methods, the plant is not corn, sorghum, or other C4 crop plants.

Certain aspects of the present disclosure relate to a genetically altered alga containing one or more genetic alterations resulting in the increase of the ability of the alga to transport bicarbonate into a lumen of a chloroplast of the alga. In some embodiments, the increase of bicarbonate transport ability is the result of overexpressing at least one green algal bestrophin polypeptide from the group of a first polypeptide with at least 70% sequence identity, at least 75% sequence identity, at least 80% sequence identity, at least 85% sequence identity, at least 90% sequence identity, or at least 95% sequence identity to SEQ ID NO:1, a second polypeptide with at least 70% sequence identity, at least 75% sequence identity, at least 80% sequence identity, at least 85% sequence identity, at least 90% sequence identity, or at least 95% sequence identity to SEQ ID NO:2, a third polypeptide with at least 70% sequence identity, at least 75% sequence identity, at least 80% sequence identity, at least 85% sequence identity, at least 90% sequence identity, or at least 95% sequence identity to SEQ ID NO:3, or any combination thereof. In some embodiments, the increase of bicarbonate transport ability is the result of overexpressing at least one green algal bestrophin polypeptide from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments, the polypeptide is localized to a chloroplast thylakoid membrane. In some embodiments, the polypeptide is overexpressed at least when the alga is under <100 ppm carbon dioxide (<0.01% [v/v] $CO_2$ in air) conditions.

In some aspects, the present disclosure relates to a green alga or part thereof with increased bicarbonate transport containing a modified nucleic acid sequence containing the coding sequence of at least one green algal bestrophin polypeptide; wherein the bestropbin polypeptide is overexpressed; wherein the bestrophin polypeptide is localized to chloroplast thylakoid membranes; and wherein when the alga is cultivated under <100 ppm carbon dioxide (<0.01% [v/v] $CO_2$ in air) conditions, the yield, growth rate, or biomass is greater than from a corresponding wild-type (WT) alga or WT part thereof that that does not overexpress the at least one bestrophin polypeptide or the yield, growth rate, or biomass is substantially similar to the yield, growth rate, or biomass from the corresponding WT alga or corresponding WT part thereof that does not overexpress the at least one bestrophin polypeptide cultivated under <100 ppm carbon dioxide (<0.01% [v/v] $CO_2$ in air) conditions. In some embodiments, the at least one green algal bestrophin polypeptide is selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

In some aspects, the present disclosure relates to a green alga or part thereof with increased growth under <100 ppm carbon dioxide (<0.01% [v/v] $CO_2$ in air) conditions containing a modified nucleic acid sequence containing the coding sequence of at least one green algal bestrophin polypeptide; wherein the bestrophin polypeptide is overexpressed; wherein the bestrophin polypeptide is localized to chloroplast thylakoid membranes; and wherein when the alga is cultivated under <100 ppm carbon dioxide (<0.01% [v/v] $CO_2$ in air) conditions, the yield, growth rate, or biomass is greater than from a corresponding wild-type (WT) alga or WT part thereof that that does not overexpress the at least one bestrophin polypeptide or the yield, growth rate, or biomass is substantially similar to the yield, growth rate, or biomass from the corresponding WT alga or corresponding WT part thereof that does not overexpress the at least one bestrophin polypeptide cultivated under <100 ppm carbon dioxide (<0.01% [v/v] $CO_2$ in air) conditions. In some embodiments, the at least one green algal bestrophin polypeptide is selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

In some embodiments of any of the above algae, the green alga is selected from the group of *Chlamydomonas reinhardtii*, *Chlamydomonas eustigma*, *Volvox carteri* f. *nagariensis*, and *Gonium pectorale*.

In some aspects, the present disclosure relates to a method of producing an alga with increased carbon use efficiency, where the steps of the method are: a) introducing a genetic alteration to the alga comprising the increase of the ability to transport bicarbonate into a lumen of a chloroplast of the alga, thereby increasing carbon use efficiency of the alga. In some embodiments, the gain of transport ability is the result of overexpressing at least one green algal bestrophin polypeptide selected from the group of a first polypeptide with at least 70% sequence identity, at least 75% sequence identity, at least 80% sequence identity, at least 85% sequence identity, at least 90% sequence identity, or at least 95% sequence identity to SEQ ID NO:1, a second polypeptide with at least 70% sequence identity, at least 75% sequence identity, at least 80% sequence identity, at least 85% sequence identity, at least 90% sequence identity, or at least 95% sequence identity to SEQ ID NO:2, a third polypeptide with at least 70% sequence identity, at least 75% sequence identity, at least 80% sequence identity, at least 85% sequence identity, at least 90% sequence identity, or at least 95% sequence identity to SEQ ID NO:3, or any combination thereof. In some embodiments, the increase of bicarbonate transport ability is the result of overexpressing at least one green algal bestrophin polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D show the similarity of the *C. reinhardtii* genes (BST1, BST2, and BST3) and proteins (BST1, BST2, and BST3) to each other, as well as the similarity of BST1-3 to other bestrophin family proteins. FIG. 1A shows a schematic representation of the BST1, BST2, and BST3 genes, where the tan boxes represent exons, the thin grey lines represent introns, the thick grey lines represent untranslated regions (UTRs), and the overlaid red lines (overlaid on exons and introns) indicate the common region shared by the three genes. FIG. 1B shows the location and orientation of the BST1, BST2, and BST3 genes on the *C. reinhardtii* genome. FIG. 1C shows an amino acid alignment of the BST1 (SEQ ID NO:1), BST2 (SEQ ID NO:2), and BST3 (SEQ ID NO:3) proteins, where the asterisks in the bottom row indicate amino acids that are identical in all three proteins. FIG. 1D shows a phylogenetic tree of the protein sequences of *C. reinhardtii* BST1, BST2 and BST3 homologs in vascular plants (group second from the top; highlighted in purple), non-vascular plants (group third from the top; highlighted in blue), diatoms (group fourth from the top; highlighted in teal), and green algae (group at bottom; highlighted in green).

FIG. 2A shows semi-quantitative RT-PCR showing BST1-3 accumulation in low $CO_2$ (<0.04% $CO_2$ in air) vs. high $CO_2$ (5% (v/v) $CO_2$ in air) in wild-type strain D66 and cia5 cells. FIG. 2B shows a semi-quantitative RT-PCR time course showing the expression of BST1-3 in cDNA obtained from cells grown in high $CO_2$ (5% $CO_2$ (v/v) in air) and in cells switched to low $CO_2$ (<0.04% $CO_2$ in air) for 2 hours (2h), 4 hours (4h), 6 hours (6h), or 12 hours (12h). Actin was used as a loading control in both FIG. 2A and FIG. 2B, and the results shown are from one of two replicates.

FIG. 3A shows the location of BST1-Venus, BST2-Venus, and BST3-Venus fusion protein expression ("Venus" column), the location of chloroplast thylakoids ("Chlorophyll" column), and the location of both relative to each other ("Merge" column) in *C. reinhardtii*. The scale bar is 5 µm. FIG. 3B shows zoomed-in images of the pyrenoid from the "BST1" row in FIG. 3A. Arrows highlight where BST1-Venus fluorescence can be seen inside the pyrenoid in the thylakoid tubules that penetrate the pyrenoid. The scale bar is 1 µm. The images for both FIG. 3A and FIG. 3B are representative images of multiple replicates.

FIG. 5A shows results of growth phenotype analysis of the strains under very low $CO_2$ (0.01% $CO_2$ (v/v) in air) conditions and a pH of 7 or 8.4. FIG. 5B shows results of growth phenotype analysis of the strains under low $CO_2$ (0.04% $CO_2$ (v/v) in air) and a pH of 7 or 8.4. FIG. 5C shows results of growth phenotype analysis of the strains under high $CO_2$ (5% $CO_2$ (v/v) in air) conditions and a pH of 7 or 8.4. The growth phenotype analysis experiment was repeated three times, and the results shown are representative.

FIG. 6A shows the $K_{0.5}$ ($C_i$) values ($C_i$ concentration needed for half maximum oxygen evolution) that were calculated from the $O_2$ evolution versus $C_i$ curves for bsti-1 and D66 acclimated to low $CO_2$ (<0.04% $CO_2$) for 12 hours at pH 8.4. FIG. 6B shows oxygen evolving activity measured at different $C_i$ amounts and at different pH values plotted as curves for bsti-1 and D66 acclimated to low $CO_2$ (<0.04% $CO_2$) for 12 hours at pH 8.4. FIG. 6C shows the $K_{0.5}$ ($C_i$) values ($C_i$ concentration needed for half maximum oxygen evolution) that were calculated from the $O_2$ evolution versus $C_i$ curves for bsti-1, bsti-2, and D66 acclimated to low $CO_2$ (<0.04% $CO_2$) for 12 hours at pH 7.8. The symbol "*" indicates that the differences in $K_{0.5}$ ($C_i$) was significant (P<0.05 by student t test). FIG. 6D shows oxygen evolving activity measured at different $C_i$ amounts and at different pH values plotted as curves for bsti-1, bsti-2, and D66 acclimated to low $CO_2$ (<0.04% $CO_2$) for 12 hours at pH 7.8. FIG. 6E shows the $K_{0.5}$ ($C_i$) values ($C_i$ concentration needed for half maximum oxygen evolution) that were calculated from the $O_2$ evolution versus $C_i$ curves for bsti-1 and D66 acclimated to high $CO_2$ (>5% $CO_2$) for 12 hours at pH 7.8. FIG. 6F shows oxygen evolving activity measured at different $C_i$ amounts and at different pH values plotted as curves for bsti-1 and D66 acclimated to high $CO_2$ (>5% $CO_2$) for 12 hours at pH 7.8. For FIGS. 6A-6F, triplicate runs were made at each $C_i$ concentration, and the error bars represent three biological replicates and are based on standard deviation. The Vmax of all the strains was set to 100% oxygen evolution activity.

FIG. 7A shows a time course of intracellular (internal) $C_i$ accumulation at pH 7.8. FIG. 7B shows a time course of $CO_2$ ($C_i$) fixation at pH 7.8. FIG. 7C shows a time course of intracellular $C_i$ accumulation at pH 8.4. FIG. 7D shows a time course of $CO_2$ fixation at pH 8.4. Cells were grown in elevated $CO_2$ (5% $CO_2$ in air) and then acclimated to low $CO_2$ (<0.04% $CO_2$) for 12 hours prior to the assays. Cells were harvested and depleted of endogenous $C_i$ before running the assays, and triplicate samples were run for each time point. The error bars in FIGS. 7A-7D represent three biological replicates.

FIG. 8A shows a schematic of the BST3 gene, where exons are depicted as blue boxes, introns are depicted as black lines, and untranslated regions are depicted as purple boxes. The location of the insert is shown as a green triangle, and primers to detect the insert are shown as small black arrows. FIG. 8B shows the results of PCR reactions using the primers shown in FIG. 8A to confirm the location of the insert in bst3. Lane 1, BST3F and BST3R primers using WT strain D66 DNA as template; lane 2, CIB1F and BST3F primers using bst3 DNA as template; lane 3, CIB1R and BST3R primers using bst3 DNA as template; lane 4, BST3F and BST3R primers using bst3 DNA as template. The size difference between lane 1 and 4 shows that there is an 1800 bp cassette. FIG. 8C shows semi-quantitative RT-PCR showing BST1-3 accumulation in low $CO_2$ (<0.04% $CO_2$ in air) vs. high $CO_2$ (5% (v/v) $CO_2$ in air) in D66 and bst3 cells. As indicated by the red box, BST3 is not expressed in bst3 cells. Actin was used as a loading control.

FIG. 9A shows growth of bst3 and WT in pH 8.6 at low $CO_2$ (<0.04% $CO_2$) over six days, which was measured using $OD_{730}$. FIG. 9B shows growth of bst3 and WT in pH 8.6 in pH 8.6 at low $CO_2$ (<0.04% $CO_2$) over six days, which was measured using chlorophyll estimation at wavelengths 645 and 663. FIG. 9C shows oxygen evolving activity measured at pH 7.4 plotted as curves for bst3 and D66. Triplicate runs were made at each $C_i$ concentration. FIG. 9D shows the $K_{0.5}$ ($C_i$) values ($C_i$ concentration needed for half maximum oxygen evolution) that were calculated from the $O_2$ evolution versus $C_i$ curves for bst3 and D66 at pH 7.4.

FIG. 10A shows structural models for *C. reinhardtii* BST1-3 and *Klebsiella pneumonia* bestrophin (Kpbest) as monomers with conserved residues lining the selective pore highlighted in red and labeled. FIG. 10B shows the secondary structure of a BST1 homopentamer model colored with the local QMEAN score (a structure quality assessment scoring function). FIG. 10C shows the outline of the channel cavity drawn on the BST1 homopentamer model in black. The conserved residues from the BST1 model in FIG. 10A are depicted as red shapes extending into the channel cavity. FIG. 10D shows the calculated electrostatic potential on the BST1 homopentamer model. The electrostatic potentials are displayed in potential scale of −4 kT/e (red, negative) to +4 kT/e (blue, positive).

DETAILED DESCRIPTION

Figure 1A:
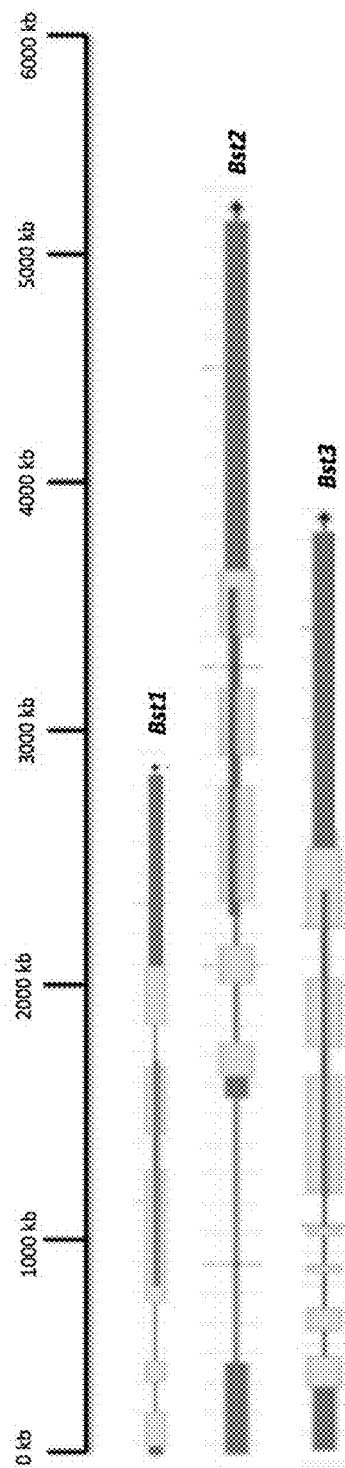

The following description sets forth exemplary methods, parameters, and the like. It should be recognized, however, that such description is not intended as a limitation on the scope of the present disclosure but is instead provided as a description of exemplary embodiments.

Genetically Altered Plants and Seeds

Certain aspects of the present disclosure relate to a genetically altered plant or part thereof containing one or more genetic alterations that increase or provide the ability for bicarbonate to cross a membrane from a plant cell cytoplasm into a stroma of at least a portion of the chloroplasts of the plant. In some aspects, the present disclosure relates to a genetically altered plant or part thereof containing one or more genetic alterations that increase or provide the ability for bicarbonate to cross a membrane from a stroma into a lumen of at least a portion of the chloroplasts of the plant. In some embodiments, the gain of the bicarbonate membrane crossing ability is the result of the expression of at least one green algal bestrophin polypeptide. In some embodiments, the gain of the bicarbonate membrane crossing ability is the result of the expression of two or three green algal bestrophin polypeptides. In some embodiments, the gain of the bicarbonate membrane crossing ability is the result of the expression of four or more (e.g., five, six, seven, eight, nine, ten) green algal bestrophin polypeptides. In some embodiments, the green algal bestrophin polypeptide is SEQ ID NO:1 (i.e., BESTROPHIN1, BST1, Cre16.g662600.t1.2), SEQ ID NO:2 (i.e., BESTROPHIN2, BST2, Cre16.g663400.t2.1), or SEQ ID NO:3 (i.e., BESTROPHIN3, BST3, Cre16.g663450.t1.2). In some embodiments, the increase or provision of the ability for bicarbonate to cross a membrane is the result of expression of at least one polypeptide selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:1, a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:2, a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:3, or any combination thereof. In some embodiments, the increase or provision of the ability for bicarbonate to cross a membrane is the result of expression of a polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

The term "BST1", and capitalization and italicized versions thereof, refer to the green algal gene and protein, as described herein. In some embodiments, this term may refer to the *C. reinhardtii* gene and protein, as described herein. In other embodiments, this term may refer to one or more homologs or orthologs of the gene and protein of any green algal species that also transport bicarbonate. In some embodiments, this term may refer to one or more paralogs of the gene and protein of any green algal species. In some embodiments, the green algal species is *C. reinhardtii, Chlamydomonas eustigma, Volvox carteri F. nagariensis*, or *Gonium pectorale*. SEQ ID NO:1 provides the *C. reinhardtii* BST1 protein. When indicated with all lower-case letters in italics, the mutant (e.g., knockout) version of the gene/protein is intended. In *C. reinhardtii*, the mutant version may be a single gene/protein. In other green algal species, the mutant version may be one, some, or all homologs, orthologs, and/or paralogs of the genes/proteins.

The term "BST2", and capitalization and italicized versions thereof, refer to the green algal gene and protein, as described herein. In some embodiments, this term may refer to the *C. reinhardtii* gene and protein, as described herein. In other embodiments, this term may refer to one or more homologs or orthologs of the gene and protein of any green algal species that also transport bicarbonate. In some embodiments, this term may refer to one or more paralogs of the gene and protein of any green algal species. In some embodiments, the green algal species is *C. reinhardtii, Chlamydomonas eustigma, Volvox carteri F. nagariensis*, or *Gonium pectorale*. SEQ ID NO:2 provides the *C. reinhardtii* BST2 protein. When indicated with all lower-case letters in italics, the mutant (e.g., knockout) version of the gene/protein is intended. In *C. reinhardtii*, the mutant version may be a single gene/protein. In other green algal species, the mutant version may be one, some, or all homologs, orthologs, and/or paralogs of the genes/proteins.

The term "BST3", and capitalization and italicized versions thereof, refer to the green algal gene and protein, as described herein. In some embodiments, this term may refer to the *C. reinhardtii* gene and protein, as described herein. In other embodiments, this term may refer to one or more homologs or orthologs of the gene and protein of any green algal species that also transport bicarbonate. In some embodiments, this term may refer to one or more paralogs of the gene and protein of any green algal species. In some embodiments, the green algal species is *C. reinhardtii, Chlamydomonas eustigma, Volvox carteri F. nagariensis*, or *Gonium pectorale*. SEQ ID NO:3 provides the *C. reinhardtii* BST3 protein. When indicated with all lower-case letters in italics, the mutant (e.g., knockout) version of the gene/protein is intended. In *C. reinhardtii*, the mutant version may be a single gene/protein. In other green algal species, the mutant version may be one, some, or all homologs, orthologs, and/or paralogs of the genes/proteins.

In some embodiments, the increase or provision of the ability for bicarbonate to cross a membrane is the result of expression of a polypeptide from, or a polypeptide with high percent identity to one of, the group SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group consisting of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. The phrases "high percent identical", "high percent identity", or "high sequence identity" and grammatical variations thereof in the context of two polynucleotides or polypeptides, refers to two or more sequences or subsequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

In some embodiments, the polypeptide is localized to a chloroplast envelope or a thylakoid membrane of at least one chloroplast within a plant cell. In some embodiments, the polypeptide is able to move bicarbonate ($HCO_3^-$) across a membrane. In some embodiments, the polypeptide is able to move chloride anions ($Cl^-$) across a membrane. In some embodiments, the polypeptide is able to move both $HCO_3^-$ and $Cl^-$ across a membrane. In some embodiments, the polypeptide is able to move negatively charged ions across a membrane. In some embodiments, the plant cell is a leaf mesophyll cell. In some embodiments, the polypeptide is expressed in at least 70% of leaf mesophyll cells of the plant. In some embodiments, the polypeptide oligomerizes to form a pentamer. In some embodiments, the polypeptide oligomerizes to form a homopentamer. In some embodiments, the pentamer or homopentamer has an entry pocket with a predominantly negative hydrostatic potential and a selective pore with a neutral/positive charge. In some embodiments, the homopentamer transports negatively charged ions.

In some aspects, the present disclosure relates to plants or parts thereof with increased carbon use efficiency containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. As used herein, the term "ambient carbon dioxide" refers to the carbon dioxide content of air without any added or removed $CO_2$. In some embodiments, ambient carbon dioxide conditions are carbon dioxide conditions of 400-500 ppm, 400-550 ppm, 400-600 ppm, 400-650 ppm, 400-700 ppm, 450-500 ppm, 450-550 ppm, 450-600 ppm, 450-650 ppm, 450-700 ppm, 500-550 ppm, 500-600 ppm, 500-650 ppm, 500-700 ppm, 550-600 ppm, 550-650 ppm, 550-700 ppm, 600-650 ppm, 600-700 ppm, or 650-700 ppm. As used herein, the term "carbon use efficiency" may refer to the proportion of carbon acquired from the environment that is incorporated into the biomass of the plant. Carbon use efficiency can be measured by any known method in the art (e.g., subtracting the amount of carbon lost through plant respiration from the total amount of carbon that is taken up by the plant, then dividing this value by the total amount of carbon that is taken up by the plant, etc.). In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with increased water use efficiency containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. As used herein, the term "water use efficiency" refers to the ratio of carbon assimilation to water consumption in a plant. Measures of water use efficiency include, but are not limited to, intrinsic water use efficiency and instantaneous water use efficiency. Instantaneous water use efficiency may be calculated by determining the ratio between plant carbon assimilation and plant transpiration. Intrinsic water use efficiency may be calculated by determining the ratio between plant carbon assimilation and plant stomatal conductance. Measures of carbon assimilation can include, but are not limited to, plant photosynthetic rate, yield, and biomass. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with increased nitrogen use efficiency containing at least one modified nucleic acid sequence with at least one coding sequence of a green algal bestropbin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. As used herein, the term "nitrogen use efficiency" refers to the ratio of nitrogen that is used by a plant for metabolism to total nitrogen supplied to the plant. Nitrogen use efficiency can be measured by any known method in the art (e.g., 15N isotope labeling, agronomic efficiency, apparent nitrogen recovery). Sources of nitrogen supplied to the plant include, but are not limited to, nitrogen contained in soil, nitrogen supplied by nitrogen-fixing bacteria, and nitrogen contained in fertilizers. In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some aspects, the present disclosure relates to plants or parts thereof with reduced photoinhibition containing at least one modified nucleic acid sequence with at least one coding sequence of a green algal bestrophin polypeptide in the plant or part thereof, where the bestrophin polypeptide is expressed in the plant or part thereof, and where when the plant is cultivated under ambient carbon dioxide conditions, the yield, growth rate, or biomass is greater than from a corresponding wild-type (WT) plant or corresponding WT part thereof that does not overexpress the bestrophin polypeptide or the yield, growth rate, or biomass is substantially similar to the yield, growth rate, or biomass from the corresponding wild-type (WT) plant or corresponding WT part thereof that does not overexpress the bestrophin polypeptide cultivated under ambient carbon dioxide conditions. As used herein, the term "photoinhibition" refers to the light-induced reduction of photosynthetic production in a plant. Photoinhibition can be measured by any known method in the art (e.g., rate of light saturated oxygen evolution, ratio of variable to maximum levels of chlorophyll a fluorescence). In some embodiments, the bestrophin polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant.

In some embodiments of any of the above embodiments the modified nucleic acid sequence is stably integrated into the nuclear genome of the plant. In some embodiments of any of the above embodiments, the at least one modified nucleic acid sequence additionally contains a second nucleic acid sequence encoding a signal peptide sequence or targeting sequence operably linked to the at least one coding sequence of a green algal bestrophin polypeptide, where expression of the signal peptide sequence or targeting sequence results in localization of the bestrophin polypeptide to a chloroplast envelope or chloroplast thylakoid membrane of at least one chloroplast of a plant cell. In some embodiments, the signal peptide sequence or targeting sequence is a leader sequence. In some embodiments, the signal peptide sequence or targeting sequence is any sequence known in the art to result in polypeptide expression in the chloroplast envelope or the chloroplast thylakoid membrane.

In some embodiments of any of the above embodiments, the increased carbon use efficiency, increased water use efficiency, increased nitrogen use efficiency, or reduced photoinhibition is the result of expression of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:1, a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:2, a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:3, or any combination thereof. In some embodiments of any of the above embodiments, the increased carbon use efficiency, increased water use efficiency, increased nitrogen use efficiency, or reduced Photoinhibition is the result of expression of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

In some embodiments of any of the above embodiments, the increase or provision of the ability for bicarbonate to cross a membrane is the result of expression of a polypeptide from the group SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group consisting of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63.

In some embodiments of any of the above embodiments, the plant is cowpea (i.e., black-eyed pea, *Vigna unguiculata*), soybean (i.e., soya bean, *Glycine max*), cassava (i.e., manioc, *Manihot esculenta*), rice (i.e., *Oryza sativa, Oryza glaberrima, Zizania* spp.), wheat (i.e., common wheat, spelt, durum, *Triticum aestivum, Triticum spelta, Triticum durum, Triticum* spp.), barley (i.e., *Hordeum vulgare*), rye (i.e., *Secale cereale*), oat (i.e., *Avena sativa*), potato (i.e., *Solanum tuberosum*), tomato (i.e., *Solanum lycopersicum*), or another C3 crop plant. In some embodiments, the plant is tobacco (i.e., *Nicotiana tabacum, Nicotiana edwardsonii, Nicotiana plumbagnifolia, Nicotiana longiflora*) or *Arabidopsis* (i.e., rockcress, thale cress, *Arabidopsis thaliana*). In some embodiments of any of the above embodiments, the plant is not corn (i.e., maize, *Zea mays*), sorghum (i.e., durra, great millet, milo, *Sorghum bicolor*), sugarcane (i.e., sugar cane, *Saccharum officinarum*), millet (i.e., finger millet, common millet, pearl millet, foxtail millet, *Eleusine coracana, Panicum miliaceum, Pennisetum glaucum, Setaria italica*), switchgrass (i.e., tall panic grass, thatchgrass, *Panicum virganum*), or another C4 crop plant.

In some embodiments, the plant part of any of the above embodiments is a leaf, a stem, a root, a flower, a seed, a fruit, a cell, or a portion thereof. In some embodiments, the plant part is a fruit. In some embodiments, the plant part is a grain, a kernel, a bean, or a tuber.

In some aspects, the present disclosure relates to a pollen grain or an ovule of any of the above embodiments.

In some aspects, the present disclosure relates to a protoplast produced from any of the above embodiments.

In some aspects, the present disclosure relates to a tissue culture produced from protoplasts or cells of any of the above embodiments, where the cells or protoplasts are produced from one of the plant parts in the group of leaf, anther, pistil, stem, petiole, root, root tip, fruit, seed, flower, cotyledon, hypocotyl, embryo, or meristematic cell.

In some aspects, the present disclosure relates to a genetically altered seed containing one or more genetic alterations that increase or provide the ability for bicarbonate to cross a membrane. In some embodiments, the seed produces a plant with the ability for bicarbonate to cross a membrane from a plant cell cytoplasm into a stroma of at least a portion of the chloroplasts of the plant. In some embodiments, the seed produces a plant with the ability for bicarbonate to cross a membrane from a stroma into a lumen of at least a portion of the chloroplasts of the plant. In some embodiments, the plant expresses at least one green algal bestrophin polypeptide. In some embodiments, the green algal bestrophin polypeptide is SEQ ID NO:1, SEQ ID NO:2, SEQ ID NO:3, or any combination thereof. In some embodiments, the plant expresses a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:1, a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:2, a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:3, or any combination thereof. In some embodiments, the plant expresses a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments, the plant expresses a polypeptide from the group SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group consisting of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. In some embodiments, the polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant. In some embodiments of any of the above embodiments, the plant is cowpea (i.e., black-eyed pea, *Vigna unguiculata*), soybean (i.e., soya bean, *Glycine max*), cassava (i.e., manioc, *Manihot esculenta*), rice (i.e., *Oryza sativa, Oryza glaberrima, Zizania* spp.), wheat (i.e., common wheat, spelt, durum, *Triticum aestivum, Triticum spelta, Triticum durum, Triticum* spp.), barley (i.e., *Hordeum vulgare*), rye (i.e., *Secale cereale*), oat (i.e., *Avena sativa*), potato (i.e., *Solanum tuberosum*), tomato (i.e., *Solanum lycopersicum*), or another C3 crop plant. In some embodiments, the plant is tobacco (i.e., *Nicotiana tabacum, Nicotiana edwardsonii, Nicotiana plumbagnifolia, Nicotiana longiflora*) or *Arabidopsis* (i.e., rockcress, thale cress, *Arabidopsis thaliana*). In some embodiments of any of the above embodiments, the plant is not corn (i.e., maize, *Zea mays*), sorghum (i.e., durra, great millet, milo, *Sorghum bicolor*), sugarcane (i.e., sugar cane, *Saccharum officinarum*), millet (i.e., finger millet, common millet, pearl millet, foxtail millet, *Eleusine coracana, Panicum miliaceum, Pennisetum glaucum, Setaria italica*), switchgrass (i.e., tall panic grass, thatchgrass, *Panicum virganum*), or another C4 crop plant.

In some embodiments of any of the above embodiments, the expression of endogenous carbonic anhydrases is modulated. In some embodiments, modulated expression may be increased expression, reduced expression, expression at a different location, or any combination thereof.

Methods of Producing and Cultivating Genetically Altered Plants

Certain aspects of the present disclosure relate to a method of producing a plant with increased carbon use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing carbon use efficiency of the plant.

In some aspects, the present disclosure relates to a method of producing a plant with increased water use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing water use efficiency of the plant.

In some aspects, the present disclosure relates to a method of producing a plant with increased nitrogen use efficiency, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing nitrogen use efficiency of the plant.

In some aspects, the present disclosure relates to a method of producing a plant with reduced photoinhibition, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby reducing photoinhibition of the plant.

In some aspects, the present disclosure relates to a method of producing a plant with increased growth or productivity, where the steps of the method are: a) introducing a genetic alteration to the plant resulting in the increase or provision of the ability for bicarbonate to cross a membrane from a plant cell cytoplasm into a stroma of at least a portion of the chloroplasts of the plant or the increase or provision of the ability for bicarbonate to cross a membrane from a stroma into a lumen of at least a portion of the chloroplasts of the plant, thereby increasing growth or productivity of the plant. Measures of increased growth can include, but are not limited to, faster growth rate, larger plants, increased biomass, increased dry mass, increased shoot mass, and increased root mass. Measures of increased productivity can include, but are not limited to, higher crop yield, greater numbers of leaves, and fewer days until crop maturity.

In some embodiments of any of the above methods, the expression of endogenous carbonic anhydrases is modulated. In some embodiments, modulated expression may be increased expression, reduced expression, expression at a different location, or any combination thereof.

In some aspects, the present disclosure relates to a method of cultivating a plant with increased carbon use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases carbon use efficiency as compared to a plant grown under the same conditions that lacks the one or more genetic alterations.

In some aspects, the present disclosure relates to a method of cultivating a plant with increased water use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases water use efficiency as compared to a plant grown under the same conditions that lacks the one or more genetic alterations.

In some aspects, the present disclosure relates to a method of cultivating a plant with increased nitrogen use efficiency, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases nitrogen use efficiency as compared to a plant grown under the same conditions that lacks the one or more genetic alterations.

In some aspects, the present disclosure relates to a method of cultivating a plant with reduced photoinhibition, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane reduces photoinhibition as compared to a plant grown under the same conditions that lacks the one or more genetic alterations.

In some aspects, the present disclosure relates to a method of cultivating a plant with increased growth or productivity, where the steps of the method are: a) providing a seed with one or more genetic alterations that increase or provide an ability for bicarbonate to cross a membrane, wherein the seed produces a plant with the ability for bicarbonate to cross a membrane from a plant cell cytoplasm into a stroma of at least a portion of the chloroplasts of the plant or a plant with the ability for bicarbonate to cross a membrane from a stroma into a lumen of at least a portion of the chloroplasts of the plant; b) cultivating the plant under conditions wherein the ability for bicarbonate to cross the membrane increases growth or productivity as compared to a plant grown under the same conditions that lacks the one or more genetic alterations.

In some aspects, the present disclosure relates to a method of cultivating a plant with increased carbon use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases carbon use efficiency as compared to a plant grown under the same conditions that lacks the one or more genetic alterations.

In some aspects, the present disclosure relates to a method of cultivating a plant with increased water use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases water use efficiency as compared to a plant grown under the same conditions that lacks the one or more genetic alterations.

In some aspects, the present disclosure relates to a method of cultivating a plant with increased nitrogen use efficiency, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases nitrogen use efficiency as compared to a plant grown under the same conditions that lacks the one or more genetic alterations.

In some aspects, the present disclosure relates to a method of cultivating a plant with reduced photoinhibition, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane reduces photoinhibition as compared to a plant grown under the same conditions that lacks the one or more genetic alterations.

In some aspects, the present disclosure relates to a method of cultivating a plant with increased growth or productivity, where the steps of the method are: a) providing a tissue culture or protoplast with one or more genetic alterations that increase or provide an ability for bicarbonate to cross a membrane; b) regenerating the tissue culture or protoplast into a plantlet; c) growing the plantlet into a plant, wherein the plant has the ability for bicarbonate to cross a membrane from a plant cell cytoplasm into a stroma of at least a portion of the chloroplasts of the plant or the ability for bicarbonate to cross a membrane from a stroma into a lumen of at least a portion of the chloroplasts of the plant; d) transplanting the plant into conditions wherein the ability for bicarbonate to cross the membrane increases growth or productivity as compared to a plant grown under the same conditions that lacks the one or more genetic alterations.

In some embodiments of any of the above methods, the seed, tissue culture, or protoplast has one or more genetic alterations that modulate the expression of endogenous carbonic anhydrases. In some embodiments, modulated expression may be increased expression, reduced expression, expression at a different location, or any combination thereof.

In some embodiments of any of the above methods, the increase or provision of the ability for bicarbonate to cross a membrane is the result of the expression of at least one polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof, of any of the above methods, the increase or provision of the ability for bicarbonate to cross a membrane is the result of the expression of at least one polypeptide selected from the group of SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, or SEQ ID NO:111, preferably selected from the group consisting of SEQ ID NO:10, SEQ ID NO:11, SEQ ID NO:15, SEQ ID NO:27, SEQ ID NO:28, SEQ ID NO:29, SEQ ID NO:42, SEQ ID NO:62, or SEQ ID NO:63. In some embodiments, the polypeptide is localized to a chloroplast envelope or a chloroplast thylakoid membrane of at least one chloroplast of a plant cell. In some embodiments, the plant cell is a leaf mesophyll cell. In some embodiments, the polypeptide is expressed in at least 70% of leaf mesophyll cells of the plant. In some embodiments of any of the above embodiments, the plant is cowpea (i.e., black-eyed pea, *Vigna unguiculata*), soybean (i.e., soya bean, *Glycine max*), cassava (i.e., manioc, *Manihot esculenta*), rice (i.e., *Oryza sativa, Oryza glaberrima, Zizania* spp.), wheat (i.e., common wheat, spelt, durum, *Triticum aestivum, Triticum spelta, Triticum durum, Triticum* spp.), barley (i.e., *Hordeum vulgare*), rye (i.e., *Secale cereale*), oat (i.e., *Avena sativa*), potato (i.e., *Solanum tuberosum*), tomato (i.e., *Solanum lycopersicum*), or another C3 crop plant. In some embodiments, the plant is tobacco (i.e., *Nicotiana tabacum, Nicotiana edwardsonii, Nicotiana plumbagnifolia, Nicotiana longiflora*) or *Arabidopsis* (i.e., rockcress, thale cress, *Arabidopsis thaliana*). In some embodiments of any of the above embodiments, the plant is not corn (i.e., maize, *Zea mays*), sorghum (i.e., durra, great millet, milo, *Sorghum bicolor*), sugarcane (i.e., sugar cane, *Saccharum officinarum*), millet (i.e., finger millet, common millet, pearl millet, foxtail millet, *Eleusine coracana, Panicum miliaceum, Pennisetum glaucum, Setaria italica*), switchgrass (i.e., tall panic grass, thatchgrass, *Panicum virganum*), or another C4 crop plant.

Genetically Altered Algae

Certain aspects of the present disclosure relate to a genetically altered alga containing one or more genetic alterations resulting in the increase of the ability of the alga to transport bicarbonate into a lumen of a chloroplast of the alga. In some embodiments, the increase of bicarbonate transport ability is the result of overexpressing at least one green algal bestrophin polypeptide selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:1, a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:2, a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:3, or any combination thereof. In some embodiments, the increase of bicarbonate transport ability is the result of overexpressing at least one green algal bestrophin polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof. In some embodiments, the polypeptide is localized to a chloroplast thylakoid membrane. In some embodiments, the polypeptide is overexpressed at least when the alga is under <100 ppm carbon dioxide (<0.01% [v/v] $CO_2$ in air) conditions.

In some aspects, the present disclosure relates to a green alga or part thereof with increased bicarbonate transport containing a modified nucleic acid sequence containing the coding sequence of at least one green algal bestrophin polypeptide; wherein the bestropbin polypeptide is overexpressed; wherein the bestrophin polypeptide is localized to chloroplast thylakoid membranes; and wherein when the alga is cultivated under <100 ppm carbon dioxide (<0.01% [v/v] $CO_2$ in air) conditions, the yield, growth rate, or biomass is greater than from a corresponding wild-type (WT) alga or WT part thereof that that does not overexpress the at least one bestrophin polypeptide or the yield, growth rate, or biomass is substantially similar to the yield, growth rate, or biomass from the corresponding WT alga or corresponding WT part thereof that does not overexpress the at least one bestrophin polypeptide cultivated under <100 ppm carbon dioxide (<0.01% [v/v] $CO_2$ in air) conditions. In some embodiments, the at least one green algal bestrophin polypeptide is selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

In some aspects, the present disclosure relates to a green alga or part thereof with increased growth under <100 ppm carbon dioxide (<0.01% [v/v] $CO_2$ in air) conditions containing a modified nucleic acid sequence containing the coding sequence of at least one green algal bestropbin polypeptide; wherein the bestrophin polypeptide is overexpressed; wherein the bestrophin polypeptide is localized to chloroplast thylakoid membranes; and wherein when the alga is cultivated under <100 ppm carbon dioxide (<0.01% [v/v] $CO_2$ in air) conditions, the yield, growth rate, or biomass is greater than from a corresponding wild-type (WT) alga or WT part thereof that that does not overexpress the at least one bestrophin polypeptide or the yield, growth rate, or biomass is substantially similar to the yield, growth rate, or biomass from the corresponding WT alga or corresponding WT part thereof that does not overexpress the at least one bestrophin polypeptide cultivated under <100 ppm carbon dioxide (<0.01% [v/v] $CO_2$ in air) conditions. In some embodiments, the at least one green algal bestrophin polypeptide is selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

In some embodiments of any of the above algae, the green alga is selected from the group of *Chlamydomonas reinhardtii, Chlamydomonas eustigma, Volvox carteri F. nagariensis*, and *Gonium pectorale*.

Methods of Producing Genetically Altered Algae

In some aspects, the present disclosure relates to a method of producing an alga with increased carbon use efficiency, where the steps of the method are: a) introducing a genetic alteration to the alga comprising the increase of the ability to transport bicarbonate into a lumen of a chloroplast of the alga, thereby increasing carbon use efficiency of the alga. In some embodiments, the gain of transport ability is the result of overexpressing at least one green algal bestrophin polypeptide selected from the group of a first polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:1, a second polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:2, a third polypeptide with at least 70% sequence identity, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or at least 95% sequence identity to SEQ ID NO:3, or any combination thereof. In some embodiments, the increase of bicarbonate transport ability is the result of overexpressing at least one green algal bestrophin polypeptide selected from the group of a first polypeptide with at least 95% sequence identity to SEQ ID NO:1, a second polypeptide with at least 95% sequence identity to SEQ ID NO:2, a third polypeptide with at least 95% sequence identity to SEQ ID NO:3, or any combination thereof.

Molecular Biological Methods to Produce Transgenic Plants and Plant Cells

One embodiment of the present invention provides a plant or plant cell comprising one or more modified plant genes and/or introduced genes. For example, the present disclosure provides transgenic plants with an increased or provided ability for bicarbonate to cross a membrane from a plant cell cytoplasm from a plant cell cytoplasm into a stroma of at least a portion of the chloroplasts of the plant. Further, the present disclosure provides transgenic plants with an increased or provided ability for bicarbonate to cross a membrane from a stroma into a lumen of at least a portion of the chloroplasts of the plant. In addition, the present disclosure provides transgenic plants with at least one modified nucleic acid sequence containing at least one coding sequence of a green algal bestrophin polypeptide. Modulated expression of other genetic elements (e.g., endogenous carbonic anhydrases) is also contemplated and described herein.

Transformation and generation of genetically altered monocotyledonous and dicotyledonous plant cells is well known in the art. See, e.g., Weising, et al., Ann. Rev. Genet. 22:421-477 (1988); U.S. Pat. No. 5,679,558; *Agrobacterium Protocols*, ed: Gartland, Humana Press Inc. (1995); and Wang, et al. Acta Hort. 461:401-408 (1998). The choice of method varies with the type of plant to be transformed, the particular application and/or the desired result. The appropriate transformation technique is readily chosen by the skilled practitioner.

Any methodology known in the art to delete, insert or otherwise modify the cellular DNA (e.g., genomic DNA and organelle DNA) can be used in practicing the inventions disclosed herein. For example, a disarmed Ti plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140, 553; Fromm et al., Bio/Technology (1990) 8, 833 839); Gordon-Kamm et al., The Plant Cell, (1990) 2, 603 618) and rice (Shimamoto et al., Nature, (1989) 338, 274 276; Datta et al., Bio/Technology, (1990) 8, 736 740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

Transgenic plants of the present invention can be used in a conventional plant breeding scheme to produce more transgenic plants with the same characteristics, or to introduce the genetic alteration(s) in other varieties of the same or related plant species. Seeds, which are obtained from the transformed plants, preferably contain the genetic alteration(s) as a stable insert in chromosomal or organelle DNA. Plants comprising the genetic alteration(s) in accordance with the invention include plants comprising, or derived from, root stocks of plants comprising the genetic alteration(s) of the invention, e.g., fruit trees or ornamental plants. Hence, any non-transgenic grafted plant parts inserted on a transformed plant or plant part are included in the invention.

Introduced genetic elements, whether in an expression vector or expression cassette, which result in the expression of an introduced gene will typically utilize a plant-expressible promoter. A 'plant-expressible promoter' as used herein refers to a promoter that ensures expression of the genetic alteration(s) of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871 2887), CabbB S (Franck et al., Cell (1980) 21, 285 294) and CabbB J I (Hull and Howell, Virology, (1987) 86, 482 493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T DNA (Velten et al., EMBO J, (1984) 3, 2723 2730).

Alternatively, a plant-expressible promoter can be a tissue-specific promoter, i.e., a promoter directing a higher level of expression in some cells or tissues of the plant, e.g., in green tissues (such as the promoter of the PEP carboxylase). The plant PEP carboxylase promoter (Pathirana et al., Plant J, (1997) 12:293-304) has been described to be a strong promoter for expression in vascular tissue and is useful in one embodiment of the current invention. Alternatively, a plant-expressible promoter can also be a wound-inducible promoter, such as the promoter of the pea cell wall invertase gene (Zhang et al., Plant Physiol, (1996) 112:1111-1117). A 'wound-inducible' promoter as used herein means that upon wounding of the plant, either mechanically or by insect feeding, expression of the coding sequence under control of the promoter is significantly increased in such plant. These plant-expressible promoters can be combined with enhancer elements, they can be combined with minimal promoter elements, or can comprise repeated elements to ensure the expression profile desired.

In some embodiments, genetic elements to increase expression in plant cells can be utilized. For example, an intron at the 5' end or 3' end of an introduced gene, or in the coding sequence of the introduced gene, e.g., the hsp70 intron. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

An introduced gene of the present invention can be inserted in host cell DNA so that the inserted gene part is upstream (i.e., 5') of suitable 3' end transcription regulation signals (i.e., transcript formation and polyadenylation signals). This is preferably accomplished by inserting the gene in the plant cell genome (nuclear or chloroplast). Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835 845), the SCSV or the Malic enzyme terminators (Schunmann et al., Plant Funct Biol, (2003) 30:453-460), and the T DNA gene 7 (Velten and Schell, Nucleic Acids Res, (1985) 13, 6981 6998), which act as 3' untranslated DNA sequences in transformed plant cells. In some embodiments, one or more of the introduced genes are stably integrated into the nuclear genome. Stable integration is present when the nucleic acid sequence remains integrated into the nuclear genome and continues to be expressed (i.e., detectable mRNA transcript or protein is produced) throughout subsequent plant generations. Stable integration into the nuclear genome can be accomplished by any known method in the art (e.g., microparticle bombardment, *Agrobacterium*-mediated transformation, CRISPR/Cas9, electroporation of protoplasts, microinjection, etc.).

The term recombinant or modified nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As used herein, the terms "overexpression" and "upregulation" refer to increased expression (e.g., of mRNA, polypeptides, etc.) relative to expression in a wild type organism (e.g., plant, alga) as a result of genetic modification. In some embodiments, the increase in expression is a slight increase of about 10% more than expression in wild type. In some embodiments, the increase in expression is an increase of 50% or more (e.g., 60%, 70%, 80%, 100%, etc.) relative to expression in wild type. In some embodiments, an endogenous gene is overexpressed. In some embodiments, an exogenous gene is overexpressed by virtue of being expressed. Overexpression of a gene in plants or algae can be achieved through any known method in the art, including but not limited to, the use of constitutive promoters, inducible promoters, high expression promoters (e.g., PsaD promoter), enhancers, transcriptional and/or translational regulatory sequences, codon optimization, modified transcription factors, and/or mutant or modified genes that control expression of the gene to be overexpressed.

Where a recombinant nucleic acid is intended for expression, cloning, or replication of a particular sequence, DNA constructs prepared for introduction into a host cell will typically comprise a replication system (i.e. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., chloroplast localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology (e.g., sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, word-length=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

Preferred host cells are plant or algal cells. Recombinant host cells, in the present context, are those which have been genetically modified to contain an isolated nucleic molecule, contain one or more deleted or otherwise non-functional genes normally present and functional in the host cell, or contain one or more genes to produce at least one recombinant protein. The nucleic acid(s) encoding the protein(s) of the present invention can be introduced by any means known to the art which is appropriate for the particular type of cell, including without limitation, transformation, lipofection, electroporation or any other methodology known by those skilled in the art.

Having generally described this invention, the same will be better understood by reference to certain specific examples, which are included herein to further illustrate the invention and are not intended to limit the scope of the invention as defined by the claims.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

Example 1: General Materials and Methods Used for Cell Culture and Growth

The following example describes the cell culture and growth conditions used in all of the following examples.

*Chlamydomonas reinhardtii* cells were maintained on either Tris-acetate-phosphate (TAP) medium or yeast-acetate (YA) medium on petri plates. Before an experiment, cells were inoculated into minimal media (i.e., not containing a carbon source) and grown on high $CO_2$ (>5% $CO_2$ in air) to a density of 2-3×10$^6$ cells mL$^{-1}$. These cells were then diluted into minimal media and grown at the pH and $CO_2$ concentrations indicated.

*Chlamydomonas reinhardtii* culture conditions were the same as described in Ma et al., Plant Physiol 156:884-896, 2011. The D66 strain (nit2$^-$, cw15, mt$^+$) was obtained from Dr. Rogene Schnell (University of Arkansas, Little Rock). CMJ030 (CC-4533; cw15, mt$^-$) and bst3 (BST3 knockout LMJ.RY0402.089365) were obtained from the CLIP collection at the *Chlamydomonas* culture collection (Zhang et al., Plant Cell 26(4):1398-1409, 2014). Tris-Acetate-Phosphate (TAP) medium, yeast-acetate (YA) medium, and Minimal (MIN; without acetate, i.e., without a carbon source) were prepared according to Sueoka, PNAS 46:83-91, 1960. Both TAP and YA petri plates were prepared by adding 1.2% (w/v) agar, and *C. reinhardtii* cells were maintained on either type of petri plate. Cell cultures were initiated by inoculating colonies from TAP plates into 100 mL TAP liquid medium in Erlenmeyer flasks for mixotrophic growth. Cultures were grown to early log phase on continuous illumination (100 µmol m$^{-2}$ s$^{-1}$) and shaking for 48 hr. The early log phase TAP-grown cultures were harvested and washed with MIN medium, then re-suspended in MIN media and bubbled with high $CO_2$ (5% [v/v] $CO_2$ in air) to reach OD$_{730}$ between 0.2 and 0.3 (~2-3×10$^6$ cells mL$^{-1}$). For CCM induction, the cells were transferred to low $CO_2$ (<0.01% [v/v] $CO_2$ in air) bubbling for 12 hr or ambient $CO_2$ (0.04%-0.045% [v/v] $CO_2$ in air).

Example 2: Phylogenetic Tree of Bestrophin Family Genes

The following example describes the construction of a phylogenetic tree depicting the evolutionary relationship of bestrophin family genes in a variety of photosynthetic organisms. In mammals, bestrophin proteins are known to conduct chloride and bicarbonate. In plants, most bestrophin proteins have not yet been characterized.

Materials and Methods

The three *C. reinhardtii* genes BESTROPHIN1 (BST1), BESTROPHIN2 (BST2), and BESTROPHIN3 (BST3) were chosen to be used in this tree for multiple reasons. For one, the BST1, BST2, and BST3 genes share a common region (see FIGS. 1A-1B). For another, the amino acid sequences of the BST1 (SEQ ID NO:1), BST2 (SEQ ID NO:2), and BST3 (SEQ ID NO:3) proteins are >80% identical to each other (see FIG. 1C). *C. reinhardtii* contains seven other predicted bestrophins, but none of these other bestrophins had more than a 45% identity with these three proteins. Finally, the three bestrophins chosen all were predicted to be targeted to the chloroplast.

Phylogenetic Tree Construction:

Amino acid sequences for BST1 (Cre16.g662600.t1.2), BST2 (Cre16.g663400.t2.1), and BST3 (Cre16.g663450.t1.2) were BLASTED against NCBI Genbank (Benson et al., Nucleic Acids Res, 21(13):2963-2965, 1993) and Phytozome v12.1 (available at phytozome DOT jgi DOT doe DOT gov under pz/portal DOT html; Goodstein et al., Nucleic Acids Res 40 (Database issue): D1178-1186, 2012). The top hits identified using these databases were downloaded. Additionally, amino acid sequences encoding *Homo sapiens* BEST1 (SJM31533.1) and *Klebsiella pneumoniae* bestrophin (pdb_4WD8_A) were downloaded from NCBI Genbank to be included as the outgroup in the phylogenetic analysis. A total of 63 initial sequences were aligned in Geneious 11.1.4 (Kearse et al., Bioinformatics 28(12):1647-1649, 2012) using a ClustalW (Thompson et al., Nucleic Acids Res 22(22):4673-4680, 1994) algorithm with the amino acid substitution matrix BLOSUM62 (Henikoff & Henikoff, PNAS 89(22):10915-10919, 1992). Duplicate sequences from the two databases (NCBI and Phytozome) and sequences with a pairwise percentage positive identity (BLOSUM62) of less than 70% were removed. The final alignment included 30 sequences and was manually trimmed to remove variable length ends from the sequences. The phylogenetic analysis was completed in MEGA X (Kumar et al., Comput Appl Biosci 10(2):189-191, 1994). The best Maximum Likelihood (ML) model for phylogenetic analysis of the alignment was calculated using the Model Selection function in MEGA X. A ML tree was constructed using the LG substitution model (Le & Gascuel, Mol Biol Evol 25(7):1307-1320, 2008) with Gamma distribution (5 discrete categories) and 500 bootstrap replicates (see FIG. 1D). Adobe Illustrator CC was used to format and shade the tree. A phylogenetic tree of the protein sequences of *C. reinhardtii* BST1, BST2 and BST3 homologs was constructed using maximum likelihood (ML).

Results

Figure 1B:
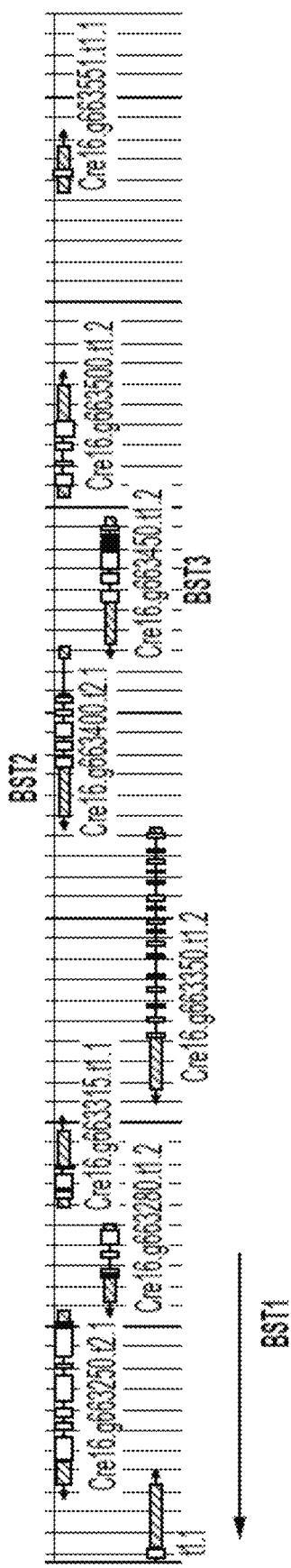

FIG. 1A shows a schematic representation of the BST1, BST2, and BST3 genes. The tan boxes represent exons, the thin grey lines represent introns, the thick grey lines represent untranslated regions (UTRs), and the red lines overlaid on the gene schematic (overlaid on exons and introns) indicate the common region shared by the three genes. Further, the lengths of each of the three bestrophin genes is shown, with BST1 being the shortest at under 3000 kb, and BST2 being the longest at over 5000 kb. In FIG. 1B, the location and orientation of the BST1, BST2, and BST3 genes on the *C. reinhardtii* genome is shown. BST1 (Cre16.g662600), BST2 (Cre16.g663400) and BST3 (Cre16.g663450) are paralogous genes located within a 130 kbp region on the 16th chromosome of *C. reinhardtii*. In addition, this image depicts the location of BST1, BST2, and BST3 relative to each other. FIG. 1C depicts an amino acid alignment of the BST1, BST2, and BST3 proteins, where the asterisks in the bottom row indicate amino acids that are identical in all three proteins. The BST1, BST2, and BST3 proteins are >80% identical to each other.

Figure 1D:
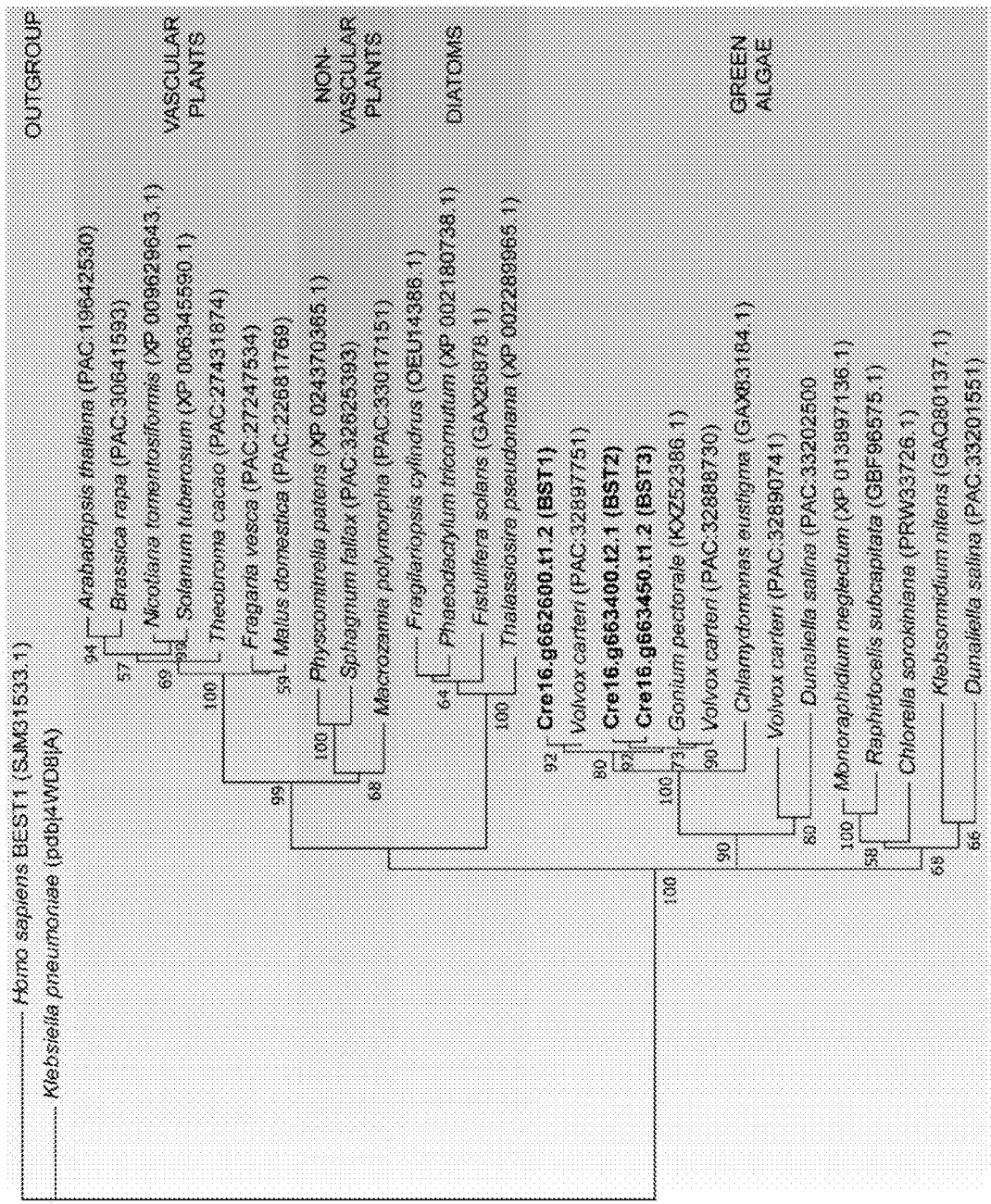

FIG. 1D shows a phylogenetic tree representing the relationship among the protein sequences of *C. reinhardtii* BST1, BST2 and BST3 homologs in a variety of photosynthetic organisms. These organisms include vascular plants (group second from the top; highlighted in purple), non-vascular plants (group third from the top; highlighted in blue), diatoms (group fourth from the top; highlighted in teal), and green algae (group at bottom; highlighted in green). The *C. reinhardtii* bestrophin proteins are shown in bold within the green-highlighted green algal group. An outgroup, consisting of proteins from the non-photosynthetic organisms human (*Homo sapiens*) and bacteria (*Klebsiella pneumoniae*), is also shown (group at top; highlighted in pink). Sequence alignment of *C. reinhardtii* BST1, BST2 and BST3 with human Bestrophin 1 (BEST1) showed low sequence identity between BEST1 and BST1-3 (21-23%). The *C. reinhardtii* bestrophin proteins show considerable sequence similarity to each other, and to other green algal bestrophin proteins, which is depicted by their proximal location within the tree and the shallower branching pattern connecting these proteins. In particular, *V. carteri* and *Chlamydomonas eustigma* are very closely related to *C. reinhardtii*, while *Dunaliella salina* is more distantly related to *C. reinhardtii*. Diatom species (highlighted in teal) are very distantly related to *C. reinhardtii*, and in fact arose from a different endosymbiotic event; this distant relationship is clearly depicted by the deeper branching pattern connecting these proteins. The vascular and non-vascular plant proteins shown in FIG. 1D have low sequence similarity of only 30-35% to the *C. reinhardtii* bestrophin proteins, which is depicted by their more distant location and the deeper branching pattern connecting these proteins. For example, the thylakoid localized VCCN1 protein of *Arabidopsis* has about a 30% sequence identity with BST1-3. Although the other proteins used to construct this tree are also bestrophin family genes, they are only distantly related to the *C. reinhardtii* bestrophins. At the amino acid level, *C. reinhardtii* bestrophins have less than 50% identity with the bestrophin proteins found in higher plants or mammals. Further, the human bestrophin protein is sufficiently different from the *C. reinhardtii* bestrophins that it can be used as an outgroup, along with the bacterial *K. pneumoniae* bestrophin protein, to anchor the phylogenetic tree.

Example 3: Bestrophins are Upregulated Under Low $CO_2$ and their Expression is Controlled by CIA5

CIA5 is a transcription factor that controls many CCM genes. In particular, CIA5 controls all of the known CCM transporters. The following example describes the analysis of bestrophin expression in a wild type (WT) D66 *C. reinhardtii* strain, and a cia5 mutant *C. reinhardtii* strain grown under either high $CO_2$ or low $CO_2$ conditions.

Materials and Methods

Cell culture and growth conditions for *C. reinhardtii* cells were as described in Example 1. For the experiment, a WT D66 *C. reinhardtii* strain and a cia5 mutant *C. reinhardtii* strain were cultured under either high $CO_2$ (5% [v/v] $CO_2$ in air) or low $CO_2$ conditions (<0.04% [v/v] $CO_2$ in air, i.e., ambient $CO_2$ conditions).

RNA samples were obtained from high $CO_2$ and low $CO_2$ acclimated cultures of both *C. reinhardtii* strains. RNA extraction was carried out using the Trizol reagent (Invitrogen) according to manufacturer's instructions. 1 ug RNA per sample was used as template for cDNA, which was made using ProtoScript® First Strand cDNA Synthesis Kit (NEB) as per manufacturer's instructions. 100 ng RNA per sample was used to conduct qRTPCR using the Luna® Universal One-Step RT-qPCR Kit from NEB as per manufacturer's instructions using QuantStudio 6. Semi-quantitative RT-PCR was performed using primers specific for BST1, BST2, or BST3, and Actin primers were as a control (listed in Table 1). PCR products were analyzed using gel electrophoresis. The experiment was replicated twice.

TABLE 1

Primers used for RT-PCR analysis.

| Gene target | Primer name | Primer sequence |
|---|---|---|
| BST1 | BST1 RT-F | GACACCAAGACCATCCTGGC (SEQ ID NO: 112) |
| | BST1 RT-R | AACAGAACTGCAGAGGTCCCG (SEQ ID NO: 113) |
| BST2 | BST2 RT-F | CGGTGCCCATGAGCTCC (SEQ ID NO: 114) |
| | BST2 RT-R | GCCACTAACCGGCCCAA (SEQ ID NO: 115) |
| BST3 | BST3 RT-F | AATCCCGTCCATGTCGCT (SEQ ID NO: 116) |
| | BST3 RT-R | CGGCTTGTGAGGACCTCG (SEQ ID NO: 117) |
| Actin | Actin RT-F | GCCAGAAGGACTCGTACGTT (SEQ ID NO: 118) |
| | Actin RT-R | CGCCAGAGTCCAGCACGATA (SEQ ID NO: 119) |

A time course analysis of BST1, BST2, and BST3 expression was also carried out. For this analysis, cells grown under high $CO_2$ were transferred to low $CO_2$ for 2 to 12 hours, and then RNA was extracted and cDNA was made as described above. This analysis was replicated twice.

Results

Figure 2A:
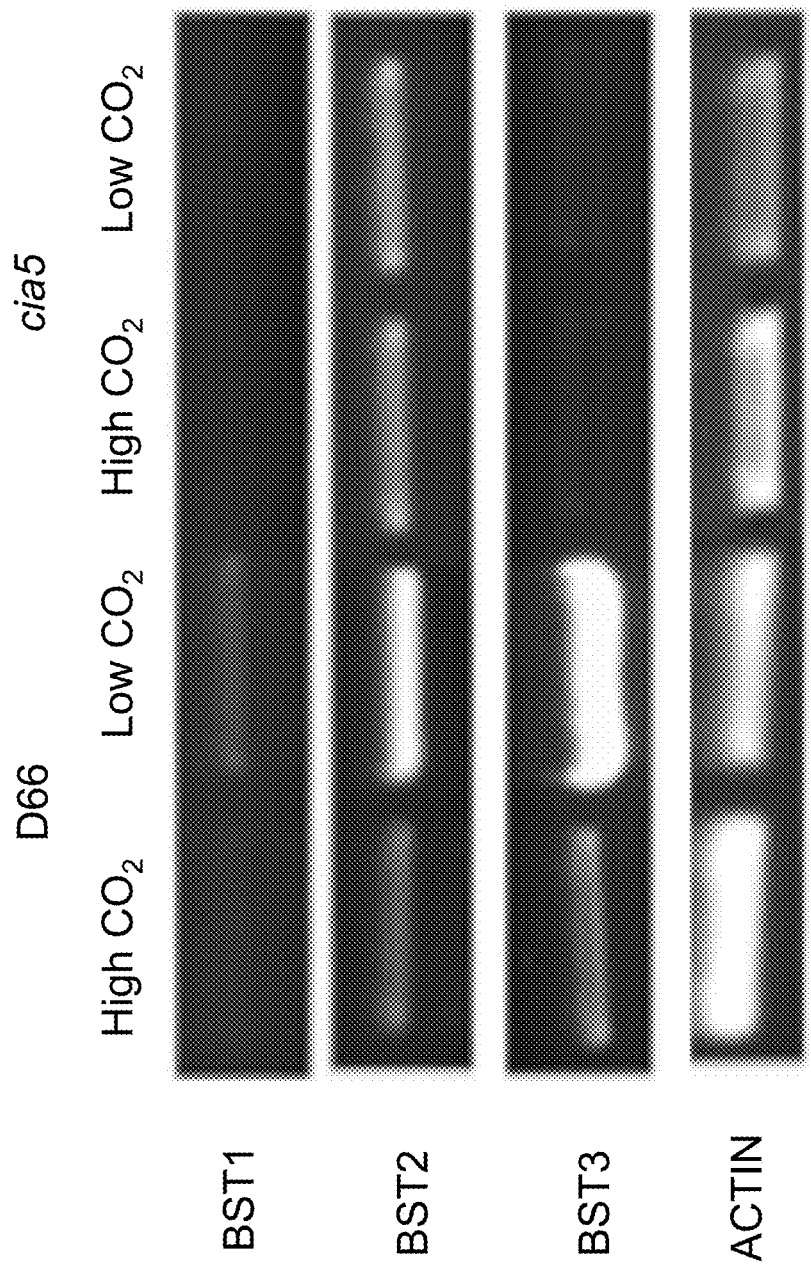
FIGS. 2A-2B show transcript analysis of the *C. reinhardtii* genes BST1, BST2, and BST3.

As shown in FIG. 2A, in D66 (WT), the expression levels of all three bestrophin genes were upregulated under low $CO_2$ conditions, as compared to high $CO_2$ conditions. In particular, BST3 expression was very low in cells grown under high $CO_2$ conditions, and much higher in cells grown under low $CO_2$ conditions. The increased intensity of the bands from the D66 cells grown in low $CO_2$ conditions as compared to the D66 cells grown in high $CO_2$ conditions clearly shows that all three genes are upregulated under low $CO_2$ conditions. In contrast to D66, the low $CO_2$ condition did not induce increased expression of BST1, BST2, or BST3 in cia5 mutants. Moreover, BST1 and BST3 were not expressed in the cia5 mutant under either condition, which is a similar transcriptional pattern to other CCM genes in the cia5 mutant (Xiang et al., PNAS 98(9):5341-5346, 2001; Fukuzawa et al., PNAS 98(9):5347-5352, 2001; Moroney et al., Plant Physiol 89(3):897-903, 1989). BST2 transcript levels in cia5 cells were the same in both high $CO_2$ and low $CO_2$ conditions, and showed no noticeable induction in low $CO_2$. This is in contrast to D66 cells, where BST2 transcript levels increase in low $CO_2$ conditions.

Figure 2B:
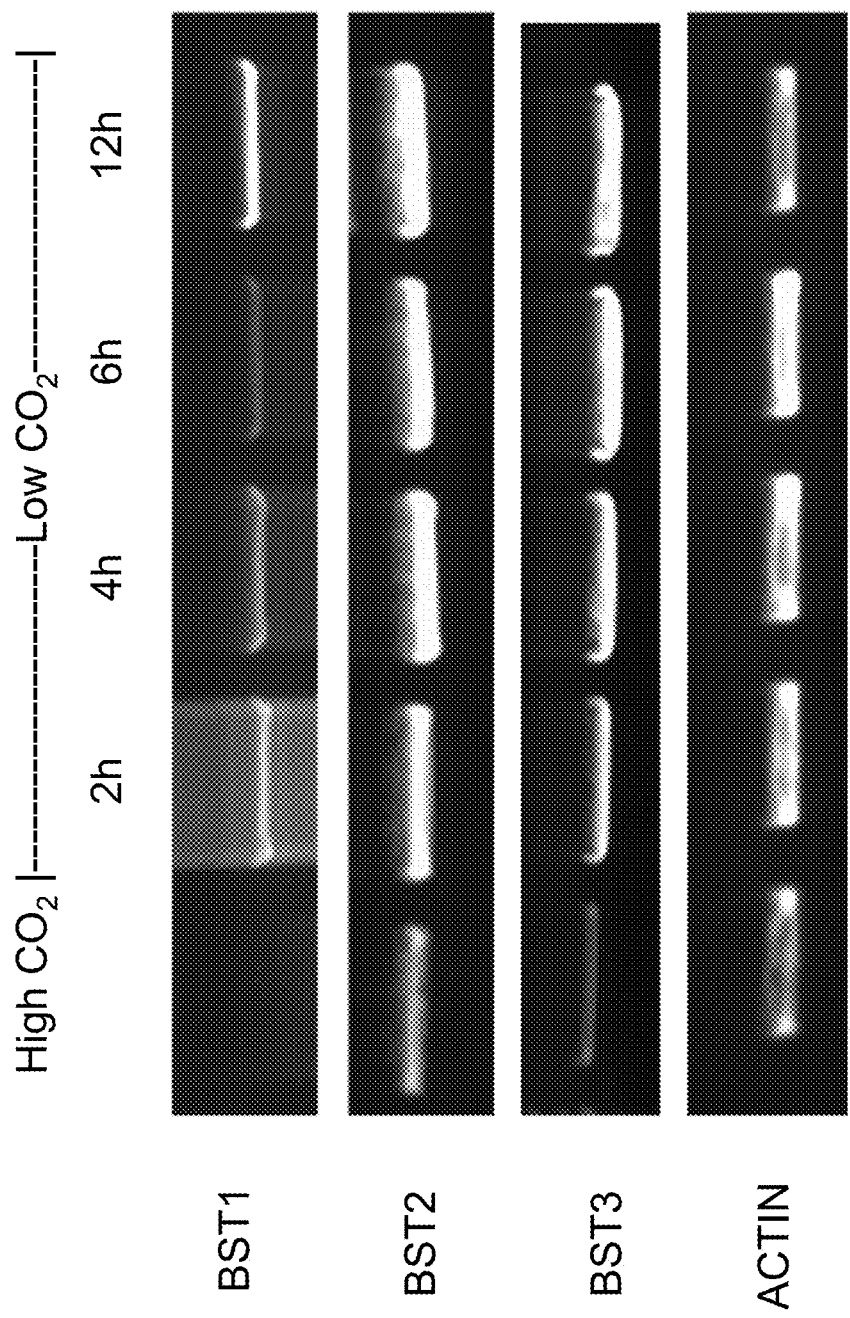

FIG. 2B shows the expression of the three BST genes in D66 at different time points after transfer from high $CO_2$ conditions to low $CO_2$ conditions. All three genes had increased transcript levels within 2 hours after the switch to low $CO_2$ and these levels of expression were maintained until at least 12 hours after induction. These results demonstrate that all three BST genes were upregulated under low $CO_2$ growth conditions known to induce CCM. Further, this upregulation was not observed in cia5 mutants, which suggests that the expression of the bestrophin genes is regulated by CIA5. Taken together, these results indicate a possible role in the CCM for the bestrophin genes.

Example 4: Localization of Bestrophins in the Chloroplast

The current CCM model indicates that bicarbonate transporters at the chloroplast thylakoid membrane are necessary for bicarbonate uptake, but these transporters have not yet been identified. The following example describes the localization of chimeric bestrophin-Venus proteins within the *C. reinhardtii* cell. A fluorescence imaging approach was chosen to identify the specific location within the chloroplast, because computational analysis predicted chloroplast targeting on the basis of the leader sequences of the three bestrophin proteins, but not a specific location within the chloroplast.

Materials and Methods

Fluorescence Protein Tagging:

For this experiment, the coding sequences of BST1, BST2, or BST3 were fused with the coding sequence of Venus in order to generate fusion proteins BST1-Venus, BST2-Venus, and BST3-Venus. The BST1-3 genes were cloned and transformed into *Chlamydomonas* strain CC-4533 as in Mackinder et al., Cell 171(1):133-147 e114, 2017. Briefly, the open reading frames of BST1-3 genes were PCR amplified from genomic DNA (primers listed in Table 2) and cloned into pLM005 with C-terminal Venus-3×FLAG and a PSAD promoter through Gibson assembly. Three separate constructs were generated, one for each BST. PSAD is a high expression promoter which drives a nuclear gene encoding an abundant chloroplast protein located on the stromal side of photosystem I in *C. reinhardtii* (Fischer and Rochaix, 2001). For transformation, wild type cultures were grown to mid-log phase and concentrated to $2 \times 10^8$ cells $mL^{-1}$. The suspension was mixed with the constructed plasmid linearized by EcoRV prior to electroporation. Then, the suspension was plated on TAP paramomycin (20 μg $mL^{-1}$) for selection. Three separate strains were generated: one expressing BST1-Venus, one expressing BST2-Venus, and one expressing BST3-Venus. Fluorescent colonies were identified using a Typhoon 8610 scanner. Laser settings for Venus were 532 nm for excitation and 555/20 for emission, and chlorophyll autofluorescence was excited at 633 nm with 670/30 emission.

TABLE 2

Primers used for generating Venus-tagged fluorescent BST1-3 proteins.

| Primer name | Primer sequence |
|---|---|
| BST1F | GCTACTCACAACAAGCCCAGTT ATGCAGATGCAAGCAAACCGTTCGTC (SEQ ID NO: 120) |
| BST1R | GAGCCACCCAGATCTCCGTTCT TGCGCTCCCCACCCATGG (SEQ ID NO: 121) |
| BST2F | GCTACTCACAACAAGCCCAGTT ATGGCCACTGGTCAGACC (SEQ ID NO: 122) |
| BST2R | GAGCCACCCAGATCTCCGTTTC TCCTTGTCTCCGCAC (SEQ ID NO: 123) |
| BST3F | GCTACTCACAACAAGCCCAGTT ATGCAAGTCAGCAAGGTTCCCTCG (SEQ ID NO: 124) |
| BST3R | GAGCCACCCAGATCTCCGTT CCGGGGCGAGATGCGCAC (SEQ ID NO: 125) |

Confocal Microscopy:

Fluorescent images of the three generated strains were then taken using a confocal microscope in order to determine bestrophin protein localization. Identified fluorescent colonies were grown heterotrophically in TAP medium until reaching mid-log phase. Cultures were then harvested and re-suspended in Tris-minimal medium overnight prior to imaging. Images were captured with Laser-scanning microscope LSM880 (Zeiss) equipped with an Airyscan module using an ×63 objectives with 1.4 NA. Argon lasers at 514 nm and 561 nm were used for excitation of Venus and chlorophyll respectively. Filters were set at 525-550 nm for the Venus emission and 620-670 nm for chlorophyll emission. Chlorophyll fluorescence was used to localize chloroplast thylakoid stacks in these strains, and an overlay of Venus and chlorophyll fluorescence was used to identify the location of bestrophin proteins relative to chloroplast thylakoid stacks. Multiple replicates were imaged.

Results

Figure 3A:
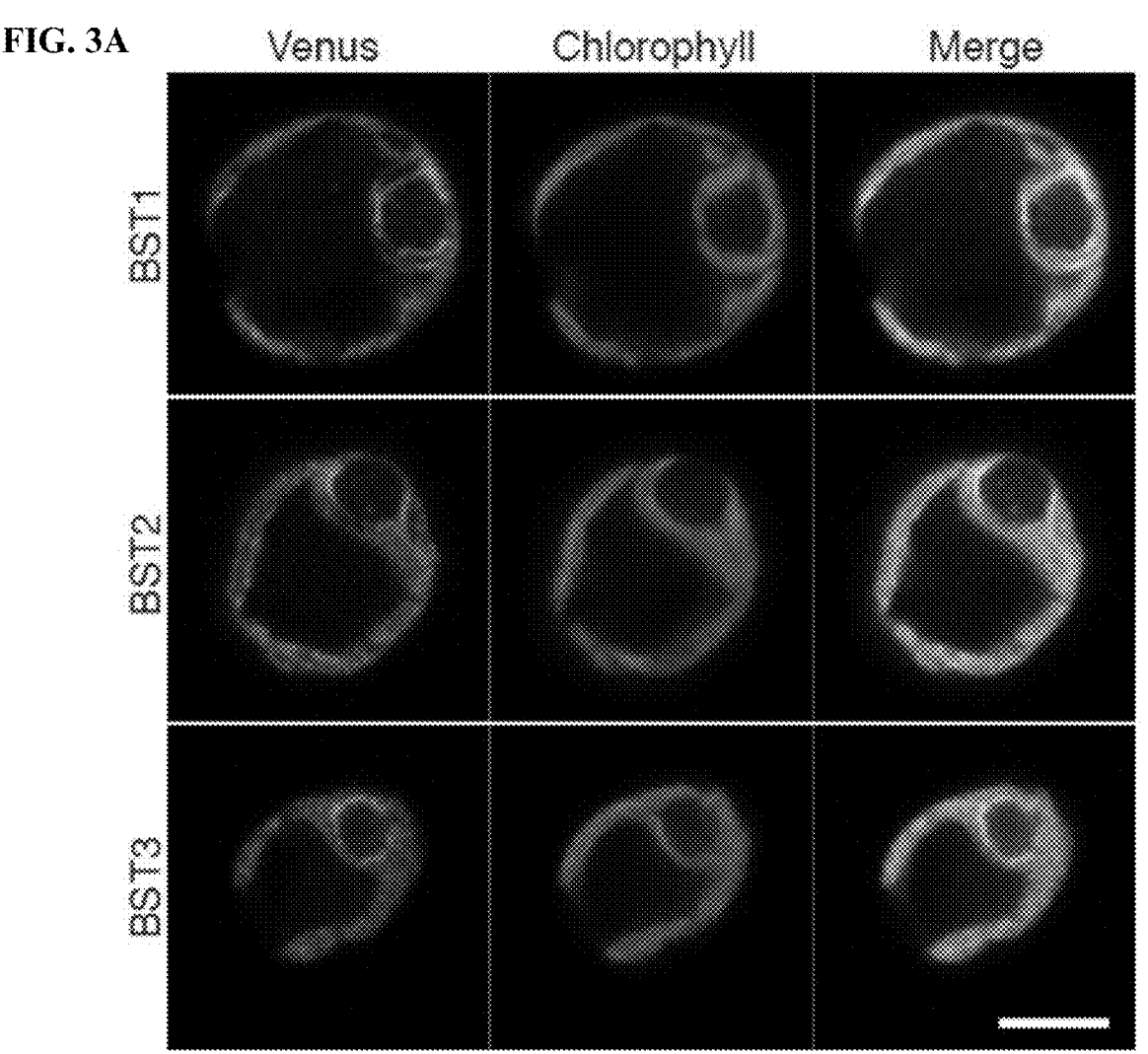
FIGS. 3A-3B show confocal microscope fluorescent protein images indicating the localization of BST1-Venus, BST2-Venus, and BST3-Venus fusion proteins in *C. reinhardtii*.
Figure 3B:
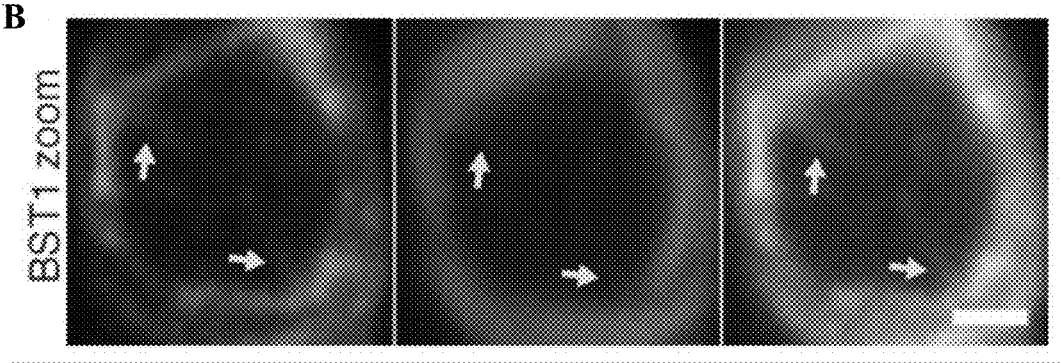

As shown in FIG. 3A, all three bestrophin fusion proteins presented non-homogenous signals within the chloroplast, indicated by Venus signals (shown in left column). When the Venus signals and the chlorophyll signals (shown in middle column) were merged, an overlap could be seen between the Venus signals and the thylakoid stacks in the chloroplast. All three BST-Venus fusion proteins localized to the thylakoid membranes of the chloroplast. In addition, the thylakoid tubules of the pyrenoid show the same overlap between the Venus signals and the chlorophyll signals. This is depicted clearly in FIG. 3B, which shows zoomed-in pyrenoid images of the BST1-Venus strain. The arrows indicate where BST1-Venus fluorescence can be seen inside the pyrenoid in the thylakoid tubules that penetrate the pyrenoid. These results both confirm the computational prediction that bestrophins are targeted to the chloroplast (based on bestrophin leader sequences), and strongly indicate a thylakoid localization for the bestrophin proteins.

Example 5: Bestrophins are Required for *C. reinhardtii* Growth Under Low $CO_2$ The following example describes the effect of reducing the expression of the three bestrophins BST1, BST2, and BST3 on the growth of *C. reinhardtii*. The growth phenotype of the triple bestrophin RNAi knockdown strain bsti-1 was compared to the WT strain D66 as well as to the mutant strains cia3 and pmp1 under growth conditions varied in $CO_2$ concentration and pH. The two mutant strains have mutations in known CCM components; the cia3 strain has a mutation in CAH3, which is a thylakoid carbonic anhydrase, while the pmp1 strain has a mutation in LCIB/LCIC, which are stromal theta carbonic anhydrases.

Materials and Methods

BST1, BST2 and BST3 Knockdown Using RNAi:

The RNAi knockdown approach was chosen in order to target all three bestrophin genes simultaneously. At present, only a bst3 knockout strain is available from the *Chlamydomonas* Culture Collection; bst1 and bst2 knockout strains are not available. Moreover, as described in more detail in Example 7, a bst3 knockout strain was tested under low $CO_2$ conditions, and found to grow normally. This means both that only the bst3 knockout strain has been tested, and that the material to generate a triple knockout strain is not currently available. The RNAi knockdown approach was therefore considered the best option.

Artificial microRNA construct for the knock-down of the BST proteins were made using the protocol of Molnar, et al. Plant J 58(1):165-174, 2009. Briefly, the Web MicroRNA Designer (WMD3) website (Available at wmd3 DOT weigelworld DOT org under cgi-bin/webapp DOTcgi) was used to design two sets of oligos complementary to different locations in the "common region" of the three BST coding sequences. Two independent constructs were designed and cloned into the pChlamyRNA3int plasmid obtained from the *Chlamydomonas* resource center. The oligos designed to target the three bestrophins that were used for RNAi knockdown are shown in Table 3. Two triple knockdown lines (BST-RNAi lines 1 and 2 or bsti-1 and bsti-2) were isolated from 400 transformants. The oligos B1 Forwards and Reverse were used to generate bsti-1 and the oligos B2 Forwards and Reverse were used to generate bsti-2.

TABLE 3

Oligos designed to target the three bestrophins.

| Oligo name | Oligo sequence |
|---|---|
| B1 Forwards | CTAGTGGGAGCGAGTTGCAAGGCATATCTCGCT GATCGGCACCATGGGGGTGGTGGTGATCAGCGC TATATGTTTTGCAACTCGCTCCCG (SEQ ID NO: 126) |
| B1 Reverse | CTAGCGGGAGCGAGTTGCAAAACATATAGCGCT GATCACCACCACCCCCATGGTGCCGATCAGCGA GATATGCCTTGCAACTCGCTCCCA (SEQ ID NO: 127) |
| B2 Forwards | CTAGTGAGAGCGTGTTGCAAGGCATATCTCGCT GATCGGCACCATGGGGGTGGTGGTGATCAGCGC TATATGTTTTGCAACACGCTCTCG (SEQ ID NO: 128) |
| B2 Reverse | CTAGCGAGAGCGTGTTGCAAAACATATAGCGCT GATCACCACCACCCCCATGGTGCCGATCAGCGA GATATGCCTTGCAACACGCTCTCA (SEQ ID NO: 129) |

The pChlamyRNA3int plasmid carrying the AphVIII gene that confers paromomycin resistance (para$^R$) was transformed into D66 by electroporation (Shimogawara et al., Genetics 148(4):1821-1828, 1998). Transformants were selected on TAP agar media containing the antibiotic paromomycin (4 μg mL$^{-1}$; Invitrogen). Resistant strains were then screened for "sick on low $CO_2$" phenotype by replica plating them on MIN plates. These were then placed in a high $CO_2$ chamber (5% [v/v]) $CO_2$ in air and a low $CO_2$ chamber (0.01% [v/v] $CO_2$ in air) with continuous illumination (100 μmol m$^{-2}$ s$^{-1}$) for 7 days. Spot tests were done by suspending growing cells in liquid MIN medium to same cell density (OD$_{730}$=0.1, 0.05 and 0.025) and 15 μL was spotted onto MIN plates. These plates were placed in high, ambient and low $CO_2$ chambers for 7 days. The $CO_2$ concentration was measured using an Environmental Gas Monitor (EGM-4, PP systems, Massachusetts).

Quantitative RT-PCR (qRT-PCR; qPCR):

RNA extraction was carried out using the Trizol reagent (Invitrogen) according to manufacturer's instructions. 1 ug RNA per sample was used as template for cDNA, which was made using ProtoScript® First Strand cDNA Synthesis Kit (NEB) as per manufacturer's instructions. 100 ng RNA per sample was used to conduct qRTPCR using the Luna® Universal One-Step RT-qPCR Kit from NEB as per manufacturer's instructions using QuantStudio 6. The primers used for qPCR are listed in Table 4; CBLP primers were used as a control.

TABLE 4

Primers used for qPCR analysis.

| Gene target | Primer name | Primer sequence |
|---|---|---|
| BST1 | qBST1F | GCTGTGTGGCATTGAGGAGA (SEQ ID NO: 130) |
| | qBST1R | GGATGAGGCTGATGAGTCCG (SEQ ID NO: 131) |
| BST2 | qBST2F | ACGGTCTACGACTTCCCTCA (SEQ ID NO: 132) |
| | qBST2R | TTGGATCACGTGGGATTGGG (SEQ ID NO: 133) |
| BST3 | qBST3F | AAGTCAGCAAGGTTCCCTCG (SEQ ID NO: 134) |
| | qBST3R | TGAATGAGCCTAGCGGGTTG (SEQ ID NO: 135) |
| CBLP | qCBLPF | ATGTGCTGTCCGTGGCTTTC (SEQ ID NO: 136) |
| | qCBLPR | CAGACCTTGACCATCTTGTCCC (SEQ ID NO: 137) |

Growth Phenotyping Under Different pH and $CO_2$ Levels:

The WT strain D66, the mutant strain cia3 (CAH3 knockout), the mutant strain pmp1 (LCIB/LCIC knockout), and bsti-1 were grown under very low $CO_2$ (0.01% $CO_2$ (v/v) in air), low (or ambient) $CO_2$ (0.04%-0.045% $CO_2$ (v/v) in air), and high $CO_2$ (5% $CO_2$ (v/v) in air). Growth in each of these three $CO_2$ conditions was tested at both pH 7 and pH 8.4. In order to inoculate the plates, three different cell concentrations were used; the highest concentration was 10,000 cells, the medium concentration was 5,000 cells, and the lowest concentration was 2,500 cells. Three spots at the three different concentrations were applied to each test plate for all four strains. The growth phenotyping experiment was replicated three times.

Results

Figure 4:
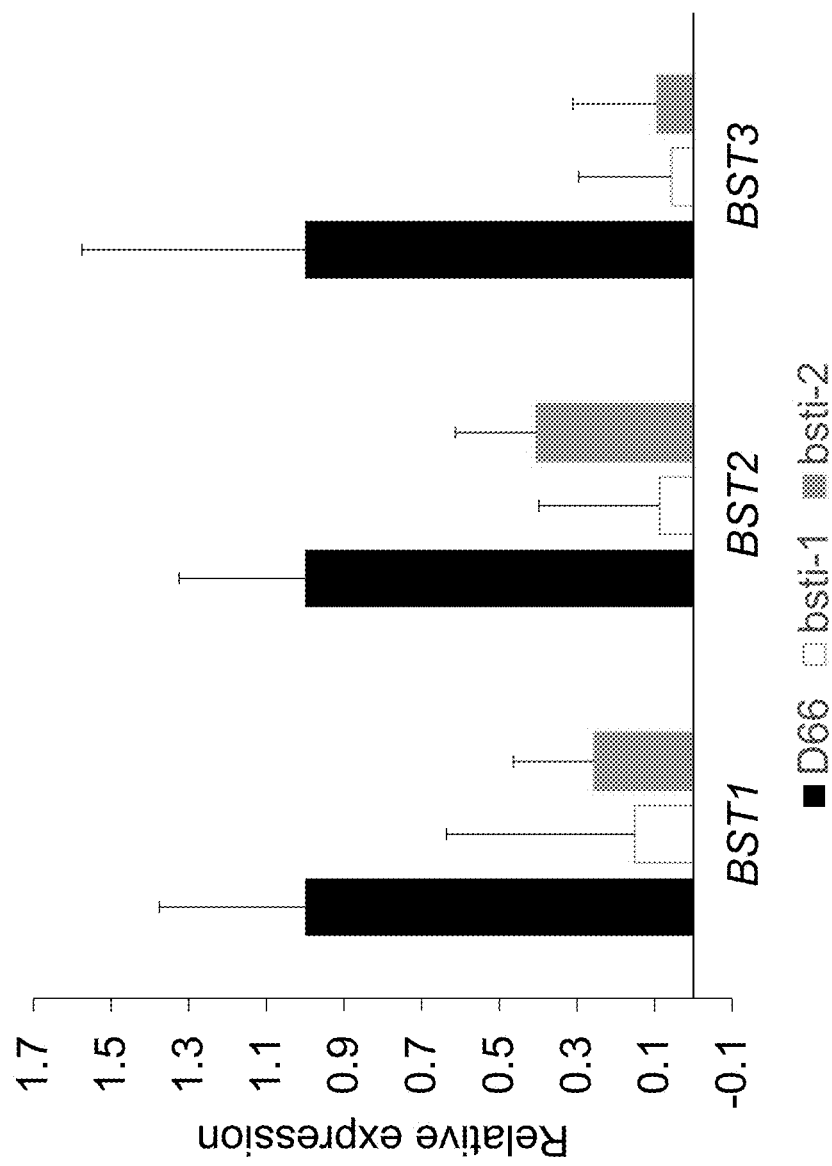
FIG. 4 shows results of qRT-PCR analysis of BST1-3 expression in the RNAi knockdown strains bsti-1 and bsti-2 as compared to the wild type strain D66. The error bars indicate the standard error for three biological replicates.

To examine the role of bestrophins in *C. reinhardtii* growth under low $CO_2$ conditions, an RNAi approach was adopted to reduce the expression of all three bestrophin genes at once. RNAi targeting BST1, BST2, and BST3 was used to generate two RNAi knockdown lines, bsti-1 and bsti-2. The expression levels of BST1, BST2, and BST3 in bsti-1, bsti-2, and in a WT control strain D66 were measured using quantitative RT-PCR. As shown in FIG. 4, the expression levels of all three bestrophin genes were lower in the bsti-1 and bsti-2 RNAi knockdown lines as compared to the WT control strain D66 (the error bars shown indicate the standard error for three biological replicates). In particular, bsti-1 and bsti-2 (BST-RNAi lines 1 and 2) showed nearly a 60-90% knockdown in the expression of BST1, BST2, and BST3 compared to D66. This result indicates that expression of all three bestrophin genes in the bsti-1 and bsti-2 RNAi knockdown lines were effectively reduced using the RNAi approach.

Figure 5A:
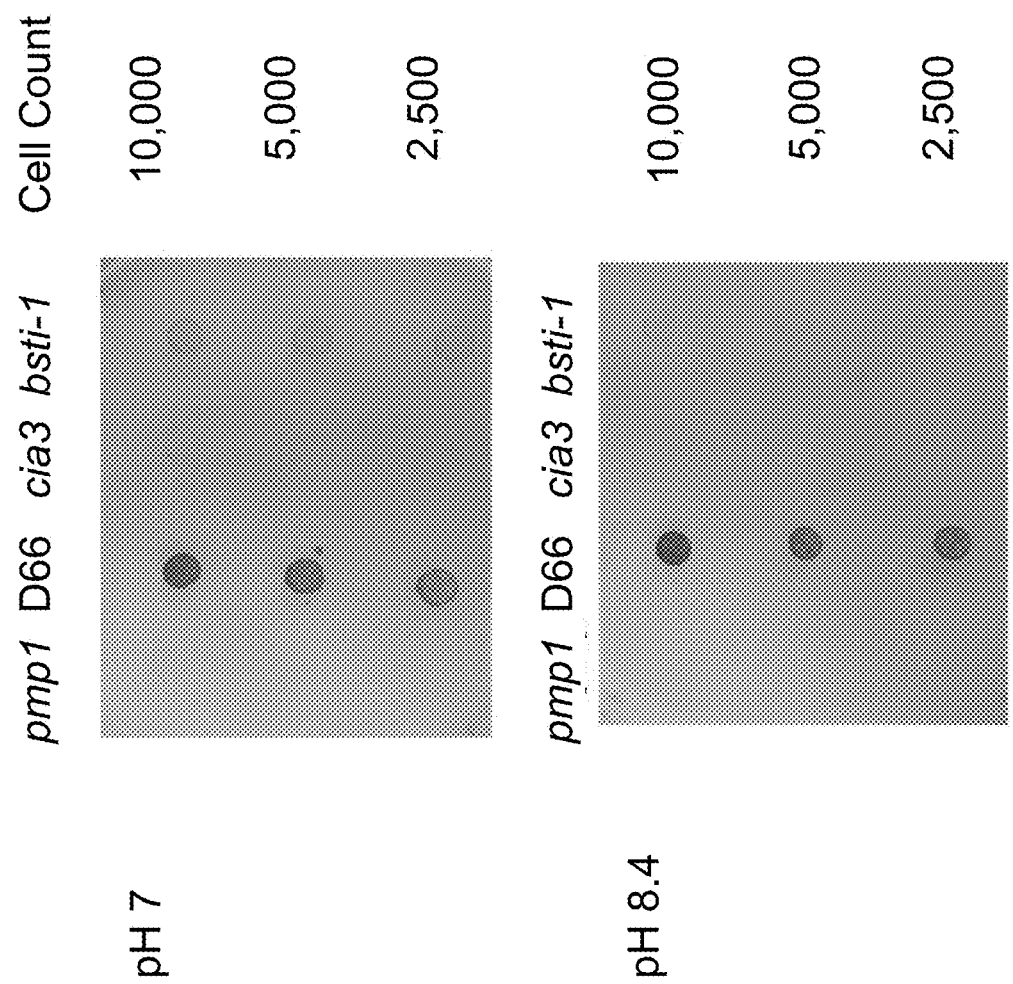
FIGS. 5A-5C show results of growth phenotype analysis of the RNAi knockdown strain bsti-1, as well as pmp1 and cia3 mutant strains as compared to the wild type strain D66 under different pH and $CO_2$ conditions. The vertical dots represent three different cell concentrations; 10,000 cells, 5,000 cells and 2,500 cells.
Figure 5B:
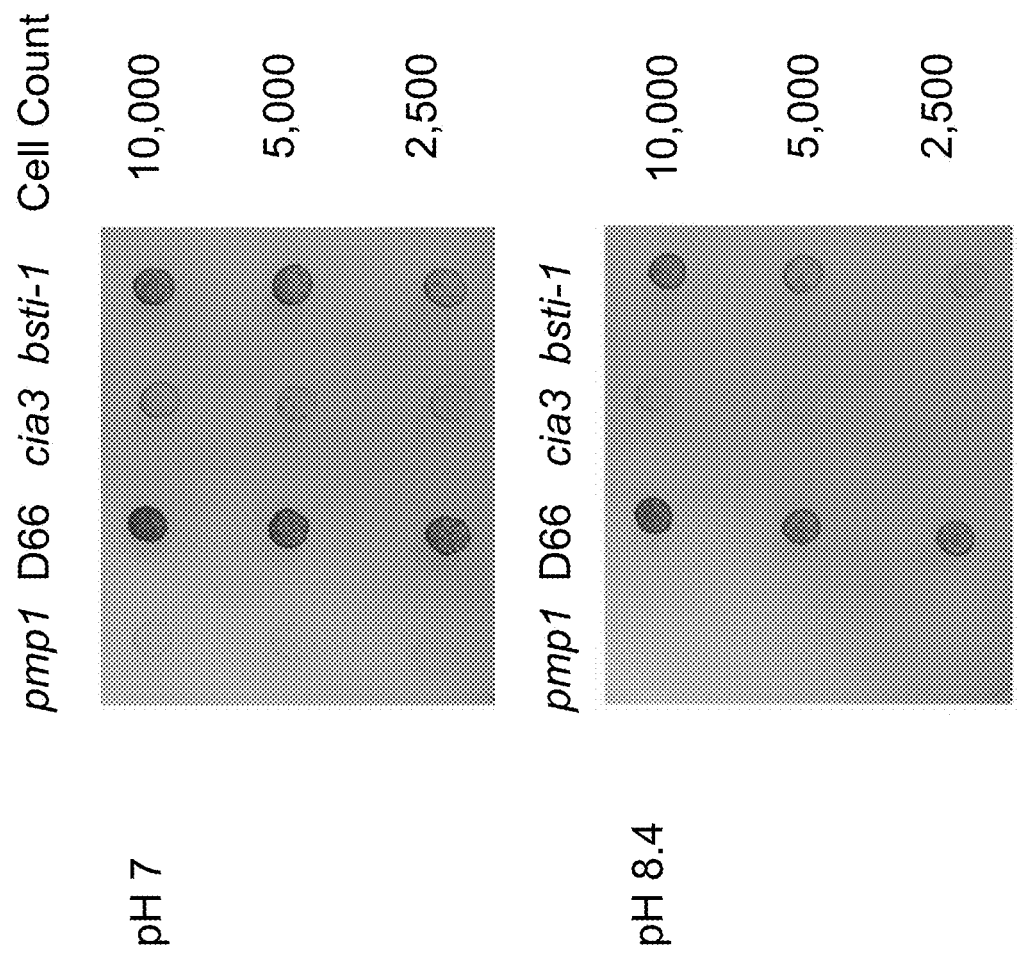
Figure 5C:
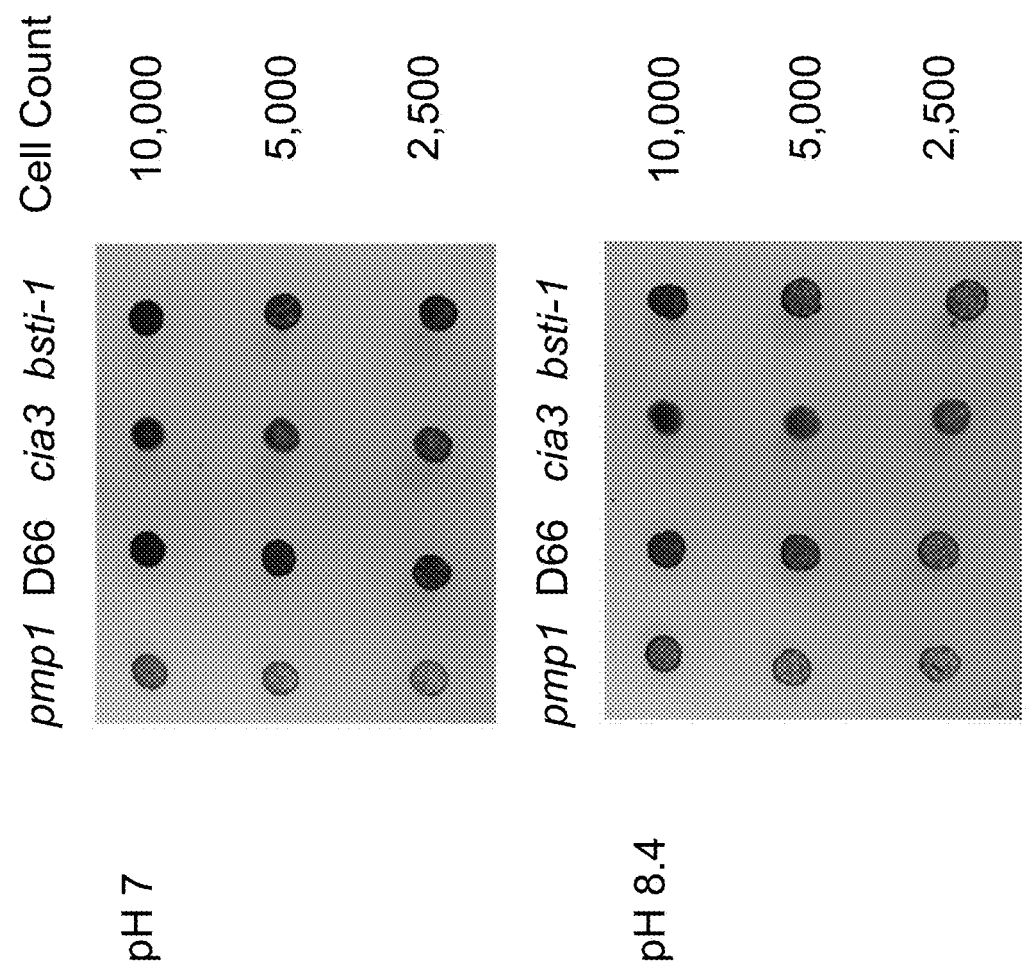

Next, the bsti-1 RNAi knockdown line, the wild type strain D66, along with the CAH3 mutant strain cia3, and the LCIB/LCIC mutant strain pmp1 were tested for their abilities to grow under different pH and $CO_2$ levels. The cultures were grown at a pH of 7 or 8.4, and under very low $CO_2$, low $CO_2$, or high $CO_2$ conditions. In very low $CO_2$ bsti-1 showed severely reduced growth that was further exacerbated at high pH, resembling the growth of CCM mutants, cia3 and pmp1 (FIG. 5A). At pH 7, the growth of bsti-1 was slightly better than at pH 8.4. In low $CO_2$, bsti-1, cia3, and pmp1 all showed reduced growth as compared to the wild type D66 strain (FIG. 5B). Again, all four strains showed slightly better growth under pH 7 as compared to pH 8.4. At high $CO_2$, however, the growth of bsti-1 was comparable to wild-type, cia3 and pmp1 (FIG. 5C). Taken together, these results show that the RNAi knockdown of all three bestrophins (bsti-1) shows a clear sick on low $CO_2$ phenotype as compared to both WT (D66) and other mutants with known sick on low $CO_2$ phenotypes (cia3, pmp1). Moreover, CAH3 (cia3 is the CAH3 knockout) is the carbonic anhydrase found within the *C. reinhardtii* thylakoid lumen, and is required for the functioning of the CCM. The three bestrophin proteins may be the proteins that deliver bicarbonate to CAH3 inside the thylakoids. Thus, these results show that all three BSTs are required for wild-type like growth of *C. reinhardtii* under low $CO_2$ conditions.

Example 6: Triple Bestrophin RNAi Knockdown Strains have a Reduced Capacity to Accumulate Inorganic Carbon ($C_i$)

The following example describes inorganic carbon affinity testing of the triple bestrophin RNAi knockdown strains bsti-1 and bsti-2 (described in Example 5) as compared to the WT strain D66.

Materials and Methods

Affinity for inorganic carbon: For this assay, the rate of photosynthesis (as $O_2$ evolution) was measured at various inorganic carbon levels (inorganic carbon=$CO_2$ & $HCO_3$). The affinity for external $C_i$ ($K_{1/2}$ [DIC]) (dissolved inorganic carbon) was estimated according to Ma et al., Plant Physiol 156:884-896, 2011. Specifically, cells with an equivalent of 100 μg of chlorophyll were suspended in HEPES-NaOH buffer (pH 7.4), HEPES-NaOH buffer (pH 7.8), or 25 mM EPPS-NaOH buffer (pH 8.4) bubbled with inert nitrogen gas, i.e. $CO_2$ free. The cells were transferred to an $O_2$ electrode chamber (Rank Brothers, Cambridge UK) illuminated at 300 μmol m$^{-2}$s$^{-1}$, and left to deplete any remaining DIC in the buffer and intracellular spaces. Upon depletion of endogenous $CO_2$, no net $O_2$ evolution is observed. Known concentrations of $NaHCO_3$ were injected into the chamber and the rate of $O_2$ evolution was measured. In this experiment, the inorganic carbon level was varied from 25 μM to 2 mM. The $K_{1/2}$ [DIC] was calculated as the DIC concentration required for half (50%) maximal rates of oxygen evolution (i.e., photosynthesis) (Badger, 1985). Chlorophyll content was measured by combining chlorophyll a and b. Chlorophyll was extracted in 100% methanol and measured using the spectrophotometer. The $K_{1/2}$ ($CO_2$) is taken as the $CO_2$ concentration needed to reach half Vmax $O_2$ evolution.

Figure 6A:
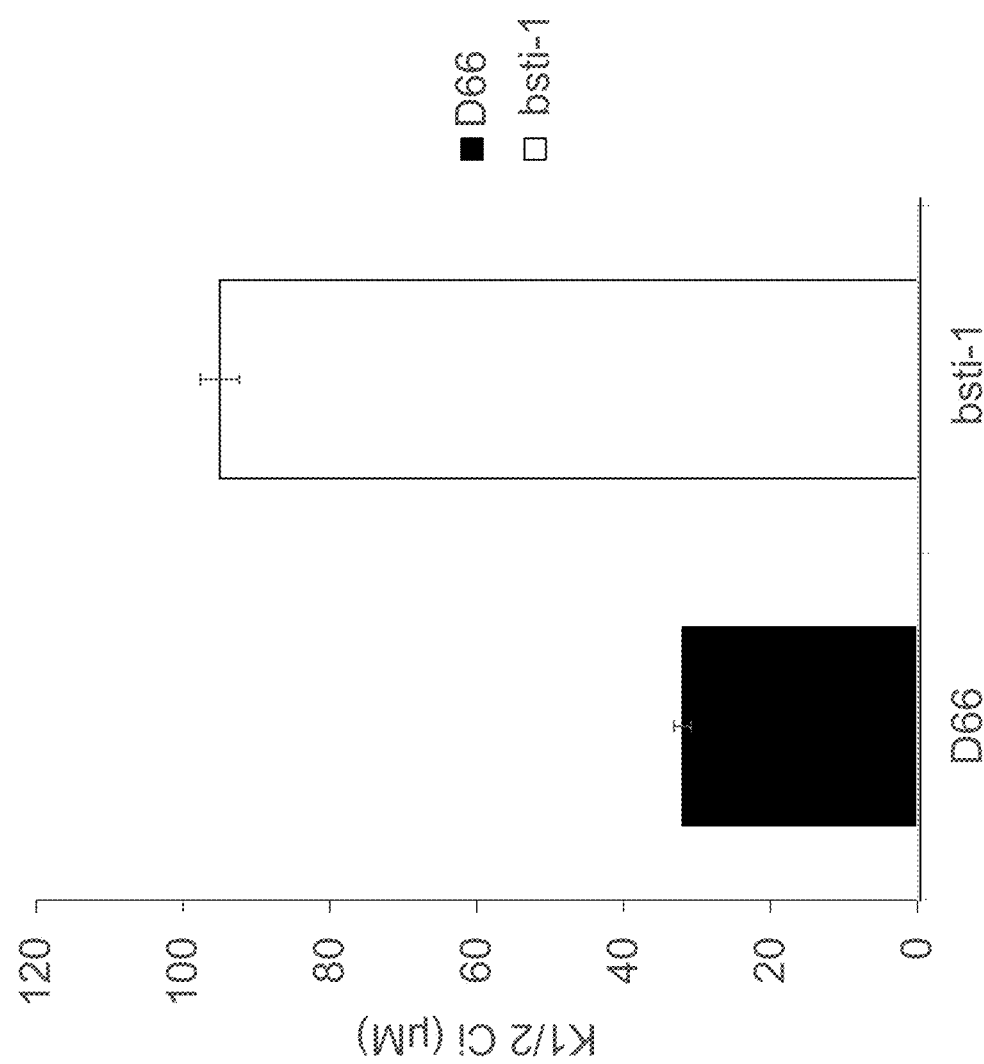
FIGS. 6A-6F show photosynthetic oxygen evolution activity of BST-RNAi lines 1 and 2, i.e., bsti-1 and bsti-2, and D66.
Figure 6B:
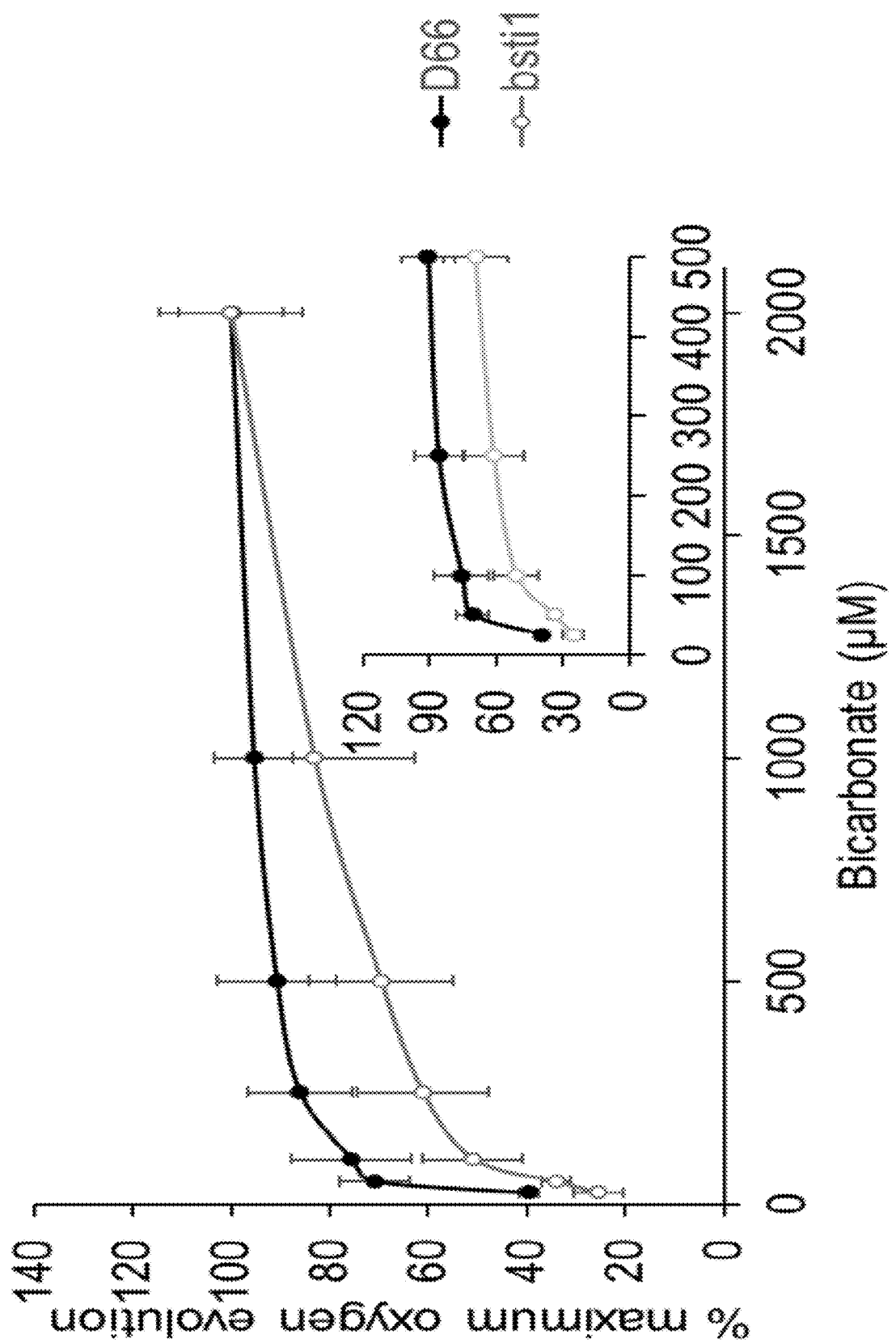
Figure 6C:
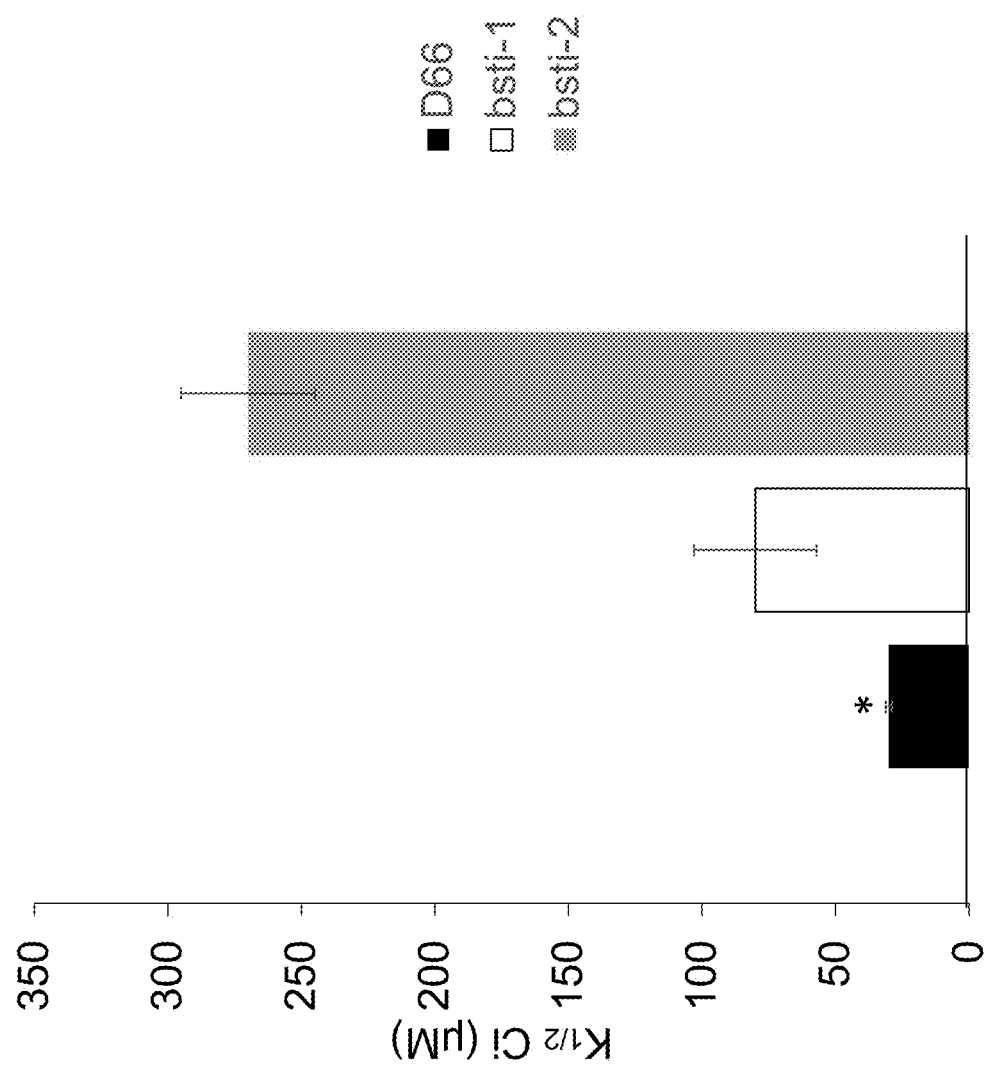
Figure 6D:
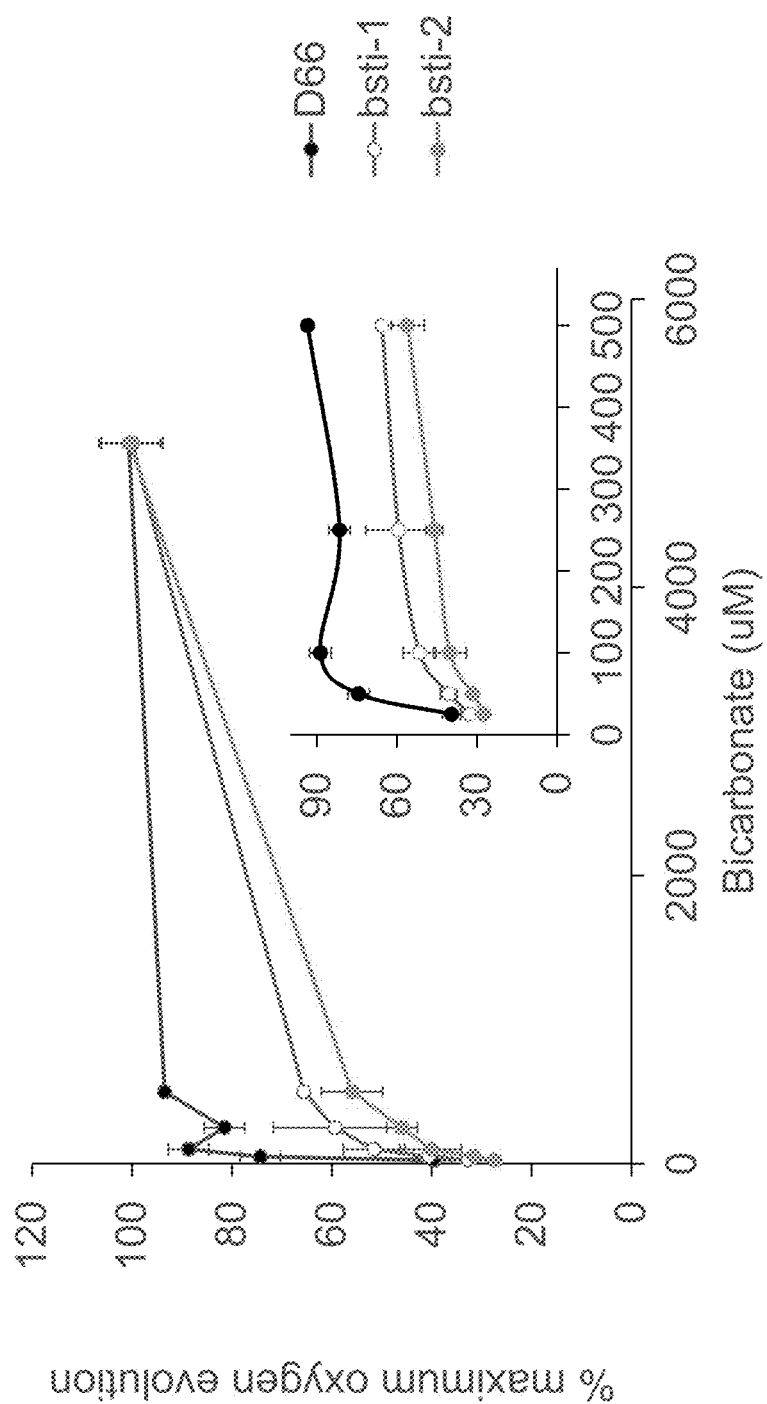
Figure 6E:
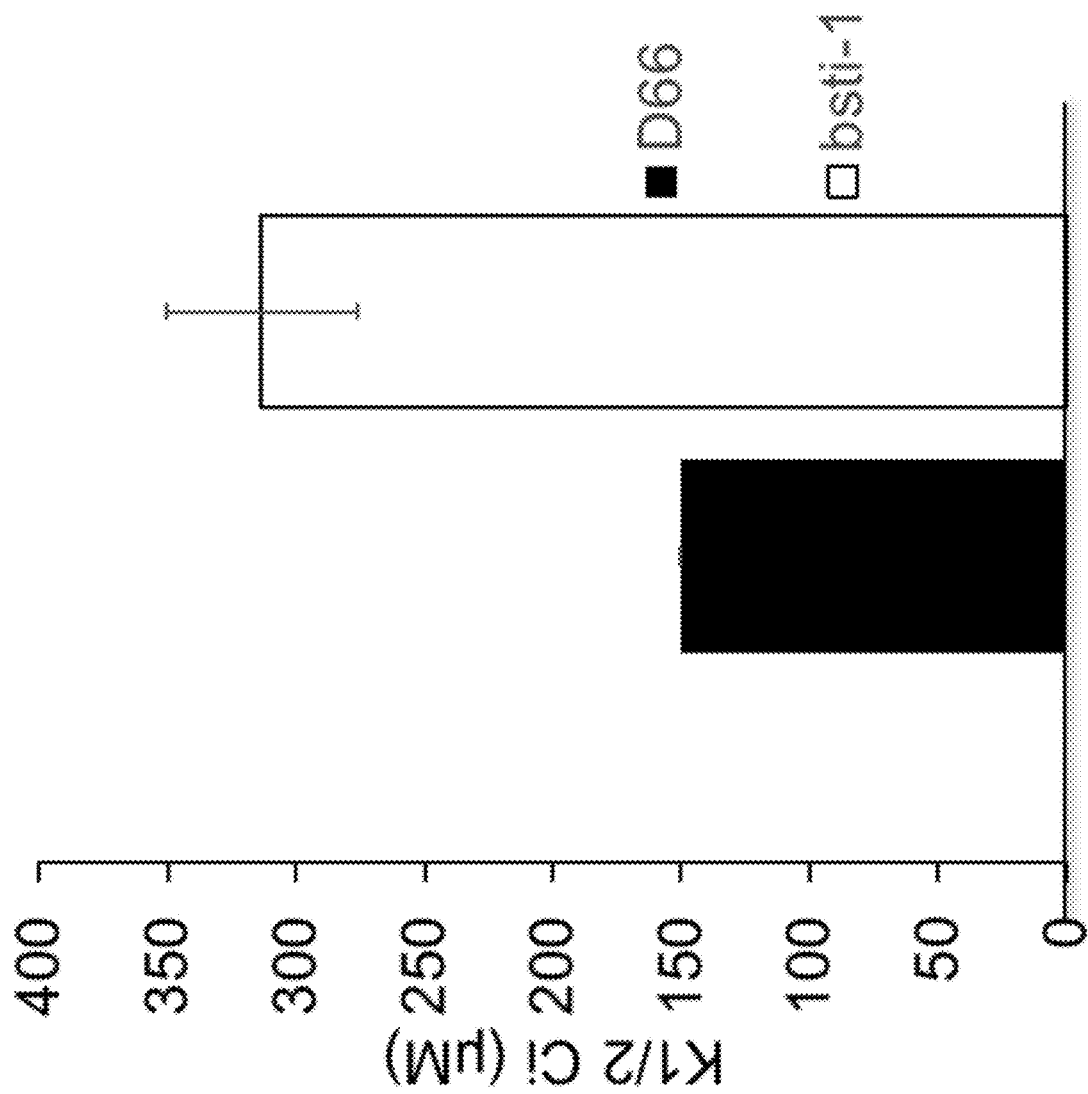
Figure 6F:
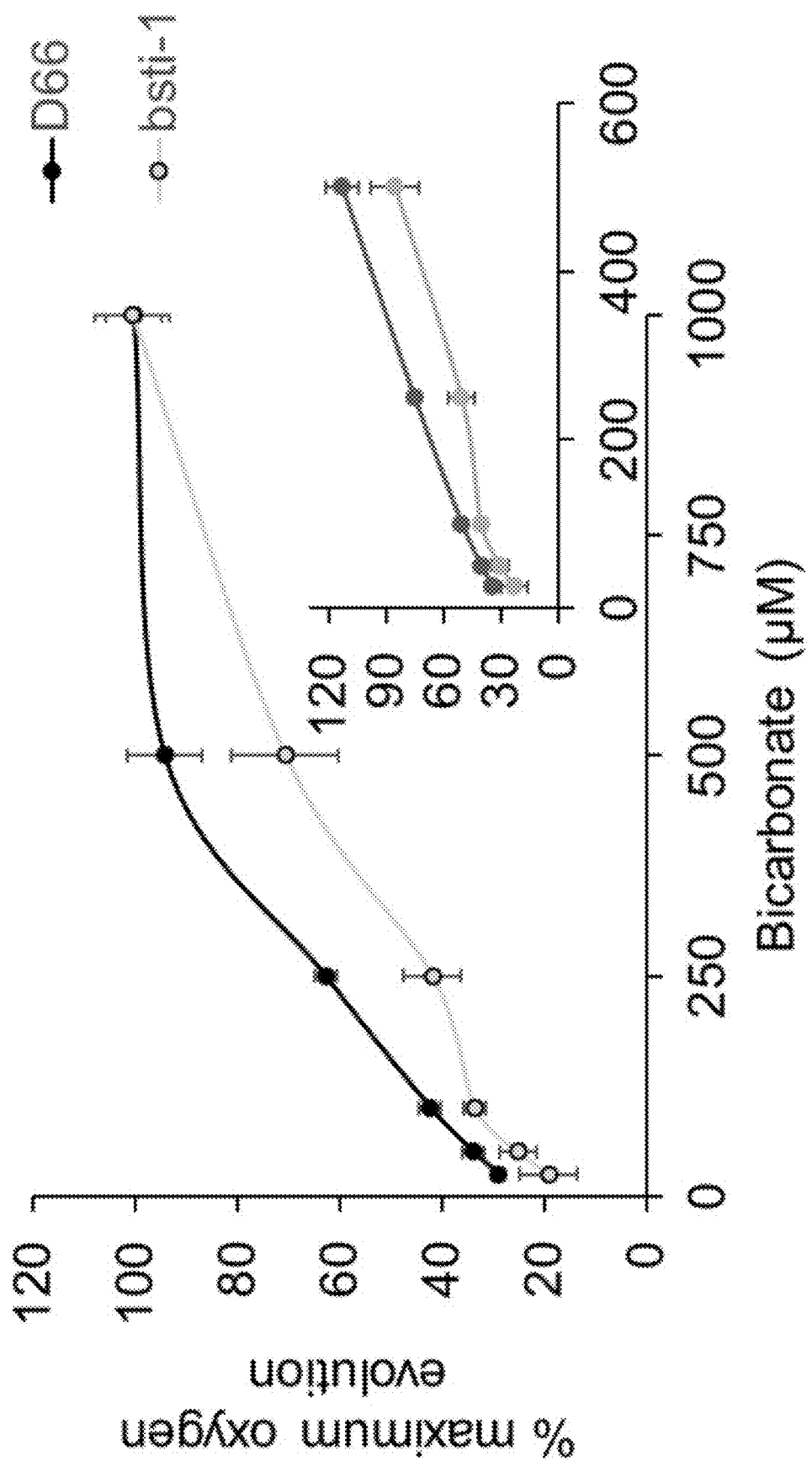
Figure 7A:
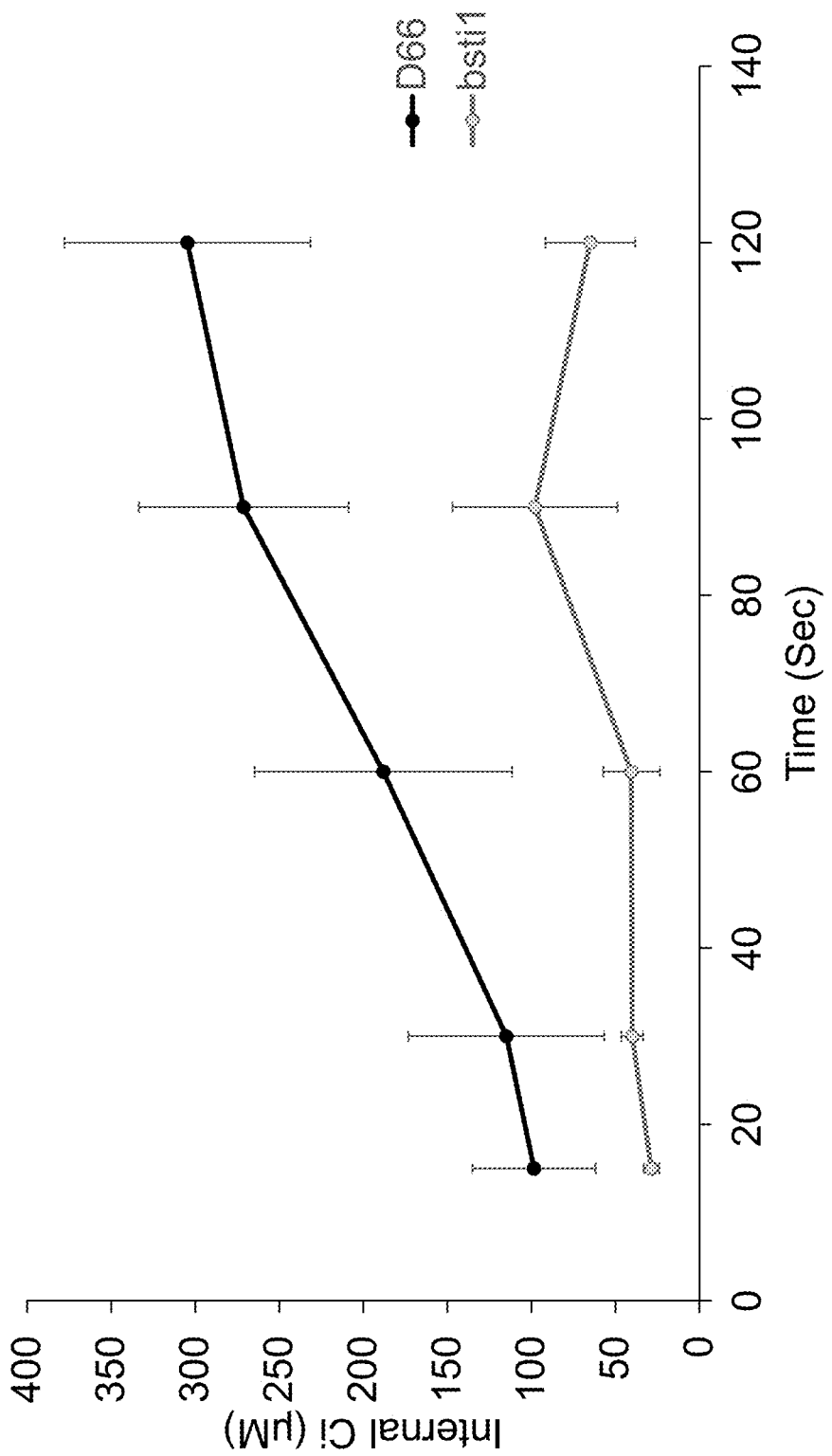
FIGS. 7A-7D show inorganic carbon uptake of bsti-1 and D66.
Figure 7B:
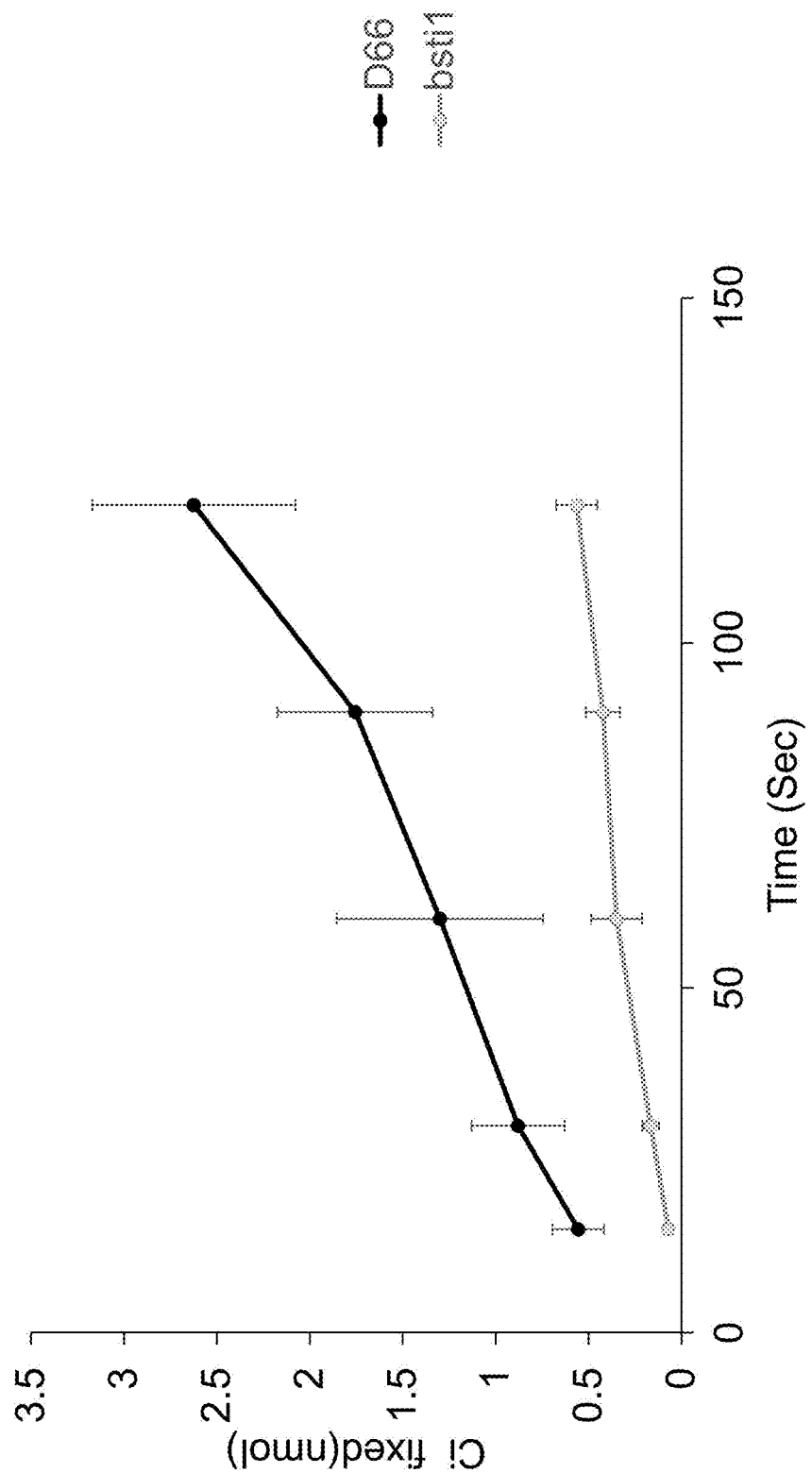
Figure 7C:
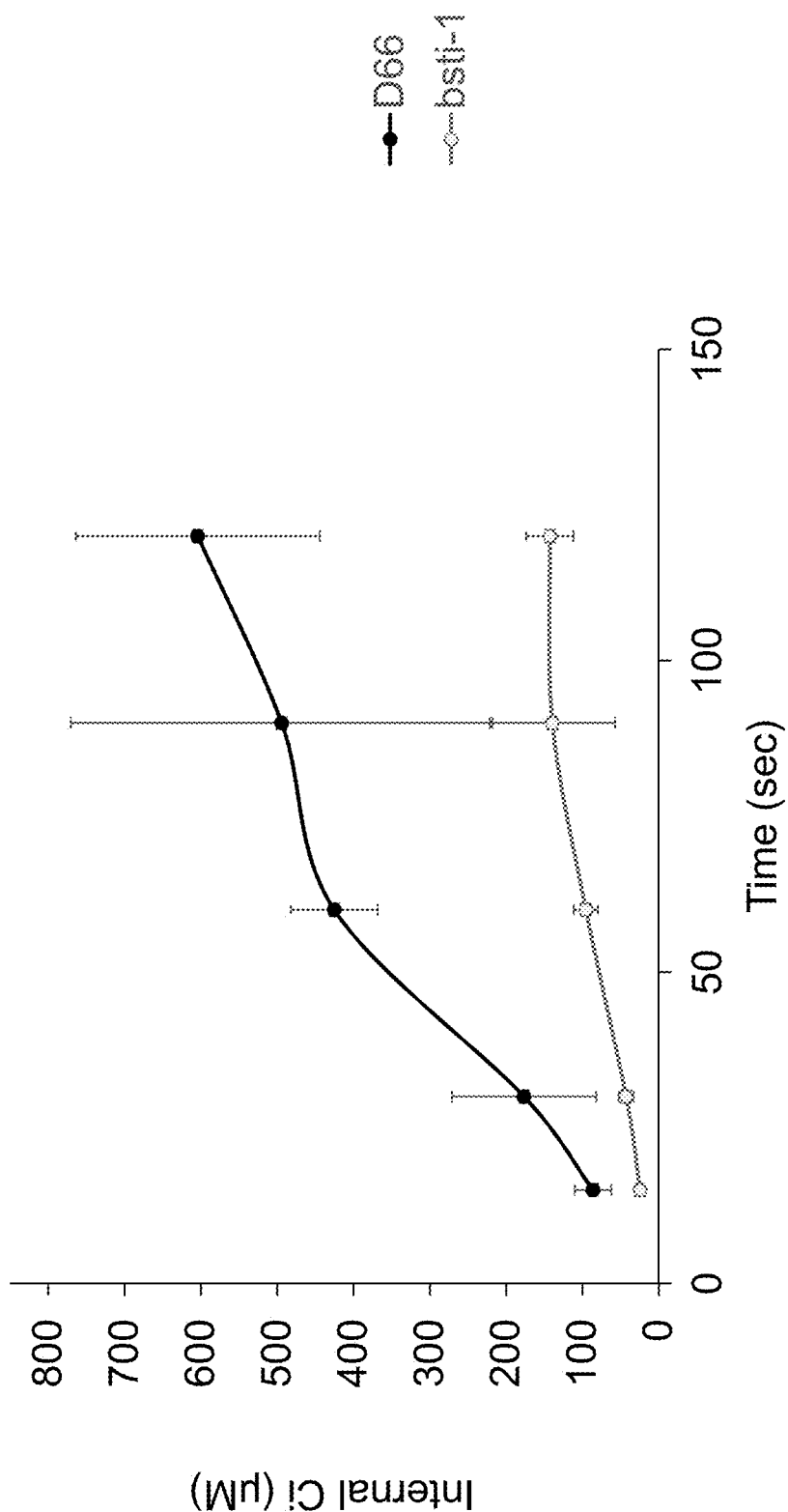
Figure 7D:
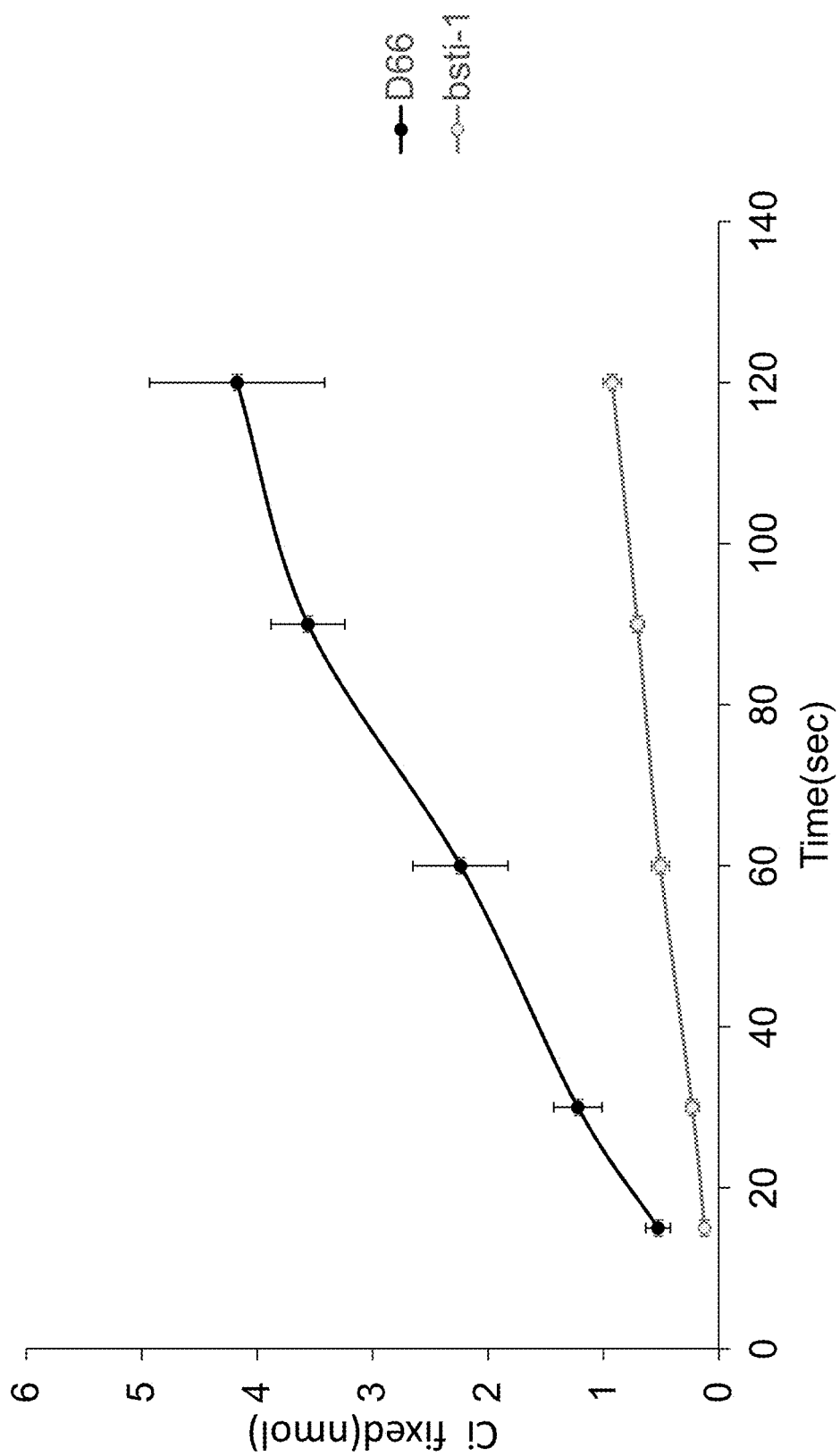

$C_i$ affinity was estimated for bsti-1 and D66 acclimated to low $CO_2$ (<0.04% $CO_2$) for 12 hours at pH 8.4 (FIG. 6A). The $K_{0.5}$ ($C_i$) values ($C_i$ concentration needed for half maximum oxygen evolution) shown in FIG. 6A was calculated from the $O_2$ evolution versus $C_i$ curves shown in FIG. 6B. In addition, $C_i$ affinity was estimated for bsti-1, bsti-2, and D66 acclimated to low $CO_2$ (<0.04% $CO_2$) for 12 hours at pH 7.8 (FIG. 6C). The $K_{0.5}$ ($C_i$) values ($C_i$ concentration needed for half maximum oxygen evolution) shown in FIG. 6C was calculated from the $O_2$ evolution versus $C_i$ curves shown in FIG. 6D. Further, $C_i$ affinity was estimated for bsti-1 and D66 acclimated to high $CO_2$ (>5% $CO_2$) for 12 hours at pH 7.8 (FIG. 6E). The $K_{0.5}$($C_i$) values ($C_i$ concentration needed for half maximum oxygen evolution) shown in FIG. 6E was calculated from the $O_2$ evolution versus $C_i$ curves shown in FIG. 6F. Triplicate runs were made at each $C_i$ concentration. The symbol "*" indicates that the differences in $K_{0.5}$($C_i$) was significant (P<0.05 by student t test). At pH 7.8 and low $CO_2$ acclimation, the Vmax of D66 is 121 μmol $O_2$ mg$^{-1}$ Chl hr$^{-1}$, the Vmax of bsti-1 is 105 μmol $O_2$ mg$^{-1}$ Chl hr$^{-1}$, and the Vmax of bsti-2 is 95 μmol $O_2$ mg$^{-1}$ Chl hr$^{-1}$. At pH 7.8 and high $CO_2$ acclimation, the Vmax of D66 is 121 μmol $O_2$ mg$^{-1}$ Chl hr$^{-1}$ and the Vmax of bsti-1 is 120 μmol $O_2$ mg$^{-1}$ Chl hr$^{-1}$. At pH 8.4 and low $CO_2$ acclimation, the Vmax of D66 is 124 μmol O2 mg$^{-1}$ Chl hr$^{-1}$ and the Vmax of bsti-1 is 85.5 μmol $O_2$ mg$^{-1}$ Chl hr$^{-1}$. The Vmax of all the strains was set to 100% oxygen evolution activity.

Uptake of Inorganic Carbon:

Silicone oil centrifugation was used to measure intracellular concentration of dissolved $C_i$ as per Moroney et al., Plant Physiol 79(1):177-183, 1985. Briefly, cells were centrifuged and suspended at 25 μg Chl mL$^{-1}$ density in $C_i$ depleted 25 mM EPPS-NaOH (pH 7.8 or 8.4) and incubated in the light until net $O_2$ evolution was zero. Cells were maintained in the light until used. 300 μL of $C_i$ depleted cells were then centrifuged in tubes containing 25 μL of 1 M glycine (pH 10) with 0.75% (w/v) SDS overlaid with 75 μL of Dow Corning AR 20 silicone oil. Assays were performed at 25° C. in 200 μmol m$^2$ s$^{-1}$ light in a Beckman Microfuge B. $C_i$ uptake was initiated by adding either 3 μl of 25 mM (for an added concentration of 25 μM) at pH 7.8 or 50 mM ((for an added concentration of 50 μM) at pH 8.4 of $NaH^{14}CO_3$ followed by the indicated time of illumination (between 15 and 120 sec at 150 μmol m$^2$ s$^{-1}$ light). Triplicate samples were run for each time point. The reaction was terminated by a 15 second centrifugation in a microfuge B (Beckman). Internal $C_i$ was calculated using the difference between total and acid stable 14C in the pellet and corrected for cell volume as described (Machingura et al., J Exp Bot 68(14):3879-3890, 2017).

Results

Two characteristics of algal cells with a CCM are first, their very high affinity for inorganic carbon ($C_i$), and second, their ability to accumulate $C_i$ to levels higher than can be obtained by diffusion. Therefore, the photosynthetic oxygen evolution activity of the RNAi knockdown lines bsti-1 and bsti-2, and the WT strain D66 were tested. The RNAi knockdown lines bsti-1 and bsti-2 acclimated to low $CO_2$ exhibited a three to tenfold lower affinity for $C_i$ at pH 7.8, respectively, as judged by their measured $K_{0.5}(C_i)$ (FIG. 6A and FIG. 6C). When acclimated to high $CO_2$, bsti-1 also had a reduction in $C_i$ affinity compared to D66 (FIG. 6E). This indicates that reducing the expression of all three BST genes caused a reduction in the cells' affinity for $C_i$. At pH 8.4, the $K_{0.5}(C_i)$ for bsti-1 is 95 μM, in sharp contrast to a low $K_{0.5}(C_i)$ of 35 μM for D66. At the higher pH of 8.4, the predominant $C_i$ species in the medium would be bicarbonate, thus the higher affinity of the D66 (WT) cells for $C_i$ reflects their ability to actively take up and utilize bicarbonate. These results, which show that bsti-1 and bsti-2 have a higher requirement for inorganic carbon for photosynthetic $O_2$ evolution, are strong evidence for a role of the bestrophins in the CCM.

$C_i$ uptake activity was also measured in D66 and bsti-1 to evaluate the importance of BST1-3 in accumulation and fixation of $C_i$. Low $CO_2$ acclimated bsti-1 had significantly lower accumulation and fixation of $^{14}C_i$ compared to D66 at both pH 7.8 as well as pH 8.4 (FIG. 7A-7D). At both pH 7.8 and 8.4, bsti-1 accumulated $^{14}C_i$ to only 20 to 25% of the levels observed in D66 cells. This difference was seen at both the earliest time point (15 seconds) and at the latest time point (up to two minutes in the light) where the D66 cells had used up most of the added $^{14}C_i$. These results indicate that BST1-3 have an important role to play in the $C_i$ uptake in low $CO_2$ conditions in *C. reinhardtii*, and again provide strong evidence for a role of the bestrophins in the CCM.

Example 7: The Bst3 Knockout Strain has Normal Growth Under Low $CO_2$ Conditions and Similar Inorganic Carbon Affinity when Compared to WT The following example describes growth under low $CO_2$ conditions and $C_i$ affinity testing of the *C. reinhardtii* bst3 knockout strain as compared to the WT strain D66.

Materials and Methods

*C. reinhardtii* knockout strains: Knockout strains are created using random insertional mutagenesis, and are part of the *Chlamydomonas* Library Project (CLiP). Strains can be ordered from the *Chlamydomonas* Resource Center (Available at www DOT chlamycollection DOT org). At present, only a bst3 knockout strain is available; bst1 and bst2 knockout strains are not available. In order to confirm the insert position in the bst3 knockout strain, PCR was performed using primers specific for the BST3 gene and for the insert (see Table 5). Insert specific primers (CIB1F and CIB1R) and the information for the flanking region were obtained from the CLIP website (Available at www DOT chlamylibrary DOT org under allMutants).

TABLE 5

Primers used to analyze the bst3 insertion.

| Primer name | Primer sequence |
|---|---|
| BST3F | TGCCCCTTCTCAGCACGT (SEQ ID NO: 138) |
| BST3R | ACTGCCTCACACTCCCCT (SEQ ID NO: 139) |
| CIB1F | GCACCAATCATGTCAAGCCT (SEQ ID NO: 140) |
| CIB1R | GACGTTACAGCACACCCTTG (SEQ ID NO: 141) |

Semi-quantitative RT-PCR analysis was performed as in Example 3.

Growth Measurement:

WT strain D66 and knockout strain bst3 were grown in pH 8.6, using methods described in the above Examples. Growth was measured using $OD_{730}$, and chlorophyll estimation was done at wavelengths 645 and 663. Measurements were done at low $CO_2$ (<0.04% $CO_2$) for six days. Cells were grown in TAP for 48 hours before transferring them to MIN at an $OD_{730}$ of 0.01.

Affinity for inorganic carbon: This was done using methods described in Example 6. Oxygen evolving activity was measured at pH 7.4 and the $K_{0.5}(C_i)$ values ($C_i$ concentration needed for half maximum oxygen evolution) were calculated from the $O_2$ evolution versus $C_i$ curves. Triplicate runs were made at each $C_i$ concentration.

Results

Figure 8A:
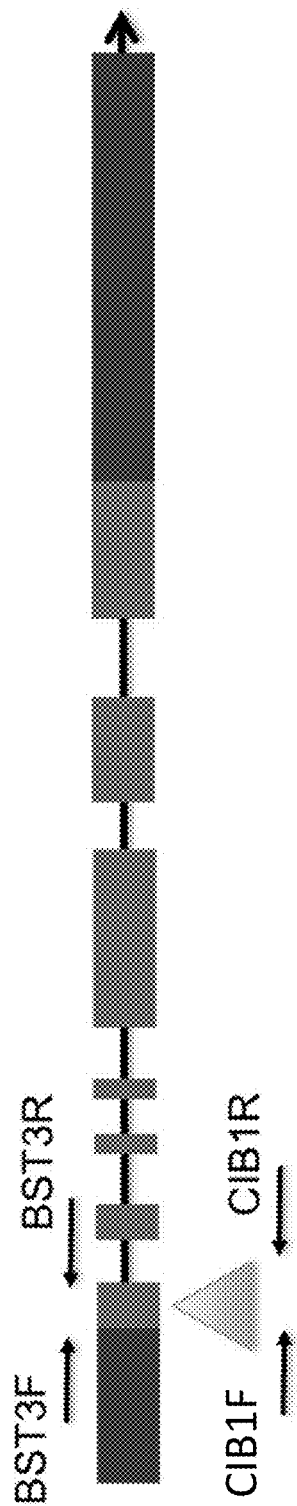
FIGS. 8A-8C show that BST3 is knocked out in the mutant bst3 from the *Chlamydomonas* Library Project (CLIP).
Figure 8B:
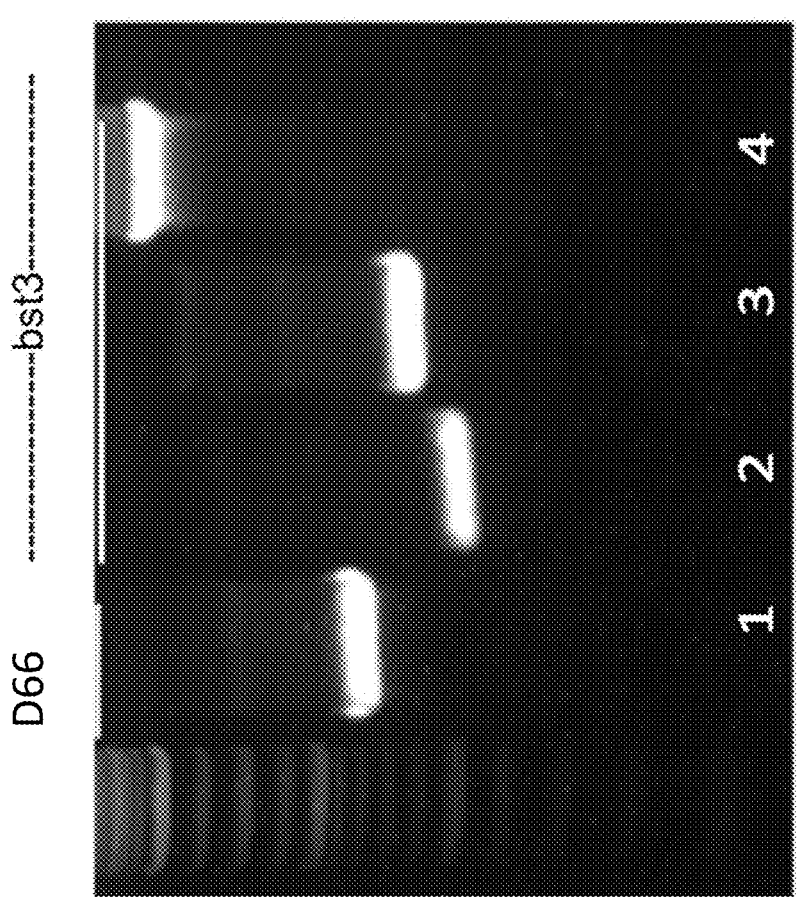
Figure 8C:
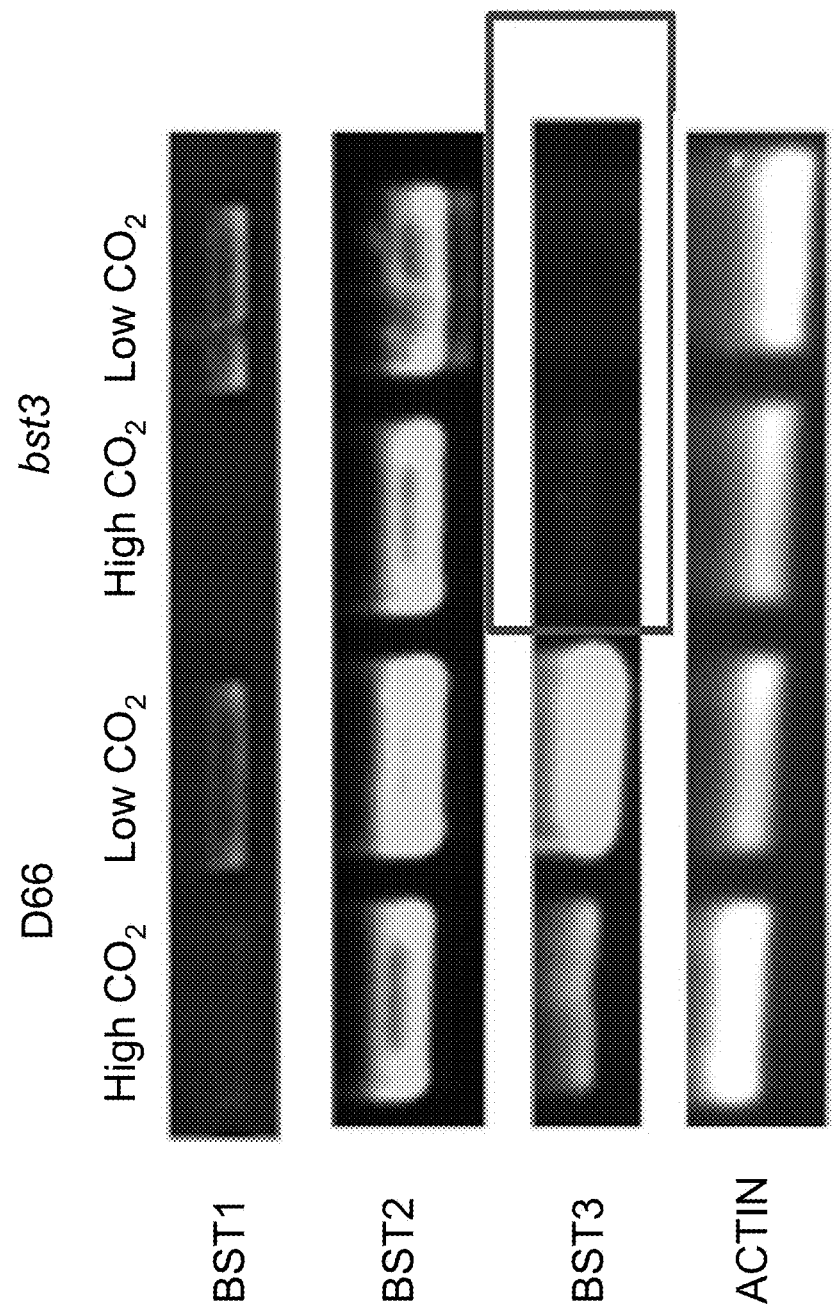

A BST3 knockout (bst3) was obtained from the CLIP mutant collection with a paromomycin insert in the first exon of the bst3 gene (FIG. 8A). The location of the insert was confirmed using PCR (FIG. 8B). In addition, BST1-3 expression was analyzed in the bst3 knockout strain under high and low $CO_2$ conditions, and compared to the WT strain D66. BST3 expression was not detected in bst3 under both conditions, while BST1 and BST2 expression were comparable between the bst3 knockout strain and the WT strain D66 under both conditions (FIG. 8C).

Figure 9A:
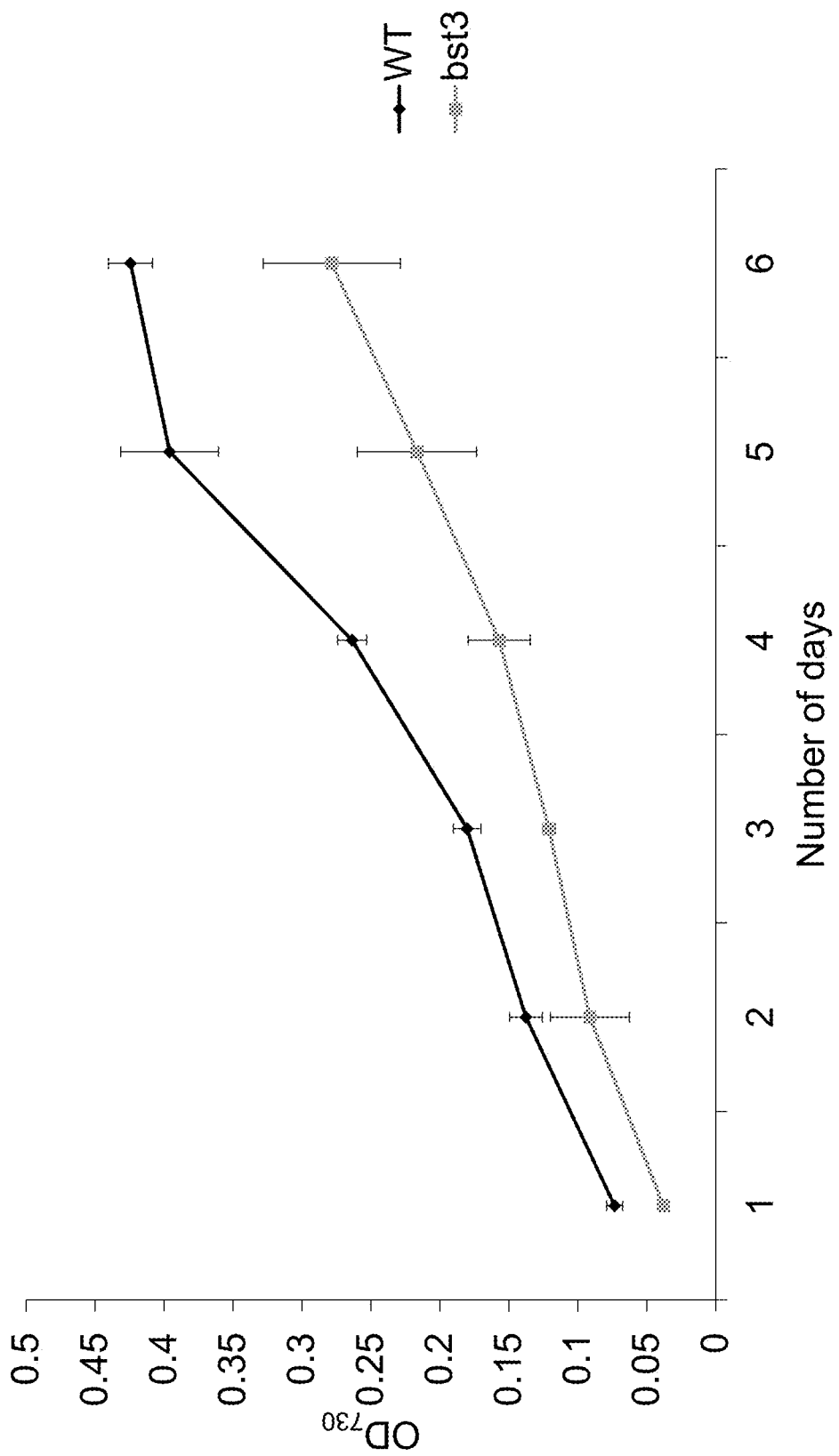
FIGS. 9A-9D show measurements of growth and inorganic carbon affinity of the knockout strain bst3 as compared to the WT strain D66.
Figure 9B:
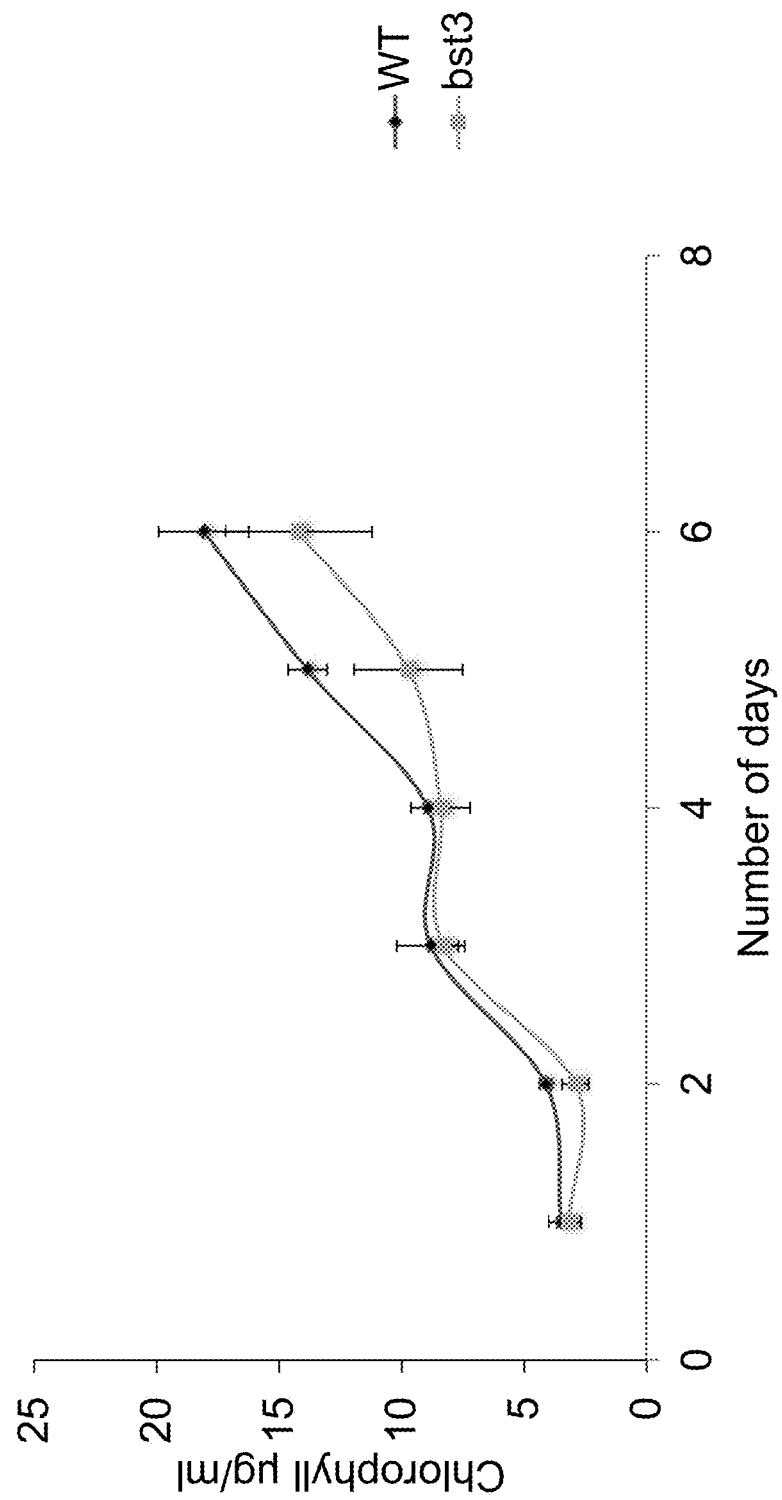
Figure 9C:
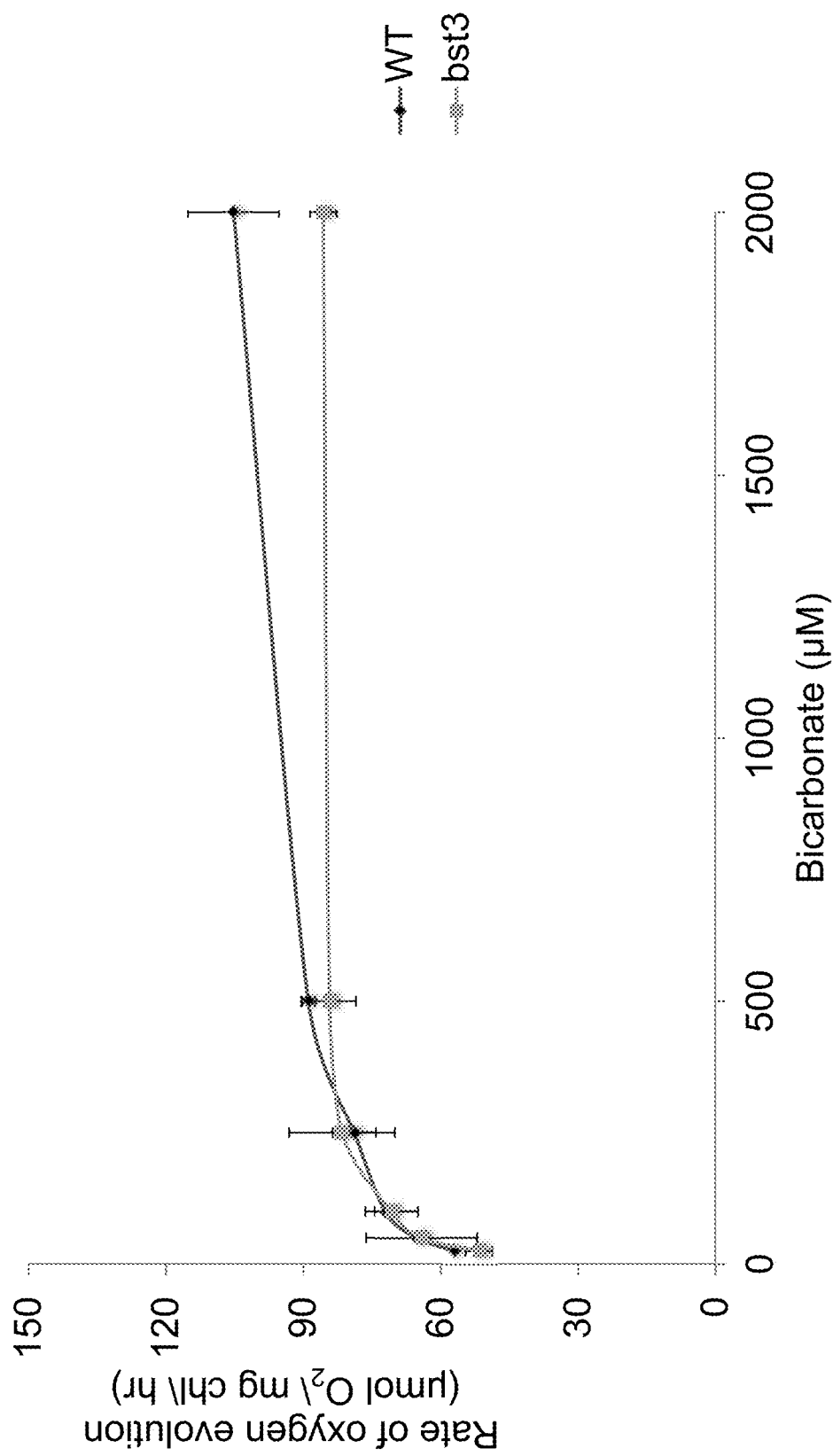
Figure 9D:
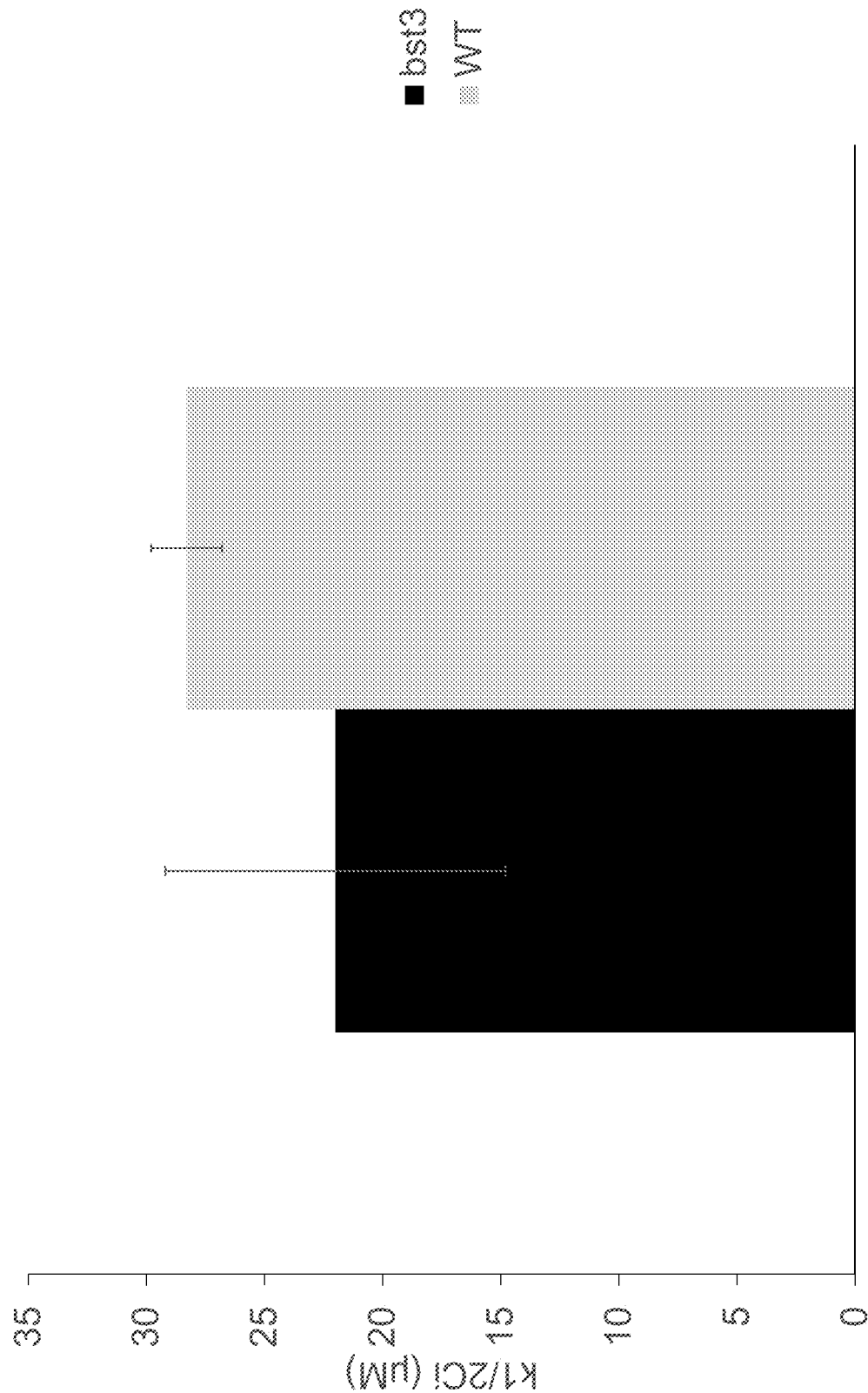

No significant growth difference for the bst3 strain was observed as compared to wild-type cells under low (<0.04% $CO_2$) (FIGS. 9A-9B), very low (0.02% $CO_2$) or high $CO_2$ (5% $CO_2$) (v/v) in air (data not shown). There also was no notable difference in $C_i$ affinity between WT and bst3 (FIG. 9C). In the RNAi knockdown line bsti-1, where the expression of all three BST genes is reduced, there is a reduced $C_i$ affinity at both pH 7.8 and pH 8.4. This is in stark contrast to bst3, the knockout strain only missing BST3 expression, which has no difference in $C_i$ affinity with WT (FIG. 9C-9D). These results support the hypothesis that the function of the three BSTs is redundant, and that the expression of all three genes must be reduced to observe physiological effects.

Example 8: Structural Characterization of BST1, BST2, and BST3 and Current *C. reinhardtii* CCM Model The following example describes the structural characterization of the *C. reinhardtii* BST1, BST2, and BST3 proteins. The example also describes the current *C. reinhardtii* CCM model.

Materials and Methods

Figure 10A:
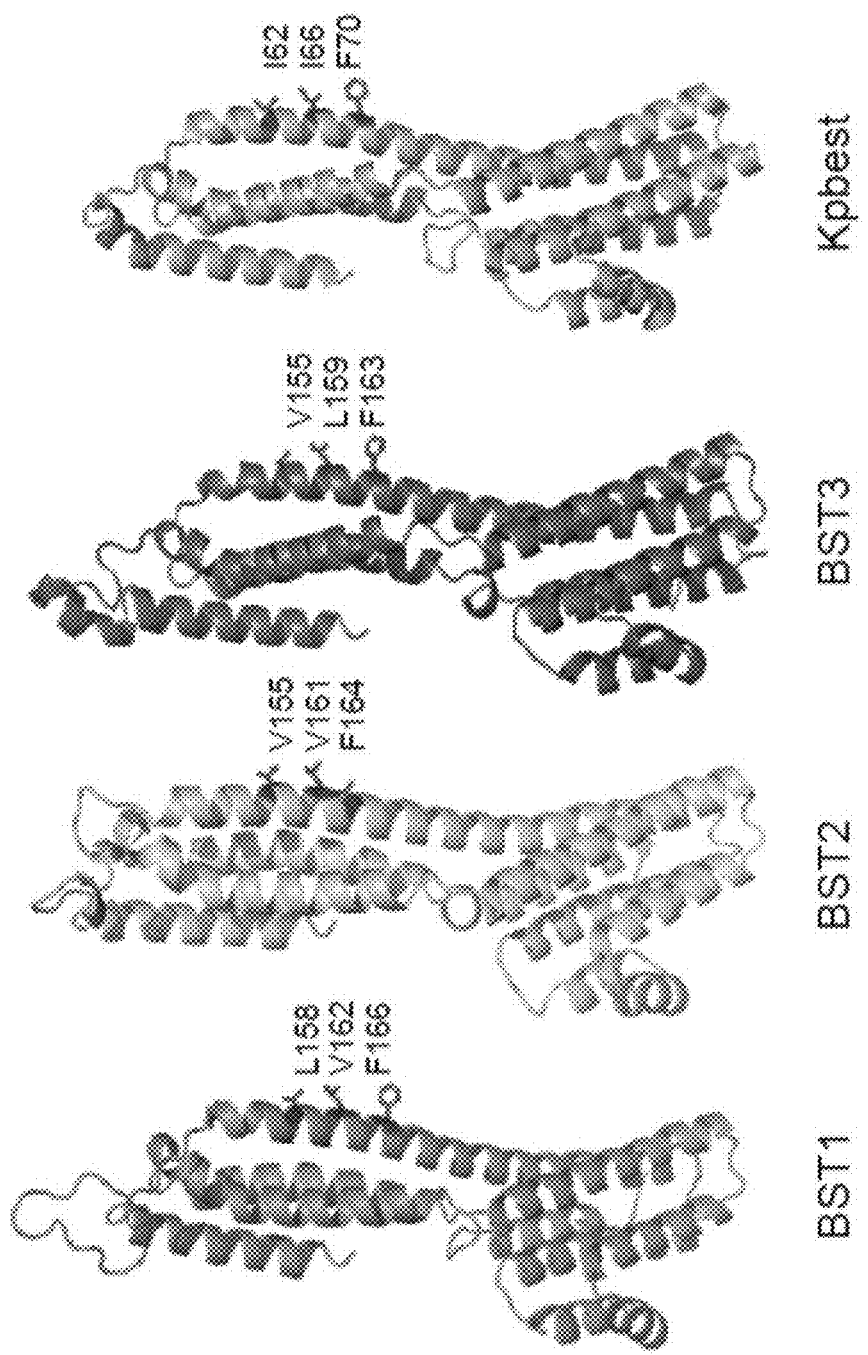
FIGS. 10A-10D show the protein structural models for *C. reinhardtii* BST1, BST2, and BST3.

Peptide sequences of BST1, BST2, and BST3 were obtained from Phytozome v12.1. Homology modelling was done using *Klebsiella pneumonia* bestrophin (Kpbest; PDB: 4DW8) as a template, and generated with Swiss-Model webserver (Yang, et al., Science 346(6216):1498-1501, 2014). Kpbest was chosen because it was identified as the highest ranking template for BST1-3 by Swiss-Model. The obtained structures and that of Kpbest are displayed as monomers with conserved residues lining the selective pore highlighted in red and labeled in FIG. 10A. The obtained BST1 homopentamer model was submitted to energy minimization with gromos 43B1 forcefield and the electrostatic potential was calculated using atom partial charge using Swiss-PDBviewer (V4.01). Then, the electric field was displayed on the BST1 homopentamer model to generate FIG. 10D. The electrostatic potentials were displayed in potential scale of -4kT/e (red, negative) to +4kT/e (blue, positive), and the cavity was highlighted in green. The BST1 homopentamer structure quality (FIG. 10B) was obtained using the QMEAN score (Benkert et al., Proteins 71(1):261-277, 2008).

Results

Figure 10B:
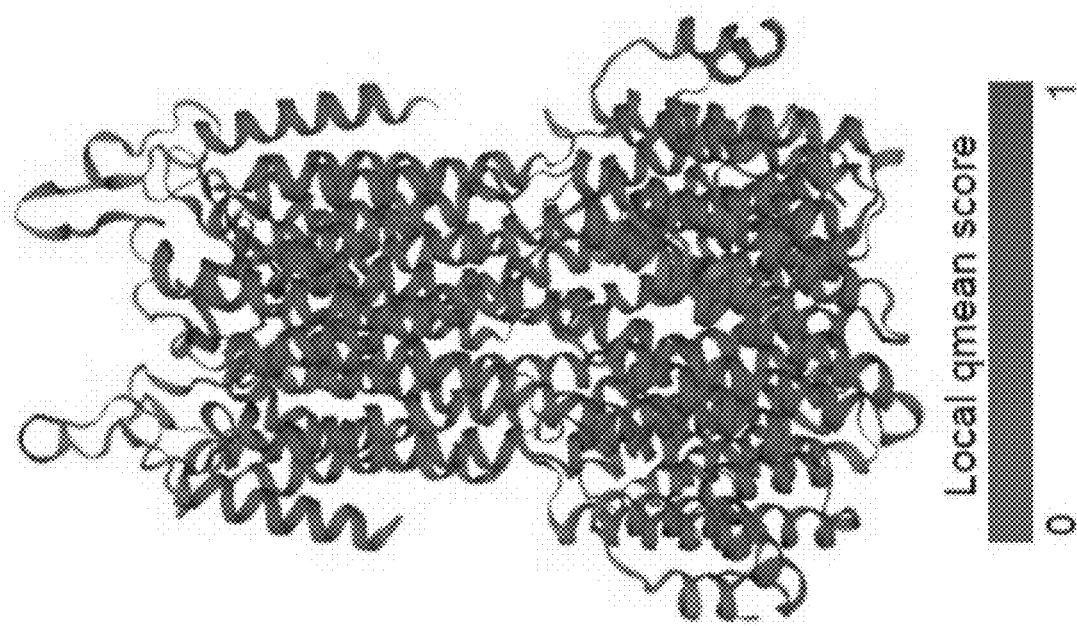
Figure 10C:
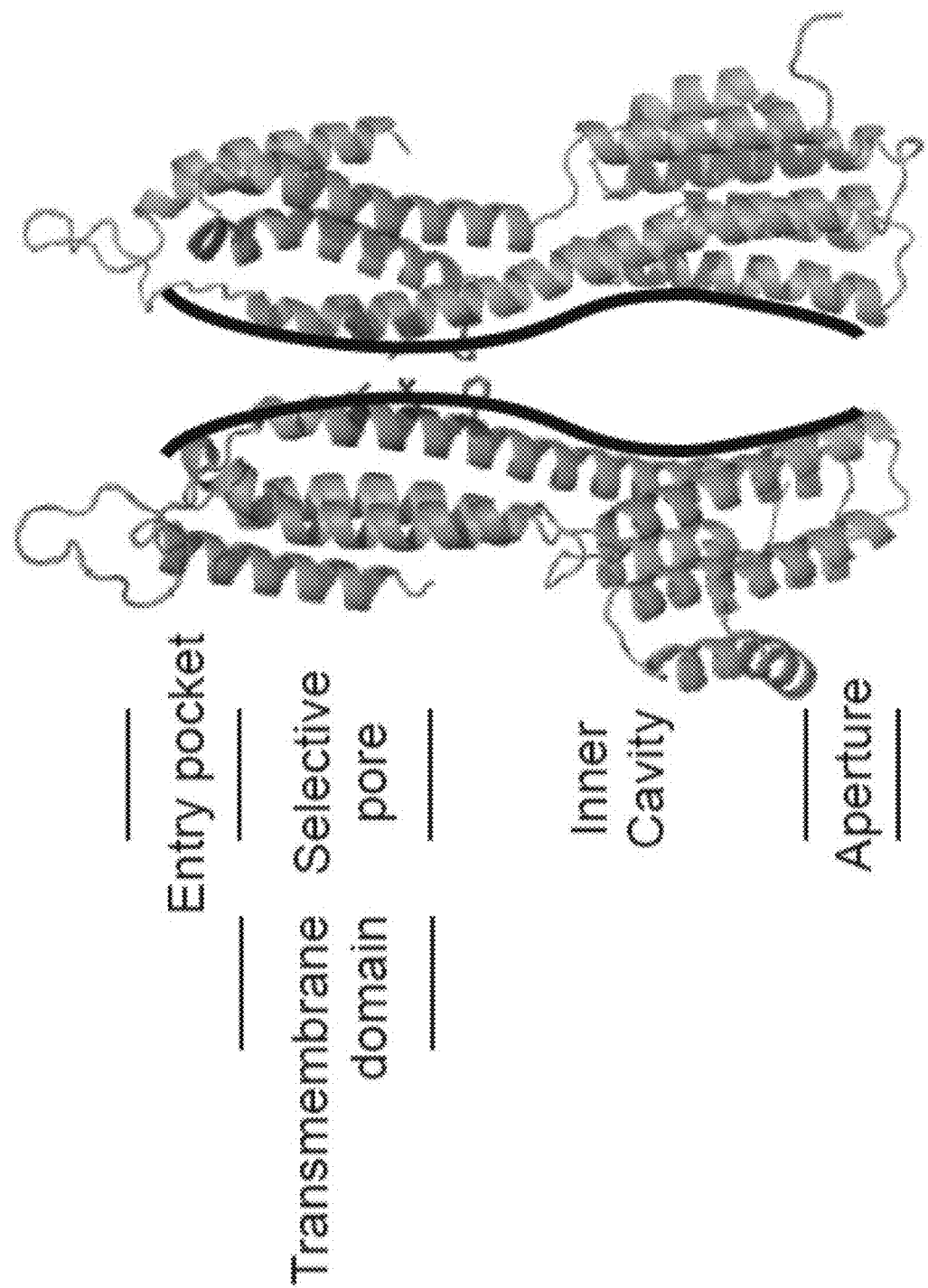
Figure 10D:
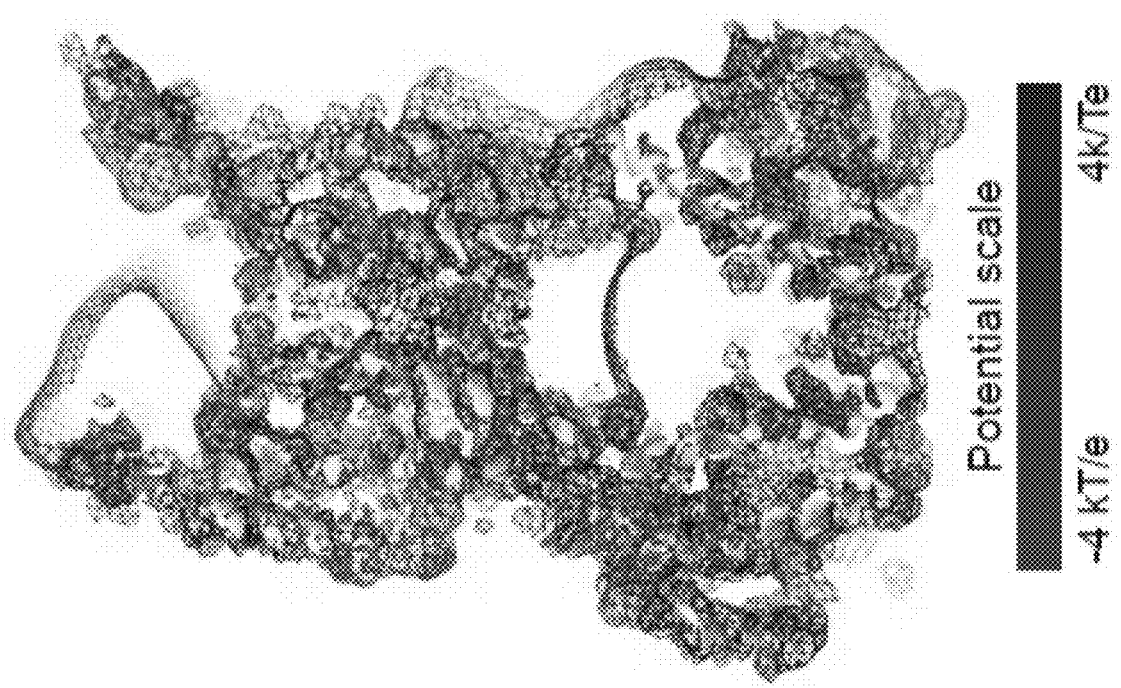

To predict whether BST1-3 might function as negative ion transporting bestrophins, homology modelling of BST1-3 using *Klebsiella pneumonia* bestrophin was done. BST1-3 contain non-polar residues along their selective pore that are conserved in proteins of the bestrophin family (FIG. 10A; Qu et al., J Neurosci 26(20):5411-5419, 2006). Structural studies show that human and *K. pneumonia* bestrophins are pentameric, and modelling of BST1 in a pentameric assembly is of high confidence (FIG. 10B). The entry pocket is bas a predominantly negative electrostatic potential and the selective pore is neutral/positively charged supporting the hypothesis that BST1-3 transport negatively charged ions (FIGS. 10C-10D; Yang, et al., Science 346(6216):1498-1501, 2014; Kane et al., Nature 516(7530):213-218, 2014). These results suggest that *C. reinhardtii* bestropbins may be anion transporters.

Figure 11:
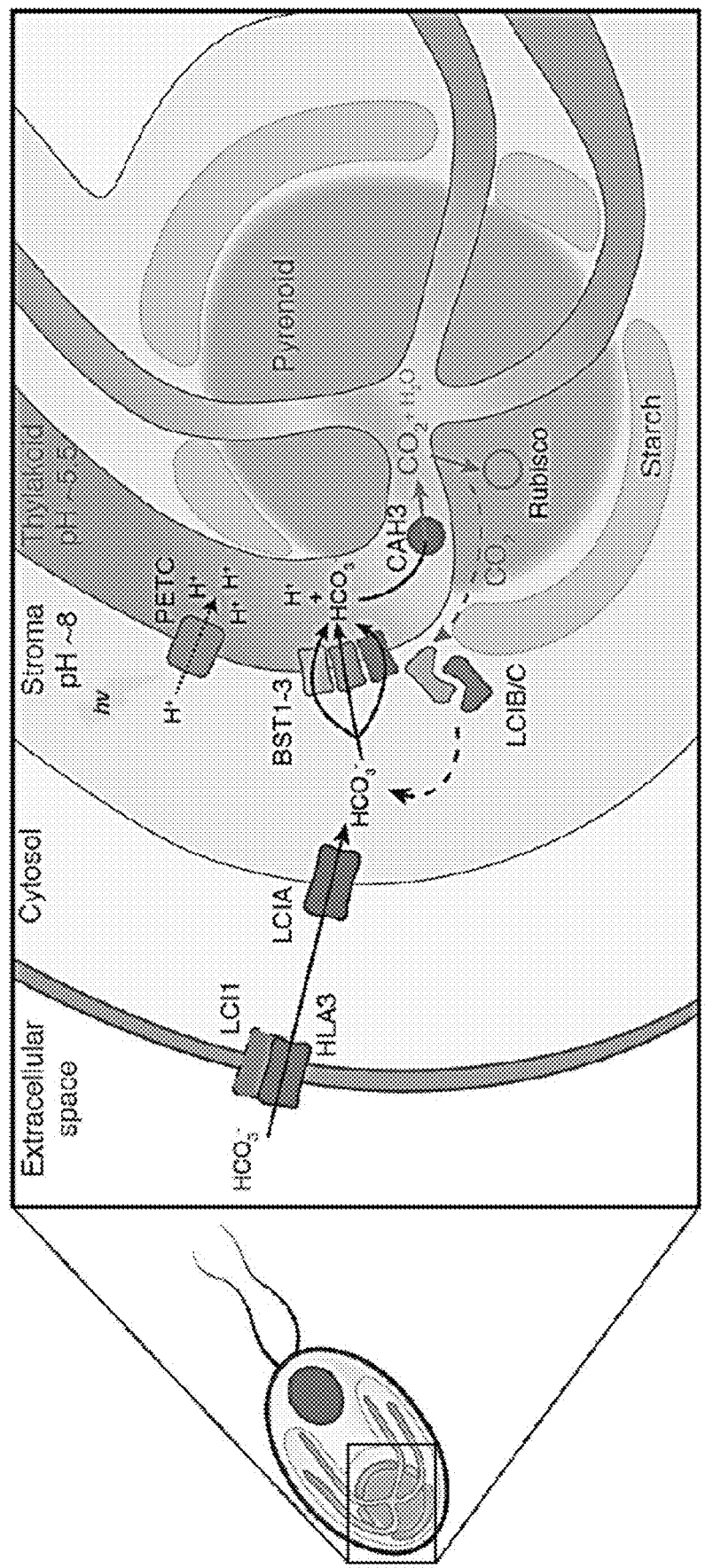
FIG. 11 shows the current *C. reinhardtii* CCM model for inorganic carbon ($C_i$) transport. BST1, BST2, and BST3 are shown as bicarbonate-transporting channels (light purple, purple, and dark purple rectangles) localized to the chloroplast thylakoid membrane.

The results described in Examples 2-8 demonstrate an important role for the three bestrophin proteins in the context of the *C. reinhardtii* CCM. Taken together, these results indicate that the three bestrophin proteins are thylakoid-localized bicarbonate-transporting channels. FIG. 11 shows the integration of BST1, BST2, and BST3 into the current *C. reinhardtii* CCM model for $C_i$ transport.

The invention claimed is:

1. A genetically altered plant or part thereof, comprising a genetic alteration comprising expression of a polypeptide with at least 95% sequence identity to SEQ ID NO:1, wherein the polypeptide transports bicarbonate and is localized to a chloroplast envelope or a thylakoid membrane of at least one chloroplast within a plant cell.

2. The plant or part thereof of claim 1, wherein the polypeptide comprises SEQ ID NO: 1.

3. The plant or part thereof of claim 1, wherein the plant cell is a leaf mesophyll cell.

4. The plant or part thereof of claim 3, wherein the polypeptide is expressed in at least 70% of leaf mesophyll cells of the plant.

5. The plant or part thereof of claim 1, wherein the plant is selected from the group consisting of cowpea, soybean, cassava, rice, soy, wheat, and other C3 crop plants, and wherein the plant is not selected from the group consisting of corn, sorghum, and other C4 crop plants.

6. A transfected plant or part thereof comprising
a transfected nucleic acid sequence comprising a coding sequence of a polypeptide with at least 95% sequence identity to SEQ ID NO:1 in the plant or part thereof;
wherein the polypeptide transports bicarbonate and is expressed in the plant or part thereof.

7. The plant or part thereof of claim 6, wherein the polypeptide is localized to a chloroplast envelope or a chloroplast thylakoid membrane of at least one chloroplast of a plant cell, wherein the plant cell is a leaf mesophyll cell, and wherein the polypeptide is expressed in at least 70% of leaf mesophyll cells of the plant.

8. The plant or part thereof of claim 6, wherein the transfected nucleic acid sequence is stably integrated into the nuclear genome of the plant.

9. The plant or part thereof of claim 8, wherein the transfected nucleic acid sequence further comprises a second nucleic acid sequence encoding a signal peptide sequence or targeting sequence operably linked to the coding sequence of the polypeptide, wherein expression of the signal peptide sequence or targeting sequence results in localization of the polypeptide to a chloroplast envelope or a chloroplast thylakoid membrane of at least one chloroplast of a plant cell.

10. The plant or part thereof of claim 6, wherein the polypeptide comprises SEQ ID NO: 1.

11. The plant or part thereof of claim 6, wherein the plant is selected from the group consisting of cowpea, soybean, cassava, rice, soy, wheat, and other C3 crop plants, and wherein the plant is not selected from the group consisting of corn, sorghum, and other C4 crop plants.

12. The plant or part thereof of claim 1, wherein the plant comprises increased carbon use efficiency, increased water use efficiency, increased nitrogen use efficiency, reduced photoinhibition, increased growth, and/or increased productivity.

13. The plant or part thereof of claim 6, wherein the plant comprises increased carbon use efficiency, increased water use efficiency, increased nitrogen use efficiency, reduced photoinhibition, increased growth, and/or increased productivity.

* * * * *

SEQUENCE LISTING

<160> NUMBER OF SEQ ID NOS: 141

<210> SEQ ID NO 1
<211> LENGTH: 438
<212> TYPE: PRT
<213> ORGANISM: Chlamydomonas reinhardtii

<400> SEQUENCE: 1

```
Met Gln Met Gln Ala Asn Arg Ser Ser Leu Arg Ala Ser Pro Val Arg
1               5                   10                  15

Gly Leu Gly Ala Arg Pro Leu Leu Arg Ala Leu Pro Ala Gly Arg Val
            20                  25                  30

Ala Arg Leu Asn Val Ser Ala Gln Ala Lys Asp Pro Asn Ala Pro Ile
        35                  40                  45

Gln Ser Asn Pro Leu Gly Thr Leu Ser Ser Gln Ser Gly Gln Val Ala
    50                  55                  60

Thr Leu Pro Arg Ser Glu Glu Ala Arg Lys Tyr Phe Arg Thr Val Tyr
65                  70                  75                  80

Asp Phe Pro Gln Trp Gln Lys His Arg Ser Ser Tyr Arg Phe Ala Glu
                85                  90                  95

Arg Leu Phe Gln Leu Ser Gln Ser His Ile Leu Gln Asn Ala Leu Pro
            100                 105                 110

Ala Ile Ser Trp Val Thr Leu Val Ala Thr Leu Val Ala Ser Tyr Gly
        115                 120                 125

Tyr Ser Tyr Asp Gln His Met Leu Pro Asp Val Phe Pro Ser Ile Ser
    130                 135                 140

Pro Asn Ala Ser Cys Thr Ala Phe Ile Ser Asn Thr Ser Val Ala Leu
145                 150                 155                 160

Ser Leu Leu Leu Val Phe Arg Thr Asn Ser Ser Tyr Gly Arg Trp Asp
                165                 170                 175

Glu Ala Arg Lys Met Trp Gly Gly Leu Leu Asn Arg Ser Arg Asp Ile
            180                 185                 190

Met Arg Gln Gly Ala Thr Cys Phe Pro Asp Asp Gln Val Glu Ala Lys
        195                 200                 205

Lys Ala Leu Ala Arg Trp Thr Val Ala Phe Ser Arg Ala Leu Arg Ile
    210                 215                 220

His Phe Gln Pro Glu Val Thr Ile Glu Ser Gly Leu Gln Asn Ile Leu
225                 230                 235                 240

Thr Pro Ala Glu Leu Gln Met Leu Ala Lys Ser Gln His Arg Pro Val
                245                 250                 255

Arg Ala Ile His Ala Ile Ser Gln Ile Ile Gln Ser Val Pro Met Ser
            260                 265                 270

Ser Ile His Gln Gln Gln Met Ser Asn Asn Leu Thr Phe Phe His Asp
        275                 280                 285

Val Leu Gly Gly Cys Glu Arg Leu Leu Arg Ala Pro Ile Pro Val Ser
    290                 295                 300

Tyr Thr Arg His Thr Ala Arg Phe Leu Phe Ala Trp Leu Thr Leu Leu
305                 310                 315                 320

Pro Phe Ala Leu Tyr Pro Thr Thr Gly Trp Gly Val Val Pro Val Cys
                325                 330                 335

Thr Gly Ile Ala Ala Val Leu Cys Gly Ile Glu Glu Ile Gly Val Gln
            340                 345                 350
```

```
Cys Glu Glu Pro Phe Gly Ile Leu Pro Leu Asp Val Ile Cys Asn Arg
            355                 360                 365

Ile Gln Ala Asp Val Met Ala Thr Leu Lys Asp Ala Asp Thr Lys
    370                 375                 380

Thr Ile Leu Ala Glu Ala Gly Leu Ile Ser Leu Ile Pro Ser Ala Thr
385                 390                 395                 400

Ser Ala Thr Pro Val Ala Ser Ala Glu Pro Val Leu Val Ser Ala Arg
                405                 410                 415

Pro Ser Ala Ala Pro Ala Pro Asn Asn Gly Leu Gln Val Arg Val Ala
                420                 425                 430

Met Gly Gly Glu Arg Lys
            435

<210> SEQ ID NO 2
<211> LENGTH: 450
<212> TYPE: PRT
<213> ORGANISM: Chlamydomonas reinhardtii

<400> SEQUENCE: 2

Met Gln Cys Leu Ser Ser Arg Pro Val Ala Met Gly Arg Ala Gly Ser
1               5                   10                  15

Ser Ala Leu Pro Arg Leu Pro Leu Arg Ala Gly Arg Val Cys His Leu
            20                  25                  30

Gly Val Arg Cys Gln Ala Ala Asn Lys Asp Pro Asn Ala Pro Ile Gln
        35                  40                  45

Ser Asn Pro Leu Gly Ser Phe Ser Ser Gln Leu Gln Asn Gln Pro Thr
    50                  55                  60

Leu Pro Arg Ser Glu Glu Ala Arg Lys Tyr Phe Arg Thr Val Tyr Asp
65                  70                  75                  80

Phe Pro Gln Trp Gln Thr His Arg Asn Gln Tyr Arg Leu Met Lys Arg
                85                  90                  95

Leu Phe Ser Ile Pro Gln Ser His Val Ile Gln Asn Ala Leu Pro Ser
            100                 105                 110

Ile Met Trp Val Ala Phe Thr Ser Thr Cys Val Ala Ala Tyr Met Tyr
        115                 120                 125

Gly Tyr Asp Gln His Met Leu Pro Glu Gly Phe Pro Thr Leu Ala Pro
    130                 135                 140

Asn Ala Ala Cys Ser Ala Phe Ile Ser Asn Thr Ser Val Ala Leu Ser
145                 150                 155                 160

Leu Leu Leu Val Phe Arg Thr Asn Ser Ser Tyr Gly Arg Trp Asp Glu
                165                 170                 175

Ala Arg Lys Met Trp Gly Gly Leu Leu Asn Arg Ser Arg Asp Ile Met
            180                 185                 190

Arg Gln Gly Ala Thr Cys Phe Pro Asp Asp Gln Val Glu Ala Lys Lys
        195                 200                 205

Ala Leu Ala Arg Trp Val Val Ala Phe Ser Arg Ala Leu Arg Ile His
    210                 215                 220

Phe Gln Pro Glu Val Thr Ile Glu Ser Glu Leu Lys Asn Ile Leu Thr
225                 230                 235                 240

Pro Ala Glu Leu Gln Met Leu Ala Lys Ser Gln His Arg Pro Val Arg
                245                 250                 255

Ala Ile His Ala Ile Ser Gln Ile Ile Gln Ser Val Pro Met Ser Ser
            260                 265                 270

Ile His Gln Gln Gln Met Ser Asn Asn Leu Thr Phe Phe His Asp Val
        275                 280                 285
```

```
Leu Gly Gly Cys Glu Arg Leu Leu Arg Ala Pro Ile Pro Val Ser Tyr
        290                 295                 300

Thr Arg His Thr Ala Arg Phe Leu Phe Ala Trp Leu Thr Leu Leu Pro
305                 310                 315                 320

Phe Ala Leu Tyr Gly Ser Cys Gly Val Ser Val Ile Pro Val Cys Ser
                325                 330                 335

Gly Ile Ala Ala Val Leu Cys Gly Ile Glu Glu Ile Gly Val Gln Cys
                340                 345                 350

Glu Glu Pro Phe Gly Ile Leu Pro Leu Asp Val Ile Cys Asn Arg Ile
            355                 360                 365

Gln Ala Asp Val Met Ala Thr Leu Lys Asp Asp Ala Asp Thr Lys Thr
        370                 375                 380

Ile Leu Ala Glu Ala Gly Leu Ile Ser Leu Arg Ala Asn Ser Ala Met
385                 390                 395                 400

Ala Val Glu Asn Ala Leu Pro Asp Leu Asp Ser Ile Asn Ala Ala Ala
                405                 410                 415

Pro Asn Gly Asn Gly Ser His Asn Gly Asn Gly Ala Ala Val Pro Val
            420                 425                 430

Ser Val Ser Ala Gly Ala Ser Gly Asn Gly Met Asn Val Arg Ile Ser
        435                 440                 445

Pro Arg
    450

<210> SEQ ID NO 3
<211> LENGTH: 466
<212> TYPE: PRT
<213> ORGANISM: Chlamydomonas reinhardtii

<400> SEQUENCE: 3

Met Gln Val Ser Lys Val Pro Ser Ser Ala Ser Ala Arg Cys Leu Pro
1               5                   10                  15

Arg Leu Pro Val Arg Thr Ser Arg Val Cys Gln Leu Ser Val Arg Cys
            20                  25                  30

Gln Ala Ala Asn Lys Asp Pro Asn Ala Pro Ile Gln Ser Asn Pro Leu
        35                  40                  45

Gly Ser Phe Ser Ser Gln Asn Ser Ser Gly Ala Val Val Thr Ala Pro
    50                  55                  60

Arg Asn Glu Asp Ala Arg Lys Tyr Phe Arg Thr Val Tyr Asp Phe Pro
65                  70                  75                  80

Gln Trp Gln Lys His Arg Ser Gln Ser Arg Leu Val Arg Arg Leu Phe
                85                  90                  95

Thr Ile Pro Gln Ser His Val Ile Gln Asn Ala Leu Pro Ser Ile Met
            100                 105                 110

Trp Val Thr Phe Thr Ser Thr Cys Val Ala Ala Tyr Met Tyr Gly Tyr
        115                 120                 125

Asp Leu His Ile Leu Pro Glu Gly Phe Pro Thr Leu Ala Pro Asn Ala
    130                 135                 140

Ala Cys Ser Ala Phe Ile Ser Asn Thr Ser Val Ala Leu Ser Leu Leu
145                 150                 155                 160

Leu Val Phe Arg Thr Asn Ser Ser Tyr Gly Arg Trp Asp Glu Ala Arg
                165                 170                 175

Lys Met Trp Gly Gly Leu Leu Asn Arg Ser Arg Asp Ile Met Arg Gln
            180                 185                 190

Gly Ala Thr Cys Phe Pro Asp Asp Gln Val Glu Ala Lys Lys Ala Leu
```

-continued

```
195 200 205

Ala Arg Trp Thr Val Ala Phe Ala Arg Ala Leu Arg Ile His Phe Gln
210 215 220

Pro Glu Val Thr Ile Glu Ser Glu Leu Gln Asn Ile Leu Thr Pro Ala
225 230 235 240

Glu Leu Gln Met Leu Ala Lys Ser Gln His Arg Pro Val Arg Ala Ile
245 250 255

His Ala Ile Ser Gln Ile Ile Gln Ser Val Arg Met Ser Ser Ile His
260 265 270

Gln Gln Gln Met Ser Asn Asn Leu Thr Phe Phe His Asp Val Leu Gly
275 280 285

Gly Cys Glu Arg Leu Leu Arg Ala Pro Ile Pro Val Ser Tyr Thr Arg
290 295 300

His Thr Ala Arg Phe Leu Phe Ala Trp Leu Thr Leu Leu Pro Phe Ala
305 310 315 320

Leu Tyr Gly Ser Cys Gly Val Ser Val Ile Pro Val Cys Thr Gly Ile
325 330 335

Ala Ala Val Leu Cys Gly Ile Glu Glu Ile Gly Val Gln Cys Glu Glu
340 345 350

Pro Phe Gly Ile Leu Pro Leu Asp Val Ile Cys Asn Arg Ile Gln Ala
355 360 365

Asp Val Met Ala Thr Leu Lys Asp Asp Ala Asp Thr Lys Thr Val Leu
370 375 380

Ala Glu Ala Gly Leu Ile Ser Leu Ile Pro Ser Met Ser Leu Pro Pro
385 390 395 400

Thr Glu His Ala Ser Pro Ser Asp Pro Val Thr Ala Ala Ala Ala Ala
405 410 415

Ala Leu Ala Ala Ala Asn Gly Asn Gly Ala Ala Ser His Ser Asn Gly
420 425 430

Asn Gly Ser Lys Pro Val Ser Thr Gln Val Pro Pro Pro Val Leu Ala
435 440 445

Pro Val Thr Val Thr Ser Ser Ser Gly Ser Met Asn Val Arg Ile Ser
450 455 460

Pro Arg
465

<210> SEQ ID NO 4
<211> LENGTH: 325
<212> TYPE: PRT
<213> ORGANISM: Helicosporidium sp. ATCC 50920

<400> SEQUENCE: 4

Met Leu Ala Ala Thr Asn Arg Ser Ala Ser Ser Pro Pro Lys Pro Pro
1 5 10 15

Phe Glu Gln Lys Gly Tyr Phe Pro Gly Ser Trp Pro His Ala Thr Phe
20 25 30

Asp Leu Ser Gln Gly Phe Tyr Ser Cys Thr Phe Ala Leu Ser Leu Leu
35 40 45

Leu Val Phe Arg Thr Asn Ala Ala Tyr Asp Arg Trp Trp Glu Ala Arg
50 55 60

Lys Thr Trp Gly Ser Leu Val Asn Arg Thr Arg Asp Phe Met Arg Gln
65 70 75 80

Ala Leu Thr Phe Phe Pro Ala Ser Glu Ser Ala Glu Ala Gly Val Leu
85 90 95

-continued

```
Leu Arg Trp Thr Val Ala Leu Pro Arg Met Leu Leu Trp Lys Leu Arg
                100                 105                 110

Glu Gln Ala Val Leu Glu Ala Glu Leu Gln Gly Val Leu Leu Pro Ala
            115                 120                 125

Glu Phe Ser Leu Leu Arg Glu Cys Asp His Arg Cys Ala Leu Ala Leu
        130                 135                 140

Ala Leu Met Ser Glu Val Val Gln Arg Ala Arg Gly Leu Asp Arg Gly
145                 150                 155                 160

Gln Arg Arg Cys Leu Asp Ala Asn Leu Thr Ala Leu Gly Asp Thr Val
                165                 170                 175

Gly Val Cys Glu Arg Ile Leu Arg Thr Pro Ile Pro Leu Ser Tyr Ser
            180                 185                 190

Arg His Thr Ser Arg Trp Leu Leu Val Trp Leu Ala Phe Leu Pro Phe
        195                 200                 205

Ser Leu Trp Arg Leu Tyr Ala Trp Gly Ser Val Pro Leu Ser Gly Leu
210                 215                 220

Leu Ala Phe Leu Met Leu Gly Ile Asp Glu Ile Gly Val Gln Ile Glu
225                 230                 235                 240

Gln Pro Phe Gln Val Leu Pro Leu Glu Ser Leu Cys Cys Thr Val Glu
                245                 250                 255

Arg Asn Leu Arg Asn Leu Ala Ala Ala Thr Pro Ala Val Lys Arg Leu
            260                 265                 270

Ala Ser Leu Ala Val Glu Ala Gln Leu Ala Leu Ala Glu Ser Asp Ala
        275                 280                 285

Thr Ala Ser Phe Arg Glu Pro Gly Lys Ser Leu Ala Cys Ser Val Phe
        290                 295                 300

Pro Pro Val Ser Pro Arg Ser Ser Leu Ile Arg Ser Cys Leu Asp Arg
305                 310                 315                 320

Pro Gln Ser Leu Pro
                325
```

<210> SEQ ID NO 5
<211> LENGTH: 422
<212> TYPE: PRT
<213> ORGANISM: Corchorus capsularis

<400> SEQUENCE: 5

```
Met Ala Gln Ser Ser Asn Pro Ser Lys Leu Ser Leu Ser Asp Phe
1               5                   10                  15

Asn Pro Lys Leu Phe Pro Asn Lys Leu His Arg Tyr Ser Ser Phe Pro
            20                  25                  30

Phe Lys Leu Ser Gln Pro Arg Ser Phe Lys Thr Leu Ser Ser Leu Ser
        35                  40                  45

Pro Pro Pro Pro Ser Ser Pro Pro Pro Ser Ser Glu Pro Thr
50                  55                  60

Thr Thr Lys Thr Leu Asn Leu Val Ser Leu Leu Arg Ala Ile Pro Asp
65                  70                  75                  80

Trp Ala Asp Arg Val Gln Glu Arg Gly Met Arg Gln Asn Arg Ala Leu
                85                  90                  95

Tyr Asn His Asp Lys Trp Ser Glu His Arg Ser Ser Leu Arg His Leu
            100                 105                 110

Arg His Leu Leu Ser Ser Leu Gln Ser Arg Val Ile Leu Ser Leu Val
        115                 120                 125

Pro Pro Val Leu Ala Phe Thr Ser Val Ala Ala Val Ile Ala Thr Tyr
    130                 135                 140
```

Asn Thr Ala Val Asp Leu His Trp Leu Pro Gly Phe Phe Pro Val Leu
145                 150                 155                 160

Arg Ala Ser Ser Leu Pro Tyr Gln Leu Thr Ala Pro Ala Leu Ala Leu
            165                 170                 175

Leu Leu Val Phe Arg Thr Glu Ala Ser Tyr Ser Arg Phe Glu Glu Gly
        180                 185                 190

Arg Lys Ala Trp Thr Lys Val Ile Ser Gly Thr Asn Asp Phe Ala Arg
    195                 200                 205

Gln Val Ile Ser Gly Val Glu Asn Ser Ser Asp Gln Ser Leu Lys
    210                 215                 220

Asp Ala Leu Leu Arg Tyr Ile Met Ala Phe Pro Val Ala Leu Lys Cys
225                 230                 235                 240

His Val Met Tyr Gly Ser Asp Ile Gly Arg Asp Leu Gln Asn Leu Leu
                245                 250                 255

Glu Val Asp Asp Leu Thr Val Val Leu Asn Ser Lys His Arg Pro Arg
            260                 265                 270

Cys Ile Ile Asp Phe Ile Ser His Ser Leu Arg Val Leu Asn Leu Lys
        275                 280                 285

Glu Ser Glu Arg Thr Val Leu Glu Ser Lys Ile Ser Cys Phe His Glu
    290                 295                 300

Gly Ile Gly Val Cys Glu Gln Leu Met Gly Ile Pro Ile Pro Leu Ser
305                 310                 315                 320

Tyr Thr Arg Leu Thr Ser Arg Phe Leu Val Leu Trp His Leu Thr Leu
                325                 330                 335

Pro Ile Ile Leu Trp Asp Asp Cys His Trp Ile Val Pro Ala Thr
            340                 345                 350

Phe Ile Ser Ala Ala Ser Leu Phe Cys Ile Glu Glu Val Gly Val Leu
        355                 360                 365

Ile Glu Glu Pro Phe Pro Met Leu Ala Leu Asp Glu Leu Cys Asn Val
    370                 375                 380

Val Gln Asn Asn Ile Arg Glu Ala Ile Ala Thr Glu Lys Val Ile Lys
385                 390                 395                 400

Ala Lys Leu Ile Gly Lys Arg Lys Arg His Ser Tyr Lys His Ser Pro
                405                 410                 415

Asn Gly Trp Pro Asn Thr
            420

<210> SEQ ID NO 6
<211> LENGTH: 406
<212> TYPE: PRT
<213> ORGANISM: Marchantia polymorpha subsp. ruderalis

<400> SEQUENCE: 6

Met Glu Asp Val Arg Leu Gly Arg Cys Glu Gly Ala Glu Gly Val Gly
1               5                   10                  15

Lys Met Gly Lys Trp Val His Lys Leu Ala Arg Phe Tyr Ala Pro Cys
            20                  25                  30

Ala Leu Pro Leu Leu Cys Val Thr Met Gly Leu Trp Ile Pro Glu Ser
        35                  40                  45

Pro Gly Ser Arg Ser Gly Arg Ser Gly Pro Glu Pro Gly Pro Tyr Asp
    50                  55                  60

Pro Asp Phe Pro Lys Glu Glu Val Phe Leu Tyr Arg Arg Thr Val Tyr
65                  70                  75                  80

Asp His Lys Asp Trp Ser Arg His Arg Ser Ser Leu Arg His Ser Arg

His Ile Leu Ser Met Arg Ser Arg Val Ile Leu Ala Leu Trp Pro
                85                  90                  95

Pro Val Phe Gly Leu Thr Thr Val Ser Ile Ala Leu Ser Ala Tyr Asn
            100                 105                 110

Glu Cys Ile Leu Ser His Trp Leu Pro Ser Phe Leu Pro Leu Leu His
        115                 120                 125

Val Ser Ala Thr Pro Phe Gln Leu Met Ala Pro Ala Leu Ala Leu Leu
145                 150                 155                 160

Leu Val Phe Arg Thr Asn Ala Ser Tyr Ala Arg Phe Asp Glu Ala Arg
                165                 170                 175

Arg Ala Trp Gly Ser Asn Val Asn Arg Thr Arg Asp Ile Thr Arg Gln
            180                 185                 190

Ala Leu Thr Trp Met Gln His Pro Ser Asp Ala Glu Lys Val Lys Lys
        195                 200                 205

Leu Ile Arg His Cys Val Ala Phe Asn Val Cys Met Lys His His Leu
210                 215                 220

Val Arg Gly Gly Asp Leu Arg Asp Asp Leu His Ser Trp Ile Asp Lys
225                 230                 235                 240

Glu Glu Ile Asp Gly Ile Leu Ala Ser Thr His Arg Pro Asn Tyr Val
                245                 250                 255

Leu Gln Val Met Ser Glu Ile Ile His Ser Cys Ser Ile Thr Glu Met
            260                 265                 270

Gln Leu Thr Arg Met Asp Val Asn Met Thr Gln Phe Ala Asp Asn Leu
        275                 280                 285

Gly Ala Cys Glu Arg Ile Phe Lys Thr Pro Ile Pro Leu Ser Tyr Thr
290                 295                 300

Arg Leu Thr Ser Arg Phe Leu Val Leu Trp His Ile Ala Leu Pro Leu
305                 310                 315                 320

Ala Leu Trp Asp His Cys Gln Trp Val Ser Val Pro Ala Thr Phe Leu
                325                 330                 335

Ser Ala Gly Ala Leu Phe Cys Ile Glu Glu Val Gly Val Leu Ile Glu
            340                 345                 350

Glu Pro Phe Gln Ile Phe Pro Leu Asp Asn Ile Cys Ser Thr Ile Lys
        355                 360                 365

Lys Asn Val Asp Gly Leu Ile Leu Ala His Thr Glu Ile His His Cys
370                 375                 380

His Lys His Pro Pro Lys Gly Cys Asp Ile Pro Lys Lys Lys Ser Ser
385                 390                 395                 400

Gly Asp Ala Pro Lys Ser
                405

<210> SEQ ID NO 7
<211> LENGTH: 453
<212> TYPE: PRT
<213> ORGANISM: Micractinium conductrix

<400> SEQUENCE: 7

Met Thr Cys Leu Thr Ser Val Leu Pro Leu Gly Gly Ala Leu Val Pro
1               5                   10                  15

Thr Arg Pro Leu Arg Ser Gly Ile His Ser Ser Thr Pro Arg Arg Arg
            20                  25                  30

Leu Ser Ala Leu Ala Pro Leu Lys Pro His Leu Val Ala Glu Pro Glu
        35                  40                  45

```
Ser Val Gln His Ala Ala Pro Ala Ala Ala Pro Pro Pro Pro
    50              55                  60

Pro Arg Asp Ala Thr Pro Ser Ala Pro Arg Gln Pro Leu Phe Gly Asp
65              70              75                  80

Ala Leu Leu Glu Ser Thr Arg Pro Gln Leu Arg Thr Val Phe Asp Ala
            85              90                  95

Asp Arg Trp Val Met His Arg Ser Val Asn Arg Tyr Phe Arg His Leu
                100             105             110

Trp Asp Leu Pro Arg Ser Arg Leu Leu Gly Leu Ala Ala Pro Leu
            115             120             125

Ala Tyr Val Leu Gly Leu Ser Ala Val Val Cys Ala Tyr Gly Ala Ala
    130             135             140

Gln Gln Ala Gly Leu Leu Pro Ser Leu Leu Pro Ser Leu Ala Gly Ala
145             150             155             160

Ala Arg Met Arg Glu Leu Tyr Asn Leu Thr Ser Pro Thr Leu Ala Leu
                165             170             175

Leu Leu Val Phe Arg Thr Asn Ala Ser Tyr Ala Arg Trp Asp Glu Gly
        180             185             190

Arg Lys Met Trp Gly Met Val Leu Asn Arg Thr Arg Asn Ile Cys Arg
        195             200             205

Leu Gly Leu Ala Trp Ile Gly Asp Asp Lys Arg Glu Leu Arg Ser Met
210             215             220

Leu Glu Glu Leu Glu Gly Ile Leu Leu Pro His Glu Ile Glu Gly Val
225             230             235             240

Leu Arg Ala Ser His Arg Pro Asn Tyr Val Leu Gln Val Leu Ala Gln
                245             250             255

Ile Val Arg Thr Ala Gly Leu Pro Thr Ala Ala Thr Leu Arg Met Glu
        260             265             270

Asp Asp Leu Thr Asn Phe Gly Asp Ser Leu Gly Gly Cys Glu Arg Leu
        275             280             285

Leu Arg Thr Pro Ile Pro Leu Phe Tyr Thr Arg His Thr Ser Arg Phe
        290             295             300

Leu Met Ile Trp Leu Thr Phe Leu Pro Ala Thr Leu Trp Pro Ala Cys
305             310             315             320

Gly Leu Leu Thr Leu Pro Leu Val Phe Leu Ile Ser Phe Leu Leu Leu
            325             330             335

Gly Val Asp Lys Ile Gly Val Ser Ile Glu Glu Pro Phe Ser Ile Leu
            340             345             350

Glu Leu Glu Thr Ile Ala Ser Arg Ala Leu Glu Asn Val His Glu Leu
            355             360             365

Ala Ala Met His Asp Gly Val Ala Asp Ile Pro Leu Gly Gly Gly Ser
    370             375             380

Ser Ser Ser Ser Ser Asn Arg Ala Ser Ser Asn Arg Gly Ala Gly
385             390             395             400

Thr Gly Arg Leu His Pro Ser Phe Gly Val Tyr Ser Ser Ser Asn Gly
            405             410             415

Ser Ser Gly Ala Asn Gly Ser Gly Gly His Gly Ser Gly Leu Ile
            420             425             430

Gly His Val Ser Ser Ile Val Ser Ala Ala Thr Met Val Ser Leu Ala
        435             440             445

Arg Pro Ala Thr Ala
450
```

<210> SEQ ID NO 8
<211> LENGTH: 803
<212> TYPE: PRT
<213> ORGANISM: Chlorella sorokiniana

<400> SEQUENCE: 8

```
Met Pro Ala Ala Leu Val Ala Ala Ala Thr Ala Cys Pro Ala
1               5                   10                  15

Ala Met Gly Arg Ala Pro Ala Ala Gly Ser Ala Ser Arg Leu Pro
        20                  25                  30

Ala Gly Leu Val Pro Ser Ser Gln Gln Leu Arg Trp Thr Leu Ala Pro
        35                  40                  45

Gln Arg His Ser Gln Pro Ser Arg Cys Arg Arg Ala Ala Arg Val Ala
        50                  55                  60

Ala Val Ala Gly Pro Gln Ala Pro Pro Arg Leu Gly Ala Pro Leu Gln
65                  70                  75                  80

Leu Gly Ser Pro Ala Ser Gln Lys Arg Arg Glu Glu Ile Leu Asn Arg
                85                  90                  95

Ile Asp Thr Leu Ile Gln Glu Glu Leu Glu Ser Gln Leu Pro Leu Pro
            100                 105                 110

Ser Val Asp Glu Leu Val Ala Asp Asp Phe Lys Glu Ser Glu Arg Arg
        115                 120                 125

Lys Leu Arg Thr Val Phe Asp Phe Asp Leu Trp Lys Arg His Arg Ser
130                 135                 140

Ser Ser Arg Tyr Ser Arg His Met Phe Gly Leu Leu Glu Ser Arg Thr
145                 150                 155                 160

Val Arg Trp Ile Gly Ala Pro Leu Ala Tyr Cys Val Ser Leu Ser Val
                165                 170                 175

Ala Val Gly Val Tyr His Asn Leu Ala Asp Ala Gly Ile Val Pro Glu
            180                 185                 190

Val Leu Pro Glu Leu Lys Thr Gln Leu Pro Ile Gln Leu Thr Ser Ala
        195                 200                 205

Ala Leu Ser Thr Leu Leu Val Leu Arg Thr Asn Thr Ser Tyr Gln Arg
    210                 215                 220

Trp Asp Glu Ala Arg Lys Met Trp Gly Leu Ile Val Asn Arg Ser Arg
225                 230                 235                 240

Asp Phe Thr Arg Gln Ala Leu Gly Tyr Ile Pro Asp Asp Gln Pro Glu
                245                 250                 255

Leu Gln Asp Met Leu Cys Arg Trp Val Val Ala Tyr Ser Arg Ser Leu
            260                 265                 270

Met Cys His Leu Arg Ser Asp Glu Asp Leu Tyr Arg Glu Leu Ala Thr
        275                 280                 285

Lys Leu Lys Pro Gln Glu Leu Glu Ala Leu Met Ser Ser Ser His Arg
    290                 295                 300

Pro Asn Tyr Thr Val Gln Val Leu Thr Ala Ile Met Gln Ala Ala Lys
305                 310                 315                 320

Leu Pro Gly Val Asp Ile Asp Pro Arg Asp Ser Gly Ala Asn Val Lys
                325                 330                 335

Ala Ser Ala Leu Val Arg Met Asp Glu Gln Leu Thr Gln Phe Ala Asp
            340                 345                 350

Val Thr Gly Gly Cys Glu Arg Ile Leu Arg Thr Pro Val Pro Leu Ala
        355                 360                 365

Tyr Ser Arg His Asn Ser Arg Met Leu Thr Leu Trp Met Thr Leu Leu
    370                 375                 380
```

-continued

```
Pro Phe Ser Leu Trp Asp Thr Cys Gly Trp Ala Thr Pro Phe Val Val
385                 390                 395                 400

Leu Ile Val Ala Phe Leu Leu Gly Val Lys Glu Ile Gly Leu Asn
            405                 410                 415

Ile Glu Glu Pro Phe Ser Ile Leu Pro Leu Glu Thr Ile Cys Asn Thr
            420                 425                 430

Ile Glu Thr Asn Val Trp Glu Leu His Arg Thr His Ser Thr Ala Ala
            435                 440                 445

Ala Glu Ala Gln Gln Glu Ala Arg Arg Gly Ser Trp Ser Gln Gln
        450                 455                 460

Ala Gln Gln Gly Pro Gln Gln Val Asp Ala Asp Leu Leu Ala Pro Ala
465                 470                 475                 480

Ala Ala Thr Gln Leu Gly Val Ala Leu Trp Arg Phe Pro Thr Gly Ala
            485                 490                 495

Ala Tyr Leu Leu Ser Arg Thr Asn Leu Ala Ser Leu Ile Glu Arg Asn
            500                 505                 510

Leu Arg Leu Arg Arg Gln Leu Gly Ile Ser Asp Ala Ala Thr Ala Thr
            515                 520                 525

Ala Leu Phe Gln Ser Gln Gly Ala Leu Val Ser Lys Phe Glu Arg Ala
            530                 535                 540

Glu Val Met Val Ala His Leu Gln Arg Leu Gln Ala Ser Gly Glu Leu
545                 550                 555                 560

Ser Ala Glu Gln Val Ala Arg Met Ala Leu Ala Pro Ser Ala Leu His
            565                 570                 575

Leu Thr Pro Ala Glu Phe Asp Arg Arg Trp His Asp Gly Gly Leu Ser
            580                 585                 590

Arg Pro Gly Ala Ser Pro Thr Asp Ile Thr Met Ser Asp Thr Ala Gly
            595                 600                 605

Arg Gln Gln Ala Ala Ala Ala Leu Gly Glu Leu Leu Gln Ala Ala
        610                 615                 620

Asp Gly Val Pro Gly Pro Leu Gln Pro Gln Tyr Leu Gln Gln Gly Glu
625                 630                 635                 640

Glu Leu Val Gln Arg Ser Ala Gly Leu Trp Arg Ala Gly Pro Ala Ala
            645                 650                 655

Leu Arg Ala Gly Trp Ala Ser Leu Gln Gln Leu Gly Leu Ser Asp Ser
            660                 665                 670

Gln Val Val Ala Ala Met Thr Met Gln Pro Ala Val Leu Ser Leu Asp
            675                 680                 685

Trp Ala Gly Glu Thr Lys Gln Arg Leu Leu Ala Trp Ala Glu Glu His
            690                 695                 700

Leu Gly Ile Asp Thr Phe Gly Phe Leu Thr Ser Tyr Thr Arg Phe Val
705                 710                 715                 720

Thr Tyr Ser Gly Ala Ser Val Ala Met Arg Ala Asp Phe Leu Gln Gln
            725                 730                 735

His His Pro Ala Met Trp Asp Gln Asn Leu Cys Arg Gly Pro Arg Thr
            740                 745                 750

Leu Phe Arg Leu Leu Thr Glu Pro Glu Arg Leu Cys Ala His Ala Gly
            755                 760                 765

Cys Thr Glu Thr Glu Leu Val Ala Phe Asn Arg Ala Trp Leu Ala Thr
            770                 775                 780

Pro Ala Gly Leu Arg Trp Gly Gly Lys Ala Gly Arg Ser Gln Arg Arg
785                 790                 795                 800

Ala Ala Ser
```

<210> SEQ ID NO 9
<211> LENGTH: 417
<212> TYPE: PRT
<213> ORGANISM: Handroanthus impetiginosus

<400> SEQUENCE: 9

Met Lys Ile Ser Pro Ser Ser Cys Ser Pro Gln Phe Leu Pro Arg Thr
1               5                   10                  15

Leu Phe Lys Phe His His Ser Pro Leu Pro Phe Ile Ser Lys Lys Pro
            20                  25                  30

His Lys Leu Ser Phe Lys Phe Ile Cys Ala Cys Gln Ser Ser Asn Asp
        35                  40                  45

Ser Asn Pro Ser Pro Ser Gln Asp Phe Thr Leu Leu Ser Leu Leu Leu
    50                  55                  60

Ala Ile Pro Asn Trp Ala Asp Gly Ile Lys Glu Arg Arg Met Lys Gln
65                  70                  75                  80

Lys Arg Ser Leu Tyr Asp His Lys Ser Trp Val Gln His Arg Ser Ser
                85                  90                  95

Leu Arg His Val Arg His Phe Leu Ser Ser Leu Ser Ser Arg Val Ile
            100                 105                 110

Leu Ser Leu Val Pro Pro Val Ile Val Phe Thr Leu Ala Val Ile
        115                 120                 125

Ile Ala Ser Tyr Asn Ser Ala Val Ser Ile His Trp Leu Pro Glu Phe
    130                 135                 140

Phe Pro Ile Leu Arg Ala Ser Ser Leu Pro Tyr Gln Leu Thr Ala Pro
145                 150                 155                 160

Ala Leu Ala Leu Leu Val Phe Arg Thr Glu Ala Ser Tyr Ser Arg
                165                 170                 175

Phe Glu Glu Gly Lys Lys Ala Trp Thr Lys Val Ile Ser Gly Thr Asn
            180                 185                 190

Asp Phe Ala Arg Gln Val Ile Ala Ser Val Ser Pro Ser Asp Ser
        195                 200                 205

Met Leu Lys Lys Ala Ile Leu Gln Tyr Ile Met Ala Phe Pro Val Ala
    210                 215                 220

Leu Lys Cys His Ile Ile Tyr Gly Ser Asp Ile Ala Gln Asp Leu Lys
225                 230                 235                 240

Asn Leu Leu Glu Ala Asp Asp Leu Ser Val Val Leu Ser Ser Lys His
                245                 250                 255

Arg Pro Arg Cys Ile Ile Glu Phe Ile Ser Gln Ser Leu Gln Leu Leu
            260                 265                 270

Asp Met Asp Ala Thr Lys Leu His Val Leu Glu Ser Lys Leu Cys Cys
        275                 280                 285

Phe His Glu Gly Ile Gly Val Cys Glu Gln Leu Met Gly Thr Pro Ile
    290                 295                 300

Pro Leu Ser Tyr Thr Arg Leu Thr Ser Arg Phe Leu Ile Leu Trp His
305                 310                 315                 320

Leu Thr Leu Pro Val Ile Leu Trp Asp Asp Cys His Trp Ile Val Val
                325                 330                 335

Pro Ala Thr Phe Ile Ser Ala Ala Ser Leu Phe Cys Ile Glu Glu Val
            340                 345                 350

Gly Val Leu Ile Glu Glu Pro Phe Pro Met Leu Ala Leu Asp Glu Leu
        355                 360                 365

Cys Leu Thr Ala Gln Ser Asn Ile Gln Asp Ile Met Arg Asn Glu Lys

```
                370             375             380
Leu Ile Lys Asp Gln Val Lys Ala Lys Arg Lys Ile His Ser Arg
385                 390             395                 400

Lys His Ser Ser Asn Gly Trp Pro Asn Pro Leu Glu Asp Arg Gln Pro
                405             410                 415

Ser
```

<210> SEQ ID NO 10
<211> LENGTH: 385
<212> TYPE: PRT
<213> ORGANISM: Chlamydomonas eustigma

<400> SEQUENCE: 10

```
Met Leu Val His Arg Val His Thr Arg Ser Leu Gly Asn Arg Asn Gln
1               5                   10                  15

Cys Gly Arg Lys Leu His Arg Val Ser Thr Phe Val Lys Thr Pro
            20              25                  30

Thr Glu Lys Pro Val Val Ala Asp Tyr Val Leu Pro Arg Ser Glu Glu
            35              40                  45

Ala Arg Arg Tyr Phe Arg Thr Val Tyr Asp Phe Pro Gln Trp Gln Lys
        50              55              60

His Arg Ser Pro Thr Arg Leu Ile Asp Arg Leu Leu Gln Ile Pro Arg
65              70              75                  80

Ser His Val Leu Gln Asn Ile Leu Pro Ser Ile Ala Trp Cys Ser Ser
                85              90                  95

Val Ala Gly Leu Leu Thr Leu Tyr Met Gln Ala Tyr Asp Ala His Ile
            100             105                 110

Leu Pro Asp Gly Phe Pro Ser Phe Ala Thr Asn Asn Ala Cys Thr Ser
        115                 120             125

Phe Val Asn Thr Thr Val Ala Leu Ser Leu Leu Val Phe Arg
        130             135             140

Thr Asn Val Ser Tyr Gly Arg Trp Asp Glu Ala Arg Lys Met Lys Gly
145                 150             155                 160

Leu Leu Val Asn Arg Ser Arg Asp Leu Met Arg Gln Val Cys Ala Met
                165             170                 175

Val Pro Glu Glu Asp Val Ala Thr Lys Ala Met Met Ala Lys Trp Thr
            180             185                 190

Ala Ala Phe Cys Arg Val Leu Arg Ile His Phe Gln Pro Glu Val Ser
        195             200             205

Leu Glu Asp Glu Met Lys Gly Leu Leu Ser Pro Glu Glu Leu Glu Trp
    210             215             220

Leu Ile Glu Ser Lys His Arg Pro Cys Ser Val Ile His Met Leu Ser
225             230                 235                 240

Gln Ile Ile Tyr Asp Ser Gln Ile Ser Ala Ile Cys Gln Ala Gln Met
                245             250                 255

Cys Asn Asn Leu Thr Ala Phe Glu Asp Val Leu Gly Gly Cys Glu Arg
            260             265                 270

Leu Leu Arg Ala Pro Ile Pro Val Ser Tyr Thr Arg His Thr Ala Arg
        275             280             285

Phe Leu Phe Thr Trp Leu Thr Leu Pro Phe Ala Leu Tyr Asn Ser
        290             295             300

Cys Gly Val Trp Thr Leu Pro Val Val Ala Gly Val Ser Ala Val Leu
305             310             315                 320

Cys Gly Ile Glu Glu Ile Gly Val Gln Ile Glu Glu Pro Phe Gly Ile
```

Leu Pro Leu Glu Ala Ile Cys Gly Arg Ile Gln Ala Asp Val Met Ala
              325                 330                 335

Thr Leu Lys Glu Asp Ala Lys Thr Arg Asn Leu Arg Asn Lys Val Leu
        340                 345                 350

Leu Ile Arg Gly Pro Glu His Trp Ala Met Val Asn Gly His Ser Asn
    355                 360                 365

370                 375                 380

Lys
385

<210> SEQ ID NO 11
<211> LENGTH: 397
<212> TYPE: PRT
<213> ORGANISM: Chlamydomonas eustigma

<400> SEQUENCE: 11

Met Asn Lys Ser Leu Leu Arg Ala Pro Glu Ser Asn Val Val Phe Arg
1               5                   10                  15

Arg Ala Cys Asn Lys Ser Phe Val Lys Arg Cys Lys Glu Val Gln Arg
            20                  25                  30

Leu Pro Ser His Val Ala Leu Ala Val Lys Asn Pro Ala Glu Lys Pro
        35                  40                  45

Val Val Ala Asp Tyr Val Leu Pro Arg Ser Glu Glu Ala Arg Arg Tyr
    50                  55                  60

Phe Arg Thr Val Tyr Asp Phe Pro Gln Trp Gln Lys His Arg Ser Gln
65                  70                  75                  80

Leu Arg Leu Ile Asp Arg Leu Leu Gln Ile Pro Arg Ser His Val Leu
                85                  90                  95

Gln Asn Ile Leu Pro Ser Ile Ala Trp Cys Ser Ser Val Ala Gly Leu
            100                 105                 110

Leu Thr Leu Tyr Met Gln Ala Tyr Asp Ala His Ile Leu Pro Asp Gly
        115                 120                 125

Phe Pro Ser Phe Thr Pro Asn Asn Ala Cys Thr Ser Phe Val Asn Thr
    130                 135                 140

Thr Thr Val Ala Leu Ser Leu Leu Val Phe Arg Thr Asn Val Ser
145                 150                 155                 160

Tyr Gly Arg Trp Asp Glu Ala Arg Lys Met Lys Gly Leu Leu Val Asn
                165                 170                 175

Arg Ser Arg Asp Leu Met Arg Gln Ala Cys Ala Met Leu Pro Ala Glu
            180                 185                 190

Asp Ile Glu Thr Lys Ala Met Met Ala Lys Trp Thr Ala Ala Phe Cys
        195                 200                 205

Arg Val Leu Arg Ile His Phe Gln Pro Glu Val Ser Leu Glu Asp Glu
    210                 215                 220

Met Lys Gly Leu Leu Ser Pro Glu Glu Leu Gln Trp Leu Gln Glu Ser
225                 230                 235                 240

Lys His Arg Pro Cys Ser Val Ile His Val Leu Ser Gln Ile Ile Tyr
                245                 250                 255

Asp Ser Gln Ile Ser Ala Ile Cys Gln Ala Gln Met Cys Asn Asn Leu
            260                 265                 270

Thr Ala Phe Glu Asp Val Leu Gly Gly Cys Glu Arg Leu Leu Arg Ala
        275                 280                 285

Pro Ile Pro Val Ser Tyr Thr Arg His Thr Ala Arg Phe Leu Phe Thr
    290                 295                 300

```
Trp Leu Thr Leu Leu Pro Phe Ala Leu Tyr Asn Ser Cys Gly Val Trp
305                 310                 315                 320

Thr Leu Pro Val Val Ala Gly Val Ser Ala Val Leu Cys Gly Ile Glu
            325                 330                 335

Glu Ile Gly Val Gln Ile Glu Glu Pro Phe Gly Ile Leu Pro Leu Glu
            340                 345                 350

Ala Ile Cys Gly Arg Ile Gln Ala Asp Val Met Ala Thr Leu Arg Glu
            355                 360                 365

Asp Glu Lys Met Arg Asn Leu Arg Lys Arg Val Ile Gln Thr Arg Thr
370                 375                 380

Thr Glu Leu Arg Glu Leu Ala Ser Gly Gly Ala Ser Lys
385                 390                 395
```

<210> SEQ ID NO 12
<211> LENGTH: 402
<212> TYPE: PRT
<213> ORGANISM: Chlamydomonas eustigma

<400> SEQUENCE: 12

```
Met Lys Val Gly Ile His Val Val Gln Thr Leu Ser Gly His Thr Ile
1               5                   10                  15

Ser Gly Gln Arg Phe Leu Asn Lys Ala Gly Cys Asn Lys Leu Arg Pro
            20                  25                  30

Ala Asn Lys Ser Ser Phe Arg Ala Gln Ser Thr Ser Ala Leu Asp Glu
        35                  40                  45

Phe Leu His Arg Ile Glu Ile Asn Ile Asp Lys Asp Lys Glu Ala Ala
    50                  55                  60

Arg Ser Glu Arg Arg Gln Ala Phe Thr His Val Asp Trp Lys Arg His
65                  70                  75                  80

Arg Ser Ser Ala Arg Phe Ile Arg His Leu Ser Thr Ile Pro Glu Ser
                85                  90                  95

Trp Val Ile Arg Gly Val Leu Trp His Val Ala Cys Phe Ile Leu Leu
            100                 105                 110

Ala Leu Gly Val Ala Ala Phe Asn Tyr Ser Tyr Ala Cys Lys Gly Leu
        115                 120                 125

Val Pro Pro Tyr Ser Ile Ala Ile Glu Pro Met Gln Leu Thr Ser Phe
    130                 135                 140

Ala Leu Ser Leu Leu Val Phe Arg Thr Asn Ala Ser Tyr Ala Arg
145                 150                 155                 160

Trp Gln Glu Ala Arg Arg Ser Phe Gly Ser Ile Thr Thr Gly Lys
                165                 170                 175

Asp Ile Met Arg Gln Ser Leu Ala Trp Phe Cys Glu Asp Trp Ala
            180                 185                 190

Gly Lys Met Ala Leu Ser Gly Trp Leu Gln Ala Leu Ala Gln Ser Ser
        195                 200                 205

Met Tyr His Leu Gln Asn Glu Gly His Leu Glu Asp Asp Ser Leu Val
    210                 215                 220

Pro Leu Gln Gly Cys Leu Ser Pro Asp Glu Leu Ala Gln Leu Arg Ile
225                 230                 235                 240

Ser Ser His Lys Pro Thr Phe Cys Ile Ala Met Ile Thr Arg Leu Val
                245                 250                 255

Ser Arg Ala Gly Met Pro Thr Glu Leu Leu Arg Met Asp Glu Asn
            260                 265                 270

Ile Ser Thr Leu Val Gln Ala Val Ser Ser Cys Glu Arg Ile Ile Asn
        275                 280                 285
```

```
Thr Pro Ile Pro Leu Ser Tyr Thr Arg His Thr Ser Arg Phe Leu Met
    290                 295                 300

Val Trp Leu Thr Cys Leu Pro Phe Ser Leu Trp Gln Tyr Cys Gly Trp
305                 310                 315                 320

Ala Met Val Pro Ile Ala Gly Leu Ile Ser Phe Val Leu Leu Gly Ile
                325                 330                 335

Glu Glu Ile Gly Val Tyr Ile Glu Glu Pro Phe Ser Leu Leu Pro Leu
                340                 345                 350

Glu Ser Leu Cys Asp Lys Leu Thr His Ser Ile Asp Asn Met Met Leu
            355                 360                 365

Glu His Arg Leu Phe Ser Glu Gly Glu Val Ile Thr Pro Lys Gly Ser
        370                 375                 380

Thr Gly Asp Ser Glu Cys Leu Ala Thr Ser Ser Lys Met Gln Arg Tyr
385                 390                 395                 400

Asn Cys

<210> SEQ ID NO 13
<211> LENGTH: 838
<212> TYPE: PRT
<213> ORGANISM: Chlamydomonas eustigma

<400> SEQUENCE: 13

Met Phe Phe Arg Lys Ala Cys Ser Gln Pro Ile Gly Arg Lys His Gln
1               5                   10                  15

Gly Gly His Arg Phe Gln Arg Leu Val Arg Pro Asn Phe Asn Cys Ser
            20                  25                  30

Val Thr Asp Ala Asp Lys Ala Ala Glu Asn Phe Val Leu Ser Arg Ser
        35                  40                  45

Glu Glu Ser Arg Arg Tyr Phe Arg Thr Val Tyr Asp Phe Pro Leu Trp
    50                  55                  60

Gln Lys His Ser Asn Gln Pro Arg Ile Ile Asp Glu Val Arg Lys Asn
65              70                  75                  80

Ser Arg Thr Asn Ile Leu Lys Ser Ile Leu Pro Ser Thr Ala Trp Cys
                85                  90                  95

Thr Gly Val Ala Ala Leu Leu Thr Ala Tyr Val Gln Ala Tyr Asp Ser
            100                 105                 110

Asn Met Leu Pro Ala Gln Phe Pro Arg Phe Glu Ser Ile Pro Ser Tyr
        115                 120                 125

Ala Ala Ile Val Asn Ile Thr Val Val Ser Leu Ser Leu Leu Leu Val
    130                 135                 140

Phe Arg Thr Asn Ala Ser Tyr Gly Gln Trp Asp Ala Ala Arg Lys Met
145                 150                 155                 160

Lys Gly Leu Leu Val Asn Arg Ser Gln Glu Leu Met Arg Glu Ala Cys
                165                 170                 175

Ser Leu Leu Pro Ala Glu Asp Thr Ala Thr Lys Ile Met Met Gly Arg
            180                 185                 190

Trp Ile Ser Ala Tyr Ala Gly Val Leu Arg Asn Gln Phe Gln Pro Glu
        195                 200                 205

Glu Ser Leu Gly Lys Ile Val Asp Gly Leu Leu Ser Thr Glu Glu Leu
    210                 215                 220

Glu Trp Leu Asn Ser Ser Asn Gln Arg Pro Ser Ser Val Ile Asp Val
225                 230                 235                 240

Leu Ser Gln Ile Ile Ser Ser Ala Ala Ile Pro Ala Pro Asn Gln Ala
                245                 250                 255
```

```
Gln Met Asn Asn Leu Ala Ala Leu Arg Gly Val Leu Gly Gly Cys
        260                 265                 270

Gln Arg Leu Leu Lys Asp Pro Ile Pro Met Ser Tyr Thr Arg Asn Ser
        275                 280                 285

Ala Arg Leu Leu Phe Leu Trp Leu Thr Leu Leu Pro Phe Ala Leu Phe
290                 295                 300

Ser Ser Cys Gly Val Trp Thr Ala Pro Val Val Ala Ala Val Ser Ala
305                 310                 315                 320

Val Leu Cys Ser Ile Glu Glu Ile Gly Val Gln Ile Glu Glu Pro Ser
            325                 330                 335

Thr Thr Gly Met Leu Pro Leu Glu Ala Ile Gly Asp Arg Ile Gln Ala
            340                 345                 350

Asp Val Ile Thr Thr Leu Leu Glu Asp Glu Lys Thr Lys Thr Met Arg
            355                 360                 365

Gly Glu Val Asp Thr Ala Ala Leu Arg Ala Ala Ala Gln Pro Ser Lys
370                 375                 380

Leu Asp Glu Val Pro Gly Lys Leu Val Leu Leu Ala Glu Gln Val Ala
385                 390                 395                 400

Val Val Gly Gln Ser Ser Asn Asn Gln Gly Thr Gly Gly Ala Gly Gln
                405                 410                 415

Lys Gly Glu Arg Arg Val Leu Leu Ser Lys Leu Glu Thr Glu Thr Lys
                420                 425                 430

Asp Met Lys Asp Asn Leu Gln Arg Leu Lys Gln Arg Ala Thr Glu Leu
            435                 440                 445

Ser Thr Lys Ala Gln Gln Ala Ser Asp Val Ala Arg Lys Glu Arg Ala
        450                 455                 460

Asn Ala Val Leu Lys Leu Gly Glu Met Asp Glu Gln Leu Lys Thr Ser
465                 470                 475                 480

Gln Glu Ala Gly Val Tyr Ser Glu Ile Thr Gln Leu Lys Asp Ser Leu
                485                 490                 495

Thr Thr Arg Glu Ser Asp Val Ala Ser Leu Val Ser Glu Leu Met Leu
            500                 505                 510

Glu Gln Gln Ser Asn Gln Leu Leu Glu Gln Val Ala Leu Leu Gln
            515                 520                 525

Met Gln Leu Ser Glu Thr Glu Asn Met Leu Thr Ser Glu Lys Ser Ile
            530                 535                 540

Gly Glu Gly Leu Ser Gln Gln Leu Gln Ile Thr Gln Val Asp Leu Asn
545                 550                 555                 560

Thr Ser Gln Ser Ser Leu Ala Asp Met Ser Gln Lys Leu Arg Glu Glu
                565                 570                 575

Glu Phe Gln Arg Ala Thr Leu Gln Ser Glu Ile Gln Ala Leu Arg Ser
            580                 585                 590

Asp Leu Asp Arg Val Thr Ala Val Glu Thr Arg Gln Lys Glu Ala
            595                 600                 605

Asp Val Tyr Arg Ala Ala Ala Glu Lys Ala Glu Gln Gln Val Val Asp
            610                 615                 620

Ala Ala Ala Leu Arg Gln Ala Met Met Ala Glu Leu Thr Glu Thr Ser
625                 630                 635                 640

Asp Ser Phe Ala Glu Leu Leu Ala Glu Ala Leu Ser Arg Ala Glu Ser
                645                 650                 655

Ala Glu Ala Asp Lys Val Lys Val Glu Ala Glu Val Arg Met Leu Gln
                660                 665                 670
```

-continued

Ser Lys Ile Val Ser Ala Asp Ala Leu Ser Arg Leu Glu Thr Gln
            675                 680                 685

Leu Leu Glu Glu Glu Arg Lys Gly Ile Pro Pro Ser Gly Ser Asn Asp
690                 695                 700

Met Glu Phe Glu Asp Val Gln Lys Arg Ile Ala Glu Leu Glu Gly Leu
705                 710                 715                 720

Leu Gly Gly Leu Leu Ser Glu Val Glu Gln Ala Thr Val Lys Gln Gly
            725                 730                 735

Arg Thr Arg Leu Thr Gln Asp Thr Ile Glu Glu Val Lys Arg Glu Ala
            740                 745                 750

Glu Leu Arg Ser Ala Arg Val Ala Ala Glu Leu Ala Ala Glu Ser Gly
            755                 760                 765

Ala Arg Ser Glu Ala Glu Asp Asn Leu Arg Val Leu Gln Ser Glu Leu
            770                 775                 780

Leu Gln Leu Lys Glu Ala Ser Gln Thr Ser Arg His Ala Ala Glu Lys
785                 790                 795                 800

Glu Leu Lys Glu Met Gln Leu Leu Ile Ser Glu Val Lys Ala Lys Ala
            805                 810                 815

Ala Glu Thr Ala Ala Phe Val Gly Lys Ala Lys Glu Gly Pro Lys
            820                 825                 830

Lys Gly Lys Ser Ala Tyr
            835

<210> SEQ ID NO 14
<211> LENGTH: 365
<212> TYPE: PRT
<213> ORGANISM: Chlamydomonas eustigma

<400> SEQUENCE: 14

Met Lys Val Cys Ile His Val Val Gln Thr Leu Ser Gly His Thr Ile
1               5                   10                  15

Ser Gly Gln Arg Phe Leu Asn Lys Ala Gly Cys Asn Lys Leu Arg Pro
            20                  25                  30

Ala Asn Lys Ser Ser Phe Arg Ala Gln Ser Thr Ser Ala Leu Asp Glu
            35                  40                  45

Phe Leu His Arg Ile Glu Ile Asn Ile Asp Lys Asp Lys Glu Ala Ala
    50                  55                  60

Arg Ser Glu Arg Arg Gln Ala Phe Thr His Val Asp Trp Lys Arg His
65                  70                  75                  80

Arg Ser Ser Ala Arg Phe Ile Arg His Leu Ser Thr Ile Pro Glu Ser
                85                  90                  95

Trp Val Ile Arg Gly Val Leu Trp His Val Ala Cys Phe Ile Leu Leu
            100                 105                 110

Ala Leu Gly Val Ala Ala Phe Asn Tyr Ser Tyr Ala Cys Lys Gly Leu
        115                 120                 125

Val Pro Pro Tyr Ser Ile Ala Ile Glu Pro Met Gln Leu Thr Ser Phe
    130                 135                 140

Ala Leu Ser Leu Leu Leu Val Phe Arg Thr Asn Ala Ser Tyr Ala Arg
145                 150                 155                 160

Trp Gln Glu Ala Arg Arg Ser Phe Gly Ser Ile Thr Thr Gly Lys
                165                 170                 175

Asp Ile Met Arg Gln Ser Leu Ala Trp Phe Cys Glu Asp Asp Trp Ala
            180                 185                 190

Gly Lys Met Ala Leu Ser Gly Trp Leu Gln Ala Leu Ala Gln Ser Ser
        195                 200                 205

```
Met Tyr His Leu Gln Asn Glu Gly His Leu Glu Asp Asp Ser Leu Val
    210                 215                 220

Pro Leu Gln Gly Cys Leu Asn Pro Asp Glu Leu Ala Gln Leu Arg Ile
225                 230                 235                 240

Ser Ser His Lys Pro Thr Phe Cys Ile Ala Met Ile Thr Arg Leu Val
                245                 250                 255

Ser Arg Ala Gly Met Pro Thr Glu Leu Leu Arg Met Asp Glu Asn
                260                 265                 270

Ile Ser Thr Leu Val Gln Ala Val Ser Ser Cys Glu Arg Ile Ile Asn
                275                 280                 285

Thr Pro Ile Pro Leu Ser Tyr Thr Arg His Thr Ser Arg Phe Leu Met
    290                 295                 300

Val Trp Leu Thr Cys Leu Pro Phe Ser Leu Trp Gln Tyr Cys Gly Trp
305                 310                 315                 320

Ala Met Val Pro Ile Ala Gly Leu Ile Ser Phe Val Leu Leu Gly Ile
                325                 330                 335

Glu Glu Ile Gly Val Tyr Ile Glu Val Ile Ile Phe Phe Leu Leu Tyr
                340                 345                 350

Leu Gly Gln Leu Ser His Asn Cys Ser His Ile Val Lys
            355                 360                 365

<210> SEQ ID NO 15
<211> LENGTH: 831
<212> TYPE: PRT
<213> ORGANISM: Chlamydomonas eustigma

<400> SEQUENCE: 15

Met Leu Val Gln Lys Thr Cys Ser Lys Pro Leu Ser Cys Lys Gln Gln
1               5                   10                  15

Ala Gly Leu Arg Thr Leu Arg Ile Phe Arg Tyr Val Phe Gln Asn Ala
                20                  25                  30

Arg Gln Asp Val Lys Ile Ala Val Ala Lys Val Val Leu Pro Pro Ser
            35                  40                  45

Glu Glu Ala Arg Arg Ser Phe Arg Thr Val Tyr Asp Phe Gln Ser Trp
50                  55                  60

Arg Lys His Arg Asn Gln Leu Arg Leu Phe Val Gln Val Gly Gln Ile
65                  70                  75                  80

Pro Arg Ser Asn Ile Leu Lys Asn Ile Leu Pro Ser Met Ala Trp Cys
                85                  90                  95

Thr Gly Val Ala Ala Leu Leu Thr Leu Tyr Met Gln Ala Tyr Asp Ser
                100                 105                 110

Asn Leu Leu Pro Glu Pro Phe Pro Ser Phe Ala Ser Asn Thr Ala Ser
            115                 120                 125

Val Thr Phe Val Asn Thr Thr Val Ala Leu Ser Leu Leu Leu Val
            130                 135                 140

Phe Arg Thr Asn Ala Ser Tyr Gly Arg Trp Asp Glu Ala Arg Lys Met
145                 150                 155                 160

Lys Gly Leu Leu Val Asn Arg Ser Arg Asp Leu Ile Arg Gln Ala Cys
                165                 170                 175

Ser Met Phe Ser Pro Glu Asp Val Glu Arg Lys Ile Met Met Gly Lys
                180                 185                 190

Trp Val Ser Val Tyr Cys Arg Val Leu Arg Ile His Phe Gln Ala Glu
            195                 200                 205

Val Ser Leu Glu Glu Glu Met Asn Gly Ile Leu Ser Met Glu Glu Val
```

-continued

```
            210                 215                 220
Glu Trp Leu Gln Ser Ser Thr His Arg Pro Cys Thr Val Ile His Val
225                 230                 235                 240

Leu Ser Gln Ile Ile Tyr Ser Ala Pro Ile Ser Ala Phe Cys Gln Ala
                    245                 250                 255

Gln Met Cys Asn Asn Leu Thr Ala Leu Glu Asp Val Leu Gly Gly Cys
                260                 265                 270

Glu Arg Ile Leu Arg Ala Pro Ile Pro Val Ser Tyr Thr Arg Asn Thr
            275                 280                 285

Ala Arg Phe Leu Phe Val Trp Leu Thr Leu Leu Pro Phe Ala Leu Phe
        290                 295                 300

Ser Ser Cys Gly Val Trp Thr Ala Pro Val Val Ala Gly Ile Ala Ala
305                 310                 315                 320

Val Leu Cys Gly Ile Glu Glu Ile Gly Val Gln Val Glu Glu Pro Phe
                    325                 330                 335

Gly Ile Leu Pro Leu Ala Ala Ile Gly Asp Arg Ile Gln Ala Asp Val
                340                 345                 350

Ile Ser Thr Leu Leu Glu Asp Gly Arg Thr Arg Thr Met Arg Ser Glu
            355                 360                 365

Val Asn Thr Ala Ala Leu Arg Ala Met Ala Gln Pro Pro Asn Gln Glu
        370                 375                 380

Gly Val Leu Gly Ser Val Asp Arg Gln Ser Thr Asn Leu Ala Asn Ser
385                 390                 395                 400

Gln Glu Ser Thr Thr Gly Ser Asn Pro Met Gly Gln Arg Val Val Leu
                    405                 410                 415

Leu Ser Lys Leu Glu Thr Glu Thr Lys Asp Met Lys Asp Asn Leu Asn
                420                 425                 430

Lys Leu Lys Gln Arg Ala Thr Glu Leu Ser Met Lys Ala Gln Leu Ala
            435                 440                 445

Ser Glu Ala Ala Gln Arg Glu Arg Ala Ser Ala Val Gln Lys Leu Gly
        450                 455                 460

Ile Met Asn Glu Gln Leu Lys Gly Phe Lys Gly Ala Glu Val Tyr Ser
465                 470                 475                 480

Glu Ile Ala Gln Leu Lys Asp Thr Leu Thr Ser Arg Glu Ser Asp Val
                    485                 490                 495

Ala Thr Val Val Ser Glu Met Gln Gln Gln Gln Leu Ser Ser Gln Gln
                500                 505                 510

Leu Phe Glu Gln Leu Ala His Leu Gln Thr Gln Leu Ser Glu Ala Glu
            515                 520                 525

Ala Leu Leu Ser Thr Glu Lys Ser Met Gly Gln Glu Leu Ser Gln Gln
        530                 535                 540

Leu Gln Leu Thr Gln Met Gly Leu Lys Thr Asn Gln Ala Ser Leu Leu
545                 550                 555                 560

Asp Val Ser His Lys Leu Gln Lys Glu Leu Gln Arg Ser Ala Phe
                    565                 570                 575

Gln Thr Glu Ile Gln Ala Leu Arg Arg Asp Leu Asp Arg Ile Thr Thr
                580                 585                 590

Ala Met Glu Ser Lys Arg Leu Glu Thr Glu Ala Phe Trp Ala Ala Ala
            595                 600                 605

Glu Ser Ala Glu Gln His Val Ala Asp Ser Ala Ala Leu Gln Ser Ala
        610                 615                 620

Met Met Ala Glu Leu Thr Glu Thr Ser Asp Ala Phe Ala Glu Arg Leu
625                 630                 635                 640
```

Ala Ala Ala Leu Ser Arg Ala Glu Thr Ala Glu Thr Asp Lys Phe Arg
            645                 650                 655

Ala Glu Gln Glu Val Lys Met Leu Gln Ser Lys Ile Ala Asp Thr Glu
        660                 665                 670

Thr Met Leu Arg Lys Leu Glu Ala Lys Ala Ala Glu Leu Glu Arg Lys
            675                 680                 685

Gly Ser Ala Pro Ser Glu Ser Thr Ala Leu Glu Phe Arg Asp Ala Gln
        690                 695                 700

Trp Lys Ile Ala Glu Leu Glu Gly Leu Leu Gly Glu Val Leu Leu Glu
705                 710                 715                 720

Val Lys His Ala Ala Ser Asn Asn Ala Thr Glu Tyr Ser Thr Gln Asp
            725                 730                 735

Lys Ile His Glu Val Gln Arg Glu Ala Asp Arg Arg Ser Ile Arg Val
        740                 745                 750

Ala Ala Glu Ile Ala Ala Glu Arg Gly Ala Arg Ser Glu Ala Glu Asp
            755                 760                 765

Asn Leu Arg Ile Leu Gln Arg Glu Leu Leu Leu Lys Glu Asp Ser
        770                 775                 780

Leu Ser Ser Arg Asn Ala Ala Glu Arg Glu Leu Lys Glu Met Gln Leu
785                 790                 795                 800

Leu Ile Cys Glu Val Lys Ala Lys Ala Ala Ser Thr Ala Thr Phe Val
            805                 810                 815

Gly Thr Ala Ala Ala Glu Gly Pro Arg Arg Gly Gln Asn Thr Tyr
        820                 825                 830

<210> SEQ ID NO 16
<211> LENGTH: 451
<212> TYPE: PRT
<213> ORGANISM: Chlorella variabilis

<400> SEQUENCE: 16

Met Thr Ala Ser Asp Ala Pro Ser Ala Ser Arg Ser Gly Gly His Ala
1               5                   10                  15

Arg Leu Val Gln Thr Ala Ala Ser Pro Arg Gly Asp Gly Ser Phe Ala
            20                  25                  30

Val Gly Ser Thr Asp Leu Glu Gln Val Ala Glu Gln Ala Val Val Asp
        35                  40                  45

Ala Val Ala Gln Thr Ala Gly Asp Arg Ala Thr Ser Ser Ser Ala Ala
    50                  55                  60

Ala Gly Ser Arg Glu Val Asp Pro Ile Lys Glu Gly Ser Arg Lys Tyr
65                  70                  75                  80

Arg Arg Thr Val Tyr Asp Phe Glu Asn Trp Arg Gln His Arg Ser Thr
            85                  90                  95

Lys Arg Tyr Met Arg His Ala Lys Gly Leu Leu Gly Ser Arg Ile Phe
        100                 105                 110

Arg Gly Leu Ala Ser Pro Leu Tyr Ile Leu Ala Val Ser Ala Ser
        115                 120                 125

Val Ala Val Trp Asn Thr Leu Val Glu Thr Gly Leu Ala Pro Asp Val
    130                 135                 140

Leu Pro Glu Leu His Met Ser Asn Asn Gly Pro Phe Gly Leu Thr Ser
145                 150                 155                 160

Phe Ala Leu Ser Leu Leu Leu Val Thr Asn Ala Ser Tyr Ala Arg Trp
            165                 170                 175

Leu Asp Ala Arg Lys Ala Trp Gly Met Leu Val Asn Arg Ser Arg Asp

```
        180             185             190
Ile Thr Arg Gln Ala Leu Thr Cys Phe Pro Ala Ala Asp Arg Pro Leu
            195                 200                 205

Leu Asp Met Leu Cys Arg Trp Thr Ala Ala Tyr Ser Arg Ala Leu Met
210                 215                 220

Cys His Val Arg Glu Asp Ser Asp Leu Glu Ala Glu Leu Arg Lys Val
225                 230                 235                 240

Leu Pro Ala His Glu Val Glu Ala Val Val Leu Ala Lys His Arg Pro
                245                 250                 255

Asn Tyr Cys Leu Gln Val Met Ser Glu Ile Val His Ser Ala His Leu
            260                 265                 270

Ser Ala Leu Pro Leu Pro Val Ala Arg Gly Ala Val Val Ala Ser Gly
        275                 280                 285

Ala Pro Ala Leu Ala Ala Ala Gly Trp Glu Gly Thr Arg Tyr Arg Met
290                 295                 300

Asp Glu Asn Leu Thr Ala Met Glu Asp Ile Leu Gly Ala Cys Glu Arg
305                 310                 315                 320

Ile Leu Arg Ala Pro Ile Pro Leu Ser Tyr Thr Arg His Thr Ser Arg
                325                 330                 335

Phe Met Met Ile Trp Leu Thr Leu Leu Pro Phe Ser Leu Trp Asp Asn
            340                 345                 350

Cys Gly Trp Ala Ser Val Pro Leu Cys Gly Ile Ile Ala Phe Leu Leu
        355                 360                 365

Leu Gly Ile Glu Glu Ile Gly Val Ser Ile Glu Glu Pro Phe Ser Ile
370                 375                 380

Leu Pro Leu Glu Val Ile Cys Asp Ile Ile Glu Ala Asn Val Arg Glu
385                 390                 395                 400

Leu Arg Ser Ile His Ala Gly Ser His Ala Glu Asp Gly Ser Gln Pro
                405                 410                 415

Arg Arg Ala Pro Ala Ala Arg Asp Leu Val Gly Arg Ala Val Ala Glu
            420                 425                 430

Ala Glu Gln Glu Glu Ala Ala Ala Ala Gly Thr Val Ala Ala Ala
        435                 440                 445

Ala Gly Ala
    450

<210> SEQ ID NO 17
<211> LENGTH: 456
<212> TYPE: PRT
<213> ORGANISM: Chlorella variabilis

<400> SEQUENCE: 17

Met Ala Ser Arg Leu His Gly Ser Arg His Gln Gly Ala Leu Leu Gly
1               5                   10                  15

Leu Gln Gln Pro Ala Gly Leu Val Pro Arg Thr Arg Ser Leu Asn Arg
            20                  25                  30

Gly Arg Leu Thr Gln Leu Arg Val Ala Ala Ala Ser Ser Pro Pro
        35                  40                  45

Leu Pro Ala Lys Leu Ser Gly Asp Asp Leu Lys Glu Ala Glu Leu Lys
    50                  55                  60

Lys Leu Arg Thr Val Ala Asp Phe Glu Phe Trp Lys Arg His Arg Ser
65                  70                  75                  80

Ser Ser Arg Tyr Trp Arg His Val Leu Gly Ile Phe Asp Ser Arg Thr
                85                  90                  95
```

```
Phe Ser Trp Val Ala Ala Pro Leu Ser Tyr Val Met Leu Leu Thr Thr
                100                 105                 110

Gly Val Cys Leu Tyr Tyr Thr Leu Ala Glu Ala Gly Ile Val Pro Glu
            115                 120                 125

Val Ile Pro Glu Ile Ser Ala Ser Ala Ala Pro Phe Gly Leu Thr
        130                 135                 140

Ser Phe Ala Leu Ser Thr Leu Leu Val Leu Arg Thr Asn Thr Ser Tyr
145                 150                 155                 160

Gln Arg Trp Asp Glu Ala Arg Lys Met Trp Gly Leu Ile Val Asn Arg
                165                 170                 175

Thr Arg Asp Ile Ser Arg Gln Ala Val Gly Tyr Ile Pro Pro His Gln
                180                 185                 190

Ala Glu Leu Gln Asp Met Phe Cys Arg Trp Leu Val Ala Tyr Cys Arg
            195                 200                 205

Ser Leu Met Cys His Leu Arg Ala Gly Glu Asp Leu Glu Ala Glu Leu
        210                 215                 220

Lys Gly Lys Leu Thr Asp Ile Glu Leu Lys Ala Leu Ala Ser Thr
225                 230                 235                 240

His Arg Pro Asn Tyr Thr Cys Gln Val Leu Thr Ala Ile Ile Arg Ala
                245                 250                 255

Ala Gln Leu Pro Gly Gly Lys Val Asp Met Asn Asp Ser Phe Ala Asn
            260                 265                 270

Val Lys Ala Ser Ala Ala Phe Arg Met Asp Glu Asn Leu Thr Gln Tyr
        275                 280                 285

Ala Asp Val Thr Gly Gly Cys Glu Arg Ile Leu Arg Thr Pro Val Pro
    290                 295                 300

Leu Ser Tyr Ser Arg His Asn Ser Arg Phe Leu Ile Ile Trp Leu Thr
305                 310                 315                 320

Leu Leu Pro Phe Thr Leu Trp Asp Gln Cys His Trp Phe Thr Leu Pro
                325                 330                 335

Val Thr Gly Leu Val Ala Phe Leu Leu Leu Gly Ile Lys Glu Ile Gly
            340                 345                 350

Val Val Val Glu Glu Pro Phe Ser Ile Leu Pro Leu Glu Arg Ile Cys
        355                 360                 365

Asp Thr Ile Glu Ala Asn Val Trp Glu Ile His Ser Ile His Ser Ala
    370                 375                 380

Lys Ala Met Lys Glu Gln Ala Glu Ala Arg Ala Ala Gly Leu Pro Ser
385                 390                 395                 400

Asp Leu Met Glu Ala Ser Asp Leu Val Ser Val Val Ser Glu Leu Ala
                405                 410                 415

Leu Ala Ala Gly Thr Gly Gly Thr Gly Thr Thr Ala Gly Asn Gly Asn
            420                 425                 430

Gly Ala Gly Asn Gly Asn Gly Ser Ala Ala Ala Ala Val Val Ala Ala
        435                 440                 445

Asn Gly Ala Val Val Val Lys Val
    450                 455

<210> SEQ ID NO 18
<211> LENGTH: 480
<212> TYPE: PRT
<213> ORGANISM: Chlorella variabilis

<400> SEQUENCE: 18

Met Leu Ala His Ser Arg Pro Gly Ala Gly Ser Arg Pro Gly Asn Gly
1               5                   10                  15
```

-continued

```
Ala Ala Lys Ala Gly Ala Gly Arg Ser Ala Pro Pro Leu Gln Pro
         20                  25                  30

Ala Pro Ala Leu Thr Arg Arg Ala Leu Val His Pro Val Pro Ser Pro
         35                  40                  45

Arg Pro Thr Pro Gly Leu Val Arg Gln Arg Pro Gln Arg Gln Arg Pro
 50                  55                  60

Gln Glu Leu Pro Gly Ala Thr Pro Glu Gln Gln Gln Phe Pro Gly
 65                  70                  75                  80

Ser Glu Leu Asp Ala Ala Ala Lys Ala Glu Ala Ala Ala Lys Leu
                 85                  90                  95

Gln Arg Tyr Pro Trp His Ser Asp Glu Trp Lys Glu Tyr Arg Lys
                100                 105                 110

Gln Val Arg Val Thr Phe Asp Phe Glu Arg Trp Arg Thr His Arg Ser
             115                 120                 125

Ser Ser Arg Phe Trp Arg His Met Ala Gly Leu Ala Gln Ser Asn Thr
130                 135                 140

Ala Gln Gly Leu Ala Gln Pro Leu Ala Tyr Val Met Ala Val Ser Leu
145                 150                 155                 160

Gly Val Ala Ala Tyr His Val Ala Ala Ala Gly Trp Leu Pro Leu
                165                 170                 175

Trp Pro Val Leu Lys Leu Ala Ala Asn Ala Pro Phe Gly Leu Thr Ser
             180                 185                 190

Phe Ala Leu Ser Leu Leu Val Phe Arg Thr Asn Ser Ser Tyr Gly
             195                 200                 205

Arg Trp Asp Glu Ala Arg Lys Met Trp Gly Leu Val Val Asn Arg Ser
210                 215                 220

Arg Asp Leu Thr Arg Gln Ala Leu Gly Tyr Ile Pro Ala His Gln Ala
225                 230                 235                 240

Glu Leu Gln Ser Met Leu Cys Arg Trp Val Ala Tyr Ser Arg Cys
                245                 250                 255

Leu Met Cys His Leu Arg Glu Gly Glu Asp Leu Glu Ala Glu Leu Arg
             260                 265                 270

Gly Val Leu Leu Pro Glu Glu Val Ala Glu Leu Ala Ala Glu His
                275                 280                 285

Arg Pro Asn Tyr Cys Cys Gln Val Leu Thr Glu Val Leu Arg Glu Ala
290                 295                 300

Gln Leu Pro Ala Ala Val Thr Ser Pro Thr Asp Ser Thr Gly Cys Val
305                 310                 315                 320

Pro Ala Gly Ala Ala Tyr Arg Met Asp Glu Asn Leu Thr Val Phe Glu
                325                 330                 335

Asp Val Thr Gly Gly Cys Glu Arg Leu Leu Arg Thr Pro Ile Pro Leu
             340                 345                 350

Ala Tyr Thr Arg His Thr Ser Arg Phe Met Met Ala Trp Leu Thr Ile
             355                 360                 365

Leu Pro Phe Ala Leu Trp Asp Thr Cys Gly Trp Ala Met Leu Pro Val
             370                 375                 380

Met Ala Ile Val Ala Phe Val Leu Leu Gly Ile Glu Glu Ile Gly Val
385                 390                 395                 400

Ser Ile Glu Glu Pro Phe Ser Ile Leu Pro Leu Glu Thr Ile Cys Arg
                405                 410                 415

Thr Ile Glu Ser Asn Val Arg Glu Ser Val Gly Ala His Cys Gln Arg
             420                 425                 430
```

Gln Ala Arg Arg Ala Gln Ala Gln His Gly Gly Val Pro Gly Asp
            435                 440                 445

Leu Pro Lys Arg His Ala His Ser Asn Gly Asn Asn Ala Val Pro Ala
450                 455                 460

Leu Leu Phe Met Pro Pro Gln Pro Val Ala Ser Ala Gly Gln Gln His
465                 470                 475                 480

<210> SEQ ID NO 19
<211> LENGTH: 318
<212> TYPE: PRT
<213> ORGANISM: Chlorella variabilis

<400> SEQUENCE: 19

Val Phe Thr Phe Glu Arg Trp Asn Lys His Arg Asn Ser Met Arg Tyr
1               5                   10                  15

Ala Lys His Leu Ala His Met Phe Thr Ser Arg Val Phe Arg Gln Leu
            20                  25                  30

Leu Gly Pro Val Leu Ala Val Met Thr Ile Ala Leu Ala Val Gly Val
        35                  40                  45

Tyr Glu Thr Leu Val Gly Ala Gly Ala Leu Pro Gly His Trp Pro His
50                  55                  60

Val Thr Leu Ala Leu Gly Gln Gly Phe Asn Leu Thr Ala Phe Ala Leu
65                  70                  75                  80

Ser Leu Leu Leu Val Phe Arg Thr Asn Ser Ser Tyr Asp Arg Trp Trp
                85                  90                  95

Glu Ala Arg Lys Leu Trp Gly Gly Val Val Asn Arg Cys Arg Asp Ile
            100                 105                 110

Val Arg Gln Val Gly Pro Gln Gly Leu Val Phe Phe Arg Asp Glu Asp
        115                 120                 125

Ala His Leu Lys Glu Leu Leu Ala Arg Trp Thr Met Ala Phe Pro Arg
130                 135                 140

Val Leu Met Cys His Leu Arg Glu Asp Met Asp Val Gly Lys Glu Val
145                 150                 155                 160

Ala His Ile Leu Thr Ala His Glu Val Ala Val Met Cys Ala Ala Ala
                165                 170                 175

His Arg Pro Asn Phe Val Leu Gln Val Met Ala Glu Thr Val Arg Ala
            180                 185                 190

Ala Arg Pro Asn Glu Leu Cys Arg Met Arg Met Asp Asp Asn Leu Thr
        195                 200                 205

Phe Phe Glu Asp Ala Met Gly Ser Cys Glu Arg Ile Leu Arg Thr Pro
210                 215                 220

Ile Pro Leu Ser Tyr Thr Arg His Thr Ser Arg Phe Leu Leu Val Trp
225                 230                 235                 240

Leu Ile Leu Leu Pro Phe Thr Leu Trp Ala Ala Tyr Ser Trp Phe Ser
                245                 250                 255

Ile Leu Leu Ser Gly Ile Phe Ala Phe Leu Met Phe Gly Ile Asp Glu
            260                 265                 270

Ile Gly Val Gln Ile Glu Glu Pro Phe Gly Trp Val Ala Ala Thr Tyr
        275                 280                 285

Thr Ala Trp His Leu Ala Cys Glu Lys Pro Gly Cys Cys Cys Trp Val
290                 295                 300

Val Leu Cys Gly Gly Val Arg Ala Ser Ala Ala His Gln Arg
305                 310                 315

<210> SEQ ID NO 20

<211> LENGTH: 433
<212> TYPE: PRT
<213> ORGANISM: Chlorella variabilis

<400> SEQUENCE: 20

```
Met Ala Ile Leu Leu Gly Ala Arg Val Gln Pro Val Ala Val Ala Ala
1               5                   10                  15

Thr Pro Ala Ala Lys Arg Gln Ala Arg Gly Ser Thr Leu Arg His Cys
            20                  25                  30

Gln Pro Ala Gly Leu Ala Ala Leu Arg Gln Arg Cys Ala Thr Ser Arg
        35                  40                  45

Cys Ser Arg Ala Ala Leu Arg Thr Leu Ala Val Ala Ser Thr Asp Lys
50                  55                  60

Thr Glu Pro Glu His Pro Tyr Phe Ser Asp Asp Trp Lys Glu Tyr Asn
65                  70                  75                  80

Arg Arg Phe Gln Arg Pro Val Phe Asp Phe Glu Arg Trp Lys Thr His
                85                  90                  95

Arg Ser Ser Ser Arg Tyr Leu Arg His Val Leu Gly Ile Phe Asp Ser
            100                 105                 110

Lys Ile Val Gln Gly Leu Ala Lys Pro Leu Ala Tyr Val Met Thr Leu
        115                 120                 125

Ala Thr Gly Val Ala Leu Tyr His Thr Leu Ala Glu Ala Gly Tyr Leu
130                 135                 140

Thr Asp Val Pro Asp Leu Lys Ala Thr Asn Ala Pro Phe Gly Leu Thr
145                 150                 155                 160

Ser Phe Ala Leu Ser Leu Leu Val Phe Arg Thr Asn Thr Ser Tyr
                165                 170                 175

Gln Arg Trp Asp Glu Ala Arg Lys Met Trp Gly Ser Met Val Asn Arg
            180                 185                 190

Ser Arg Asp Phe Thr Arg Gln Ala Leu Gly Tyr Val Pro Glu Ser Gln
        195                 200                 205

Pro Glu Leu Arg Ser Met Leu Val Arg Trp Ser Ile Ala Tyr Pro Arg
210                 215                 220

Ala Leu Met Cys His Leu Arg Pro Gly Glu Asn Ile Glu Glu Val
225                 230                 235                 240

Lys Asp Ile Leu Lys Pro Glu Val Lys Ala Leu Ala Ala Ser Thr
                245                 250                 255

His Arg Pro Asn Tyr Cys Met Gln Val Leu Thr Ala Cys Leu Lys Gln
            260                 265                 270

Ala Gln Leu Pro Ala Ala Val Thr Ser Asn Arg Asp Ser Tyr Gly Ala
        275                 280                 285

Val Pro Ala Gly Ala Ala Tyr Arg Met Asp Glu Asn Leu Thr Val Tyr
290                 295                 300

Ser Asp Val Thr Gly Gly Cys Glu Arg Ile Leu Arg Thr Pro Val Pro
305                 310                 315                 320

Leu Ser Tyr Thr Arg His Thr Ser Arg Phe Met Met Ile Trp Leu Thr
                325                 330                 335

Leu Leu Pro Phe Thr Leu Trp Asp Asn Cys Gly Trp Ala Met Leu Pro
            340                 345                 350

Ile Thr Phe Ile Val Ser Phe Leu Leu Gly Ile Glu Glu Ile Gly
        355                 360                 365

Val Ser Ile Glu Glu Pro Phe Thr Ile Leu Pro Leu Glu Thr Ile Ala
370                 375                 380

Arg Thr Ile Glu Ala Asn Leu Arg Glu Leu Glu Ala Thr His Gly Pro
```

```
                385                 390                 395                 400
Ala Thr Leu Gly Lys Ala Gly Pro Gly Gln Val Asn Ala Thr Glu Leu
                    405                 410                 415

Leu Tyr Asp Met Ile Pro Ser Ala Ala Asn Gly Arg Ile Ser Ile Asn
                420                 425                 430

Ala

<210> SEQ ID NO 21
<211> LENGTH: 503
<212> TYPE: PRT
<213> ORGANISM: Chlorella variabilis

<400> SEQUENCE: 21

Met Gln Leu Gly Ala Gly Arg Gln Val Ser Ala Pro Val Ala Gly
1               5                   10                  15

Pro Ala Ser Arg Leu Pro Cys Gly Leu Gly Leu Ala Ser Pro Arg His
                20                  25                  30

Pro Trp Pro Ala Ser Arg Gly Pro Leu Thr His His Gln Arg Arg
            35                  40                  45

Gln Leu Arg Val Ala Val Ala Gly Gly Pro Gly Gln Gln Pro Glu Glu
50                  55                  60

Ala Pro Glu Arg Pro Ala Phe Pro Ala Ala Ala Ala Val Arg Arg
65                  70                  75                  80

Gln Gln Ile Gln Arg Glu Arg Ala Ala Ile Arg Asn Arg Ile Glu Asn
                85                  90                  95

Leu Val Ala Thr Asp Phe Asp Glu Glu Asp Ala Ala Leu Ile Asp Leu
            100                 105                 110

Val Gly Asp Glu Phe Lys Glu Ala Asp Arg Lys Asn Leu Arg Thr Val
        115                 120                 125

Phe Asp Phe Asp Arg Trp Lys Lys His Arg Ser Gly Ser Arg Tyr Met
130                 135                 140

Arg His Ala Arg Ala Thr Phe Thr Ser Arg Ile Thr Gln Gly Leu Ala
145                 150                 155                 160

Ala Pro Leu Leu Tyr Val Thr Gly Leu Ser Ile Ala Val Ala Ser Trp
                165                 170                 175

His Thr Ala Ala Glu Val Arg Trp Ala Gly Pro Met Gly Ile Leu Ser
            180                 185                 190

Pro Ile Pro Glu Leu Lys Ile Asp Thr Thr Phe Ser Leu Thr Ser Phe
        195                 200                 205

Ala Leu Ser Leu Leu Ala Tyr Arg Thr Asn Ala Gly Tyr Gly Arg
    210                 215                 220

Trp Asp Glu Ala Arg Lys Met Trp Gly Leu Val Val Asn Arg Ser Arg
225                 230                 235                 240

Asp Met Thr Arg Gln Val Gly Ala Arg Leu Ala Gly Ala Gly Gln Cys
                245                 250                 255

Val His Asn Ile Phe Ile Thr Val Cys Thr Cys Ser Arg Ser Leu Met
            260                 265                 270

Cys His Leu Arg Gly Gly Glu Asp Ile Glu Ser Glu Leu Ala Gly Val
        275                 280                 285

Leu Thr Pro Arg Glu Leu Asp Ala Leu Lys Ala Ser His Arg Pro
    290                 295                 300

Asn Tyr Cys Val Gln Val Arg Gly Arg Val Ala Arg Gly Ser Ala
305                 310                 315                 320

Val Gly Gly Ser Leu Pro Pro Leu Pro Pro Ala Ala Ala Ser Pro Gln
```

```
            325                 330                 335
Asp Val Thr Gly Gly Cys Glu Arg Ile Leu Arg Thr Pro Ile Pro Leu
            340                 345                 350

Ser Tyr Thr Arg His Thr Ser Arg Phe Met Met Ile Trp Leu Thr Val
            355                 360                 365

Met Pro Phe Thr Leu Trp Asp Ala Ala Gly Trp Ala Met Val Pro Leu
        370                 375                 380

Ala Met Thr Val Ala Phe Leu Leu Gly Ile Glu Glu Ile Gly Val
385                 390                 395                 400

Met Ile Glu Glu Pro Phe Ser Val Leu Pro Leu Glu Val Ile Ser Arg
                405                 410                 415

Thr Ile Glu Gly Asn Val Arg Glu Leu Glu Arg Ala His Gly Leu Glu
                420                 425                 430

Ala Ala Ala Met Lys Glu Arg Glu Ala Ala Leu Ala Ala Ala Arg Asp
                435                 440                 445

Gly Gly Gly Ala Ala Pro Ala Ala Pro Ala Asp Gly Gln Val Asp
450                 455                 460

Ala Leu Asp Leu Val Leu Ser Ile Leu Pro Glu Glu Leu Arg Gln
465                 470                 475                 480

Pro Trp Gly Pro Gly Leu Ala Met Leu Ser Gly Thr Ala Gly Pro Ala
                485                 490                 495

Thr Val Pro Ala Gly Asn Ser
                500

<210> SEQ ID NO 22
<211> LENGTH: 444
<212> TYPE: PRT
<213> ORGANISM: Chlorella variabilis

<400> SEQUENCE: 22

Met Gly Ala Ala Ala Pro Pro Ser Ala Ala Leu Ala Arg Pro Ala Ala
1               5                   10                  15

Gly Gln Arg Pro Leu Ala Ala Gln Leu Arg Gln Arg Gln Pro Gly Leu
            20                  25                  30

Ala Ala Leu Thr Gln Arg His His Ala Ala Ala Cys Arg Cys Asn Arg
        35                  40                  45

Cys Gly Arg Gly Val Ala Leu Arg Thr Ser Ala Val Ala Asn Thr Asp
    50                  55                  60

Lys Arg Glu Gln Pro His Pro Tyr Phe Thr Asp Glu Trp Lys Glu Tyr
65              70                  75                  80

Asn Arg Gln Phe Gln Arg Pro Val Phe Asp Phe Glu Arg Trp Lys Thr
                85                  90                  95

His Arg Ser Ser Arg Tyr Leu Arg His Val Leu Gly Met Gly Asp
            100                 105                 110

Ser Lys Ile Val Gln Gly Leu Ala Lys Pro Leu Ala Tyr Val Met Thr
        115                 120                 125

Leu Ala Thr Gly Val Ala Leu Tyr His Thr Leu Ala Glu Ala Gly Tyr
    130                 135                 140

Leu Thr Asp Val Pro Asp Leu Lys Ala Thr Asn Ala Pro Phe Gly Leu
145                 150                 155                 160

Thr Ser Phe Ala Leu Ser Leu Leu Val Phe Arg Thr Asn Thr Ser
                165                 170                 175

Tyr Gln Arg Trp Asp Glu Ala Arg Lys Met Trp Gly Ser Met Val Asn
            180                 185                 190
```

```
Arg Ser Arg Asp Phe Thr Arg Gln Ala Leu Gly Tyr Val Pro Tyr Ser
            195                 200                 205

Gln Pro Glu Leu Arg Ser Met Leu Val Arg Trp Ser Ile Ala Tyr Pro
    210                 215                 220

Arg Ala Leu Met Cys His Leu Arg Pro Gly Glu Asn Ile Glu Glu Glu
225                 230                 235                 240

Val Lys Asp Ile Leu Lys Pro Glu Val Lys Ala Leu Ala Ala Ser
                245                 250                 255

Thr His Arg Pro Asn Tyr Cys Met Gln Val Leu Thr Ala Cys Ile Lys
                260                 265                 270

Gln Ala Gln Leu Pro Ala Ala Val Thr Ser Asn Arg Asp Ser Tyr Gly
        275                 280                 285

Ala Val Pro Ala Gly Ala Ala Tyr Arg Met Asp Glu Asn Leu Thr Val
    290                 295                 300

Tyr Ser Asp Val Thr Gly Gly Cys Glu Arg Ile Leu Arg Thr Pro Val
305                 310                 315                 320

Pro Leu Ser Tyr Thr Arg His Thr Ser Arg Phe Met Met Ile Trp Leu
                325                 330                 335

Thr Leu Leu Pro Phe Thr Leu Trp Asp Asn Cys Gly Trp Ala Met Leu
                340                 345                 350

Pro Ile Thr Phe Ile Val Ser Phe Leu Leu Leu Gly Ile Glu Glu Ile
        355                 360                 365

Gly Val Ser Ile Glu Glu Pro Phe Thr Ile Leu Pro Leu Glu Thr Ile
    370                 375                 380

Ala Arg Thr Ile Glu Ala Asn Leu Arg Glu Leu Glu Ala Thr His Gly
385                 390                 395                 400

Pro Ala Thr Leu Gly Lys Ala Pro Glu Gly Ala Met Asn Ala Thr Glu
                405                 410                 415

Leu Leu Tyr Glu Val Ile Pro Ser Ala Ala Pro Ala Asp Thr Val Asn
                420                 425                 430

Ala Asn Ser Asn Gly Ala Gln Ile Ala Val Lys Ala
            435                 440

<210> SEQ ID NO 23
<211> LENGTH: 273
<212> TYPE: PRT
<213> ORGANISM: Chlorella variabilis

<400> SEQUENCE: 23

Ser Thr Phe Thr Phe Arg Arg Trp Ala Phe His Arg Ser Thr Ser Arg
1               5                   10                  15

Tyr Val Arg His Met Ser Gly Ile Phe Gln Ser Arg Ile Val Arg Gly
            20                  25                  30

Leu Ala Gln Pro Leu Leu Ser Ser Cys Ala Thr Ala Thr Ile Val Cys
        35                  40                  45

Val Tyr Glu Gln Ala Leu Gln Asp Gly Trp Leu Pro Ser Phe Leu Pro
    50                  55                  60

Thr Phe Ile Met Pro Ser Leu Pro Phe Asp Ile Thr Ala Ser Ser Leu
65                  70                  75                  80

Gly Leu Leu Leu Val Phe Arg Thr Asn Ser Ser Tyr Asp Arg Trp Gln
                85                  90                  95

Gln Ala Val Ser Ala Trp Gly Asp Ile Glu Thr Arg Ala Arg Asp Thr
            100                 105                 110

Leu Arg Gln Leu Leu Ala Ala Ala Ser His Ser Ser Ala Gly His Gly
        115                 120                 125
```

```
Gly Ala Arg Gln Ala Ala Leu Trp Leu Val Ala Phe Ser Arg Ser Leu
        130                 135                 140

Lys Ala Gln Leu Thr Glu Asp Ser Asp Val Gln Ala Glu Leu Arg Glu
145                 150                 155                 160

Val Leu Thr Gly Gln Glu Leu Ala Leu Leu Gly Ala Gln His Arg
                165                 170                 175

Pro Ser Phe Ala Leu Ala Val Leu Ser Glu Leu Ala Glu Ala Pro
            180                 185                 190

Leu Arg Asp Ala Gln Arg Val Arg Val Asp Glu Asn Leu Ser Cys Phe
        195                 200                 205

Gln Asp Ala Ala Gly Arg Cys Glu Arg Ile Leu Arg Thr Pro Ile Pro
    210                 215                 220

Leu Ser Tyr Thr Arg His Ser Ser Arg Phe Met Val Ile Trp Leu Ser
225                 230                 235                 240

Ala Leu Pro Leu Gly Leu Trp Ser Gln Cys Gly Phe Gly Thr Ile Pro
                245                 250                 255

Leu Thr Val Ile Ser Pro Ser Cys Cys Trp Ala Leu Arg Arg Leu Gly
            260                 265                 270

Val

<210> SEQ ID NO 24
<211> LENGTH: 668
<212> TYPE: PRT
<213> ORGANISM: Chlamydomonas reinhardtii

<400> SEQUENCE: 24

Met Gln Cys Gln Leu Lys His Gly Ala Arg Pro Gln Ser Gln Arg Pro
1               5                   10                  15

Asn Trp Leu Pro Ala Arg Ala Ala Thr Leu Arg Pro Ala Val Gln His
            20                  25                  30

Gly Val Arg Arg Gly Leu Thr Leu Gly Val Lys Ala Ala Ala Ala Pro
        35                  40                  45

Leu Glu Asp Lys Lys Met Pro Ala Asp Met Thr Thr Arg Gln Tyr Arg
50                  55                  60

Arg Val Val Tyr Asp Phe Ala Leu Trp Ala Lys His Arg Asp Val Asn
65                  70                  75                  80

Arg Tyr Leu Tyr Asn Leu Arg Thr Ile Pro Gly Ser Arg Ile Ile Arg
                85                  90                  95

Gln Leu Ser Gln Pro Met Gly Val Val Leu Ala Trp Ala Ala Leu Phe
            100                 105                 110

Gly Phe Tyr Glu Thr Cys Leu Glu Ala Gly Val Leu Pro Ser Tyr Leu
        115                 120                 125

Pro Lys Met Thr Leu Met Ser Ala Glu Pro Gln Gly Leu Thr Ser Phe
    130                 135                 140

Ala Leu Ser Leu Leu Leu Val Phe Arg Thr Asn Ser Ser Tyr Gly Arg
145                 150                 155                 160

Phe Asp Glu Ala Arg Lys Ile Trp Gly Gly Ile Leu Asn Arg Ala Arg
                165                 170                 175

Asn Ile Ala Asn Gln Ala Val Thr Phe Ile Pro Ala Glu Asp Gln Ala
            180                 185                 190

Gly Arg Glu Ala Val Gly Lys Trp Thr Val Gly Phe Thr Arg Ala Leu
        195                 200                 205

Gln Ala His Leu Gln Glu Asp Ile Asp Leu Arg Lys Glu Leu Glu Lys
    210                 215                 220
```

```
Ala Thr Pro Arg Trp Ser Lys Glu Glu Ile Asp Met Leu Val Asn Ala
225                 230                 235                 240

Gln His Arg Pro Ile Lys Ala Ile Ser Val Leu Ser Glu Leu Thr Arg
            245                 250                 255

Gln Leu Ser Ile Thr Gln Phe Gln Ala Leu Gln Met Gln Glu Asn Cys
        260                 265                 270

Thr Phe Phe Tyr Asp Ala Leu Gly Gly Cys Glu Arg Leu Leu Arg Thr
    275                 280                 285

Pro Ile Pro Val Ser Tyr Thr Arg His Thr Ala Arg Phe Leu Thr Ile
290                 295                 300

Trp Leu Ala Met Leu Pro Leu Gly Leu Trp Glu Arg Tyr His Trp Ser
305                 310                 315                 320

Met Leu Pro Val Ile Ala Leu Ile Gly Phe Leu Leu Leu Gly Ile Asp
                325                 330                 335

Glu Ile Gly Ile Ser Ile Glu Glu Pro Phe Gly Ile Leu Pro Leu Asp
            340                 345                 350

Ala Ile Cys Gly Arg Ala Gln Thr Asp Val Asn Ser Leu Leu Lys Glu
        355                 360                 365

Asp Pro Ala Val Met Lys Tyr Val Asp Val Arg Ser Gly Arg Val
    370                 375                 380

Lys Ser Pro Pro Leu Pro Ala Pro Ala Pro Ala Ala
385                 390                 395                 400

Ala Ala Ala Ala Ala Ala Ala Arg Ser Val Ser Pro Gln Pro Asp
            405                 410                 415

Val Ala Lys Thr Leu Gly Ser Leu Phe Thr Asn Val Arg Ala Gly Val
            420                 425                 430

Gly Ala Val Ala Pro Gly Ala Pro Leu Met Pro Gln Ala Pro Val Arg
            435                 440                 445

Ser Pro Ser Pro Thr Arg Ser Val Ser Pro Ser Phe Pro Arg Ala Ser
            450                 455                 460

Ala Gly Thr Gly Met Pro Pro Val Gly Met Asn Gly Ala Thr Pro
465                 470                 475                 480

Arg Val Ala Ala Ala Pro Pro Thr Pro Pro Val Ser Arg Pro Ala
                485                 490                 495

Ala Pro Ala Ala Ala Pro Ala Ala Gly Ser Gly Phe Thr Met Pro Asn
                500                 505                 510

Phe Ser Ala Ser Leu Ser Gly Leu Thr Gly Gly Ala Ala Ala Ala
        515                 520                 525

Lys Ser Ala Ala Asp Ala Ala Ser Ser Lys Leu Thr Lys Met Ala Asp
        530                 535                 540

Ser Met Ser Ser Gly Ala Ala Pro Ala Pro Pro Ala Ala Pro Ala
545                 550                 555                 560

Arg Pro Ser Thr Ser Pro Arg Pro Ser Ala Ser Ser Pro Ile Ser Ser
            565                 570                 575

Ser Ala Asp Ala Asp Arg Ser Asp Ser Ser Arg Arg Pro Val Asn Trp
        580                 585                 590

Arg Asp Glu Leu Gln Ser Leu Lys Ala Thr Arg Glu Pro Asn Gly Asn
        595                 600                 605

Gly Asn Gly Ser Gly Val Ala Pro Ala Gly Arg Ala Asp Ala Asp
        610                 615                 620

Glu Glu Ala Leu Arg Arg Phe Gly Asn Leu Ala Gly Arg Ser Arg Ser
625                 630                 635                 640
```

```
Gly Asn Gly Gly Gly Ser Ser Asp Thr Glu Leu Ser Glu Ala Asn
                645                 650                 655

Arg Pro Arg Thr Arg Pro Asp Trp Arg Asn Gln Leu
            660                 665

<210> SEQ ID NO 25
<211> LENGTH: 381
<212> TYPE: PRT
<213> ORGANISM: Chlamydomonas reinhardtii

<400> SEQUENCE: 25

Met Asn Asn Leu Arg Lys Lys Arg Phe Glu Glu Lys Thr Val Glu Arg
1               5                   10                  15

Val Tyr Glu Ala Asp Val Tyr Pro Ala Val Phe Asp Phe Glu Ala Trp
            20                  25                  30

His Asn His Arg Ser Arg Lys Arg Tyr Leu Glu His Cys Ile Thr Leu
        35                  40                  45

Phe Arg Ser Tyr Phe Phe Arg Asp Leu Leu Gly Pro Leu Ala Val Leu
    50                  55                  60

Val Gly Thr Ala Val Ala Val Gly Cys Tyr Glu Gln Ala Leu Gln Asp
65                  70                  75                  80

His Leu Leu Pro Gly Ala Leu Pro Ser Phe Ser Gly Val Ser Asp Thr
                85                  90                  95

Pro Phe Gln Leu Thr Ser Phe Ala Leu Ser Leu Met Leu Val Phe Arg
            100                 105                 110

Thr Asn Ser Ser Tyr Ala Arg Trp Leu Asp Ala Arg Gln Gln Trp Gly
        115                 120                 125

Leu Ile Val Asn Thr Ser Arg Thr Phe Ile Arg Gln Val Met Thr Thr
    130                 135                 140

Leu Pro Glu Ser Ser Cys Ser Glu Leu Arg Asp Ala Ile Ala Arg Trp
145                 150                 155                 160

Thr Ile Ala Phe Val Arg Leu Ser Lys Leu His Leu Arg Glu His Gly
                165                 170                 175

Asp Val Arg Leu Glu Met Ala Gly Val Leu Arg Gly Glu Glu Leu Pro
            180                 185                 190

Leu Val Ala Ala Ala His Arg Pro Leu Ala Ala His Val Leu
        195                 200                 205

Ser Glu Leu Leu Arg Ser Ala Glu Ala Gly Arg Leu Ser Asp Gln
    210                 215                 220

Ser Arg Ala Arg Leu Glu Ala Asp Val Asn Met Leu Ser Gln Ala Leu
225                 230                 235                 240

Gly Ala Cys Glu Lys Ile Leu Arg Asn Pro Ile Pro Leu Ser Tyr Thr
                245                 250                 255

Arg His Thr Ser Arg Phe Leu Val Leu Trp Leu Leu Trp Leu Pro Ile
            260                 265                 270

Ala Leu Trp Gly Lys Val Ser Trp Gly Val Val Pro Val Glu Ala Ile
        275                 280                 285

Leu Cys Tyr Leu Leu Leu Gly Ile Asp Glu Ile Ala Ile Gln Met Glu
    290                 295                 300

Glu Pro Phe Gly Ile Leu Pro Leu Glu Asn Phe Cys Asp Ala Val Gln
305                 310                 315                 320

Gln Ser Val Glu Gln Val Ala Ser Met Asp His Gly Val Gln Asp Val
                325                 330                 335

Val Ala Ser Tyr Val Cys His Ile Val Gln Gln Asp Ser Gly Asn Gly
            340                 345                 350
```

```
Thr Gly Ala Ser Glu Pro Ala Pro Ala Glu Asp Gly Gly Asn Gly
        355                 360                 365

Phe Ala Asn Ile Phe Phe Arg Met Pro Ala Asp Arg Cys
370                 375                 380
```

<210> SEQ ID NO 26
<211> LENGTH: 401
<212> TYPE: PRT
<213> ORGANISM: Chlamydomonas reinhardtii

<400> SEQUENCE: 26

```
Met Gly Ser Gly Pro Arg Thr Ile Gly Leu Asp Ser Pro Thr Thr Thr
1               5                   10                  15

Ile Arg Ser Ala Ala Arg Asp Gln Arg Gln Leu Tyr Glu Val Glu Gly
            20                  25                  30

Arg Gly Thr Val Pro Phe Asp His Tyr Lys Glu Gly Ser Arg His Ala
        35                  40                  45

Arg Arg Met Thr Phe Thr Phe Asp Asp Trp Lys Arg His Arg Ser Ser
    50                  55                  60

Asn Arg Tyr Leu Tyr His Leu Lys Thr Leu Thr Glu Ser Gly Ile Val
65                  70                  75                  80

Arg Gly Ile Trp Ala Pro Val Ala Trp Val Thr Leu Phe Thr Ala Val
                85                  90                  95

Val Ala Thr Leu Asn Val Ala His Gly Ala Ala Met Leu Pro Pro Trp
            100                 105                 110

Val Pro Ala Met Pro Gln Ile Ala Ile Glu Pro Val Gln Leu Thr Ser
        115                 120                 125

Ile Ala Leu Ser Leu Leu Leu Val Phe Arg Thr Asn Ala Ser Tyr Ser
    130                 135                 140

Arg Trp Asp Glu Gly Arg Arg Ser Phe Gly Ser Ile Thr Thr Val Ser
145                 150                 155                 160

Arg Asp Ile Ala Arg Gln Ala Phe Ala Trp Phe Arg Pro Asp Asp Tyr
                165                 170                 175

Glu Ser Arg Val Arg Val Gly Arg Trp Leu Val Ala Leu Gly Arg Ser
            180                 185                 190

Thr Met Val His Leu Arg Glu Glu His Asp Met Glu Asp Glu Leu Arg
        195                 200                 205

Glu Val Leu Lys Pro Ala Glu Val Gln Ala Val Val Ser Ala Val His
    210                 215                 220

Ala Pro Ser Phe Cys Leu Gln Met Ile Thr Leu Ile Ile Arg Thr Ala
225                 230                 235                 240

Gly Leu Pro Gln Glu Leu Val Ile Arg Met Asp Glu Asn Val Ser Arg
                245                 250                 255

Leu Thr Asp Ala Val Ser Ala Cys Glu Arg Ile Leu Asn Thr Pro Ile
            260                 265                 270

Pro Leu Ser Tyr Thr Arg His Thr Ala Arg Phe Leu Met Ala Trp Leu
        275                 280                 285

Ala Cys Leu Pro Phe Cys Leu Trp Thr Tyr Cys Gly Pro Ala Met Val
    290                 295                 300

Pro Ile Ala Ala Leu Val Ala Phe Val Leu Leu Gly Ile Glu Glu Ile
305                 310                 315                 320

Gly Val Tyr Ile Glu Glu Pro Phe Ser Ile Leu Ala Leu Glu Lys Leu
                325                 330                 335

Val Asn Lys Leu Glu Asn Ile Val Asn Ala Met Leu Arg Asp Ser Gln
```

```
            340                 345                 350
Glu Leu Asp Arg Leu Val Lys Val Gly Ser Pro Thr Ala Ser Pro Arg
        355                 360                 365

Pro Glu Pro Ala Ser Thr Asn Ser Asn Asn Ala Val Thr Asp Thr Ala
    370                 375                 380

Phe Gly Leu Gly Ala Ala Gly Gly Phe Ser Pro Ala Val Ala Gly Ala
385                 390                 395                 400

Met

<210> SEQ ID NO 27
<211> LENGTH: 438
<212> TYPE: PRT
<213> ORGANISM: Chlamydomonas reinhardtii

<400> SEQUENCE: 27

Met Gln Met Gln Ala Asn Arg Ser Ser Leu Arg Ala Ser Pro Val Arg
1               5                   10                  15

Gly Leu Gly Ala Arg Pro Leu Leu Arg Ala Leu Pro Ala Gly Arg Val
            20                  25                  30

Ala Arg Leu Asn Val Ser Ala Gln Ala Lys Asp Pro Asn Ala Pro Ile
        35                  40                  45

Gln Ser Asn Pro Leu Gly Thr Leu Ser Ser Gln Ser Gly Gln Val Ala
    50                  55                  60

Thr Leu Pro Arg Ser Glu Ala Arg Lys Tyr Phe Arg Thr Val Tyr
65                  70                  75                  80

Asp Phe Pro Gln Trp Gln Lys His Arg Ser Ser Tyr Arg Phe Ala Glu
                85                  90                  95

Arg Leu Phe Gln Leu Ser Gln Ser His Ile Leu Gln Asn Ala Leu Pro
            100                 105                 110

Ala Ile Ser Trp Val Thr Leu Ala Thr Leu Val Ala Ser Tyr Gly
        115                 120                 125

Tyr Ser Tyr Asp Gln His Met Leu Pro Asp Val Phe Pro Ser Ile Ser
    130                 135                 140

Pro Asn Ala Ser Cys Thr Ala Phe Ile Ser Asn Thr Ser Val Ala Leu
145                 150                 155                 160

Ser Leu Leu Leu Val Phe Arg Thr Asn Ser Ser Tyr Gly Arg Trp Asp
                165                 170                 175

Glu Ala Arg Lys Met Trp Gly Gly Leu Leu Asn Arg Ser Arg Asp Ile
            180                 185                 190

Met Arg Gln Gly Ala Thr Cys Phe Pro Asp Asp Gln Val Glu Ala Lys
        195                 200                 205

Lys Ala Leu Ala Arg Trp Thr Val Ala Phe Ser Arg Ala Leu Arg Ile
    210                 215                 220

His Phe Gln Pro Glu Val Thr Ile Glu Ser Glu Leu Gln Asn Ile Leu
225                 230                 235                 240

Thr Pro Ala Glu Leu Gln Met Leu Ala Lys Ser Gln His Arg Pro Val
                245                 250                 255

Arg Ala Ile His Ala Ile Ser Gln Ile Ile Gln Ser Val Pro Met Ser
            260                 265                 270

Ser Ile His Gln Gln Gln Met Ser Asn Asn Leu Thr Phe Phe His Asp
        275                 280                 285

Val Leu Gly Gly Cys Glu Arg Leu Leu Arg Ala Pro Ile Pro Val Ser
    290                 295                 300

Tyr Thr Arg His Thr Ala Arg Phe Leu Phe Ala Trp Leu Thr Leu Leu
```

```
                305                 310                 315                 320
Pro Phe Ala Leu Tyr Pro Thr Thr Gly Trp Gly Val Pro Val Cys
                325                 330                 335
Thr Gly Ile Ala Ala Val Leu Cys Gly Ile Glu Glu Ile Gly Val Gln
                340                 345                 350
Cys Glu Glu Pro Phe Gly Ile Leu Pro Leu Asp Val Ile Cys Asn Arg
                355                 360                 365
Ile Gln Ala Asp Val Met Ala Thr Leu Lys Asp Ala Asp Thr Lys
                370                 375                 380
Thr Ile Leu Ala Glu Ala Gly Leu Ile Ser Leu Ile Pro Ser Ala Thr
385                 390                 395                 400
Ser Ala Thr Pro Val Ala Ser Ala Glu Pro Val Leu Val Ser Ala Arg
                405                 410                 415
Pro Ser Ala Ala Pro Ala Pro Asn Asn Gly Leu Gln Val Arg Val Ala
                420                 425                 430
Met Gly Gly Glu Arg Lys
                435
```

<210> SEQ ID NO 28
<211> LENGTH: 450
<212> TYPE: PRT
<213> ORGANISM: Chlamydomonas reinhardtii

<400> SEQUENCE: 28

```
Met Gln Cys Leu Ser Ser Arg Pro Val Ala Met Gly Arg Ala Gly Ser
1               5                   10                  15
Ser Ala Leu Pro Arg Leu Pro Leu Arg Ala Gly Arg Val Cys His Leu
                20                  25                  30
Gly Val Arg Cys Gln Ala Ala Asn Lys Asp Pro Asn Ala Pro Ile Gln
                35                  40                  45
Ser Asn Pro Leu Gly Ser Phe Ser Ser Gln Leu Gln Asn Gln Pro Thr
                50                  55                  60
Leu Pro Arg Ser Glu Glu Ala Arg Lys Tyr Phe Arg Thr Val Tyr Asp
65                  70                  75                  80
Phe Pro Gln Trp Gln Thr His Arg Asn Gln Tyr Arg Leu Met Lys Arg
                85                  90                  95
Leu Phe Ser Ile Pro Gln Ser His Val Ile Gln Asn Ala Leu Pro Ser
                100                 105                 110
Ile Met Trp Val Ala Phe Thr Ser Thr Cys Val Ala Ala Tyr Met Tyr
                115                 120                 125
Gly Tyr Asp Gln His Met Leu Pro Glu Gly Phe Pro Thr Leu Ala Pro
                130                 135                 140
Asn Ala Ala Cys Ser Ala Phe Ile Ser Asn Thr Ser Val Ala Leu Ser
145                 150                 155                 160
Leu Leu Leu Val Phe Arg Thr Asn Ser Ser Tyr Gly Arg Trp Asp Glu
                165                 170                 175
Ala Arg Lys Met Trp Gly Gly Leu Leu Asn Arg Ser Arg Asp Ile Met
                180                 185                 190
Arg Gln Gly Ala Thr Cys Phe Pro Asp Asp Gln Val Glu Ala Lys Lys
                195                 200                 205
Ala Leu Ala Arg Trp Val Val Ala Phe Ser Arg Ala Leu Arg Ile His
                210                 215                 220
Phe Gln Pro Glu Val Thr Ile Glu Ser Glu Leu Lys Asn Ile Leu Thr
225                 230                 235                 240
```

```
Pro Ala Glu Leu Gln Met Leu Ala Lys Ser Gln His Arg Pro Val Arg
                245                 250                 255

Ala Ile His Ala Ile Ser Gln Ile Ile Gln Ser Val Pro Met Ser Ser
            260                 265                 270

Ile His Gln Gln Gln Met Ser Asn Asn Leu Thr Phe Phe His Asp Val
        275                 280                 285

Leu Gly Gly Cys Glu Arg Leu Leu Arg Ala Pro Ile Pro Val Ser Tyr
    290                 295                 300

Thr Arg His Thr Ala Arg Phe Leu Phe Ala Trp Leu Thr Leu Leu Pro
305                 310                 315                 320

Phe Ala Leu Tyr Gly Ser Cys Gly Val Ser Val Ile Pro Val Cys Ser
                325                 330                 335

Gly Ile Ala Ala Val Leu Cys Gly Ile Glu Glu Ile Gly Val Gln Cys
            340                 345                 350

Glu Glu Pro Phe Gly Ile Leu Pro Leu Asp Val Ile Cys Asn Arg Ile
        355                 360                 365

Gln Ala Asp Val Met Ala Thr Leu Lys Asp Asp Ala Asp Thr Lys Thr
    370                 375                 380

Ile Leu Ala Glu Ala Gly Leu Ile Ser Leu Arg Ala Asn Ser Ala Met
385                 390                 395                 400

Ala Val Glu Asn Ala Leu Pro Asp Leu Asp Ser Ile Asn Ala Ala Ala
                405                 410                 415

Pro Asn Gly Asn Gly Ser His Asn Gly Asn Gly Ala Ala Val Pro Val
            420                 425                 430

Ser Val Ser Ala Gly Ala Ser Gly Asn Gly Met Asn Val Arg Ile Ser
        435                 440                 445

Pro Arg
    450

<210> SEQ ID NO 29
<211> LENGTH: 466
<212> TYPE: PRT
<213> ORGANISM: Chlamydomonas reinhardtii

<400> SEQUENCE: 29

Met Gln Val Ser Lys Val Pro Ser Ser Ala Ser Ala Arg Cys Leu Pro
1               5                   10                  15

Arg Leu Pro Val Arg Thr Ser Arg Val Cys Gln Leu Ser Val Arg Cys
            20                  25                  30

Gln Ala Ala Asn Lys Asp Pro Asn Ala Pro Ile Gln Ser Asn Pro Leu
        35                  40                  45

Gly Ser Phe Ser Ser Gln Asn Ser Ser Gly Ala Val Val Thr Ala Pro
    50                  55                  60

Arg Asn Glu Asp Ala Arg Lys Tyr Phe Arg Thr Val Tyr Asp Phe Pro
65                  70                  75                  80

Gln Trp Gln Lys His Arg Ser Gln Ser Arg Leu Val Arg Arg Leu Phe
                85                  90                  95

Thr Ile Pro Gln Ser His Val Ile Gln Asn Ala Leu Pro Ser Ile Met
            100                 105                 110

Trp Val Thr Phe Thr Ser Thr Cys Val Ala Ala Tyr Met Tyr Gly Tyr
        115                 120                 125

Asp Leu His Ile Leu Pro Glu Gly Phe Pro Thr Leu Ala Pro Asn Ala
    130                 135                 140

Ala Cys Ser Ala Phe Ile Ser Asn Thr Ser Val Ala Leu Ser Leu Leu
145                 150                 155                 160
```

Leu Val Phe Arg Thr Asn Ser Ser Tyr Gly Arg Trp Asp Glu Ala Arg
            165                 170                 175

Lys Met Trp Gly Gly Leu Leu Asn Arg Ser Arg Asp Ile Met Arg Gln
        180                 185                 190

Gly Ala Thr Cys Phe Pro Asp Asp Gln Val Glu Ala Lys Lys Ala Leu
    195                 200                 205

Ala Arg Trp Thr Val Ala Phe Ala Arg Ala Leu Arg Ile His Phe Gln
210                 215                 220

Pro Glu Val Thr Ile Glu Ser Glu Leu Gln Asn Ile Leu Thr Pro Ala
225                 230                 235                 240

Glu Leu Gln Met Leu Ala Lys Ser Gln His Arg Pro Val Arg Ala Ile
            245                 250                 255

His Ala Ile Ser Gln Ile Ile Gln Ser Val Arg Met Ser Ser Ile His
        260                 265                 270

Gln Gln Gln Met Ser Asn Asn Leu Thr Phe Phe His Asp Val Leu Gly
    275                 280                 285

Gly Cys Glu Arg Leu Leu Arg Ala Pro Ile Pro Val Ser Tyr Thr Arg
290                 295                 300

His Thr Ala Arg Phe Leu Phe Ala Trp Leu Thr Leu Leu Pro Phe Ala
305                 310                 315                 320

Leu Tyr Gly Ser Cys Gly Val Ser Val Ile Pro Val Cys Thr Gly Ile
            325                 330                 335

Ala Ala Val Leu Cys Gly Ile Glu Glu Ile Gly Val Gln Cys Glu Glu
        340                 345                 350

Pro Phe Gly Ile Leu Pro Leu Asp Val Ile Cys Asn Arg Ile Gln Ala
    355                 360                 365

Asp Val Met Ala Thr Leu Lys Asp Asp Ala Asp Thr Lys Thr Val Leu
370                 375                 380

Ala Glu Ala Gly Leu Ile Ser Leu Ile Pro Ser Met Ser Leu Pro Pro
385                 390                 395                 400

Thr Glu His Ala Ser Pro Ser Asp Pro Val Thr Ala Ala Ala Ala Ala
            405                 410                 415

Ala Leu Ala Ala Ala Asn Gly Asn Gly Ala Ala Ser His Ser Asn Gly
        420                 425                 430

Asn Gly Ser Lys Pro Val Ser Thr Gln Val Pro Pro Pro Val Leu Ala
    435                 440                 445

Pro Val Thr Val Thr Ser Ser Ser Gly Ser Met Asn Val Arg Ile Ser
450                 455                 460

Pro Arg
465

<210> SEQ ID NO 30
<211> LENGTH: 456
<212> TYPE: PRT
<213> ORGANISM: Chrysochromulina sp. CCMP291

<400> SEQUENCE: 30

Met Arg Glu His Pro Leu Ser Tyr Glu Glu Tyr Met Arg Gln Arg Ser
1               5                   10                  15

Ala Gly Arg Asp Pro Leu Ala Glu Ala Val Gln Gly Gln Ser Ala Ser
            20                  25                  30

Met Glu Arg Gly Val Val Pro Pro Pro Val Lys Ala Thr Pro Glu
        35                  40                  45

Arg Thr Glu Ala Ala Phe Thr Pro Pro Ala Glu Phe Asp Phe Phe Gln

```
            50                  55                  60
Asp Val Phe Lys Pro Thr Val Glu Ser Val Lys Ala Val Val Ser
 65                  70                  75                  80

Pro Gly Ala Gln Gln Asp Ser Asp Glu Ser Tyr Met Arg Val Pro Trp
                     85                  90                  95

Trp Glu Gln Gly Ser Thr Tyr Ser Glu Asp Gln Arg Lys Asp Arg Arg
                    100                 105                 110

Thr Val Phe Met His Asp Asp Trp Lys Arg His Arg Ser Ser Glu Arg
                    115                 120                 125

Phe Phe Arg Asn Ile Lys Thr Trp Pro Ser Ser Gly Ile Asn Gln Ala
                    130                 135                 140

Leu Arg Lys Glu Leu Thr Phe Val Thr Ser Val Ser Val Phe Val Val
145                 150                 155                 160

Leu Ala Asn Met Leu Leu Tyr Gln Tyr Gln Asp Phe Gly Gly Val Val
                    165                 170                 175

His Pro Gly Pro Leu Ser Phe Leu Asp Gly Pro Ile Lys Ser Leu Ser
                    180                 185                 190

Leu Pro Ala Leu Pro Phe Ser Met Ala Ser Pro Val Leu Ser Leu Leu
                    195                 200                 205

Leu Val Phe Arg Thr Asn Thr Ala Tyr Phe Arg Trp Asn Glu Ala Arg
                    210                 215                 220

Thr Leu Trp Gly Gly Leu Ile Asn Asn Cys Arg Asn Ile Val Arg Gln
225                 230                 235                 240

Thr Thr Thr Met Phe Pro Asn Asp Ala Tyr His Asn Ala Leu Lys Lys
                    245                 250                 255

Arg Leu Ala Thr Glu Thr Ala Thr Phe Ile Lys Ser Leu Arg Asn Phe
                    260                 265                 270

Leu Arg Gly Pro Glu Asp Asp Ala Thr Leu Arg Lys Glu Leu Tyr Ala
                    275                 280                 285

Tyr Val Asn Gln Gly Leu Met Thr Ser Ala Gln Ala Glu Ala Thr Leu
                    290                 295                 300

Ala Ala Lys Asn Arg Pro Met Phe Ala Leu Ala Met Ser Ala Thr
305                 310                 315                 320

Leu Arg Lys Ala Asn Ile Asp Glu Met Tyr Ile Ser Arg Met Asp Ser
                    325                 330                 335

Thr Ile Ser Val Leu Val Asp Leu Thr Gly Ala Asn Glu Arg Ile Phe
                    340                 345                 350

Lys Ser Pro Ile Pro Leu Val Tyr Thr Arg Leu Thr Ala Arg Phe Leu
                    355                 360                 365

Ser Val Phe Leu Thr Leu Leu Pro Leu Ala Met Trp Ala Ala Leu Gly
                    370                 375                 380

Glu Ser Trp Asn His Trp Ala Thr Ile Pro Ala Thr Phe Ile Leu Ser
385                 390                 395                 400

Val Phe Leu Phe Gly Val Glu Glu Val Gly Ile Gln Ile Glu Pro
                    405                 410                 415

Phe Ser Ile Leu Pro Leu Glu Ala Met Cys Asn Gly Ala Ile Glu Ala
                    420                 425                 430

Val Gln Leu Glu Met Leu Ala Ala Glu Gln Ser Gln Val Phe Glu Ala
                    435                 440                 445

Ala Gly Asp Ala Val Ala Val Ala
    450                 455

<210> SEQ ID NO 31
```

<211> LENGTH: 415
<212> TYPE: PRT
<213> ORGANISM: Fistulifera solaris

<400> SEQUENCE: 31

```
Met Arg Phe Thr Thr Arg Gln Leu Ile Val Gly Ile Ala Leu Thr Ala
1               5                   10                  15

Ser Leu His Gly Ala Phe Ala Phe Val Thr Pro Ser Val Val Gly Ser
            20                  25                  30

Ser Lys Ala Ser Lys Ser Ala Leu Asp Val Ser Thr Val Pro Arg Asn
        35                  40                  45

Asp Gly Ser Gly Leu Ser Tyr Gly Glu Arg Ser Arg Pro Phe Arg Arg
    50                  55                  60

Asn Phe Tyr Thr Gln Pro Asp Trp Glu Lys His Arg Ser Arg Asn Arg
65                  70                  75                  80

Phe Lys Gly Asn Leu Leu Ser Ile Thr Arg Ser Gly Val Ile Arg Gln
                85                  90                  95

Leu Thr Asn Glu Val Leu Phe Ile Thr Ala Val Ala Thr Ala Val Trp
            100                 105                 110

Ala Ile Asn Cys Leu Thr Ala Ala Gly Tyr Asp Asp Leu Asn Gly Val
        115                 120                 125

His His Glu Gly Leu Leu Pro Phe Pro Thr Leu Gln Met Pro Ser
    130                 135                 140

Glu Phe Phe Thr Phe Ser Ser Pro Ala Leu Ser Leu Leu Val Phe
145                 150                 155                 160

Lys Thr Asn Thr Ser Tyr Gly Arg Trp Asp Glu Ala Arg Lys Ala Trp
                165                 170                 175

Gly Val Ile Val Asn Ser Ser Arg Thr Ile Leu Arg Gln Gly Ala Ala
            180                 185                 190

Trp Leu Gln Glu Thr Asn Ile Pro Glu Arg Asp Lys Ile Arg Leu Ile
        195                 200                 205

Ala Arg Leu Ala Ala Ala Val Trp Cys Phe Pro Arg Ser Met Thr Arg
    210                 215                 220

His Val Leu Ser Ala Arg Glu Asp Asp Ala Ala Tyr Ala Glu Asp Cys
225                 230                 235                 240

Arg Ala Asn Leu Arg Pro Asp Leu Ala Glu Asp Leu Ile Ala Ala Arg
                245                 250                 255

His Lys Pro Thr Arg Ala Thr Tyr Glu Ile Ser Cys Ala Ile Asn Asp
            260                 265                 270

Leu Pro Leu Ser Asp Ile Gln Lys Ala Thr Leu Glu Tyr Ser Val Asn
        275                 280                 285

Gln Leu Cys Asp Ala Met Gly Ala Asn Asp Arg Ile Leu Ser Ser Pro
    290                 295                 300

Val Pro Leu Val Tyr Thr Arg His Leu Ala Arg Phe Leu Glu Val Trp
305                 310                 315                 320

Leu Leu Met Leu Pro Leu Gly Leu Trp Pro Asp Phe Thr Asn Ser Trp
                325                 330                 335

Asn His Ile Ala Met Ile Pro Ile Thr Val Leu Leu Ser Tyr Phe Leu
            340                 345                 350

Leu Gly Ile Glu Glu Leu Gly Val Gln Leu Glu Pro Phe Ser Val
        355                 360                 365

Leu Pro Leu His Lys Ile Thr Ser Gly Ile Gly Leu Ser Ala Glu Glu
    370                 375                 380

His Val Gln Trp Phe Leu Asn Asp Ser Ala Lys Ser Glu Met Lys Thr
```

```
              385                 390                 395                 400
Asn Ser Ala Gly Ser Thr Ser Pro Asn Tyr Gln Ser Leu Ser Pro
                405                 410                 415

<210> SEQ ID NO 32
<211> LENGTH: 430
<212> TYPE: PRT
<213> ORGANISM: Fistulifera solaris

<400> SEQUENCE: 32

Met Met Leu Arg Leu Ser Asn Ala Val Phe Ala Leu Ile Ala Leu Ala
1               5                   10                  15

Ser Val Ser Gln Gly Ser Ala Phe Ala Pro Ser Ser Thr Ser Ser Arg
            20                  25                  30

Val Asp Thr Ala Leu Phe Gly Asn Thr Gln Ser Pro Pro Pro Ile Pro
        35                  40                  45

Met Pro Lys Ala Ile Ser Tyr Gly Glu Glu Ser Arg Lys Tyr Arg Arg
    50                  55                  60

Thr Val Phe Thr His Asp Asp Trp Val Lys His Arg Ser Pro Glu Arg
65                  70                  75                  80

Phe Val Arg Asn Leu Ser Ser Ile Trp Ser Ser Val Tyr Lys Asn
                85                  90                  95

Leu Ala Asn Glu Val Met Ala Thr Thr Gly Val Ala Thr Phe Val Val
            100                 105                 110

Leu Tyr Asn Ala Leu Val Gly Gly Tyr Thr Asp Phe Ser Gly Val Ala
        115                 120                 125

His Ala Ala Pro Ile Gln Gly Leu Met Gln Val Gly Leu Pro Leu Ala
    130                 135                 140

Pro Phe Thr Leu Ser Ser Pro Ser Leu Gly Leu Leu Leu Val Phe Arg
145                 150                 155                 160

Thr Asn Thr Ser Tyr Gln Arg Trp Asp Glu Ala Arg Lys Asn Trp Gly
                165                 170                 175

Met Asn Ile Asn His Thr Arg Asp Leu Val Arg Met Gly Thr Ala Met
            180                 185                 190

Tyr Asp Arg Gln Gly Val Ser Pro Glu Lys Val Glu Lys Asp Leu Lys
        195                 200                 205

Thr Leu Ser Leu Cys Thr Trp Ala Phe Val Arg Ala Met Lys Arg His
    210                 215                 220

Leu Ser Pro Glu Ser Glu Asp Glu Ala Phe Lys Arg Glu Leu Tyr
225                 230                 235                 240

Glu Lys Leu Pro Ser Ala Gln Ala Ala Ile Ile Lys Ala Ala His
                245                 250                 255

Arg Pro Asn Arg Ala Leu Phe Asp Leu Ser Leu Ala Ile Glu Asn Leu
            260                 265                 270

Asn Met His Phe Met Arg Lys Asn Glu Ile His Lys Ala Ala Thr Ile
        275                 280                 285

Phe Glu Asp Asn Leu Gly Ser Ser Glu Arg Leu Leu Thr Ser Pro Val
    290                 295                 300

Pro Leu Phe Tyr Ser Arg His Leu Ala Arg Phe Leu Ser Leu Trp Leu
305                 310                 315                 320

Leu Leu Ile Pro Phe Ala Leu Tyr Asp Thr Leu Gly Gly Thr Trp Asn
                325                 330                 335

His Val Gly Leu Ile Pro Thr Thr Ala Val Leu Ser Thr Phe Leu Phe
            340                 345                 350
```

-continued

Gly Ile Glu Glu Leu Ala Ala Gln Met Glu Pro Phe Thr Ile Leu
            355                 360                 365

Pro Met Gln Ala Phe Cys Asp Lys Ile Gly Asn Trp Cys Asn Glu Ile
370                 375                 380

Val Ser Trp Ser Pro Gly Asp Asn Gly Met Glu Val Thr Ile Pro Ser
385                 390                 395                 400

Ala Val Glu Gln Asp His Val Val Glu Glu Met Val Ala Asn Gly
            405                 410                 415

Ser Thr Arg Pro Ser Leu Arg Lys Val Leu Gly Leu Lys Lys
            420                 425                 430

<210> SEQ ID NO 33
<211> LENGTH: 430
<212> TYPE: PRT
<213> ORGANISM: Fistulifera solaris

<400> SEQUENCE: 33

Met Met Leu Arg Leu Ser Ser Ala Val Phe Ala Leu Ile Ala Leu Ala
1               5                   10                  15

Ser Val Ser Gln Gly Ser Ala Phe Thr Pro Ser Ser Thr Ser Ser Arg
            20                  25                  30

Val Asp Thr Ala Leu Phe Gly Asn Thr Gln Ser Pro Pro Ile Pro
        35                  40                  45

Met Pro Lys Ala Ile Ser Tyr Gly Glu Ser Arg Lys Tyr Arg Arg
    50                  55                  60

Thr Val Phe Thr His Asp Asp Trp Val Lys His Arg Ser Pro Glu Arg
65                  70                  75                  80

Phe Val Arg Asn Leu Ser Ser Ile Trp Ser Ser Gly Val Tyr Lys Asn
                85                  90                  95

Leu Ala Asn Glu Val Met Ala Thr Thr Gly Val Ala Thr Phe Val Val
            100                 105                 110

Ile Tyr Asn Ala Leu Val Gly Gly Tyr Thr Asp Phe Ser Gly Val Ala
        115                 120                 125

His Ala Ala Pro Ile Gln Gly Leu Leu Gln Val Gly Leu Pro Leu Ala
    130                 135                 140

Pro Phe Thr Leu Ser Ser Pro Ser Leu Gly Leu Leu Leu Val Phe Arg
145                 150                 155                 160

Thr Asn Thr Ser Tyr Gln Arg Trp Asp Glu Ala Arg Lys Asn Trp Gly
                165                 170                 175

Met Asn Ile Asn His Thr Arg Asp Leu Val Arg Met Gly Thr Ala Met
            180                 185                 190

Tyr Asp Arg Gln Gly Val Pro Pro Glu Lys Val Glu Lys Asp Leu Lys
        195                 200                 205

Met Leu Ser Leu Cys Thr Trp Ala Phe Val Arg Ala Met Lys Arg His
    210                 215                 220

Leu Ser Pro Glu Ser Glu Asp Glu Glu Ala Phe Lys Arg Glu Leu Tyr
225                 230                 235                 240

Glu Lys Leu Pro Ser Ala Gln Ala Glu Ala Ile Ile Lys Ala Ala His
                245                 250                 255

Arg Pro Asn Arg Ala Leu Phe Asp Leu Ser Leu Ala Ile Glu Asn Leu
            260                 265                 270

Asn Met His Phe Met Arg Lys Asn Glu Ile His Lys Ala Ala Thr Ile
        275                 280                 285

Phe Glu Asp Asn Leu Gly Ser Ser Glu Arg Leu Leu Thr Ser Pro Val
    290                 295                 300

```
Pro Leu Phe Tyr Ser Arg His Leu Ala Arg Phe Leu Ser Leu Trp Leu
305                 310                 315                 320

Leu Leu Ile Pro Phe Ala Leu Tyr Asp Pro Leu Ala Gly Thr Trp Asn
            325                 330                 335

His Val Gly Leu Ile Pro Thr Thr Ala Met Leu Ser Val Phe Leu Phe
            340                 345                 350

Gly Ile Glu Glu Leu Ala Ala Gln Met Glu Glu Pro Phe Thr Ile Leu
            355                 360                 365

Pro Met Gln Ala Phe Cys Asp Lys Ile Gly Asn Trp Cys Asn Glu Ile
370                 375                 380

Val Ser Trp Ser Pro Gly Asp Asn Gly Met Glu Val Thr Ile Pro Ser
385                 390                 395                 400

Ala Val Glu Glu Asp His Val Val Glu Glu Met Met Val Ala Asn Gly
                405                 410                 415

Ser Thr Arg Pro Ser Leu Arg Lys Val Leu Gly Leu Lys Lys
            420                 425                 430

<210> SEQ ID NO 34
<211> LENGTH: 505
<212> TYPE: PRT
<213> ORGANISM: Fistulifera solaris

<400> SEQUENCE: 34

Met Val Arg Phe Thr Cys Ile Phe Pro Leu Val Ala Ala Leu Ile Ser
1               5                   10                  15

Asn Ala Ser Ala Phe Val Thr Pro Ala Asn Ser Val Ala Lys His Ala
            20                  25                  30

Thr Pro Arg Phe Glu Gly Asn Glu Arg Arg Leu Ile Ser Ala Pro Ser
        35                  40                  45

Asp Gly Ser Val Ala Lys Arg Ser Thr Ser Arg Phe Ser Ser Glu Gly
    50                  55                  60

Thr Gly Trp Asp Ser Phe Lys Gly Leu Arg Asp Phe Thr Asn Ile Pro
65                  70                  75                  80

Ser Gly Glu Glu Gln Arg Lys Phe Arg Arg Thr Val Tyr Thr His Lys
                85                  90                  95

Asp Trp Lys Lys His Arg Ser Gln Asp Arg Phe Val Phe Tyr Leu Leu
            100                 105                 110

Ala Met Phe Lys Ser Gly Val Tyr Lys Asn Ile Gly Arg Glu Val Ile
            115                 120                 125

Thr Ile Thr Ala Val Ala Ala Phe Val Cys Ile Tyr Asn Ser Leu Val
        130                 135                 140

Gly Gly Phe Thr Asp Leu Asn Gly Val Gln Gln Ala Ala Leu Leu Gln
145                 150                 155                 160

Ser Gln Phe Leu Pro Lys Leu Thr Leu Pro Leu Ser Leu Phe Thr Ile
                165                 170                 175

Thr Ser Ser Ser Leu Gly Leu Leu Leu Val Phe Arg Thr Asn Thr Ser
            180                 185                 190

Tyr Gln Arg Trp Asp Glu Ala Arg Lys Asn Trp Gly Met Asn Ile Asn
        195                 200                 205

His Thr Arg Asp Leu Val Arg Met Ala Asn Ala Tyr Tyr Asp Ser Thr
    210                 215                 220

Gly Val Pro Pro Glu Val Arg Ala Asp Met Asn His Val Ala Leu
225                 230                 235                 240

Cys Thr Trp Ala Phe Val Arg Cys Met Lys Arg His Leu Ser Pro Glu
```

```
                    245                 250                 255
Glu Glu Asp Glu Ala Asp Phe Gln Lys Glu Ile Leu Glu Lys Leu Pro
            260                 265                 270
Arg Gln Gln Ala Glu Met Ile Ile Ala Ala Ala His Arg Pro Asn Arg
        275                 280                 285
Ala Leu Gln Asp Leu Ser Tyr Ala Ile Asp Asp Leu Pro Met His Phe
    290                 295                 300
Ile Arg Lys Asn Glu Ile His Arg Ala Val Thr Ile Phe Glu Asp Asn
305                 310                 315                 320
Leu Gly Ser Ser Glu Arg Leu Leu Ser Ser Pro Val Pro Val Phe Tyr
            325                 330                 335
Ser Arg His Leu Ala Arg Phe Leu Ala Val Trp Leu Leu Phe Val Pro
        340                 345                 350
Phe Ala Leu Tyr Asp Ser Phe Asn Ala Ser Trp Asn His Ile Ala Met
    355                 360                 365
Val Pro Ala Thr Ala Val Met Ser Ile Phe Leu Val Gly Ile Glu Glu
370                 375                 380
Leu Gly Thr Gln Leu Glu Glu Pro Phe Thr Ile Leu Pro Met Gln Gly
385                 390                 395                 400
Phe Cys Asp Lys Ile Tyr Asn Trp Cys Met Glu Ile Ala Ser Trp Gln
            405                 410                 415
Pro Gly Asp Asn Gly Arg Pro Met Arg Pro Val Lys Pro Glu His Ala
        420                 425                 430
Tyr Phe Thr Ser Thr Ser Glu Gly Val Asn Gly Tyr Ala Asn Asn Tyr
    435                 440                 445
Tyr Thr Pro Gln Gln Ser Tyr Tyr Asn Glu Pro Ala Gln Pro Gln Gln
    450                 455                 460
Ser Tyr Tyr Ser Glu Pro Thr Pro Ala Pro Gln Tyr Tyr Asn Glu Pro
465                 470                 475                 480
Thr Pro Ala Gln Pro Ala Ala Asn Gln Gly Trp Val Asp Met Ala Glu
            485                 490                 495
Phe Leu Arg Arg Gln Gly Ser Gly Val
            500                 505

<210> SEQ ID NO 35
<211> LENGTH: 502
<212> TYPE: PRT
<213> ORGANISM: Fistulifera solaris

<400> SEQUENCE: 35

Met Val Arg Met Ile Cys Ile Leu Pro Leu Val Ala Ala Leu Ile Gly
1               5                   10                  15
Ser Ala Asn Ala Leu Val Ala Pro Ala Asn Asn Val Ala Lys Gln Ala
            20                  25                  30
Met Pro Arg Phe Ser Asn Asn Val Ala Lys Ser Ala Val Pro Arg Leu
        35                  40                  45
Leu Thr Ser Glu Gly Thr Arg Leu Phe Ser Ser Glu Gly Thr Gly Trp
    50                  55                  60
Asp Ser Phe Lys Gly Val Arg Asp Phe Thr Asn Ile Pro Ser Gly Glu
65                  70                  75                  80
Glu Gln Arg Lys Phe Arg Arg Thr Val Tyr Thr His Lys Asp Trp Lys
                85                  90                  95
Lys His Arg Ser Gln Asp Arg Phe Ile Tyr Tyr Leu Leu Ala Ile Phe
            100                 105                 110
```

```
Lys Ser Gly Val Tyr Lys Asn Ile Gly Arg Glu Val Ile Thr Ile Thr
            115                 120                 125

Ala Val Ala Ala Leu Val Cys Val Tyr Asn Ser Leu Val Gly Gly Tyr
        130                 135                 140

Thr Asp Leu Asn Gly Val Gln Ala Ala Leu Leu Gln Ser Gln Phe
145                 150                 155                 160

Leu Pro Lys Leu Thr Leu Pro Leu Ser Leu Phe Thr Ile Thr Ser Ser
                165                 170                 175

Ser Leu Gly Leu Leu Val Phe Arg Thr Asn Thr Ser Tyr Gln Arg
            180                 185                 190

Trp Asp Glu Ala Arg Lys Asn Trp Gly Met Asn Ile Asn His Thr Arg
        195                 200                 205

Asp Leu Val Arg Met Ala Asn Ala Tyr Tyr Asp Ser Thr Gly Val Pro
    210                 215                 220

Pro Glu Val Arg Ala Asp Asp Met Asn His Ile Ala Leu Cys Thr Trp
225                 230                 235                 240

Ala Phe Val Arg Cys Met Lys Arg His Leu Ser Pro Glu Glu Asp
            245                 250                 255

Glu Leu Asp Phe Gln Lys Glu Ile Leu Glu Lys Leu Pro Arg Lys Gln
        260                 265                 270

Ala Glu Met Ile Ile Ala Ala His Arg Pro Asn Arg Ala Leu Gln
    275                 280                 285

Asp Leu Ser Tyr Ala Ile Asp Asp Leu Pro Met His Phe Met Arg Lys
    290                 295                 300

Asn Glu Ile His Arg Ala Val Thr Ile Phe Glu Asp Asn Leu Gly Ser
305                 310                 315                 320

Ser Glu Arg Leu Leu Ser Ser Pro Val Pro Val Phe Tyr Ser Arg His
            325                 330                 335

Leu Ala Arg Phe Leu Ala Val Trp Leu Leu Phe Val Pro Phe Ala Leu
        340                 345                 350

Tyr Asp Ser Phe Asn Ala Ser Trp Asn His Ile Ala Met Val Pro Ala
    355                 360                 365

Thr Ala Val Met Ser Ile Phe Leu Val Gly Ile Glu Glu Leu Gly Thr
370                 375                 380

Gln Leu Glu Glu Pro Phe Thr Ile Leu Pro Met Gln Gly Phe Cys Asp
385                 390                 395                 400

Lys Ile Tyr Asn Trp Cys Met Glu Ile Ala Ser Trp Gln Pro Gly Asp
            405                 410                 415

Asn Gly Arg Ser Met Arg Pro Val Lys Pro Glu His Ala Tyr Phe Thr
        420                 425                 430

Ser Thr Ser Glu Gly Val Asn Gly Tyr Ser Asn Asn Tyr Tyr Thr Pro
    435                 440                 445

Gln Gln Ser Tyr Tyr Asn Glu Pro Ala Gln Pro Gln Gln Ser Tyr Tyr
    450                 455                 460

Ser Glu Pro Thr Pro Ala Pro Tyr Tyr Asn Glu Pro Thr Pro Ala
465                 470                 475                 480

Gln Pro Ala Gly Asn Gln Gly Trp Val Asp Met Ala Glu Phe Leu Arg
            485                 490                 495

Arg Gln Gly Ser Gly Val
            500

<210> SEQ ID NO 36
<211> LENGTH: 433
<212> TYPE: PRT
```

<213> ORGANISM: Fragilariopsis cylindrus CCMP1102

<400> SEQUENCE: 36

| | | | | | | | | | | | |
|---|---|---|---|---|---|---|---|---|---|---|---|
| Met | Gly | Leu | Ala | Ser | Thr | Leu | Ile | Glu | Glu | Val | Val | Glu | Glu | Val |
| 1 | | | | 5 | | | | | 10 | | | | | 15 |

Met Gly Leu Ala Ser Thr Leu Ile Glu Glu Val Val Glu Glu Val
1               5                   10                  15

Trp Val Pro Pro Ser Ser Phe Ser Thr Pro Asp Gln Tyr Asn Ser Ser
                20                  25                  30

Pro Thr Leu Ser Ala Gln Ser Pro Thr Ile Ser Val Thr Leu Pro Val
            35                  40                  45

Gly Leu Arg Pro Pro Lys Phe Gly Pro Lys Lys Asp Ile Thr Tyr Gly
50                  55                  60

Glu Asn Ser Arg Lys Phe Arg Arg Thr Val Tyr Thr His Glu Asp Trp
65                  70                  75                  80

Val Arg His Arg Ser Pro Asp Arg Phe Phe Arg Tyr Ile Ala Ser Val
                85                  90                  95

Pro Thr Ser Gly Ile Ala Lys Asn Leu Ala Arg Glu Leu Tyr Phe Leu
            100                 105                 110

Thr Ala Ile Thr Ala Ile Val Val Leu Tyr Asn Gly Leu Ile Thr Gly
            115                 120                 125

Tyr Gln Asp Ile Asn Gly Ile Ala His Gly Pro Val Trp Ser Ser Pro
130                 135                 140

Phe Leu Pro Pro Leu Thr Leu Pro Met Gln Pro Phe Ala Leu Ala Ser
145                 150                 155                 160

Pro Ser Leu Gly Leu Leu Leu Val Phe Arg Ser Asn Thr Ala Tyr Gln
            165                 170                 175

Arg Trp Asp Glu Ala Arg Lys Asn Trp Gly Met Asn Ile Asn His Thr
            180                 185                 190

Arg Asp Leu Asn Arg Met Ala Asn Ala Tyr Tyr Asp Lys Thr Gly Ile
            195                 200                 205

Ser Asp Glu Lys Arg Lys Asp Asp Leu Glu Arg Leu Ser Leu Cys Thr
210                 215                 220

Trp Ala Phe Val Arg Ala Met Lys Arg His Leu Ser Pro Ala Asp Glu
225                 230                 235                 240

Asp Glu Ala Ala Phe Lys Ala Glu Leu Tyr Gln Lys Leu Pro Lys Leu
            245                 250                 255

Gln Ala Gln Gln Ile Ile Lys Ala Ala His Arg Pro Asn Arg Ala Leu
            260                 265                 270

Tyr Asp Leu Ser Leu Ala Ile Glu Asn Leu Pro Met His Phe Leu Arg
            275                 280                 285

Lys Asn Lys Leu His Ala Ala Leu Thr Ile Phe Glu Asp Thr Leu Gly
            290                 295                 300

Ser Ser Glu Arg Leu Leu Thr Ser Pro Val Pro Leu Ile Tyr Asn Arg
305                 310                 315                 320

His Thr Ser Arg Phe Leu Leu Val Trp Leu Leu Leu Pro Phe Ala
            325                 330                 335

Leu Trp Glu Glu Phe Gly Phe Met Trp Asn His Ile Gly Met Ile Pro
            340                 345                 350

Gly Met Ser Ile Leu Gly Leu Leu Phe Gly Ile Glu Glu Leu Ala
            355                 360                 365

Thr Gln Leu Glu Glu Pro Phe Thr Ile Leu Pro Met Gln Ala Phe Cys
            370                 375                 380

Asp Lys Ile Trp Asn Trp Cys Asn Glu Ile Ala Ser Trp Glu Asp Gly
385                 390                 395                 400

```
Gln Asn Gly Ile Thr Thr Asn Arg Ser Tyr Gln Gly Arg Thr Glu Val
                405                 410                 415
Tyr Val Asp Asn Ser Tyr Glu Asn Glu Asn Ala Tyr Thr Thr Pro Thr
                420                 425                 430
Pro

<210> SEQ ID NO 37
<211> LENGTH: 430
<212> TYPE: PRT
<213> ORGANISM: Fragilariopsis cylindrus CCMP1102

<400> SEQUENCE: 37

Met Arg Phe Val Gly Val Ser Ser Leu Met Ser Met Ala Ala Val Met
 1               5                  10                  15
Thr Val Val Val Ser Cys His Val Gly Ser Ala Ser Ala Phe Val
                20                  25                  30
Pro Pro Ser Gly Lys Thr Ser Ser Trp Asn Ser Val Ala Ser Gln
                35                  40                  45
Gln Ala Lys Asp Pro Leu His Ile Leu Pro Pro Asp Ala Thr Asp Ile
        50                  55                  60
Pro Tyr Gly Glu Glu Ser Arg Lys Phe Arg Thr Val Tyr Thr His
65                  70                  75                  80
Asp Asp Trp Ile Lys His Arg Ser Pro Asp Arg Phe Phe Lys Thr Leu
                85                  90                  95
Arg Thr Thr Thr Thr Ser Gly Ile Tyr Lys Asn Val Gly Arg Glu Val
                100                 105                 110
Leu Ala Val Thr Phe Ile Ala Thr Phe Val Met Leu Trp Asn Met Leu
            115                 120                 125
Thr Gly Glu Tyr Thr Asp Leu Val Gly Leu Val His Pro Gly Ile Met
        130                 135                 140
Arg Gly Gln Phe Thr Pro Ser Leu Ala Leu Pro Met Ser Pro Phe Thr
145                 150                 155                 160
Leu Ser Ser Gly Phe Leu Gly Leu Leu Leu Val Phe Arg Thr Asn Lys
                165                 170                 175
Ala Tyr Gln Arg Trp Asp Glu Ala Arg Lys Asn Trp Gly Met Asn Ile
                180                 185                 190
Asn His Thr Arg Asp Leu Val Arg Met Gly Thr Thr Phe Tyr Asp Asp
            195                 200                 205
Ala Gln Ile Ser Asn Pro Glu Gln Arg Asp Ile Asp Leu Glu Arg Leu
        210                 215                 220
Ser Leu Cys Thr Trp Ala Phe Val Arg Ser Met Lys Arg His Leu Ser
225                 230                 235                 240
Pro Glu Trp Glu Asp Glu Gln Glu Phe Lys Met Glu Leu Tyr Gln Arg
                245                 250                 255
Leu Pro Ser Gln Gln Ala Gln Thr Ile Leu Asp Ala Ala His Arg Pro
                260                 265                 270
Asn Arg Ala Leu Tyr Asp Leu Ser Leu Ala Ile Glu Gln Leu Pro Met
            275                 280                 285
His Phe Ile Arg Lys Asp Gln Met His Lys Ala Leu Thr Ile Phe Glu
        290                 295                 300
Asp Asn Leu Gly Ser Ser Glu Arg Leu Leu Thr Ser Pro Val Pro Ile
305                 310                 315                 320
Phe Tyr Asn Arg His Val Ala Arg Phe Leu Phe Val Trp Leu Ala Phe
                325                 330                 335
```

```
Leu Pro Phe Ala Leu Tyr Asp Pro Phe Lys Glu Ser Trp Asn His Val
                340                 345                 350

Met Met Ile Pro Thr Thr Ala Leu Leu Ser Leu Phe Leu Phe Gly Ile
            355                 360                 365

Glu Glu Leu Ala Thr Gln Met Glu Glu Pro Phe Thr Ile Leu Pro Met
370                 375                 380

Gln Ala Phe Cys Asp Lys Ile Gly Asn Trp Cys Asn Glu Ile Val Ser
385                 390                 395                 400

Trp Lys Asp Gly Asp Asn Gly Val Tyr Asn Lys Pro Ser Asn Asn Phe
                405                 410                 415

Pro Ala Lys Gly His Asn Ser Val Tyr Phe Glu Ser Glu Leu
                420                 425                 430

<210> SEQ ID NO 38
<211> LENGTH: 393
<212> TYPE: PRT
<213> ORGANISM: Fragilariopsis cylindrus CCMP1102

<400> SEQUENCE: 38

Met Cys Phe Ala Phe Cys Glu Arg Leu Leu Asp Val Met Ser Ser Ser
1               5                   10                  15

Cys Asp Thr Ala Met Leu Leu Glu Lys Tyr Gln Val Thr Thr Lys Asp
            20                  25                  30

Ile Pro Tyr Gly Glu Thr Ser Arg Gln Phe Arg Arg Thr Val Tyr Thr
        35                  40                  45

His Asp Asp Trp Val Lys His Arg Ser Pro Asn Arg Phe Ile Lys Asn
    50                  55                  60

Leu Ser Thr Ile Val Ser Ser Gly Val Tyr Lys Asn Val Gly Arg Glu
65                  70                  75                  80

Val Ala Ser Thr Thr Ser Ile Ala Thr Phe Val Val Leu Trp Asn Met
                85                  90                  95

Leu Thr Val Gly Tyr Asp Asp Leu Asn Gln Ile His His Leu Pro Leu
            100                 105                 110

Ile Asn Ser Tyr Tyr Val Pro Gly Leu Thr Leu Pro Leu Gln Pro Phe
        115                 120                 125

Thr Leu Ala Ser Gly Ser Leu Gly Leu Leu Val Phe Arg Thr Asn
    130                 135                 140

Thr Ala Tyr Gln Arg Trp Asp Glu Ala Arg Lys Asn Trp Gly Met Asn
145                 150                 155                 160

Ile Asn His Thr Arg Asp Leu Val Arg Met Gly Asn Thr Phe Tyr Asp
                165                 170                 175

Arg Thr Gly Val Ser Asp Glu Thr Arg Lys Glu Asp Leu Gln Arg Leu
            180                 185                 190

Ser Val Cys Thr Trp Ser Phe Val Arg Cys Met Lys Arg His Leu Ser
        195                 200                 205

Pro Glu Trp Glu Asp Glu Ala Ala Phe Arg Leu Glu Met Phe Glu Arg
    210                 215                 220

Leu Pro Glu Ser Gln Ala Asn Ala Val Ile Asn Ala Ala His Arg Pro
225                 230                 235                 240

Asn Arg Ala Leu Phe Asp Leu Ser Met Ala Ile Glu Asn Leu Pro Met
                245                 250                 255

His Phe Met Arg Lys Asn Glu Met His Lys Ala Leu Thr Ile Phe Glu
            260                 265                 270

Asp Asn Leu Gly Ser Ser Glu Arg Leu Leu Thr Ser Pro Val Pro Leu
        275                 280                 285
```

```
Ile Tyr Asn Arg His Thr Leu Arg Phe Leu Ser Ile Trp Leu Leu Leu
            290                 295                 300

Met Pro Phe Ser Leu Tyr Lys Pro Phe Asp Ser Thr Trp Asn His Ile
305                 310                 315                 320

Gly Met Ile Pro Ala Thr Ala Met Ile Ser Leu Phe Leu Phe Gly Ile
                325                 330                 335

Glu Glu Leu Ala Thr Gln Met Glu Pro Phe Thr Ile Leu Pro Met
                340                 345                 350

Gln Ala Phe Cys Asp Lys Ile Gly His Ser Glu Val Tyr Phe Glu Asn
                355                 360                 365

Leu Gly Ser Ser Pro Gly Val Val Asp Gly Ser Asn Ala Phe Val Glu
            370                 375                 380

Gln Gln Pro Glu Ile Val Arg Val Pro
385                 390

<210> SEQ ID NO 39
<211> LENGTH: 467
<212> TYPE: PRT
<213> ORGANISM: Gonium pectorale

<400> SEQUENCE: 39

Met Leu Arg Pro Leu Pro Gly Cys Val Thr Ala Arg Arg Pro Ser Ala
1               5                   10                  15

Ser Cys Pro Ala Leu Trp Ser Val Glu Ala Val Leu Ser Thr Leu Arg
                20                  25                  30

Lys Lys Arg Leu Glu Pro Asn Thr Val Glu Arg Val Tyr Glu Ala Asp
            35                  40                  45

Val Tyr Pro Ala Val Phe Asp Phe Ala Ala Trp Thr Gln His Arg Ser
    50                  55                  60

Arg Gly Arg Tyr Leu Glu His Cys Ile Thr Leu Phe Arg Ser Tyr Phe
65                  70                  75                  80

Phe Arg Asp Leu Leu Gly Pro Leu Leu Val Leu Gly Ala Ala Val
                85                  90                  95

Ala Val Gly Leu Tyr Glu Thr Phe Leu Gln Glu Gly Leu Leu Pro Glu
                100                 105                 110

Trp Val Pro Asp Phe Gly Gly Val Ser Asp Thr Pro Phe Gln Leu Thr
            115                 120                 125

Ser Phe Ala Leu Ser Leu Met Leu Val Phe Arg Thr Asn Ser Ser Tyr
130                 135                 140

Ala Arg Trp Leu Asp Ala Arg Gln Gln Trp Gly Leu Ile Val Asn Thr
145                 150                 155                 160

Ala Arg Thr Phe Val Arg Gln Ala Met Thr Thr Leu Pro Glu Asp Ser
                165                 170                 175

Cys Ser Glu Leu Arg Asp Ala Val Ala Arg Trp Thr Ile Ala Phe Val
                180                 185                 190

Arg Leu Ser Lys Leu His Leu Arg Glu His Gly Asp Val Arg Ala Glu
            195                 200                 205

Met Gln Gly Val Leu Arg Gly Glu Leu Pro Leu Val Ala Ala Ala
            210                 215                 220

Ala His Arg Pro Leu Ala Ala Cys His Val Leu Ser Gln Leu Met Ala
225                 230                 235                 240

Ala Ala Gly Ala Gly Ala Ile Ser Asp Gln Ser Arg Gln Arg Leu
                245                 250                 255

Glu Ala Asp Ile Asn Gly Leu Ser Gln Ala Leu Gly Ala Cys Glu Lys
```

```
                260                 265                 270
Ile Leu Arg Asn Pro Ile Pro Leu Ser Tyr Thr Arg His Thr Ser Arg
                275                 280                 285
Phe Leu Ile Leu Trp Leu Leu Trp Leu Pro Val Ala Leu Trp Gly Lys
                290                 295                 300
Ala Gly Trp Cys Val Val Pro Val Glu Ala Ile Leu Thr Tyr Leu Leu
305                 310                 315                 320
Leu Gly Ile Asp Glu Ile Ala Ile Gln Met Glu Glu Pro Phe Gly Ile
                325                 330                 335
Leu Pro Leu Glu Asn Phe Cys Asp Ala Val Gln Gln Ser Val Glu Gln
                340                 345                 350
Val Thr Arg Met Asp His Ser Val His Asp Val Val Ser Ser Tyr Val
                355                 360                 365
Cys Ala Leu Val Pro Ala Ala Pro Ala Thr Ala Ala Pro Pro Val
370                 375                 380
Ala Ala Pro Pro Ala Thr Ala Met Gly Gly Thr Ala Ser Ala Val Val
385                 390                 395                 400
Ala Ala Ala Ala Ala Glu Glu Ser Ser Pro Val Ala Ala Ser Val Thr
                405                 410                 415
Ala Thr Ala Ala Pro Gly Asp Leu Asn Arg Ala Ala Arg Asp Gln Gly
                420                 425                 430
Ser Gly Met Glu Gly Ser Gly Val Gly Asp Gly Ser Gly Asp Gly Arg
                435                 440                 445
Thr Gly Gln Gly Phe Trp Gln Ala Ile Trp Thr Pro Asn Ile Pro Ser
                450                 455                 460
Asp Arg Cys
465

<210> SEQ ID NO 40
<211> LENGTH: 481
<212> TYPE: PRT
<213> ORGANISM: Gonium pectorale

<400> SEQUENCE: 40

Met Gln Gly Arg Ala Gly Ala Ala Val Glu Glu Gly Val Ser Leu Pro
1               5                   10                  15
Thr Pro Thr Arg Asn Pro Val Phe Asn Pro Thr Arg Trp Ser Tyr His
                20                  25                  30
Arg Ser Thr Ser Arg Tyr Gly Arg His Leu Thr Thr Ile Phe Lys Ser
                35                  40                  45
Val Thr Phe Arg Asn Leu Gln Ala Pro Leu Ser Phe Leu Thr Met Met
            50                  55                  60
Ala Cys Leu Val Val Leu Tyr Arg Thr Ser Val Glu Leu Glu Gln Leu
65                  70                  75                  80
Pro Asp Phe Phe Glu Gly Val Thr Phe Thr Asp Val Pro Phe Gln Leu
                85                  90                  95
Thr Ser Phe Ala Leu Ser Leu Leu Leu Val Phe Arg Thr Asp Ala Gly
                100                 105                 110
Tyr Gly Arg Trp Cys Ala Ala Met Asp Ala Trp Gly Thr Leu Arg Asn
                115                 120                 125
Ala Ser Ala Asp Leu Ile Arg Lys Ala Ser Ala Trp Val Asp Asp Gly
            130                 135                 140
Pro His Leu Arg Arg Leu Val Arg Trp Val Ala Ala Phe Pro Leu Cys
145                 150                 155                 160
```

```
Leu Met Val Glu Leu Arg His Asp Gln Gly Asp Pro Ala Met Glu Gly
            165                 170                 175

Ala Leu Arg Ala Glu Leu Ala Arg Val Leu Arg Pro Tyr Glu Leu Gln
        180                 185                 190

Gln Val Leu Ala Ala Gly Pro Tyr His His Gln Phe Cys Leu Ser Val
        195                 200                 205

Leu Thr Ala Leu Val Glu Ala Gln Leu Gly Glu Ser Arg Glu Thr
        210                 215                 220

Ala Met Leu Glu Asp Leu His Gly Phe Asn Asp Ala Cys Glu Cys
225                 230                 235                 240

Glu Lys Ile Leu Arg Phe Pro Ile Pro Leu Thr Tyr Thr Arg His Thr
                245                 250                 255

Ser Arg Phe Met Leu Ile Tyr Leu Ser Ala Leu Pro Leu Ala Leu Tyr
                260                 265                 270

Asp Ser Cys Asp Trp Ala Val Ile Pro Val Thr Ala Val Ile Ala Phe
            275                 280                 285

Leu Leu Leu Gly Ile Glu Asp Ile Gly Val Gln Ile Glu Glu Pro Phe
        290                 295                 300

Ser Ile Leu Pro Leu Pro Asp Ile Cys Ala Asp Leu His Met Thr Ala
305                 310                 315                 320

Gln Arg Ala Val Ala Gln Arg Asp Met Val Arg Cys Leu Ala Asp Pro
                325                 330                 335

Ala Val Cys Arg Val Arg Asp Glu Asp Leu Glu Pro Thr Ala Arg Arg
            340                 345                 350

His Ala Ala Ala His Gly Gly Pro Gly Thr Ser Tyr Gly Glu Gly Arg
        355                 360                 365

Gly His Ala Ala Thr Gly His Pro Gly Ala Gly Pro Asp Ala Trp Gln
        370                 375                 380

Gly Asp Glu Tyr Val Val Glu Ala Gly Phe Gly Ser Gly Gly Val Ala
385                 390                 395                 400

Gly Gly Gly Gly Val Gly Ala Gly Ala Gly Ala Gly Ser Ala Arg
                405                 410                 415

Ser Asn Gly Asn Gly Ala Gly Gly Ala Gly Gly Gly Gly Lys
                420                 425                 430

Gly Val Gly Ala Arg Gly Arg Phe Val Glu Ser Gly Lys Gly Pro Gly
        435                 440                 445

Leu Val Ala Ala Ile Ser Glu Asn Gly Asn Gly Asn Gly Tyr Asn Gly
        450                 455                 460

Asn Gly Asn Gly Tyr Ser Gly Gly Thr Ala Ser Gly Trp Pro His Arg
465                 470                 475                 480

Pro

<210> SEQ ID NO 41
<211> LENGTH: 308
<212> TYPE: PRT
<213> ORGANISM: Gonium pectorale

<400> SEQUENCE: 41

Met Arg Val Ala Trp Ser Gly Ile Val Arg Gly Ile Ser Ala Pro Val
1               5                   10                  15

Leu Phe Val Thr Ala Phe Thr Ala Val Val Ala Ala Leu Asn Ala Ala
                20                  25                  30

His Ala Ala Ser Leu Leu Pro Ala Trp Val Pro Ala Met Pro Ala Ile
            35                  40                  45
```

```
Ala Ile Glu Pro Val Gln Leu Thr Ser Ile Ala Leu Ser Leu Leu Leu
 50                  55                  60

Val Phe Arg Thr Asn Ala Ser Tyr Ser Arg Trp Asp Glu Gly Arg Arg
 65                  70                  75                  80

Ser Phe Gly Ser Ile Thr Thr Val Ser Arg Asp Ile Ala Arg Gln Ala
                 85                  90                  95

Phe Ala Trp Phe Arg Pro Asp Asp Gly His Asn Arg Arg Arg Leu Gly
            100                 105                 110

Arg Trp Leu Val Ala Leu Gly Arg Ser Thr Met Val His Leu Arg Glu
        115                 120                 125

Glu His Lys Met Glu Asp Glu Leu Lys Tyr Val Leu Glu Pro Gln Glu
    130                 135                 140

Val Glu Ala Val Leu Ser Ser Val His Ala Pro Ser Phe Cys Leu Gln
145                 150                 155                 160

Met Ile Thr Trp Ile Ile Arg His Ala Gly Leu Pro Gln Glu Leu Val
                165                 170                 175

Ile Arg Met Asp Glu Asn Val Ser Arg Leu Thr Asp Ala Val Ser Ala
            180                 185                 190

Cys Glu Arg Ile Leu Asn Thr Pro Ile Pro Leu Ser Tyr Thr Arg His
        195                 200                 205

Thr Ala Arg Phe Leu Met Ala Trp Leu Val Cys Leu Pro Phe Cys Leu
    210                 215                 220

Trp Pro Tyr Cys Gly Pro Ala Met Ile Pro Ile Ala Ala Leu Ile Ala
225                 230                 235                 240

Phe Val Leu Leu Gly Ile Glu Glu Ile Gly Val Tyr Ile Glu Glu Pro
                245                 250                 255

Phe Ser Ile Leu Ala Leu Glu Lys Leu Val Asn Lys Leu Glu Asn Ile
            260                 265                 270

Ile Asn Ala Met Leu His Glu Trp Gln Asn Leu Asp Glu Leu Ser Arg
        275                 280                 285

Thr Ala Met Gly Thr Ala Asn Gly Ser Gln Pro Val Ser Ala Ala Ala
    290                 295                 300

Ser Ala Thr Ala
305

<210> SEQ ID NO 42
<211> LENGTH: 447
<212> TYPE: PRT
<213> ORGANISM: Gonium pectorale

<400> SEQUENCE: 42

Met Gln Leu Ser Gly Arg Gln Gln Ala Leu Ser Ala Arg Gly Val Ala
 1               5                  10                  15

Pro Leu Pro Ser Arg Leu Cys Arg Lys Arg Leu Ile Ile Ala Ala Asn
                20                  25                  30

Ala Ala Lys Asp Pro Asn Ala Pro Ile Gln Ser Asn Pro Leu Gly Thr
            35                  40                  45

Leu Ser Ser Gln Gly Asn Thr Met Ala Thr Pro Pro Arg Ser Glu Ala
 50                  55                  60

Ala Arg Lys Tyr Phe Arg Thr Val Tyr Asp Phe Pro Gln Trp Gln Glu
 65                  70                  75                  80

His Arg Ser Gln Phe Arg Leu Met Lys Arg Leu Phe Thr Ile Pro Gln
                85                  90                  95

Ser His Val Ile Gln Asn Ala Leu Pro Ser Ile Ser Trp Val Gly Val
            100                 105                 110
```

```
Val Ser Thr Ala Leu Thr Leu Tyr Met Thr Ala His Asp Gln His Ile
        115                 120                 125

Leu Pro Glu Gly Phe Pro Ser Leu Val Pro Asn Ala Ser Cys Ser Ala
        130                 135                 140

Phe Ile Ser Asn Thr Ser Val Ala Leu Ser Leu Leu Val Phe Arg
145                 150                 155                 160

Thr Asn Ser Ser Tyr Gly Arg Trp Asp Glu Ala Arg Lys Met Trp Gly
                165                 170                 175

Gly Leu Leu Asn Arg Ser Arg Asp Ile Met Arg Gln Gly Ala Thr Cys
                180                 185                 190

Phe Pro Asp Asp Gln Val Glu Ala Lys Lys Ala Leu Ala Arg Trp Val
        195                 200                 205

Val Ala Phe Ala Arg Ala Leu Arg Ile His Phe Gln Pro Glu Val Thr
        210                 215                 220

Ile Glu Ser Glu Leu Lys Asn Ile Leu Thr Pro Ala Glu Leu Glu Met
225                 230                 235                 240

Leu Ala Lys Ser Gln His Arg Pro Val Arg Ala Ile His Ala Ile Ser
                245                 250                 255

Gln Ile Ile Gln Ser Val Pro Met Ser Ser Ile His Gln Met Gln Met
        260                 265                 270

Ser Asn Asn Leu Thr Phe Phe His Asp Val Leu Gly Gly Cys Glu Arg
        275                 280                 285

Leu Leu Arg Ala Pro Ile Pro Val Ser Tyr Thr Arg His Thr Ala Arg
        290                 295                 300

Phe Leu Phe Thr Trp Leu Ser Leu Leu Pro Phe Ala Leu Tyr Gly Gln
305                 310                 315                 320

Cys Gly Ala Gly Val Ile Pro Val Ser Thr Gly Ile Ala Ala Val Leu
                325                 330                 335

Cys Gly Ile Glu Glu Ile Gly Val Gln Cys Glu Glu Pro Phe Gly Ile
                340                 345                 350

Leu Pro Leu Asp Val Ile Cys Asn Arg Ile Gln Ala Asp Val Met Ala
        355                 360                 365

Thr Leu Lys Asp Asp Ala Asp Thr Lys Thr Ile Leu Ala Glu Ala Gly
        370                 375                 380

Leu Val Ser Leu Leu Pro Ser Ala Ala Ser Ala Met Ala His Thr Ser
385                 390                 395                 400

Ala Ser Ser Asn Gly Asn Gly Asn Gly Ala Asn Gly Asn Gly Ala Asn
                405                 410                 415

Gly Asn Gly Ala Asn Gly Asn Gly Ala Ala Val Ala Ala Pro Gln Val
                420                 425                 430

Pro Val Ser Ala Ser Ala Gly Met Thr Val Gln Ile Ser Pro Arg
        435                 440                 445

<210> SEQ ID NO 43
<211> LENGTH: 1866
<212> TYPE: PRT
<213> ORGANISM: Gonium pectorale

<400> SEQUENCE: 43

Met Glu His Thr Gly Pro Ser Leu Ala Gly Pro Pro Pro Pro Pro Pro
1               5                   10                  15

Leu Ala Ser Ala Pro Ser Val Ala Val Glu Arg Ser Gly Ser Glu Met
            20                  25                  30

Gly Ser Ala Leu Pro Tyr Arg Arg Arg Ser Thr Ala Pro Ala Val Ala
```

-continued

```
                35                  40                  45
Ala Pro Pro Pro Ser Val Met Val Pro Ala Ala Ala Gly Pro
 50                  55                  60

Ala Ala Ala Thr Ala Leu Ala Arg His Gln Pro Gln Ala Ala Ala
 65                  70                  75                  80

Ala Gly Ala Ala Pro Phe Pro Gly Ala Ala Pro Leu Pro Pro Ala
                 85                  90                  95

Leu Gln Ala Ser Thr Ser Arg Val Gly Arg Leu Leu Gln Glu Arg Phe
                100                 105                 110

Arg Arg Cys Arg Ser His Gln Ala Phe Asn Trp Thr Pro Glu Glu Ala
                115                 120                 125

Pro Leu Ser Pro Pro Pro Pro Pro Pro Leu Ser Pro Pro Leu Pro
    130                 135                 140

Ala Val Gln Lys Trp Ala Ala Ser Thr Val Pro Lys Pro Gly Pro Ala
145                 150                 155                 160

Ala Ala Ala Ala Ala Ala Ala Pro Pro Thr Pro Tyr Leu Ser Pro
                165                 170                 175

Ser Pro Ser Thr Ser Pro Ser Pro Ser Pro Pro Pro Gln
                180                 185                 190

Ala Thr Ala Ala Ala Ser Ala Ala Ser Gly Ala Asp Gly Asp Phe Met
                195                 200                 205

Thr Ala Ala Val Ser Glu Leu Val Glu Arg Pro Phe Arg Leu Val Val
    210                 215                 220

Val Ala Asn Arg Leu Pro Val Thr Cys Val Gln Asp Ala Pro Gly Gly
225                 230                 235                 240

Glu Trp Gln Leu Lys Ala Ser Ser Gly Gly Leu Val Ser Ala Leu Arg
                245                 250                 255

Gly Leu Gly Phe Arg Ser Ser Met Trp Ile Gly Trp Pro Gly Val Trp
                260                 265                 270

Leu Pro Pro Gly Ser Asp Arg Asn Arg Leu Thr Glu Leu Leu Arg Arg
    275                 280                 285

Asp Gly Tyr Glu Pro Val Trp Leu Glu Ser Lys Leu Met Asp Leu Phe
    290                 295                 300

Tyr Lys Gly Phe Cys Asn Ser Val Leu Trp Gln Leu Phe His Tyr Asp
305                 310                 315                 320

Pro Pro Ser Leu Glu Gly Trp Ala Arg Ser Ala Glu Gln Gln Ala Ser
                325                 330                 335

Ser Gln Ala Ala Gln Trp Gly Ala Tyr Val Glu Ala Asn Gly Arg Phe
                340                 345                 350

Ala Asp Ala Val Leu Ala Thr His Gly Ser Ala Asp Met Val Trp Val
    355                 360                 365

His Asp Tyr His Leu Met Leu Leu Pro Gly Ile Leu Lys Arg Ala Val
    370                 375                 380

Pro Lys Met Arg Val Gly Phe Phe Leu His Thr Pro Phe Pro Ser Ser
385                 390                 395                 400

Glu Val Tyr Arg Ala Leu Pro Val Arg Glu Gln Val Ser Gly Gly Gly
                405                 410                 415

Gly Gly Gly Glu Ser Arg Leu Trp Ile Leu Ser Gly Leu Ala Ala
                420                 425                 430

Asp Leu Val Gly Phe His Thr Tyr Asp Tyr Ala Arg His Phe Ile Ser
    435                 440                 445

Ala Cys Ala Arg Ile Leu Gly Leu Glu Gly Thr Pro Glu Gly Val Glu
450                 455                 460
```

```
Thr His Gly Ser Leu Thr Arg Val Gly Thr Phe Pro Ile Gly Ile Glu
465                 470                 475                 480

Thr Cys Arg Phe Val Arg Ala Ala Ala Asp Pro Asp Val Val Arg Gln
                    485                 490                 495

Val Ala Ala Leu Arg Thr Arg Phe Val Gly Arg Lys Ile Val Leu Gly
                500                 505                 510

Val Asp Arg Leu Asp Pro Ile Lys Gly Leu Pro His Lys Leu Leu Ala
                515                 520                 525

Phe Glu Lys Leu Leu Glu Glu Gln Pro Tyr Trp Arg Asp Lys Val Val
530                 535                 540

Leu Val Gln Ile Ala Val Pro Ser Arg Thr Asp Val Pro Glu Tyr Gln
545                 550                 555                 560

His Leu Ser Ser Ile Val His Glu Ile Val Gly Arg Val Asn Gly Leu
                565                 570                 575

Tyr Gly Ser Leu Thr His Val Pro Ile His Tyr Leu Asp Thr Cys Leu
                580                 585                 590

Ala Phe Ser Gln Leu Val Ala Leu Tyr Gly Ala Thr Asp Val Ala Leu
                595                 600                 605

Val Thr Ser Leu Arg Asp Gly Met Asn Leu Val Ser Tyr Glu Phe Val
610                 615                 620

Ala Cys Gln Gly Asp Gly Ser Gly Pro Glu Pro Gly Val Leu Leu
625                 630                 635                 640

Leu Ser Glu Phe Ala Gly Ala Ala Gln Thr His Thr Ala Gln His Trp
                645                 650                 655

Ala Asp Thr Phe Leu Ser Glu Leu Asn Asp Thr His Ile Glu Ala Asp
                660                 665                 670

Leu Arg Gly Arg Ala Ala Pro Gln Leu Asp Val Arg Gln Val Leu
                675                 680                 685

Glu Ala Tyr Gly Ser Ser Arg Arg Arg Leu Phe Val Leu Ser Tyr Ser
690                 695                 700

Ala Val Leu Thr Ala Gly Gly Glu Ala Ala Gly Pro Asp Pro Ala
705                 710                 715                 720

Asn Val Val Val Leu Met Gly Gly Cys Glu Ala Gly Arg Met Glu Ala
                725                 730                 735

Leu Ala Gly Arg Gln Leu Ala Gly Ala Trp Leu Ala Ala Glu Asn Gly
                740                 745                 750

Leu Leu Val Arg Pro Pro Val Pro Pro Glu Ala Leu Asp Gly Asp Asp
                755                 760                 765

Asp Ser Gly Gly Ala Pro Ala Ala Ala Thr Thr Val Pro Ala Arg
                770                 775                 780

Gln Ala Ala Tyr Ser Pro Ser Ser Ser Gly His Pro Thr Ala Ser
785                 790                 795                 800

Gln Pro Pro Gln Pro Pro Leu Pro Arg Gly Trp Arg Trp Leu Pro Gly
                805                 810                 815

Gly Pro Pro Ala Ser Leu Pro Pro Ser Ala Leu Pro Ser Ala Ser Pro
                820                 825                 830

Ser Thr Ser Pro Ser Pro Arg Gly Leu Ala Ala Ala Arg Cys Val Leu
                835                 840                 845

Asp Tyr Phe Cys Glu Arg Thr Pro Gly Ser Phe Val Glu Ala Arg Gln
                850                 855                 860

Thr Ser Leu Val Trp Asn Tyr Lys Tyr Thr Asp Ala Glu Phe Gly Ser
865                 870                 875                 880
```

```
Leu Gln Ala Arg Asp Leu Leu Gln His Leu Arg Ala Gly Pro Ile Gly
            885                 890                 895

Asn Glu Pro Leu Glu Val Val Gln Ser Gly Arg Ser Val Glu Ile Arg
        900                 905                 910

Pro Val Gly Val Thr Lys Gly Thr Ser Met Met Arg Leu Leu Gly Leu
        915                 920                 925

Leu Ala Gly Gly Gly Gly Gly Pro Pro Ser Gly Gly Gly Ala
        930                 935                 940

Ala Ala Ala Ser Thr Pro Asp Ser Gly Gly Arg Ser Ala Ser Arg
945                 950                 955                 960

Gly Tyr Gly Gly Phe Asn Gly His Gly Asn Gly Thr Ser Arg Asn Gly
            965                 970                 975

Gly Gly Gly Gly Ser Trp Arg Arg Val Gly Ala Gly Arg Arg Arg Leu
            980                 985                 990

Ser Ile Asp Gly Gly Arg Pro Ser Val Asp Gly Gly Arg Gly Thr Leu
            995                 1000                1005

Leu Pro Phe Arg Ala Gly Gly Ala Gly Gly Ala Ser Gly Ala Pro
        1010                1015                1020

Ala Val Gly Gly Gly Ser Asp Gly Arg Gly Gly Ser Arg Glu Val Glu
1025                1030                1035                1040

Gln Gly Ser Ser Gly Gly Asp Gly Gly Gly Arg Asp Ala Ala Thr
        1045                1050                1055

Ala Ala Ala Ala Ala Ala Gly Phe Asp Phe Ala Leu Val Val Cys Gly
        1060                1065                1070

His Leu Thr Pro Arg Asp Glu Asp Met Phe Ile Leu Phe Arg Asp Asp
        1075                1080                1085

Gly Asn Ser Gly Gly Gly Gly Cys Gly Ala Ser Ala Ser Ala Val Arg
        1090                1095                1100

Ala Pro Asp Ala Ser Gly Pro Ala Asn Gly Phe Ala Ala Asn Gly Leu
1105                1110                1115                1120

Val Gln Asn Gly Gly Gly Gly Gln Ala Ile Pro His Ala Pro Ala Pro
        1125                1130                1135

Ala Ser Arg Pro Gln Val Ala Glu Gly Leu Gly Ala Asn Ala Gly Gly
        1140                1145                1150

Gly Gly Gly Ile Gly Gly Thr Gly Gly Thr Gly Gly Asp Gly
        1155                1160                1165

Gly Ala Pro Gly Asn Arg Arg Arg Cys Ala Ser Phe Thr Val Ala Leu
        1170                1175                1180

Gly Arg Arg Pro Ser Cys Ala Ser Ser Ser Leu Gly Gly Gly Gln
1185                1190                1195                1200

Leu Val Asp Leu Leu Gln Ala Leu Ala Ala Gly Arg Ala Ala Ala Pro
        1205                1210                1215

Ser Gln Gly Glu Pro Pro Gly Ala Ala Ala Gly Thr Ala Ala Pro Ile
        1220                1225                1230

Ser Asp Pro Asn Asn Arg Arg Arg Gln Gly Val Val Ala Asp Ala Pro
        1235                1240                1245

Pro Gln Pro His Ser His Glu Arg Trp Gln Pro Lys Ala Gly Gly Thr
        1250                1255                1260

Ser Ala Ile Arg Thr Gln Arg Arg Gly Ser Asp Gly Asp Leu Gly Ala
1265                1270                1275                1280

Ala Gly Thr Ala Ala Gly Ala Ala Ala Gly Val Thr Thr Gly Asn Gly
        1285                1290                1295

Ile Ala Glu Cys Thr Ala Gly Arg Arg Ser Ala Arg Val His Glu Pro
```

-continued

```
                1300                1305                1310
His Thr Thr Val Arg Gln Ala Ser Glu Pro Ser Glu Gly Glu Ser Pro
            1315                1320                1325
Phe Thr Ala Asp Gly Ala Gly Gly Gly Arg Ser Gly Ser Asp Ala
            1330                1335                1340
Asp Ala Asp Ala Asp Ala Pro Asp Ala Asn Asp Gly Asp Gly Asp Gly
1345                1350                1355                1360
Gly Asp Gly Asp Gly Pro Leu Arg Pro Leu Ala Glu Pro Leu Ser Ala
            1365                1370                1375
Phe Pro Ser Pro Val Leu Pro Ala Ala Ala Ser Pro Leu Ala Phe Gly
            1380                1385                1390
Gly Thr Pro Leu Gln Ala Phe Ala Arg Trp Ala Ala Ala Pro Ala Ala
            1395                1400                1405
Ala Gly Ala Ala Ala Val His Ser Gly Ser Ser Asn Ser Gly Gly Gly
            1410                1415                1420
Arg Ser Gly Gly Arg Gly Phe Gly Ser Gly Ala Ala Gly Gly Gly Gly
1425                1430                1435                1440
Gly Gly Gly Cys Val Ala Arg Arg Ser Leu Val Val Ala Asn Ala
            1445                1450                1455
Ala Lys Asp Pro Asn Ala Pro Ile Gln Ser Asn Pro Leu Gly Thr Leu
            1460                1465                1470
Ser Ser Gln Ser Gly Thr Val Ser Val Leu Pro Arg Ser Glu Glu Ala
            1475                1480                1485
Arg Arg Tyr Trp Arg Thr Val Tyr Asp Phe Pro Gln Trp Gln Lys His
            1490                1495                1500
Arg Ser Ser Tyr Arg Phe Ala Glu Arg Leu Phe Gln Leu Ser Gln Ser
1505                1510                1515                1520
His Ile Leu Gln Asn Ala Leu Pro Ser Ile Ser Trp Val Thr Leu Val
            1525                1530                1535
Ala Thr Ala Val Ala Ala Tyr Gly Thr Ala Tyr Asp Ala Glu Met Leu
            1540                1545                1550
Pro Glu Ile Leu Pro Ser Ile Ala Pro Asn Ala Ser Cys Thr Ala Phe
            1555                1560                1565
Ile Ser Asn Thr Ser Val Ala Leu Ser Leu Leu Val Phe Arg Thr
            1570                1575                1580
Asn Ser Ser Tyr Gly Arg Trp Asp Glu Ala Arg Lys Met Trp Gly Gly
1585                1590                1595                1600
Leu Leu Asn Arg Ser Arg Asp Ile Met Arg Gln Gly Ala Thr Cys Phe
            1605                1610                1615
Pro Asp Asp Gln Val Glu Ala Lys Lys Ala Leu Ala Arg Trp Val Val
            1620                1625                1630
Ala Phe Ala Arg Ala Leu Arg Ile His Phe Gln Pro Glu Val Thr Leu
            1635                1640                1645
Glu Ser Glu Leu Lys Asn Ile Leu Thr Pro Ala Glu Leu Glu Met Leu
            1650                1655                1660
Ala Lys Ser Gln His Arg Pro Val Arg Ala Ile His Ala Ile Ser Gln
1665                1670                1675                1680
Ile Ile Gln Ser Val Pro Met Ser Ser Ile His Gln Met Gln Met Ser
            1685                1690                1695
Asn Asn Leu Thr Phe Tyr His Asp Val Leu Gly Gly Cys Glu Arg Leu
            1700                1705                1710
Leu Arg Ala Pro Ile Pro Val Ser Tyr Thr Arg His Thr Ala Arg Phe
            1715                1720                1725
```

```
Leu Phe Ala Trp Leu Thr Leu Leu Pro Phe Ala Leu Tyr Pro Thr Val
    1730                1735                1740

Gly Trp Gly Val Val Pro Val Cys Thr Gly Ile Ala Ala Val Leu Cys
1745                1750                1755                1760

Gly Ile Glu Glu Ile Gly Val Gln Cys Glu Glu Pro Phe Gly Ile Leu
            1765                1770                1775

Pro Leu Asp Val Ile Cys Asn Arg Ile Gln Ala Asp Val Met Ala Thr
            1780                1785                1790

Leu Lys Asp Asp Ala Asp Thr Lys Thr Val Leu Ala Glu Ala Gly Leu
        1795                1800                1805

Leu Asn Leu Val Pro Ser Ala Ala Ala Val Pro Val Ala Ser Ala
    1810                1815                1820

Ala Pro Ala Ala Pro Ala Ala Gln Gln Pro Ala Met Ala Gly Ser
1825                1830                1835                1840

Ala Ser Ser Ser Ser Ala Gly Arg Gly Pro Ser Asn Gly Leu Gln Val
                1845                1850                1855

Arg Val Ala Ile Gly Ser Gln Asp Lys Gln
            1860                1865

<210> SEQ ID NO 44
<211> LENGTH: 381
<212> TYPE: PRT
<213> ORGANISM: Klebsormidium nitens

<400> SEQUENCE: 44

Met Asn Ala Pro Lys Ile Asp Pro Glu Pro Leu Leu Glu Tyr Leu Gln
1               5                   10                  15

Asp Glu Thr Lys Lys Thr Ile Phe Asp Phe Val Arg Trp Ala Thr His
            20                  25                  30

Arg Asn Thr Arg Arg Tyr Ala Arg His Val Ser Gly Leu Trp Arg Ser
        35                  40                  45

Gly Ile Ile Arg Ser Leu Arg Ser Pro Leu Leu Phe Val Phe Phe Ser
    50                  55                  60

Ser Leu Ser Leu Val Leu Tyr His Thr Ala Lys Asp Arg Ala Trp Ile
65                  70                  75                  80

Ser Pro Ser Phe Pro Thr Leu Ser Leu Ser Ser Thr Gln Pro Phe Thr
                85                  90                  95

Leu Ser Ser Leu Ala Leu Ser Leu Leu Val Phe Arg Thr Asn Ala
            100                 105                 110

Ser Tyr Ala Arg Phe Asp Glu Ala Arg Thr Ile Leu Gly Ala Ile Leu
        115                 120                 125

Cys Arg Thr Arg His Leu Ala Arg Gln Gly Leu Ala Trp Ile Asp Pro
    130                 135                 140

Lys Asp Ala Asp Leu Ile Ala Leu Leu Glu Arg Trp Thr Ile Ala Phe
145                 150                 155                 160

Thr Phe Ala Leu Ala Val His Leu Arg Pro Asp Gly Asp Val Arg Lys
                165                 170                 175

Glu Leu Gln Gly Val Leu Leu Pro Ser Glu Leu Ala Ala Leu Glu Glu
            180                 185                 190

Ala Glu His Lys Pro Ser Phe Val Leu Ser Val Leu Gln His Ile Leu
        195                 200                 205

Pro Gln Ala Gly Val Ser Asp Tyr Leu Gln Gly Cys Met Asn Glu Ser
    210                 215                 220

Leu Ala Gln Leu Glu Thr Ser Leu Gly Ser Cys Glu Arg Ile Phe Asn
```

```
           225                 230                 235                 240
Thr Pro Ile Pro Leu Met Tyr Thr Arg His Thr Ser Arg Phe Leu Met
                245                 250                 255

Leu Trp Ile Gly Ile Ile Pro Phe Met Met Trp Glu Ala Cys Gly Phe
                260                 265                 270

Ala Ser Leu Ile Leu Ser Pro Ala Ile Ala Phe Phe Leu Leu Gly Ile
                275                 280                 285

Glu Glu Ile Gly Val Gln Ile Glu Pro Phe Ser Ile Leu Pro Ile
                290                 295                 300

Thr Tyr Ile Ala Ser Val Ala Glu Arg Asn Ile Arg Glu Met Val Lys
305                 310                 315                 320

Lys Arg Glu Leu Thr Arg Gly Ile Val Gly Arg Gly Arg Gly Val
                325                 330                 335

Ser Trp Glu Gly Gly Leu Gly Gly Pro Leu Asp Gly Val Met Asn Gly
                340                 345                 350

Cys Asn Ala Val Ser Gly Gln Gln Ser Glu Gly His Phe Glu Arg Ala
                355                 360                 365

Gln Lys Arg Cys Leu Phe Arg Thr His Phe Ser Ser Leu
                370                 375                 380

<210> SEQ ID NO 45
<211> LENGTH: 460
<212> TYPE: PRT
<213> ORGANISM: Klebsormidium nitens

<400> SEQUENCE: 45

Met Ala Thr Ser Ala His Val Ala Met Arg Pro Gln Ala Leu Trp Thr
1               5                   10                  15

Gly Gly Gly Pro Ala Ser Ala Arg Ser Ala Pro Ala Phe Asn Pro Leu
                20                  25                  30

Pro Ala Gln Val Gly Cys Pro Leu Ala Thr Lys Glu Lys Trp Gln Arg
                35                  40                  45

Met Trp Gly His Ala Ser Leu Arg Ala Ser Leu Asp Leu Ala Asp Ser
    50                  55                  60

Lys Glu Glu Ala Ala Arg Lys Thr Arg Thr Pro Ser Leu Pro Gln Arg
65                  70                  75                  80

Arg Ser Val Arg Cys Gln Ser Ala Pro Lys Ser Asn Ser Pro Pro
                85                  90                  95

Val Ala Leu Lys His Tyr Leu Thr Pro Ile Ser Ala Asp Val Lys Lys
                100                 105                 110

Glu Glu Ser Met Val Tyr Arg Thr Val Phe Gly His Pro Glu Trp
                115                 120                 125

Leu Arg His Arg Ser Ser Thr Arg His Tyr Arg His Ile Leu Ser Ile
                130                 135                 140

Ser Ser Ser Arg Val Ile Leu Ala Leu Gly Pro Val Leu Ala Leu
145                 150                 155                 160

Thr Gly Gly Ala Leu Ala Met Ala Leu Tyr Asn Glu Ala Ile Val His
                165                 170                 175

Asp Ile Leu Pro His Glu Leu Pro Leu Leu Lys Ala Ser Ala Leu Pro
                180                 185                 190

Leu Gln Leu Thr Ala Pro Ala Leu Ala Leu Leu Val Phe Arg Thr
                195                 200                 205

Asn Ala Ser Tyr Ser Arg Phe Asp Glu Ala Arg Lys Met Trp Gly Ala
                210                 215                 220
```

```
Thr Leu Asn Arg Val Arg Asp Leu Ala Arg Gln Ala Leu Ser Tyr Met
225                 230                 235                 240

Asp Asp Asn Glu Glu Arg Glu Glu Val Leu Arg Tyr Leu Met Ala Phe
            245                 250                 255

Pro Tyr Ala Phe Lys Asn His Leu Leu Arg Glu Asp His Ile Val Asp
        260                 265                 270

Asp Met Arg Asn Val Gly Leu Asn Ser Asp Glu Ile Glu Ile Leu Thr
    275                 280                 285

Ser Thr Glu His Arg Pro Asn Tyr Cys Leu Gln Val Met Ser Gln Val
290                 295                 300

Ile Ser Lys Asn Thr Asp Leu Thr Asp Phe Gln Arg Val Asn Leu Asp
305                 310                 315                 320

His Asn Leu Thr His Phe His Asp Gln Val Gly Gly Cys Glu Arg Ile
            325                 330                 335

Phe Lys Thr Pro Leu Pro Leu Ser Tyr Thr Arg Leu Thr Ser Arg Phe
        340                 345                 350

Leu Val Leu Trp His Phe Leu Pro Leu Ala Leu Trp Asp Ala Cys
    355                 360                 365

His Trp Met Val Val Pro Ala Thr Phe Leu Ser Ala Ala Leu Phe
370                 375                 380

Cys Ile Glu Glu Val Gly Val Leu Ile Glu Glu Pro Phe Ser Ile Leu
385                 390                 395                 400

Pro Leu His Ala Ile Cys Asn Thr Ala Glu Lys Asn Val Arg Glu Leu
            405                 410                 415

Thr Arg Leu Gln Gly Glu His Leu Asn Lys Arg Ala Ile Gly Gly Lys
        420                 425                 430

Lys Gln Ala Gln Leu Asn Gly Ala Ser Gln Asn Gly Val Ala Asp Gly
    435                 440                 445

Ala Ala Ala Arg Arg Thr Asn Val Gln Val Thr Asn
450                 455                 460

<210> SEQ ID NO 46
<211> LENGTH: 428
<212> TYPE: PRT
<213> ORGANISM: Marchantia polymorpha

<400> SEQUENCE: 46

Met Glu Thr Leu Cys Ser Ile Pro Lys Leu Thr Ser Arg Cys Leu Ser
1               5                   10                  15

Phe Ser Thr Ser Leu Leu Glu Leu Ser Arg Phe His Ser Phe Cys Pro
            20                  25                  30

Gly Leu Pro Gln Glu Leu Asn Val Arg Arg Gly Arg Thr Ala Phe Arg
        35                  40                  45

Leu Arg Ala Gln Pro Cys Ser Gly Ile Ser Thr Ile His Val Lys Glu
    50                  55                  60

Ser Arg Val Ser Arg Arg Gln Thr Ile Arg Cys Val Gly Ser Gly Pro
65                  70                  75                  80

Glu Pro Glu Pro Tyr Asp Pro Asp Phe Pro Lys Glu Val Phe Leu
            85                  90                  95

Tyr Arg Arg Thr Val Tyr Asp His Lys Asp Trp Ser Arg His Arg Ser
        100                 105                 110

Ser Leu Arg His Ser Arg His Ile Leu Ser Met Arg Ser Ser Arg Val
    115                 120                 125

Ile Leu Ala Leu Trp Pro Pro Val Phe Gly Leu Thr Val Ser Ile
130                 135                 140
```

```
Ala Leu Ser Ala Tyr Asn Glu Cys Ile Leu Ser His Trp Leu Pro Ser
145                 150                 155                 160

Phe Leu Pro Leu Leu His Val Ser Ala Thr Pro Phe Gln Leu Met Ala
                165                 170                 175

Pro Ala Leu Ala Leu Leu Leu Val Phe Arg Thr Asn Ala Ser Tyr Ala
            180                 185                 190

Arg Phe Asp Glu Ala Arg Arg Ala Trp Gly Ser Asn Val Asn Arg Thr
        195                 200                 205

Arg Asp Ile Thr Arg Gln Ala Leu Thr Trp Met Gln His Pro Ser Asp
    210                 215                 220

Ala Glu Lys Val Lys Leu Ile Arg His Cys Val Ala Phe Asn Val
225                 230                 235                 240

Cys Met Lys His His Leu Val Arg Gly Gly Asp Leu Arg Asp Leu
                245                 250                 255

His Ser Trp Ile Asp Lys Glu Ile Asp Gly Ile Leu Ala Ser Thr
            260                 265                 270

His Arg Pro Asn Tyr Val Leu Gln Val Met Ser Glu Ile Ile His Ser
        275                 280                 285

Cys Ser Ile Thr Glu Met Gln Leu Thr Arg Met Asp Val Asn Met Thr
    290                 295                 300

Gln Phe Ala Asp Asn Leu Gly Ala Cys Glu Arg Ile Phe Lys Thr Pro
305                 310                 315                 320

Ile Pro Leu Ser Tyr Thr Arg Leu Thr Ser Arg Phe Leu Val Leu Trp
                325                 330                 335

His Ile Ala Leu Pro Leu Ala Leu Trp Asp His Cys Gln Trp Val Ser
            340                 345                 350

Val Pro Ala Thr Phe Leu Ser Ala Gly Ala Leu Phe Cys Ile Glu Glu
        355                 360                 365

Val Gly Val Leu Ile Glu Glu Pro Phe Gln Ile Phe Pro Leu Asp Asn
    370                 375                 380

Ile Cys Ser Thr Ile Lys Lys Asn Val Asp Gly Leu Ile Leu Ala His
385                 390                 395                 400

Thr Glu Ile His His Cys His Lys His Pro Lys Gly Cys Asp Ile
                405                 410                 415

Pro Lys Lys Lys Ser Ser Gly Asp Ala Pro Lys Ser
            420                 425

<210> SEQ ID NO 47
<211> LENGTH: 337
<212> TYPE: PRT
<213> ORGANISM: Monoraphidium neglectum

<400> SEQUENCE: 47

Met Gly Ala Ala Ala Val Val Ala Tyr Glu Ala Leu Arg Thr Gly
1               5                   10                  15

Ala Leu Thr Phe Leu Pro Ser Leu His Val Ser Pro Gln Leu Ile Ser
                20                  25                  30

Leu Thr Ser Phe Ala Leu Ser Leu Leu Val Phe Arg Thr Asn Ala
            35                  40                  45

Ser Tyr Glu Arg Trp Asp Gly Ala Arg Lys Thr Trp Gly Leu Ile Ile
        50                  55                  60

Asn Arg Ser Arg Asp Ile Val Arg Gln Gly Leu Thr His Ile Pro Arg
65                  70                  75                  80

Asp Lys Pro Asp Leu Arg Ala Met Leu Cys Arg Trp Val Pro Ala Phe
```

```
                85                  90                  95
Ser Lys Ala Leu Met Cys His Leu Arg Arg Asp Lys Ser Leu Arg Gln
            100                 105                 110

Glu Leu Gln Gly Val Leu Leu Pro Ala Glu Val Asp Glu Val Met Arg
            115                 120                 125

Ser Gln His Arg Pro Asn Tyr Val Leu Gln Val Leu Ala Glu Ile Ile
130                 135                 140

Arg Thr Gly Arg Val Arg Ala Pro Ala Ile Arg Met Glu Glu Asn
145                 150                 155                 160

Leu Thr Ser Phe Glu Asp Cys Leu Gly Gly Cys Glu Arg Val Leu Lys
                165                 170                 175

Thr Pro Ile Pro Leu Ser Tyr Thr Arg His Thr Ser Arg Ser Leu Met
            180                 185                 190

Ile Trp Leu Thr Leu Leu Pro Phe Ala Leu Val Ser Thr Cys Gly Leu
            195                 200                 205

Ala Thr Ile Pro Leu Cys Gly Phe Val Ala Phe Leu Leu Leu Gly Glu
            210                 215                 220

Thr Ile Arg Ile Glu Glu Ile Gly Val Ser Ile Glu Glu Pro Phe Ser
225                 230                 235                 240

Thr Leu Pro Leu Ala Ala Ile Cys Gly Ser Val Leu Thr Asn Val Arg
                245                 250                 255

Glu Leu Gln Ala Thr His Ala Ala Asp Thr Thr Gly Ser Ser Ala Ala
            260                 265                 270

Asp Val Asn Pro Leu Pro Leu Ser Ala Ser Gln Leu Val Thr Arg Tyr
            275                 280                 285

Gly Val Ala Ala Ala Glu Ala Glu Val Arg Gly Met Asp Val Ala Val
            290                 295                 300

Ser Gly Ala Ala Ala Ala Ala Ala Ile Arg Ala Gly Val Pro Gly
305                 310                 315                 320

Asn His Ala Val Trp Pro Gln Ile Arg Ala Gly Leu Ala Ala Ala Gln
                325                 330                 335

Ser

<210> SEQ ID NO 48
<211> LENGTH: 430
<212> TYPE: PRT
<213> ORGANISM: Monoraphidium neglectum

<400> SEQUENCE: 48

Met Gln His Ala Ala Arg Leu Gln His Ala Ala Ala Pro Gln Leu
1               5                   10                  15

Met Arg Pro Pro Thr His Gln Arg Ala Leu Cys Ala Thr Ile Ser Ala
            20                  25                  30

Tyr Val Arg Ser Ile Glu Lys Gly Asp Asp Leu Ala Lys Asn Gln Leu
        35                  40                  45

Cys His Val Lys Arg Ala Ser Val Arg Ala Lys Ala Ser Ala Lys Asp
50                  55                  60

Pro Arg Val Phe Asp His Asp Asn Trp Asp Val His Arg Ser Thr Thr
65                  70                  75                  80

Arg His Ala Arg His Ile Ala Gly Leu Cys Arg Ser Gln Thr Val Ala
                85                  90                  95

Asn Leu Val Arg Pro Leu Ser Tyr Val Met Gly Val Ala Val Thr Val
            100                 105                 110

Val Ala Val Glu Ala Leu Arg Ala Ala Gly Cys Ala Pro Ala Phe Leu
```

```
                115                 120                 125
Pro Ser Leu Gln Val Asn Ser Ala Leu Phe Gly Leu Thr Ser Phe Ala
130                 135                 140

Leu Ser Leu Leu Val Phe Arg Thr Asn Ala Ser Tyr Glu Arg Trp
145                 150                 155                 160

Asp Ser Ala Arg Lys Met Trp Gly Leu Val Leu Asn Arg Ser Arg Asp
                165                 170                 175

Ile Val Arg Gln Gly Leu Thr His Ile Pro Arg Asp Lys Pro Asp Leu
                180                 185                 190

Arg Ala Met Leu Cys Arg Trp Val Pro Ala Phe Ser Lys Ala Leu Met
                195                 200                 205

Cys His Leu Arg Arg Asp Lys Asn Leu Ser Gln Glu Leu Gln Gly Val
                210                 215                 220

Leu Leu Pro Ala Glu Val Asp Glu Val Met Arg Ala Gln His Arg Pro
225                 230                 235                 240

Asn Tyr Val Leu Gln Val Leu Ala Glu Ile Ile Arg Thr Gly Arg Val
                245                 250                 255

Arg Ala Thr Ala Ala Ile Arg Met Glu Glu Asn Leu Thr Ser Phe Glu
                260                 265                 270

Asp Cys Leu Gly Gly Cys Glu Arg Ile Leu Lys Thr Pro Ile Pro Leu
                275                 280                 285

Ser Tyr Thr Arg His Thr Ser Arg Thr Met Met Ile Trp Leu Thr Leu
                290                 295                 300

Leu Pro Ser Ala Leu Val Ser Thr Cys Gly Leu Ala Thr Ile Pro Leu
305                 310                 315                 320

Cys Gly Phe Val Ala Phe Leu Leu Gly Ile Glu Ile Gly Val
                325                 330                 335

Ser Ile Glu Glu Pro Phe Ser Ile Leu Pro Leu Asp Ala Ile Ser Gly
                340                 345                 350

Ser Val Leu Thr Asn Val Arg Glu Leu Gln Ala Thr His Asp Ala Ala
                355                 360                 365

Ala Gly Ala Thr Gly Ala Ala Asp Ala Ala Pro Leu Pro Leu Ser Ala
370                 375                 380

Ser Gln Leu Val Thr Arg Tyr Gly Val Ala Ala Ala Glu Ala Gln Val
385                 390                 395                 400

Arg Gly Met His Val Gly Val Asn Gly Ala Ala Ala Val Ala Ala
                405                 410                 415

Asn Gly Thr Ala Val Arg Ser Thr His Ala Val Trp Pro Gln
                420                 425                 430

<210> SEQ ID NO 49
<211> LENGTH: 318
<212> TYPE: PRT
<213> ORGANISM: Monoraphidium neglectum

<400> SEQUENCE: 49

Met Thr Ser Pro Ile His Ser Tyr Gly Arg Trp Asp Glu Ala Arg Lys
1               5                   10                  15

Met Trp Gly Leu Val Leu Asn Arg Ser Arg Asp Ile Ala Arg Gln Gly
                20                  25                  30

Leu Ser Tyr Ile Pro Asp Asp Arg Gln Asp Leu Arg Asp Met Leu Cys
                35                  40                  45

Arg Trp Thr Pro Ala Phe Ser Arg Ser Leu Met Thr His Leu Arg Lys
                50                  55                  60
```

Gly Glu Asp Leu Arg Glu Leu Lys Asp Ile Leu Arg Pro His Glu
65                  70                  75                  80

Leu Asp Ser Leu Leu Met Ser Thr His Arg Pro Asn Tyr Cys Leu Gln
            85                  90                  95

Val Leu Ser Gln Val Val Lys Asp Ala Asn Ala Gly Thr Ala Ala Thr
            100                 105                 110

Ile Arg Met Asp Asp Asn Ile Thr Ala Phe Glu Asp Cys Leu Gly Gly
            115                 120                 125

Cys Glu Arg Ile Leu Lys Thr Pro Val Pro Leu Ser Tyr Thr Arg His
            130                 135                 140

Thr Ser Arg Phe Leu Ile Ile Trp Leu Thr Met Leu Pro Phe Thr Leu
145                 150                 155                 160

Tyr Gly Ser Cys Gly Phe Ala Thr Val Pro Leu Cys Cys Val Ile Ala
                165                 170                 175

Phe Leu Leu Leu Gly Ile Glu Glu Ile Gly Val Ser Ile Glu Glu Pro
            180                 185                 190

Phe Ser Ile Leu Ala Leu Gln Ala Ile Cys Asp Ser Ala Leu Asn Asn
            195                 200                 205

Val Arg Glu Leu Gln Ala Gln His Asp Ile Ser Lys Ala Lys Ser Asp
210                 215                 220

Gln Tyr Ser Ala Ile Glu Leu Val Ser Met Ala Ala Glu Ala Ala
225                 230                 235                 240

Gly Ala Ser Ala Thr Ala Ala Ala Glu Ser His Asn Gly Asn Gly
                245                 250                 255

Asn Gly Asn Gly Ser Arg Ala Pro Ser Pro Ala Phe Ala Thr Ala Gly
            260                 265                 270

Val Ala Asn Gly Gly Asn Arg Phe Ala Val Ala Pro Pro Gly Ser Asn
            275                 280                 285

Gly Thr Ala Ala Ser Ser Asp Gly Ala Gly Ser Gly Gly Ser Asn Val
            290                 295                 300

Trp Pro Arg Lys Gly Asn Tyr Ser Ser Val Ser Phe Arg Lys
305                 310                 315

<210> SEQ ID NO 50
<211> LENGTH: 363
<212> TYPE: PRT
<213> ORGANISM: Monoraphidium neglectum

<400> SEQUENCE: 50

Met Glu Leu Arg Cys Ala Pro Ala Ser Ala Pro Gly Ile Ala Pro Asn
1               5                   10                  15

Asp Thr Ala Ala Ala Ala Ser Phe Gly Gly Ala Pro Ile Ser His
            20                  25                  30

Gly Gly Ala Ala Ala Ala Asn Thr Lys Gly Gly Arg Glu Gln Ser
            35                  40                  45

Val Gly Gly Thr Ala Arg Pro Arg Ser Ala Leu Gly Arg Leu Ser Arg
            50                  55                  60

Ser Lys Ile Leu Asn Leu Gly Ala Pro Glu Phe Val Lys Tyr Val Leu
65                  70                  75                  80

Asp Lys Asp Gly His Asp Arg His Glu Thr Asp Ile Thr Arg Arg
            85                  90                  95

Phe Trp His Asn Val Arg Arg Glu Ala Gly Met Arg Gly Lys Gln
            100                 105                 110

Thr Ser Lys Phe Phe Ser Ala Ala Gly Ser Gly Val Leu Ala Pro Ala
            115                 120                 125

Asp Leu Val Phe Thr Phe Asp Arg Trp Asn Lys His Arg Asn Ser Leu
    130                 135                 140

Arg Tyr Val Lys His Leu Thr His Val Phe Thr Ser Arg Ile Phe Arg
145                 150                 155                 160

Asn Leu Arg Gly Pro Val Val Val Met Ala Met Ala Val Leu Val
                165                 170                 175

Gly Thr Tyr Glu Thr Leu Arg Thr Thr Gly Tyr Leu Pro Gly Phe Pro
            180                 185                 190

His Leu Ala His Ser Ala Leu Asp Glu Gly Phe Gln Leu Thr Ala Phe
        195                 200                 205

Ala Leu Ser Leu Leu Val Phe Arg Thr Asn Ser Ser Tyr Asp Arg
    210                 215                 220

Trp Trp Glu Ala Arg Lys Ile Trp Gly Gly Val Val Asn Arg Ser Arg
225                 230                 235                 240

Asp Val Val Arg Gln Gly Leu Val Phe Phe Ala Asp Glu Asp Thr His
                245                 250                 255

Leu Lys Glu Thr Leu Ala Cys Trp Ala Met Ala Phe Pro Lys Val Leu
            260                 265                 270

Met Cys His Leu Arg Asp Ser Met Asp Val Lys Lys Glu Val Gly His
        275                 280                 285

Leu Leu Ser Pro Leu Glu Leu Glu Leu Leu Cys Ser Ser Ala His Arg
    290                 295                 300

Pro Asn Phe Ile Leu Gln Val Ile Ser Glu Thr Ile Arg Ala Ala Lys
305                 310                 315                 320

Pro His Glu Leu Tyr Arg Ile Arg Met Asp Glu Asn Leu Thr Phe Phe
                325                 330                 335

His Asp Ala Leu Gly Ser Cys Glu Arg Ile Leu Arg Thr Pro Ile Pro
            340                 345                 350

Leu Ser Tyr Thr Arg His Thr Ser Arg Phe Leu
    355                 360

<210> SEQ ID NO 51
<211> LENGTH: 406
<212> TYPE: PRT
<213> ORGANISM: Monoraphidium neglectum

<400> SEQUENCE: 51

Met Met Val Cys Gly Leu Met Ala Gly Arg Val Gln Leu Thr Asp Leu
1               5                   10                  15

Gly Arg Pro Val Ala Gly Asp Tyr Glu Asp Ala Ile Lys Glu Glu Ser
                20                  25                  30

Arg Arg Tyr Arg Arg Thr Val Phe Asp Ile Gln Ala Trp Glu Gly His
            35                  40                  45

Arg Ser Thr Thr Arg Tyr Gly Arg His Leu Val Gly Ile Leu Thr Ser
    50                  55                  60

Arg Val Val Trp Gly Leu Ala Arg Pro Leu Leu Tyr Val Ala Ala Val
65                  70                  75                  80

Ala Ala Ala Val Val Ala Tyr Glu Ser Leu Arg Gln Ala Gly Leu Leu
                85                  90                  95

Pro Ala Ala Leu Pro Ser Val Gln Leu Thr Ser Lys Glu Pro Phe Gly
            100                 105                 110

Leu Thr Ser Phe Ala Leu Ser Leu Leu Val Phe Arg Thr Asn Ser
    115                 120                 125

Ser Tyr Gly Arg Trp Asp Glu Ala Arg Lys Met Trp Gly Leu Val Leu 130                 135                 140
Asn Arg Ser Arg Asp Ile Val Arg Gln Gly Leu Ser Tyr Ile Ser Pro
145                 150                 155                 160

Asp Cys Trp Gln Leu Arg Asp Met Leu Cys Arg Trp Thr Pro Ala Phe
                165                 170                 175

Ser Arg Ala Leu Met Cys His Leu Arg Lys Gly Asn Asp Leu Arg Gln
                180                 185                 190

Glu Leu Gln Asp Ile Leu Leu Pro His Glu Leu Asp Ser Leu Leu Lys
                195                 200                 205

Ala Thr His Arg Pro Asn Tyr Val Leu Gln Val Leu Ser Gln Ile Ile
                210                 215                 220

Ser Ser Ala Asn Leu Ser Val Ala Ala Thr Ile Arg Met Asp Gln Asn
225                 230                 235                 240

Leu Thr Ser Phe Ala Asp Cys Leu Gly Gly Cys Glu Arg Ile Leu Arg
                245                 250                 255

Thr Pro Ile Pro Leu Ser Tyr Thr Arg His Thr Ser Arg Phe Leu Met
                260                 265                 270

Ile Trp Leu Thr Leu Leu Pro Phe Ser Leu Phe Gly Ser Cys Gly Leu
                275                 280                 285

Ser Thr Ile Pro Leu Ser Val Ala Ile Ala Phe Leu Leu Leu Gly Ile
                290                 295                 300

Glu Glu Ile Gly Val Ser Ile Glu Ala Glu Pro Phe Ser Ile Leu Ala
305                 310                 315                 320

Leu Glu Val Ile Cys Asp Ser Val Leu Ser Asn Val Arg Glu Ile Gln
                325                 330                 335

Ser Thr His Ala Ala Asn Gly Asn Gly Ser Ser Thr Gly Val Ser
                340                 345                 350

Gly Asn Gly Asn Gly Ser Gly Ala Pro Pro Ala Gln Arg Arg Glu
                355                 360                 365

Gln Leu Ser Ala Ala Gln Leu Val Gly Leu Ala Arg Ser Gly Pro Gln
                370                 375                 380

Gly Gln Lys Glu Trp Pro Pro Val Gln Ala Val Asn Arg Tyr Pro Val
385                 390                 395                 400

Pro Gln Ala Ala Gly Val
                405

<210> SEQ ID NO 52
<211> LENGTH: 358
<212> TYPE: PRT
<213> ORGANISM: Physcomitrella patens

<400> SEQUENCE: 52

Met His Arg Asn Ala Val Tyr Gly His Asp Glu Trp Ala Lys His Lys
1               5                   10                  15

Ser Cys Trp Arg His Gly Arg His Leu Lys Thr Ile Phe Ala Ser Arg
                20                  25                  30

Pro Ile Val Ala Thr Gly Pro Pro Val Ala Phe Cys Thr Leu Ile Ala
                35                  40                  45

Val Phe Val Ile Phe Asn His Ser Val Leu Val Gly His Phe Pro
    50                  55                  60

Val Trp Val Pro Val Ile Gln Val Ala Ser Ile Pro Phe Ala Leu Thr
65                  70                  75                  80

Ser Ser Val Leu Ser Leu Leu Leu Val Phe Arg Thr Asn Ser Ser Tyr
                85                  90                  95

Asn Arg Phe Asp Glu Ala Arg Lys Ala Trp Gly Ser Asn Val Asn Arg
                100                 105                 110

Thr Arg Asp Leu Ala Arg Gln Ala Leu Thr Trp Ile Arg Ser Pro Ala
            115                 120                 125

Asp Leu Pro Lys Leu His Cys Leu Leu Arg His Ile Lys Ala Tyr Ser
        130                 135                 140

Tyr Cys Leu Lys Asp His Leu Thr Gln Asp Asn Thr Leu Arg Glu Glu
145                 150                 155                 160

Leu Ala Lys Val Leu Glu Pro Thr Glu Leu Val Leu Ser Ser
                165                 170                 175

Lys His Arg Pro Asn Tyr Val Met Gln Val Met Ser Glu Leu Ile Lys
                180                 185                 190

Gln Cys Lys Val Ser Glu Trp Glu Ser Met Ser Met Asp Arg Asn Leu
            195                 200                 205

Thr Gln Phe His Asp Asn Val Gly Ala Cys Glu Arg Leu Phe Lys Thr
        210                 215                 220

Pro Ile Pro Val Ala Tyr Thr Arg Leu Thr Ser Arg Val Leu Ser Leu
225                 230                 235                 240

Trp His Ile Ser Leu Pro Phe Ala Leu Trp Asn Ser Cys His Trp Leu
                245                 250                 255

Thr Ile Pro Ala Thr Phe Phe Ser Ser Ala Ala Leu Phe Tyr Ile Glu
            260                 265                 270

Glu Val Gly Val Leu Ile Glu Pro Phe Trp Ile Leu Ala Leu Met
        275                 280                 285

Ser Ile Ser Asp Gly Ile Cys Ser Ala Leu Asp Gly Leu Val Ala Ala
290                 295                 300

His Gln Glu Thr Arg Leu Val Trp Gly Val His Pro Gln Ala Val Cys
305                 310                 315                 320

Lys Lys Asp His Val Val Ile Thr Phe Glu Asn Ser Arg Ser Cys Ala
                325                 330                 335

Ser Asp Gly Phe Arg Pro Gln His Asp Tyr Ile Asp Val Ala Met Thr
            340                 345                 350

Arg Val Asn Ser Val Ser
        355

<210> SEQ ID NO 53
<211> LENGTH: 416
<212> TYPE: PRT
<213> ORGANISM: Physcomitrella patens

<400> SEQUENCE: 53

Met Ala Pro Gly Gln Val His Thr Asp Cys Leu Trp Met Lys Tyr Ser
1               5                   10                  15

Cys Leu Arg Asn Thr Tyr Ser Lys Leu Gln Ala Leu Gln Met Lys Asp
                20                  25                  30

Leu Asp Phe Arg His Trp Ala Ser Gln Glu Phe Ser Leu Val Thr Pro
            35                  40                  45

Glu Glu Gln Ala Val Leu Gly Ser Gly Leu Glu Pro Gln Lys Ile Met
        50                  55                  60

His Arg Asn Lys Val Tyr Gly His Leu Glu Trp Ala Arg His Lys Ser
65                  70                  75                  80

Ser Trp Arg His Gly Arg His Ile Phe Ser Ile Leu Ser Ser Gly Val
                85                  90                  95

Ile Phe Ala Val Phe Pro Pro Val Leu Val Cys Thr Leu Phe Gly Thr
                100                 105                 110

```
Phe Val Thr Ile Phe Asn His Phe Val Gln Asn Gly His Leu Pro Thr
            115                 120                 125

Trp Met Pro Ile Leu His Val Ala Ser Leu Pro Phe Thr Leu Thr Ser
    130                 135                 140

Ser Val Leu Ser Leu Leu Leu Val Phe Arg Thr Asn Ser Ser Tyr Asn
145                 150                 155                 160

Arg Phe Glu Glu Ala Arg Lys Phe Trp Gly Ser Asn Val Asn Arg Thr
                165                 170                 175

Arg Asp Leu Val Arg Gln Ser Leu Thr Trp Ile Ser Gln Pro Gly Asp
            180                 185                 190

Ser Leu Ile Leu Leu Ser Leu Leu Arg His Ile Lys Ala Tyr Ser Phe
        195                 200                 205

Cys Leu Lys Asp His Leu Thr Glu Asp Glu Thr Leu Arg Asp Asp Leu
    210                 215                 220

Val Gly Ile Val Glu Pro His Glu Leu Glu Ser Ile Leu Ser Ser Pro
225                 230                 235                 240

His Arg Pro Asn Tyr Ile Leu Gln Val Leu Ser Glu Leu Ile Asn Gln
                245                 250                 255

Cys His Ile Ser Gln Trp Glu Lys Met Ser Met Asp Glu Asn Ile Thr
            260                 265                 270

Thr Phe His Asp Asn Val Gly Ala Cys Glu Arg Ile Leu Lys Thr Pro
        275                 280                 285

Ile Pro Ile Ala Tyr Thr Leu Val Thr Ser Arg Phe Leu Ile Leu Trp
    290                 295                 300

His Ser Ala Leu Pro Leu Ala Leu Trp Asn Asp Cys Gly Trp Leu Thr
305                 310                 315                 320

Ile Pro Ala Thr Phe Leu Thr Gly Met Ala Leu Phe Tyr Ile Glu Glu
                325                 330                 335

Val Gly Val Val Ile Glu Glu Pro Phe Trp Ile Leu Pro Leu Gly Ser
            340                 345                 350

Ile Cys Thr Gly Ile Val Ser Ala Ile Asp Gly Leu Ser Ala Ala His
        355                 360                 365

Lys Thr Ser Asn Leu Leu Trp Ser Leu His Gln Pro Met Thr Asp His
    370                 375                 380

Val Val Gln Ile Ala Phe Glu Arg Ser Lys Thr Asp Gly Phe Ser Lys
385                 390                 395                 400

Thr Arg Asp Gln Ile Asp Val Met Leu Thr Arg Ile Asn Ser Ile Ala
                405                 410                 415

<210> SEQ ID NO 54
<211> LENGTH: 297
<212> TYPE: PRT
<213> ORGANISM: Physcomitrella patens

<400> SEQUENCE: 54

Met Gly Leu His Lys Ser Ser Trp Arg His Gly Arg His Ile Gln Thr
1               5                   10                  15

Ala Phe Ser Thr Gly Val Ile Ser Ser Ile Pro Arg Val Phe Phe
                20                  25                  30

Cys Thr Leu Ile Ser Val Leu Val Thr Ile Phe Asn His Ala Val Met
            35                  40                  45

Glu Gly Val Leu Pro His Trp Val Pro Ser Leu Arg Val Pro Thr Leu
        50                  55                  60

Pro Met Ser Leu Thr Ala Pro Val Leu Ser Leu Leu Leu Val Phe Arg
```

```
                65                  70                  75                  80
Thr Asn Ser Ser Tyr Asn Arg Leu Asp Glu Ala Arg Lys Ala Trp Gly
                    85                  90                  95

Ser Asn Val Asn Arg Thr Arg Asp Val Ser Arg Gln Ala Leu Ser Trp
                100                 105                 110

Ile Cys Asp Pro Asp Ala Asp Lys Leu Gln Ser Leu Leu Arg His
            115                 120                 125

Ile Lys Ala Phe Ser Tyr Cys Leu Lys Asp His Leu Thr Gln Glu Asn
        130                 135                 140

Leu Leu Gln Glu Glu Leu Ala Arg Val Leu Glu Pro Arg Glu Val Glu
145                 150                 155                 160

Leu Val Leu Lys Ser Ser His Arg Pro Asn Tyr Val Leu His Val Met
                165                 170                 175

Ser Asp Thr Ile Lys His Cys Arg Ile Ser Lys Trp Glu Ser Lys Ser
            180                 185                 190

Met Asp Arg Asn Ile Thr Gln Phe His Asp Asn Val Gly Ala Cys Glu
        195                 200                 205

Arg Leu Phe Lys Thr Pro Ile Pro Val Ala Tyr Thr Arg Met Ile Ser
    210                 215                 220

Arg Phe Leu Ser Ile Trp His Phe Leu Leu Pro Leu Ala Leu Trp Asn
225                 230                 235                 240

Ser Cys Arg Trp Leu Thr Ile Pro Val Thr Phe Val Ser Gly Val Gly
                245                 250                 255

Leu Phe Cys Ile Glu Glu Val Gly Val Leu Ile Glu Asp Pro Ser Thr
            260                 265                 270

Ser Leu Leu Cys Cys Gln Ser Ala Met Ala Phe Pro Gln Leu Trp Met
        275                 280                 285

Ala Ser Ala Arg Leu Met Lys Glu Leu
    290                 295

<210> SEQ ID NO 55
<211> LENGTH: 669
<212> TYPE: PRT
<213> ORGANISM: Raphidocelis subcapitata

<400> SEQUENCE: 55

Met Leu Ala Thr Ala Pro Cys Ala Ala Ala Cys Thr Pro Ser Arg Arg
1               5                   10                  15

Gly Gly Arg Cys His Arg Arg Leu Trp Thr Pro Pro Arg Thr Ala Ala
            20                  25                  30

His Gly Gln His Ala Ala Ala Asp Gly Asp Lys Gln Gln Pro Asp
        35                  40                  45

Gln Pro Pro Pro Pro Ala Thr Ala Ala Ala Gly Ser Asp Pro
    50                  55                  60

Ala Pro Pro Ser Pro Ala Ala Pro Pro Thr Pro Gly Gly
65                  70                  75                  80

Phe Thr Pro Tyr Trp Pro Ser Asn Tyr Arg Lys Arg Leu Glu Ala Ala
                85                  90                  95

Thr Leu Glu Arg Ala His Glu Ala Asp Val Thr Pro Thr Val Phe Asp
            100                 105                 110

Phe Ala Leu Trp Arg Arg His Arg Ser Arg Leu Arg Tyr Val Glu His
        115                 120                 125

Leu Val Thr Leu Thr Gly Ser Tyr Phe Val Leu Asp Leu Ala Ala Pro
    130                 135                 140
```

```
Val Ile Val Leu Thr Ala Ala Ala Ala Val Gly Leu Tyr Glu Thr
145                 150                 155                 160

Val Leu Gln Gly Gly Met Leu Pro Ser Phe Leu Pro Asn Ile Ala Met
            165                 170                 175

Ala Ala Glu Gly Pro Phe Asn Ala Ala Ser Phe Ala Met Ser Leu Met
            180                 185                 190

Leu Ala Phe Lys Thr Asn Val Ser Tyr Ala Arg Trp Asn Glu Ala Arg
            195                 200                 205

Cys Leu Trp Gly Ser Leu Val Asn Arg Ser Arg Asn Leu Val Arg Gln
            210                 215                 220

Gly Leu Met Leu Ile Pro Arg Glu His Ala Ala Leu Lys Pro Val Leu
225                 230                 235                 240

Ala Arg Trp Ser Ile Ala Phe Ala Arg Ala Leu Lys Thr His Leu Arg
            245                 250                 255

Glu Asp Gly Asp Val Ala Gly Glu Leu Ala Ala Ile Leu Glu Pro His
            260                 265                 270

Glu Val Ala Val Val Ala Ala Asn Leu Asn Arg Pro Leu Ala Cys Leu
            275                 280                 285

Gln Ala Met Ser Ala Val Val Arg Ala Ala Arg Leu Asp Pro Ile Gly
            290                 295                 300

Thr Ser Arg Leu Asp Ile Asn Leu Glu Thr Phe Glu Asp Ile Met Gly
305                 310                 315                 320

Ala Cys Glu Arg Ile Leu Lys Thr Pro Ile Pro Leu Ser Tyr Thr Arg
            325                 330                 335

His Thr Ser Arg Phe Leu Thr Leu Trp Leu Ala Thr Leu Pro Phe Val
            340                 345                 350

Leu Trp Asn His Ile His Trp Gly Val Ile Pro Ser Thr Ala Val Ile
            355                 360                 365

Ser Phe Leu Leu Phe Gly Ile Asp Glu Ile Ala Ile Gln Leu Glu Glu
            370                 375                 380

Pro Phe Gly Ile Leu Pro Leu Glu Ala Ile Cys Asp Thr Ile Gln Arg
385                 390                 395                 400

Asn Ile Glu Glu Leu Val Asn Ser Glu Gly Ala Val Ala Leu Ala Leu
            405                 410                 415

Asp Ala Ser Met His Glu Ala Arg Ala Arg Leu Ala Gln Glu Glu Glu
            420                 425                 430

Leu Ala Arg Met Leu Glu Glu Gln Leu Pro Phe Asn Trp Gly Pro Arg
            435                 440                 445

Gly Leu Ser Gln Pro His Ser Pro Ala Ala Pro Gly Thr Pro Gly
450                 455                 460

Ala Ala Gly Gly Ala Gly Ala Ala Ala Ala Ala Ala Leu Ile Ala
465                 470                 475                 480

Ala Asn Arg Pro Arg Pro Phe Gln Asp Phe Pro Ala Gly Gln Pro Ala
            485                 490                 495

Thr Arg Ile Glu Pro Trp Arg Glu Glu Pro Val Gly Ala Thr Ala Pro
            500                 505                 510

Pro Pro Val Ser Glu Glu Gly Gln Pro Gln Trp Arg Pro Gly Trp
            515                 520                 525

Gly Arg Gly Gly Asp Gly Phe Gly Gln Gln Pro Glu Cys Pro Pro Asn
            530                 535                 540

Cys Ser Cys Arg Met Ala Glu Pro Gly Ala Ala Gly Gly Gln Gln His
545                 550                 555                 560

Ser Ser Pro Ala Leu Arg Arg Glu Asp Ala Asp Arg Leu Arg Arg Ala
```

-continued

```
                565                 570                 575

Leu Gly Glu Val Ala Ala Arg Arg Ala Ala Gln Ser Glu Ala Arg Ala
                580                 585                 590

Ala Pro Leu Glu Pro Val Glu Met Pro Trp Tyr Ala Asp Asp Val Ala
            595                 600                 605

Ser Asp Ser Leu Leu Gly Ala Ala Ala Glu Ala Asp Pro Arg Glu
        610                 615                 620

Ala Gly Val Val Glu Phe Leu Leu Gly Arg Ala His Gly Ala Asn Ala
625                 630                 635                 640

Val Arg His Pro Gly Thr Pro Met Gly Thr His Glu Glu Glu Glu
                645                 650                 655

Gly Pro Ala Ala Ala Gly Pro Ala Pro Pro Ala Gly Gly
            660                 665

<210> SEQ ID NO 56
<211> LENGTH: 564
<212> TYPE: PRT
<213> ORGANISM: Raphidocelis subcapitata

<400> SEQUENCE: 56

Met Arg Ser Ser Leu Ala Ala Pro Pro Ala His Ala Ser Ser Pro Arg
1               5                   10                  15

Gly Leu Arg Ala Ala Ala Pro Pro Arg Pro Arg Ala Gly Ala Arg Gly
                20                  25                  30

Gly Arg Pro Ala Val Val Val Ala Ala Leu Ser Gln Glu Asp Asp Gln
            35                  40                  45

Ile Lys Glu Gln Ser Arg Lys Phe Arg Arg Thr Val Phe Thr Phe Glu
        50                  55                  60

Asp Trp Glu Lys His Arg Ser Thr Ser Arg Tyr Ser Arg His Leu Ser
65                  70                  75                  80

Gly Met Phe Ser Ser Arg Val Val Trp Gly Leu Gln Arg Pro Leu Val
                85                  90                  95

Tyr Val Cys Gly Val Ser Leu Ala Val Ile Leu Tyr Glu Lys Ser Leu
                100                 105                 110

Glu Leu Leu Ser Arg Glu Pro Phe Gly Leu Thr Ser Phe Ala Leu Ser
            115                 120                 125

Leu Leu Leu Val Phe Arg Thr Asn Val Ser Tyr Glu Arg Trp Asp Ser
        130                 135                 140

Ala Arg Lys Met Trp Gly Leu Leu Leu Asn Arg Ser Arg Asp Leu Val
145                 150                 155                 160

Arg Gln Gly Ile Thr Tyr Ile Pro Glu Asp Arg Pro Glu Leu Arg Thr
                165                 170                 175

Leu Leu Val Arg Trp Thr Pro Ala Phe Ala Arg Ala Leu Leu Cys His
            180                 185                 190

Leu Arg Lys Asp Gly Asp Trp Glu Gly Gln Leu Gly Leu Thr Leu Lys
        195                 200                 205

Pro His Glu Val Glu Gln Val Leu Lys Ala Thr His Arg Pro Asn Tyr
    210                 215                 220

Val Leu Gln Val Leu Ser Gln Ile Ile Arg Glu Ala Asp Leu Gly Val
225                 230                 235                 240

Ala Pro Thr Thr Arg Met Asp Glu Asn Leu Thr Gln Phe Glu Asp Val
                245                 250                 255

Leu Gly Gly Cys Glu Arg Ile Leu Lys Thr Pro Val Pro Leu Ser Tyr
            260                 265                 270
```

```
Thr Arg His Thr Ser Arg Phe Leu Met Ile Trp Leu Thr Leu Leu Pro
            275                 280                 285

Phe Thr Leu Tyr Ser Thr Val Gly Leu Gly Thr Ala Pro Leu Cys Ala
    290                 295                 300

Ile Ile Ala Phe Leu Leu Gly Ile Glu Glu Ile Gly Val Ser Ile
305                 310                 315                 320

Glu Glu Pro Phe Ser Ile Leu Ala Leu Glu Ala Ile Ser Asp Ser Ser
                325                 330                 335

Leu Asn Asn Ser Arg Glu Leu Ala Ala Met His Ala Thr Asp Ala Ala
            340                 345                 350

Val Pro Leu Pro Glu Gly Ala Asp Pro Pro Ala Tyr Thr Ser Ala
    355                 360                 365

Arg Asp Leu Ile Ala Leu Ala Ser Ala Ala Val Ala Ser Ala Ala
370                 375                 380

Ala Asp Ala Leu Ala Ala Pro Ala His Ala Pro Ala Pro Ala Ser His
385                 390                 395                 400

Ser Ala Pro Ala Pro Gln Glu Pro Ala Ala Pro Ala Ala Pro Ala Ala
                405                 410                 415

Val Ala Pro Ala Ala Ala Ala Pro Ala Pro Ala Ala Pro Ala Pro Thr
            420                 425                 430

Ala Pro Ala His Ser Ala Pro Val Pro Lys Glu Pro Ala Ala Glu Pro
            435                 440                 445

Glu Arg Val Pro Val Leu Ala Gly Val Gly Ala Gly Arg Ala Pro Val
    450                 455                 460

His Leu Asn Gly Lys Ser Gly Asn Gly Ala Thr Ala Tyr Glu Pro Ala
465                 470                 475                 480

Ala Ala Pro Ala Arg Ala Asn Gly Ala Arg Pro Ala Ala Ala Ser
                485                 490                 495

Pro Lys Pro Ala Ala Ala Ala Pro Ala Ala Ala Ser His Ala Ala
                500                 505                 510

Pro Ala Ala Pro Ala Ala Ala Ala Ala Pro Gln Ala Ala Ala Ala Pro
            515                 520                 525

Gln Ala Ala Ala Pro Ala Pro Ala Pro Ala Ala Lys Pro Leu Pro Asn
    530                 535                 540

Thr Gly Arg Ala Gly Ser Leu Arg Arg Thr Gly Gly Tyr Gly Leu Ile
545                 550                 555                 560

Arg Phe Arg Ser

<210> SEQ ID NO 57
<211> LENGTH: 513
<212> TYPE: PRT
<213> ORGANISM: Raphidocelis subcapitata

<400> SEQUENCE: 57

Met Gln Cys Ala Ile Gly Asn Ala Ala Val Gln Pro Leu Gly Arg Pro
1               5                   10                  15

Leu Gly Val Pro Arg Ser Arg Ala Ala Ala Ala Ala Ala Ala Ala Val
            20                  25                  30

Arg Ala Arg Ser Trp Pro Arg Leu Thr Ala Leu Arg Ala Ala Pro Gly
        35                  40                  45

Asp Gly Pro Glu Pro Ser Ala Pro Ser Thr Ala Gly Ser Leu Gln Ser
    50                  55                  60

Leu Ala Glu Arg Leu Arg Ala Thr Ala Thr Pro Gly Glu Val Gln Ser
65                  70                  75                  80
```

```
Asp Leu Asn Tyr Tyr Gly Leu Ala Asn Leu Glu Asp Ala Arg Arg Ser
                85                  90                  95

Gly Asp Glu Ala Gln Asp Leu Leu Trp Arg Thr Pro Val Ser Glu
            100                 105                 110

Leu Ala Ala Arg Arg Arg Gly Leu Gly Leu Val Ala Ala Asp Leu Ser
            115                 120                 125

Thr Glu Gln Glu Arg Lys Leu Arg Arg Ala Val Phe Gly Phe Asp Arg
            130                 135                 140

Trp Ala Ala His Arg Ser Thr Ser Arg Tyr Leu Arg His Leu Lys Gly
145                 150                 155                 160

Ile Val Ser Ser Arg Thr Met Arg Ala Leu Leu Pro Pro Leu Ala Phe
                165                 170                 175

Phe Gly Ala Val Ala Val Ala Ala Gly Trp Tyr Thr Leu Glu Leu Ala
            180                 185                 190

Pro Gln Tyr Gly Leu Pro Lys Val Val Leu Asn Asp Ser Ser Leu Glu
            195                 200                 205

Ile Thr Ser Phe Ala Leu Ser Leu Leu Leu Val Phe Arg Thr Asp Ser
            210                 215                 220

Ser Tyr Ala Arg Trp Glu Gln Ala Leu Asn Ala Trp Gln Ser Val Arg
225                 230                 235                 240

Ala Glu Ser Lys Asn Leu Ala Arg Gln Ala Cys Tyr Phe Val Glu Glu
                245                 250                 255

Pro Ile Arg Arg Ala Met Leu Met Arg Trp Thr Val Ala Phe Pro His
            260                 265                 270

Ala Leu Leu Ser His Val Arg Cys Asp Ala Pro Leu Arg Ala Gln Leu
            275                 280                 285

Ala Gly Val Leu Ala Pro His Glu Val Glu Ala Val Glu Ala Val Gly
            290                 295                 300

Ala Ala Ser Ala Pro Glu Phe Val Leu Gln Val Met Ser Glu Leu Val
305                 310                 315                 320

Glu Gln Cys Arg Leu Gly Asp Ser His Arg Ala Glu Gln Leu Tyr Phe
                325                 330                 335

Ser Ile Lys Ala Leu Gly Gly Ala Val Gly Thr Cys Asp Lys Leu Leu
            340                 345                 350

Arg Tyr Pro Ile Pro Leu Ala Tyr Ser Arg His Thr Ser Arg Phe Met
            355                 360                 365

Cys Val Trp Leu Ser Ala Leu Pro Phe Ala Leu Phe Ser Ser Gly Leu
            370                 375                 380

Gly Trp Gly Ala Val Pro Val Thr Leu Val Thr Ala Tyr Leu Leu Leu
385                 390                 395                 400

Ala Val Asp Glu Ile Gly Val Gln Ile Glu Glu Pro Phe Ser Ile Leu
                405                 410                 415

Pro Leu Glu Asp Ile Leu Phe Asp Ile Gln Ser Glu Thr Ala Ala Leu
            420                 425                 430

Gly Glu Arg Gln Gly Ala Val Ala Glu Ile Leu Arg Ala Gly Gly Ile
            435                 440                 445

Glu Cys Thr Pro Arg Thr Pro Phe Asp Asp Ala Ala Cys Ala Ala Cys
            450                 455                 460

Gly Ala Leu Val Ser Pro Ala Gly Ser Leu Asp Asp Gly Asp Asp Ala
465                 470                 475                 480

Gly Gly Gly Gly Ala Gly Ala Gly Ala Gly Glu Ala Leu Pro Gly Leu
                485                 490                 495

Pro Leu Arg Pro Arg Ala Pro Gly Gly Arg Arg Val Val Arg Thr Ser
```

-continued

```
                500             505             510
Arg

<210> SEQ ID NO 58
<211> LENGTH: 469
<212> TYPE: PRT
<213> ORGANISM: Raphidocelis subcapitata

<400> SEQUENCE: 58

Met Lys Leu Ser Ala Gly Pro Met Gln Ser Arg Ala Ala Phe Ala Gly
1               5                   10                  15

Gln Arg Leu Ala Val Arg Pro Ala Leu Arg Ser Arg Ala Ala Lys Arg
            20                  25                  30

Thr Pro Ala Val Gln Thr Ser Cys Gly Ala Ala Pro Lys Gly Leu Pro
        35                  40                  45

Ser Ser Val Thr Ser Tyr Asp Asp Ile Lys Glu Lys Ser Arg Lys
    50                  55                  60

Phe Arg Arg Thr Val Phe Thr Phe Glu Ser Trp Glu Gly His Arg Ser
65                  70                  75                  80

Thr Glu Arg Tyr Ala Arg His Ile Ile Ser Met Phe Ser Ser Arg Val
                85                  90                  95

Val Arg Gly Leu Ser Lys Pro Leu Phe Tyr Met Val Gly Val Ser Ser
            100                 105                 110

Phe Val Val Ala Tyr Glu Thr Ala Arg Leu Ala Gly Leu Leu Pro Leu
        115                 120                 125

Trp Ala Pro Ser Val Gln Leu Asn Ser Lys Glu Val Phe Gly Leu Thr
130                 135                 140

Ser Phe Ala Leu Ser Leu Leu Val Phe Arg Thr Asn Ala Ser Tyr
145                 150                 155                 160

Glu Arg Trp Asp Gly Ala Arg Lys Met Trp Gly Leu Val Leu Asn Arg
                165                 170                 175

Ser Arg Asp Ile Val Arg Gln Gly Leu Thr Tyr Phe Pro Ser Asp Arg
            180                 185                 190

Pro Glu Leu Lys Asp Met Leu Val Arg Trp Thr Pro Ala Phe Ser Lys
        195                 200                 205

Ser Leu Met Cys His Leu Arg Lys Asp Asp Tyr Arg Glu Val Leu
    210                 215                 220

Gln Asp Ile Leu Leu Pro His Glu Leu Asp Ser Ile Met Met Ala Thr
225                 230                 235                 240

His Arg Pro Asn Tyr Ala Leu Gln Val Leu Ser Glu Ile Val Arg Glu
                245                 250                 255

Ala Asn Cys Gly Thr Ala Pro Thr Met Arg Met Asp Asp Asn Ile Thr
            260                 265                 270

Ser Phe Glu Asp Cys Leu Gly Gly Cys Glu Arg Ile Leu Lys Thr Pro
        275                 280                 285

Val Pro Leu Ser Tyr Thr Arg His Thr Ser Arg Phe Leu Met Ile Trp
    290                 295                 300

Leu Ser Leu Leu Pro Phe Ala Leu Tyr Gly Thr Cys Gly Val Ser Thr
305                 310                 315                 320

Ile Pro Leu Cys Val Ile Ala Phe Leu Leu Gly Ile Glu Glu
                325                 330                 335

Ile Gly Val Ser Ile Glu Glu Pro Phe Ser Ile Leu Ala Leu Glu Ala
            340                 345                 350

Ile Ser Asp Ser Ala Leu Asn Asn Ser Arg Glu Leu Lys Ala Gln His
```

```
                    355                 360                 365
Asp Ala Glu Val Arg Asn Gly Asn Gln Met Ser Ala Thr Asp Leu Ile
    370                 375                 380

Ala Phe Glu Ala Ala Ala Arg Gly Arg Thr Pro Leu Ser Lys Leu Ser
385                 390                 395                 400

Gly Ala Pro Ala Ala Pro Ala Val Pro Ala Ala Pro Ala
                405                 410                 415

Pro Ala Ala Ala Pro Ala Pro Ala Pro Ala Val Pro Ala Ala Ala
                420                 425                 430

Pro Ala Tyr Val Ala Ala Ala Thr Asn Gly Ser Ala Asn Gly Ala
            435                 440                 445

Ala Pro Asn Thr Trp Pro Arg Pro Ser Pro Val Pro Thr Ser Gly
            450                 455                 460

Val Ser Phe Arg Lys
465

<210> SEQ ID NO 59
<211> LENGTH: 443
<212> TYPE: PRT
<213> ORGANISM: Raphidocelis subcapitata

<400> SEQUENCE: 59

Met Ala Leu Ala Ala Ala Arg Pro Ala Leu Cys Ala Gly Pro Ser Gln
1               5                   10                  15

Leu Arg Arg Ala Gly Gln Pro Ala Ala Gln Ala Ala Arg Pro Leu Leu
                20                  25                  30

Pro Leu Arg Arg Ala Arg Ala Pro Leu Arg Val Gln Ala Ser Lys Ala
            35                  40                  45

Asn Pro Tyr Ala His Met Asn Val Asp Asp Ala Ile Lys Glu Gln Thr
        50                  55                  60

Arg Lys Thr Ala Arg Thr Val Phe Asp Phe Glu Arg Trp Glu Ala His
65                  70                  75                  80

Arg Cys Ser Gly Arg Tyr Phe Arg His Ile Leu Gly Val Phe Asn Ser
                85                  90                  95

Arg Ile Ile Phe Gly Leu Leu Arg Pro Leu Met Leu Val Ile Leu Thr
            100                 105                 110

Ala Thr Ala Val Val Met Trp Glu Ser Leu Arg Gln Ala Gly Val Leu
        115                 120                 125

Pro Pro Val Val Pro Ser Val Gln Leu Ala Trp Ser Lys Glu Leu Phe
130                 135                 140

Gly Leu Thr Ser Phe Ala Leu Ser Leu Leu Val Phe His Thr Asn
145                 150                 155                 160

Ala Gly Tyr Glu Arg Trp Asp Gly Ala Arg Lys Ile Trp Gly Leu Met
                165                 170                 175

Leu Asn Arg Ser Arg Asp Ile Ala Arg Gln Gly Leu Thr Tyr Ile Pro
            180                 185                 190

Arg Asp Gln Pro His Leu Arg Ala Met Leu Cys Arg Trp Val Pro Ala
        195                 200                 205

Phe Ser Arg Thr Leu Met Cys His Leu Arg Gln Asp Ser Asp Phe Gly
210                 215                 220

Ala His Leu Lys Gly Val Leu Tyr Pro His Glu Ile Glu Ala Val Leu
225                 230                 235                 240

Ser Ser Thr His Arg Pro Asn Tyr Val Leu Gln Val Ile Ser Glu Ile
                245                 250                 255
```

-continued

```
Val Lys Ser Ala Arg Leu Pro Leu Ala Ala Arg Val Lys Met Asp Gln
            260                 265                 270

Asn Ile Thr Thr Phe His Asp Asp Leu Gly Gly Cys Glu Arg Ile Leu
        275                 280                 285

Lys Thr Pro Ile Pro Leu Ser Tyr Thr Arg His Thr Gly Arg Phe Leu
    290                 295                 300

Met Ile Trp Leu Leu Leu Leu Pro Phe Thr Leu Val Gly Gly Cys Gly
305                 310                 315                 320

Val Thr Thr Ile Pro Leu Cys Ala Thr Ile Gly Phe Leu Leu Met Gly
                325                 330                 335

Ile Asp Glu Ile Gly Val Ala Ile Glu Glu Pro Phe Ser Ile Leu Pro
            340                 345                 350

Leu Glu Ala Ile Ala Asn Ser Ala Leu Val Asn Ile Arg Glu Leu Glu
        355                 360                 365

Ala Ala His Gln Ala Asp Pro Glu Pro Asp Phe Ser Ala Ala Glu Asp
    370                 375                 380

His His Thr Arg Thr Ala Leu Asp Leu Val Ser Ala Thr Ala Thr Ala
385                 390                 395                 400

Gly Thr Ala Gln Arg Ala Ala Ala Ala Ala Thr Ala Ala Ser Ala
                405                 410                 415

Ala Ala Val Ala Ala Ala Ala Ala Ala Ala Ala Gly Ala Pro
            420                 425                 430

Arg Ser Trp Pro Ser Ser Pro Ala Phe Ala Asn
        435                 440

<210> SEQ ID NO 60
<211> LENGTH: 1146
<212> TYPE: PRT
<213> ORGANISM: Tetrabaena socialis

<400> SEQUENCE: 60

Met Gln Ala Leu Arg Leu Lys Gly Gln Arg Pro Gly Leu Arg Ala Ser
1               5                   10                  15

Leu Gln Pro Arg Arg Thr Val Val Arg Ile Val Ala Asn Ala Ala Lys
            20                  25                  30

Asp Pro Asn Ala Pro Ile Gln Ser Asn Pro Leu Gly Thr Leu Ser Ser
        35                  40                  45

Gln Ser Gly Thr Val Ala Pro Leu Leu Arg Ser Glu Ala Arg Arg
    50                  55                  60

Tyr Trp Arg Thr Val Tyr Asp Phe Pro Gln Trp Gln Lys His Arg Ser
65                  70                  75                  80

Ser Tyr Arg Phe Met Glu Arg Leu Phe Gln Leu Leu Gln Ser His Ile
                85                  90                  95

Leu Gln Asn Ala Leu Pro Ser Ile Ser Trp Val Thr Leu Val Ala Thr
            100                 105                 110

Leu Val Ala Ala Tyr Gly Thr Ser Phe Asp Gln Gly Leu Leu Pro Asp
        115                 120                 125

Gly Leu Pro Asn Ile Ser Pro Asn Ala Ser Cys Thr Ala Phe Ile Ser
    130                 135                 140

Asn Thr Ser Ile Ala Leu Ser Leu Leu Val Phe Arg Thr Asn Ser
145                 150                 155                 160

Ser Tyr Gly Arg Trp Asp Glu Ala Arg Lys Met Trp Gly Gly Leu Leu
                165                 170                 175

Asn Arg Ser Arg Asp Ile Met Arg Gln Gly Ala Thr Cys Phe Pro Asp
            180                 185                 190
```

-continued

```
Asp Gln Val Glu Ala Lys Lys Ala Leu Ala Arg Trp Val Ala Tyr
        195                 200                 205

Ala Arg Ala Leu Arg Ile His Phe Gln Pro Glu Val Thr Leu Glu Ser
    210                 215                 220

Glu Leu Lys Asn Ile Leu Thr Ala Pro Glu Leu Glu Met Leu Ala Arg
225                 230                 235                 240

Ser Gln His Arg Pro Val Arg Ala Ile His Ser Ile Ser Gln Ile Ile
                245                 250                 255

Gln Ser Val Pro Met Ser Ser Ile His Gln Met Gln Met Ser Asn Asn
                260                 265                 270

Leu Thr Phe Phe His Asp Val Leu Gly Gly Cys Glu Arg Leu Leu Arg
            275                 280                 285

Ala Pro Ile Pro Val Ser Tyr Thr Arg His Thr Ala Arg Phe Leu Phe
        290                 295                 300

Ala Trp Leu Thr Leu Leu Pro Phe Ala Leu Tyr Pro Thr Val Gly Trp
305                 310                 315                 320

Gly Val Val Pro Val Ser Thr Gly Ile Ala Ala Val Leu Cys Gly Ile
                325                 330                 335

Glu Glu Ile Gly Val Gln Cys Glu Glu Pro Phe Gly Ile Leu Pro Leu
            340                 345                 350

Asp Val Ile Cys Asn Arg Ile Gln Ala Asp Val Met Ala Thr Leu Lys
        355                 360                 365

Asp Asp Gln Asp Thr Lys Ile Val Leu Ser Glu Ala Gly Leu Leu Gly
    370                 375                 380

Leu Leu Pro Ser Ala Val Ala Thr Val Pro Val Ala Ala Ala Ala Ala
385                 390                 395                 400

Ala Ala Ala Ala Ala Ala Ala Pro Ala Asn Gly Asn Gly Asn Gly
                405                 410                 415

Asn Gly Asn Gly Asn Gly Ala Tyr Ala Gln Pro Ala Gly Ala Val Ala
                420                 425                 430

Ser Lys Asp Met Gln Val Arg Val Ala Ile Gly Ala Glu Lys His Gln
    435                 440                 445

Arg Val Cys Ala Pro Arg Gly Leu Arg Ala Pro Ala Leu Cys Gly Arg
        450                 455                 460

Arg Leu Arg Leu Val Val Ser Ala Asp Ala Ala Lys Asp Pro Asn Ala
465                 470                 475                 480

Pro Ile Gln Ser Asn Pro Leu Gly Thr Leu Ser Ser Gln Ser Gly Leu
                485                 490                 495

Val Ser Thr Thr Pro Arg Ser Glu Met Ala Arg Lys Tyr Phe Arg Thr
                500                 505                 510

Val Tyr Asp Phe Pro Gln Trp Gln Lys His Arg Asn Gln Tyr Arg Leu
    515                 520                 525

Met Lys Arg Leu Ile Thr Ile Pro Gln Ser His Ile Ile Gln Asn Ala
530                 535                 540

Leu Pro Ser Ile Ala Trp Val Gly Leu Val Ser Thr Ala Leu Ala Val
545                 550                 555                 560

Tyr Met Thr Ala Leu Asp Gln His Leu Leu Pro Glu Gly Leu Pro Ser
                565                 570                 575

Phe Ala Pro Asn Ala Ser Cys Ser Ala Phe Ile Ser Asn Thr Ser Val
                580                 585                 590

Ala Leu Ser Leu Leu Leu Val Phe Arg Thr Asn Thr Ser Tyr Ser Arg
                595                 600                 605
```

```
Trp Asp Glu Ala Arg Lys Met Trp Gly Gly Leu Leu Asn Arg Ser Arg
610                 615                 620
Asp Ile Met Arg Gln Ala Ala Thr Cys Phe Pro Asp Asp Gln Val Glu
625                 630                 635                 640
Ala Lys Lys Ala Leu Ala Arg Trp Val Val Ala Tyr Ala Arg Ala Leu
                645                 650                 655
Arg Ile His Phe Gln Pro Glu Val Thr Leu Glu Ser Glu Leu Lys Asn
                660                 665                 670
Ile Leu Thr Pro Ala Glu Leu Glu Met Leu Ala Arg Ser Gln His Arg
                675                 680                 685
Pro Val Arg Ala Ile His Ser Ile Ser Gln Ile Ile Gln Ser Val Pro
690                 695                 700
Met Ser Ser Val His Gln Met Gln Met Ser Asn Asn Leu Thr Phe Phe
705                 710                 715                 720
His Ala Lys Asp Pro Asn Ala Pro Ile Gln Ser Asn Pro Leu Gly Thr
                725                 730                 735
Leu Ser Ser Gln Ser Gly Leu Val Ser Thr Thr Pro Arg Ser Glu Met
                740                 745                 750
Ala Arg Lys Tyr Phe Arg Thr Val Tyr Asp Phe Pro Gln Trp Gln Lys
                755                 760                 765
His Arg Asn Gln Tyr Arg Leu Met Lys Arg Leu Ile Thr Ile Pro Gln
770                 775                 780
Ser His Ile Ile Gln Asn Ala Leu Pro Ser Ile Ala Trp Val Gly Leu
785                 790                 795                 800
Val Ser Thr Ala Leu Ala Val Tyr Met Thr Ala Leu Asp Gln His Leu
                805                 810                 815
Leu Pro Glu Gly Leu Pro Ser Phe Ala Pro Asn Ala Ser Cys Ser Ala
                820                 825                 830
Phe Ile Ser Asn Thr Ser Val Ala Leu Ser Leu Leu Leu Val Phe Arg
                835                 840                 845
Thr Asn Thr Ser Tyr Ser Arg Trp Asp Glu Ala Arg Lys Met Trp Gly
                850                 855                 860
Gly Leu Leu Asn Arg Ser Arg Asp Ile Met Arg Gln Ala Ala Thr Cys
865                 870                 875                 880
Phe Pro Asp Asp Gln Val Glu Ala Lys Lys Ala Leu Ala Arg Trp Val
                885                 890                 895
Val Ala Tyr Ala Arg Ala Leu Arg Ile His Phe Gln Pro Glu Val Thr
                900                 905                 910
Leu Glu Ser Glu Leu Lys Asn Ile Leu Thr Pro Ala Glu Leu Glu Met
                915                 920                 925
Leu Ala Arg Ser Gln His Arg Pro Val Arg Ala Ile His Ser Ile Ser
                930                 935                 940
Gln Ile Ile Gln Ser Val Pro Met Ser Ser Val His Gln Met Gln Met
945                 950                 955                 960
Ser Asn Asn Leu Thr Phe Phe His Asp Val Leu Gly Gly Cys Glu Arg
                965                 970                 975
Leu Leu Arg Ala Pro Ile Pro Val Ser Tyr Thr Arg His Thr Ala Arg
                980                 985                 990
Phe Leu Phe Ala Trp Leu Thr Leu Leu Pro Phe Ala Leu Tyr Gly Gln
                995                 1000                1005
Leu Gly Tyr Ala Val Val Pro Thr Cys Leu Gly Ile Ala Ala Val Leu
                1010                1015                1020
Cys Gly Ile Glu Glu Ile Gly Val Gln Cys Glu Glu Pro Phe Gly Ile
```

```
                1025           1030           1035           1040
Leu Pro Leu Asp Val Ile Cys Asn Arg Ile Gln Ala Asp Val Met Ala
                    1045           1050           1055

Thr Leu Lys Asp Asp Glu Asp Thr Lys Ile Val Leu Ala Glu Ala Gly
                    1060           1065           1070

Leu Leu Asn Leu Leu Pro Arg Pro Ala Ala Leu Ala Leu Glu Pro Ala
                    1075           1080           1085

Val Gln Tyr Ala Ala Ala Ser Asn Gly Asn Gly Asn Gly Ala Ser Thr
                    1090           1095           1100

Asn Gly Asn Gly Ala Ser Thr Asn Gly Asn Gly Ala Ser Thr Asn Gly
1105           1110           1115           1120

Asn Gly Asn Gly Lys Pro Ala Leu Val Thr Val Gly Ala Ser Ser Ala
                    1125           1130           1135

Ala Ala Met Lys Val Glu Ile Thr Pro Arg
                    1140           1145

<210> SEQ ID NO 61
<211> LENGTH: 705
<212> TYPE: PRT
<213> ORGANISM: Volvox carteri f. nagariensis

<400> SEQUENCE: 61

Met Gln Ser Gln Leu Gln Pro Arg Leu Gln Leu Gln Gly Thr Arg Leu
1               5                   10                  15

Asn Trp Leu Pro Gln Arg Ser Cys Val Gln Arg Arg Ser Leu Arg Val
                20                  25                  30

Asp Ala Thr Ser Gly Ala Ala Pro Pro Pro Ala Gly Lys Glu Leu
            35                  40                  45

Ser Asn Asp Met Val Thr Arg Gln Tyr Arg Arg Thr Val Tyr Asp Phe
50                  55                  60

Ser Leu Trp Ala Lys His Arg Asp Val Asn Arg Tyr Leu Tyr Asn Leu
65                  70                  75                  80

Lys Thr Ile Pro Gly Ser Arg Ile Ile Arg Thr Leu Gly Gln Pro Met
                85                  90                  95

Gly Ile Val Leu Ala Trp Ala Ala Met Phe Gly Phe Tyr Glu Thr Cys
            100                 105                 110

Leu Glu Ser Gly Val Leu Pro Ser Tyr Phe Pro Lys Leu Thr Leu Met
        115                 120                 125

Ser Ala Glu Pro Gln Gly Leu Thr Ser Phe Ala Leu Ser Leu Leu Leu
    130                 135                 140

Val Phe Arg Thr Asn Ser Ser Tyr Gly Arg Phe Asp Glu Ala Arg Lys
145                 150                 155                 160

Ile Trp Gly Gly Ile Leu Asn Arg Ala Arg Asn Ile Ala Asn Gln Ala
                165                 170                 175

Val Thr Phe Ile Pro Ala Glu Asp Val Ala Gly Arg Glu Ala Val Gly
            180                 185                 190

Lys Trp Ala Val Gly Phe Cys Arg Ala Leu Gln Ala His Leu Gln Glu
        195                 200                 205

Asp Ala Asn Leu Arg Glu Glu Leu Gln Lys Ala Gln Pro Arg Trp Ser
    210                 215                 220

Arg Glu Glu Ile Asp Met Leu Cys Ser Ala Gln His Ser Trp Gln Gln
225                 230                 235                 240

Leu Gln Ser Cys Val Asn Ala Phe Trp Pro Ile Lys Ala Ile Ser Met
                245                 250                 255
```

```
-continued

Leu Ser Glu Leu Thr Arg Gln Leu Pro Ile Ser Gln Phe Gln Ala Leu
            260                 265                 270

Gln Met Gln Glu Asn Val Thr Phe Phe Tyr Asp Ala Leu Gly Gly Cys
        275                 280                 285

Glu Arg Leu Leu Arg Thr Pro Ile Pro Val Ser Tyr Thr Arg Ile Leu
    290                 295                 300

Pro Leu Asp Ala Ile Cys Thr Arg Ala Gln Thr Asp Val Val Ser Leu
305                 310                 315                 320

Leu Lys Asp Asp Pro Ala Val Val Lys Tyr Ile Ser Asp Val Arg Gln
                325                 330                 335

Gly Arg Ile Ala Pro Pro Thr Glu Pro Pro Val Ala Gly Ala Ala Pro
            340                 345                 350

Val Ala Ala Pro Pro Pro Pro Pro Ala Ser Ala Gly Gly Gly
        355                 360                 365

Ile Ser Arg Ser Gly Ser Pro Thr Ala Gln Gln Pro Asp Val Met
    370                 375                 380

Lys Thr Val Thr Ser Met Leu His Asn Val Lys Ala Gly Ile Gly Ala
385                 390                 395                 400

Val Ala Pro Ala Pro Pro Arg Pro Pro Ser Pro Gln Pro Arg Ala Arg
                405                 410                 415

Ser Pro Arg Ala Ala Ser Pro Gly Gly Pro Ser Pro Phe Pro Arg Ala
            420                 425                 430

Ser Ala Gly Thr Gly Gly Ala Ala Ala Val Pro Ser Pro Pro Pro
        435                 440                 445

Ile Lys Pro Leu Thr Ser Ser Ser Ser Ser Gly Ala Val Ser
    450                 455                 460

Lys Asp Ser Asn Asn Ser Thr Ala Thr Ala Lys Lys Pro Ala Ser Ala
465                 470                 475                 480

Pro Ala Ala Ser Ser Ala Gly Phe Ser Met Gly Phe Ser Gly Leu Ala
                485                 490                 495

Asp Gly Ala Ala Ala Ala Lys Ser Ala Ser Ala Ala Ala Lys
            500                 505                 510

Phe Ser Lys Ile Ala Asp Ser Val Val Ala Gly Thr Pro Ala Ala Pro
        515                 520                 525

Ala Ser Glu Ala Lys Arg Glu Thr Ala Ala Ala Ala Met Gln Ala
    530                 535                 540

Gln Pro Arg Asn Thr Pro Ser Ser Ser Ser Thr Pro Ser Ala Ala
545                 550                 555                 560

Pro Ala Asn Gly Ser Ser Asp Asp Arg Ser Ser Gly Arg Arg
                565                 570                 575

Thr Ala Ala Ala Val Asn Trp Arg Glu Glu Leu Ala Ala Leu Arg Ala
            580                 585                 590

Gly Arg Glu Asp Ala Glu Glu Pro Ala Ser Ala Ser Ala Ser Tyr Asp
        595                 600                 605

Arg Glu Phe Pro Ser Ser Trp Ser Phe Ser Ser Ala Ser Ser Ala
    610                 615                 620

Ala Val Val Gln Ser Gly Asp Ala Glu Asp Glu Ala Arg Arg Phe
625                 630                 635                 640

Gly Gly Leu Ala Gly Arg Gly Ala Arg Ser Asp Thr Thr Thr Ser Ala
                645                 650                 655

Ala Ala Val Met Arg Gly Asn Gly Asn Gly Leu Ser Glu Asn Gly Tyr
            660                 665                 670

Gly Asn Gly Tyr Gly Asn Asp Asn Gly Asn Gly Asn Gly Asn Thr Val
```

```
                675                 680                 685
Glu Ala Arg Gly Ala Arg Pro Arg Thr Arg Pro Asp Trp Arg Asn Gln
        690                 695                 700
Leu
705

<210> SEQ ID NO 62
<211> LENGTH: 403
<212> TYPE: PRT
<213> ORGANISM: Volvox carteri f. nagariensis

<400> SEQUENCE: 62

Met Ser Ser Ser Met Met Val Cys Gly Arg Gln Gln Arg Leu Ser Met
1               5                   10                  15

Pro Arg Gly Leu Gly Ser Ala Leu Pro Gly Ser Arg Leu Cys Arg Ser
            20                  25                  30

Arg Leu Ile Ile Val Ala Ser Ala Ala Lys Asp Pro Asn Ala Pro Ile
        35                  40                  45

Gln Ser Asn Pro Leu Gly Ala Leu Ser Ser Gln Ala Gly Thr Val Thr
    50                  55                  60

Pro Leu Pro Arg Ser Glu Glu Ala Arg Lys Tyr Phe Arg Thr Val Tyr
65                  70                  75                  80

Asp Phe Pro Gln Trp Gln Thr His Arg Ser Gln Phe Arg Leu Met Lys
                85                  90                  95

Arg Leu Phe Thr Ile Pro Gln Ser His Val Ile Gln Asn Ala Leu Pro
            100                 105                 110

Ser Ile Leu Trp Val Gly Ile Val Ser Ser Ala Leu Ala Ala Tyr Met
        115                 120                 125

Thr Ala His Asp Gln His Ile Leu Pro Glu Gly Phe Pro Ser Leu Ser
    130                 135                 140

Pro Asn Ala Ser Cys Ser Ala Phe Ile Ser Asn Thr Ser Val Ala Leu
145                 150                 155                 160

Ser Leu Leu Leu Val Phe Arg Thr Asn Ser Ser Tyr Gly Arg Trp Asp
                165                 170                 175

Glu Ala Arg Lys Met Trp Gly Gly Leu Leu Asn Arg Ser Arg Asp Ile
            180                 185                 190

Met Arg Gln Gly Ala Thr Cys Phe Pro Asp Asp Gln Val Glu Ala Lys
        195                 200                 205

Lys Ala Leu Ala Arg Trp Val Val Ala Phe Arg Ala Leu Arg Ile
    210                 215                 220

His Phe Gln Pro Glu Val Ser Ile Glu Ser Glu Leu Lys Asn Ile Leu
225                 230                 235                 240

Thr Pro Ala Glu Leu Glu Met Leu Ala Lys Ser Gln His Arg Pro Val
                245                 250                 255

Arg Ala Ile His Ala Ile Ser Gln Ile Ile Gln Ser Val Pro Met Ser
            260                 265                 270

Ser Ile His Gln Met Gln Met Ser Asn Asn Leu Thr Phe Phe His Asp
        275                 280                 285

Val Leu Gly Gly Cys Glu Arg Leu Leu Arg Ala Pro Ile Pro Val Ser
    290                 295                 300

Tyr Thr Arg His Thr Ala Arg Phe Leu Phe Met Trp Leu Thr Leu Leu
305                 310                 315                 320

Pro Phe Ala Leu Tyr Gly Gln Cys Gly Leu Gly Val Pro Val Cys
                325                 330                 335
```

-continued

```
Thr Gly Ile Ala Ala Val Leu Cys Gly Ile Glu Glu Ile Gly Val Gln
            340                 345                 350

Cys Glu Glu Pro Phe Gly Ile Leu Pro Leu Glu Val Ile Cys Asn Arg
        355                 360                 365

Ile Gln Ala Asp Val Met Ala Thr Leu Lys Asp Asp Ala Asp Thr Lys
    370                 375                 380

Thr Val Leu Ala Glu Ala Gly Leu Glu Arg Pro Gln Pro Gln Pro Gln
385                 390                 395                 400

Arg Gly Glu

<210> SEQ ID NO 63
<211> LENGTH: 446
<212> TYPE: PRT
<213> ORGANISM: Volvox carteri f. nagariensis

<400> SEQUENCE: 63

Met Gln Ile Gly Thr Pro Met Arg Ala Ala Ser Gln Arg Pro Leu
1               5                   10                  15

Gly Leu Arg Tyr Ser Cys Leu Pro Arg Lys Leu Ile Arg Val Val Ala
            20                  25                  30

Asn Ala Ala Lys Asp Pro Asn Ala Pro Ile Gln Ser Asn Pro Leu Gly
        35                  40                  45

Thr Leu Ser Ser Gln Ser Gly Thr Val Asn Pro Leu Pro Arg Ser Glu
    50                  55                  60

Glu Ala Arg Arg Tyr Trp Arg Thr Val Tyr Asp Phe Pro Gln Trp Gln
65                  70                  75                  80

Lys His Arg Ser Pro Tyr Arg Phe Met Glu Arg Leu Phe Gln Leu Ser
                85                  90                  95

Gln Ser His Ile Leu Gln Asn Ala Leu Pro Ala Ile Ser Trp Val Thr
            100                 105                 110

Leu Val Ala Thr Met Val Ala Ala Tyr Gly Thr Ser Tyr Asp Gln His
        115                 120                 125

Leu Leu Pro Asp Gly Phe Pro Ser Ile Ser Pro Asn Ala Ser Cys Ser
    130                 135                 140

Ala Phe Val Ser Asn Thr Ser Val Ala Leu Ser Leu Leu Val Phe
145                 150                 155                 160

Arg Thr Asn Ser Ser Tyr Gly Arg Trp Asp Glu Ala Arg Lys Met Trp
                165                 170                 175

Gly Gly Leu Leu Asn Arg Ser Arg Asp Ile Met Arg Gln Gly Ala Thr
            180                 185                 190

Cys Phe Pro Asp Asp Gln Val Glu Ala Lys Lys Ala Leu Ala Arg Trp
        195                 200                 205

Val Val Ala Phe Ala Arg Ala Leu Arg Ile His Phe Gln Pro Glu Val
    210                 215                 220

Thr Ile Glu Ser Glu Leu Lys Asn Ile Leu Thr Pro Ala Glu Leu Glu
225                 230                 235                 240

Met Leu Ala Lys Ser Gln His Arg Pro Val Arg Ala Ile His Ala Ile
                245                 250                 255

Ser Gln Ile Ile Gln Ser Val Pro Met Ser Ser Ile His Gln Met Gln
            260                 265                 270

Met Ser Asn Asn Leu Thr Phe Phe His Asp Val Leu Gly Gly Cys Glu
        275                 280                 285

Arg Leu Leu Arg Ala Pro Ile Pro Val Ser Tyr Thr Arg His Thr Ala
    290                 295                 300
```

-continued

```
Arg Phe Leu Phe Ala Trp Leu Thr Leu Leu Pro Ala Leu Tyr Pro
305                 310                 315                 320

Ser Ala Gly Trp Gly Val Val Pro Val Cys Thr Gly Ile Ala Ala Val
            325                 330                 335

Leu Cys Gly Ile Glu Glu Ile Gly Val Gln Cys Glu Glu Pro Phe Gly
            340                 345                 350

Ile Leu Pro Leu Asp Val Ile Cys Asn Arg Ile Gln Ala Asp Val Met
            355                 360                 365

Ala Thr Leu Lys Asp Asp Ala Asp Thr Lys Thr Val Leu Ala Glu Ala
    370                 375                 380

Gly Leu Ala Ala Thr Gly Ala Ala Val Ala Ala Pro Arg Trp Leu Met
385                 390                 395                 400

Arg Arg Ala Pro Arg Ser Gly Trp Glu Glu Gly Ala Arg Glu Leu Val
            405                 410                 415

Val Cys Arg Arg Ala Arg Ile Thr Ser Ser Ser Asp Ser Glu Cys
            420                 425                 430

Glu Val Val Ala Ser Pro Cys Val Arg Phe Leu Ile Glu Pro
            435                 440                 445

<210> SEQ ID NO 64
<211> LENGTH: 398
<212> TYPE: PRT
<213> ORGANISM: Volvox carteri f. nagariensis

<400> SEQUENCE: 64

Met Gln Ala Asp Leu Ala Gly Phe His Ala Arg Pro Thr Phe Lys Arg
1               5                   10                  15

Thr Arg Asn Asn Cys Leu Arg His Ala His Arg Lys Pro Pro Phe Ala
            20                  25                  30

Arg Pro Val Ala Phe Gly Ser Pro Ile Gln Pro Leu Asp Arg Ser Ser
        35                  40                  45

Leu Trp Thr Ser Ser Ala Leu Trp Thr Val Glu Ser Val Leu Val Asn
    50                  55                  60

Leu Arg Arg Lys Arg Phe Glu Pro Lys Thr Val Glu Arg Val Tyr Glu
65                  70                  75                  80

Ala Asp Val Tyr Pro Ala Val Phe Asp Phe Ala Ser Trp Thr Gln His
                85                  90                  95

Arg Ser Arg Gly Arg Tyr Leu Glu His Cys Ile Thr Leu Phe Arg Ser
            100                 105                 110

Tyr Phe Phe Arg Asp Leu Leu Gly Pro Leu Leu Val Leu Val Gly Ala
        115                 120                 125

Ala Met Thr Val Ala Ser Tyr Glu Thr Ala Leu Gln Thr Gly Leu Leu
    130                 135                 140

Pro Arg Trp Leu Pro Asp Phe Gly Gly Ser Ser Asp Thr Pro Phe Gln
145                 150                 155                 160

Leu Thr Ser Phe Ala Leu Ser Leu Met Leu Val Phe Arg Thr Asn Ser
                165                 170                 175

Ser Tyr Ala Arg Trp Leu Asp Ala Arg Gln Gln Trp Gly Leu Ile Val
            180                 185                 190

Asn Thr Ala Arg Thr Phe Val Arg Gln Val Met Thr Thr Leu Pro Glu
        195                 200                 205

Thr Ser Cys Cys Glu Val Arg Ser Ala Leu Ala Arg Trp Thr Val Ala
    210                 215                 220

Phe Val Arg Leu Gly Lys Leu His Leu Arg Glu His Gly Asp Val Gly
225                 230                 235                 240
```

```
Ala Glu Val Gln Gly Leu Leu Asp Gly Glu Val Pro Leu Val Leu
            245                 250                 255

Ala Ala Ser His Arg Pro Leu Ala Ala Cys His Val Met Ser Gly Leu
            260                 265                 270

Leu Arg Ser Ala Glu Gly Ser Gly Gln Leu Ser Glu Gln Ala Arg Met
            275                 280                 285

Arg Leu Glu Ala Asp Ile Asn Leu Met Ser Gln Ala Leu Gly Ala Cys
            290                 295                 300

Glu Lys Ile Leu Arg Asn Pro Ile Pro Leu Ser Tyr Thr Arg His Thr
305                 310                 315                 320

Ser Arg Phe Leu Ile Leu Trp Leu Leu Trp Leu Pro Leu Ala Leu Trp
                325                 330                 335

Gly Lys Val Gly Trp Cys Val Val Pro Val Glu Ala Val Met Thr Tyr
                340                 345                 350

Leu Leu Leu Gly Ile Asp Glu Ile Ala Val Gln Met Glu Glu Pro Phe
                355                 360                 365

Gly Gly Ser Gly Leu Gly Gly Ala Gly Arg Ser Ala Ala Ser Cys Arg
            370                 375                 380

Trp Lys Thr Cys Val Arg Leu Tyr Asn Asn Pro Trp Ser Asn
385                 390                 395
```

<210> SEQ ID NO 65
<211> LENGTH: 389
<212> TYPE: PRT
<213> ORGANISM: Volvox carteri f. nagariensis

<400> SEQUENCE: 65

```
Met Ser Thr Asp Phe Val Ala Tyr Ser Val Cys Thr Ser Ala Leu Val
1               5                   10                  15

Cys Val Thr Phe Thr Phe Asp Asp Trp Lys Arg His Arg Ser Ser Asn
            20                  25                  30

Arg Tyr Leu Tyr His Leu Lys Thr Leu Ser Glu Ser Gly Ile Val Arg
        35                  40                  45

Gly Ile Ala Ala Pro Val Leu Phe Val Thr Ala Phe Thr Ala Gly Met
    50                  55                  60

Thr Leu Leu Tyr Val Val Ala Ala Leu Asn Val Ala His Ala Ala Arg
65                  70                  75                  80

Met Leu Pro Ala Trp Leu Pro Pro Leu Pro Asn Ile Ala Ile Glu Pro
                85                  90                  95

Ile Gln Leu Thr Ser Ile Ala Leu Ser Leu Leu Leu His Met Leu Thr
            100                 105                 110

Gly Val Arg His Glu Ser Ser Glu Thr Pro Pro Lys Pro Arg His Pro
        115                 120                 125

Arg Leu Leu Thr Cys Arg Arg Phe Pro Cys Ala Pro Leu Ser Leu Pro
    130                 135                 140

Val Leu Phe Tyr Asp Met Glu Lys Val Phe Arg Thr Asn Ala Ser Tyr
145                 150                 155                 160

Ser Arg Trp Asp Glu Gly Arg Arg Ser Phe Gly Ser Ile Thr Thr Val
                165                 170                 175

Ser Arg Asp Ile Ala Arg Gln Ala Phe Ala Trp Phe Arg Thr Asp Asp
            180                 185                 190

Met Thr Asn Arg Ser Arg Leu Gly Arg Trp Leu Val Ala Leu Gly Arg
        195                 200                 205

Val Thr Met Val His Leu Arg Glu Glu His Gly Met Gln Glu Glu Leu
```

Lys Gly Val Leu Lys Pro Gln Glu Ile Asp Ala Val Thr Ser Ser Ile
225                 230                 235                 240

His Ala Pro Ser Phe Cys Leu Gln Met Ile Thr Trp Thr Ile Arg Thr
                245                 250                 255

Ala Gly Leu Pro Gln Glu Leu Val Ile Arg Met Asp Glu Asn Val Ser
                260                 265                 270

Arg Leu Thr Asp Ala Val Ser Ala Cys Glu Arg Ile Leu Asn Thr Pro
            275                 280                 285

Ile Pro Leu Ser Tyr Thr Arg His Thr Ala Arg Phe Leu Met Ala Trp
            290                 295                 300

Leu Val Cys Leu Pro Phe Cys Leu Trp Ser Tyr Cys Gly Leu Ala Met
305                 310                 315                 320

Val Pro Ile Ala Ala Leu Val Ala Phe Val Leu Leu Gly Ile Glu Glu
                325                 330                 335

Ile Gly Val Tyr Ile Glu Glu Pro Phe Ser Ile Leu Ala Leu Glu Lys
                340                 345                 350

Leu Val Asn Lys Leu Glu Asn Ile Val Asn Ala Met Leu Arg Glu Ser
            355                 360                 365

Gln Trp Gln Thr Gln Ser Phe Ala Leu His Ile Leu Phe Val Gly Pro
370                 375                 380

Phe Pro Val Ser Val
385

<210> SEQ ID NO 66
<211> LENGTH: 929
<212> TYPE: PRT
<213> ORGANISM: Micractinium conductrix

<400> SEQUENCE: 66

Met Gln Arg Val Leu Ala Ala Ser Gly Ser Thr Thr His Met Ala Ala
1               5                   10                  15

Arg Pro Gly Leu Ser Gly Ser Ser Arg Ala Arg Ala Ala Thr Ala Ala
            20                  25                  30

Ala Thr Ala Arg Leu Thr Pro Ala Gly Arg Gly Asn Ala Leu Arg Leu
        35                  40                  45

Ala Met Pro Gln His Ala Gly Ala Ala Ala Gly Pro Arg Thr Arg
    50                  55                  60

Ala Pro Val Arg Val Ser Ala Ala Asp Pro Ala Val Lys Leu Thr
65                  70                  75                  80

Gly Asp Asp Leu Lys Glu Ala Asn Arg Lys Gln Met Arg Thr Val Phe
            85                  90                  95

Asp Phe Glu Leu Trp Arg Lys His Arg Ser Ser Ala Arg Tyr Trp Arg
            100                 105                 110

His Ile Thr Gly Ile Phe Glu Ser Arg Ile Val Ser Gly Leu Ala Ala
        115                 120                 125

Pro Leu Gly Tyr Val Ala Ala Leu Ser Thr Thr Val Ala Leu Tyr His
    130                 135                 140

Val Leu Ala Glu Ala Gly Tyr Ile Met Asp Val Pro Asp Leu Lys Leu
145                 150                 155                 160

Ala Ser Asn Ala Pro Phe Gly Leu Thr Ser Phe Ala Leu Ser Leu Leu
            165                 170                 175

Leu Val Phe Arg Thr Asn Ser Ser Tyr Gly Arg Trp Asp Glu Ala Arg
            180                 185                 190

```
Lys Met Trp Gly Leu Ile Val Asn Arg Ser Arg Asp Phe Val Arg Gln
        195                 200                 205

Gly Leu Gly Tyr Ile Pro Asp Ser Gln Pro Glu Leu Gln Asn Met Leu
    210                 215                 220

Cys Arg Trp Thr Val Ala Tyr Ser Arg Ser Leu Met Cys His Leu Arg
225                 230                 235                 240

Pro Gly Glu Asn Leu Glu Glu Glu Leu Lys Glu Thr Leu Pro Ala His
                245                 250                 255

Glu Leu Lys Ala Leu Leu Ser Ser Thr His Arg Pro Asn Tyr Val Val
            260                 265                 270

Gln Val Leu Thr Ala Val Leu Lys Glu Ala Gln Leu Pro Thr Ala Val
        275                 280                 285

Thr Ser Ser Arg Asp Ser Thr Ala Val Val Pro Ala Gly Ala Ala Tyr
    290                 295                 300

Arg Met Asp Glu Asn Leu Thr Val Phe Ala Asp Val Thr Gly Gly Cys
305                 310                 315                 320

Glu Arg Ile Leu Arg Thr Pro Ile Pro Leu Ser Tyr Thr Arg His Thr
                325                 330                 335

Ser Arg Phe Met Met Ile Trp Leu Thr Leu Leu Pro Phe Thr Leu Trp
            340                 345                 350

Asp Ser Cys Arg Trp Ala Met Val Pro Ile Ser Leu Ile Val Ser Phe
        355                 360                 365

Leu Leu Leu Gly Ile Glu Glu Ile Gly Val Ser Ile Glu Glu Pro Phe
    370                 375                 380

Thr Ile Leu Pro Leu Glu Val Ile Ser Arg Thr Ile Glu Gly Asn Val
385                 390                 395                 400

Lys Glu Leu Gln Lys Met His Ser Ser Glu Gly Lys Ala Val Met Gly
                405                 410                 415

Ala Ser Ala Glu Gly Asp Asn Leu Ser Ala Gln Ala Leu Val Asp Ala
            420                 425                 430

Val Leu Pro Ala Ile Ser Gly Asn Gly Asn Gly Ala Leu Ser Ala
        435                 440                 445

Ala Gly Ser Ser Gly Ser Ser Arg Ile Val Ile Lys Pro Ala Met
450                 455                 460

Ala Met Gln Gln Arg Ala Ser Ala Ala Pro Lys Arg Ser Ala Ala Thr
465                 470                 475                 480

Gly Ala Arg Ala Leu Val Ala His Pro Ala Ala Cys Arg Cys Ala Ala
                485                 490                 495

His Arg Arg Gly Arg Ser Leu Val Val Arg Ala Ala Ser Asp Asn Val
            500                 505                 510

Met Glu Val Gly Gly Arg Thr Ile Val Val Glu Asp Asp Gly Thr Ile
        515                 520                 525

Ile Ile Ser Gln Pro Ala Ala Ser Ala Ala Val Asp Val Lys Glu Ser
    530                 535                 540

Ala Glu Val Glu Tyr Leu Thr Ala Arg Ser Ala Ile Val Asn Lys His
545                 550                 555                 560

Phe Glu Gly Ser Leu Gly Ala Asp Asp Phe Ile Gln Arg Val Glu Met
                565                 570                 575

Ala Leu Tyr Ala Phe Gly Phe Thr Gly Glu Asn Ser Ile Ala Met Val
            580                 585                 590

Asn Leu Cys Arg Asp Glu Val Thr Val Thr Leu Lys Gln Lys Ile Asp
        595                 600                 605

Ala Val Phe Gly Ala Ser Phe Ser Thr Asn Gly Leu Gly Gly Val Leu
```

```
                610             615             620
Thr Cys Gly Ala Val Gly Met Gly Ala Gly Phe Ser His Ser Pro Ile
625                 630                 635                 640

Cys Asp Thr Thr Gly Lys Glu Arg Tyr Ile Phe Phe Ser Phe Pro His
                645                 650                 655

Ile Ser Ile Asn Ser Lys Gly Glu Val Gly Pro Met Ser Arg Pro Gly
                660                 665                 670

Arg Pro Gly Gln Ser Cys Ala Cys Gly Ala Leu Ile Lys Ser Trp Thr
                675                 680                 685

Glu Leu Arg Ser Glu Gly Val Ser Cys Asn Cys Lys Ile Pro Gly Val
                690                 695                 700

His Asp Ala Glu Asn Pro Glu Tyr Ser Ile Leu Lys Gln Arg Ile Ala
705                 710                 715                 720

Arg Arg Leu Arg His Glu Gly Glu Thr Asp Glu Ser Val Gln Gln Leu
                725                 730                 735

Ser Leu Val Asp Ile Thr Lys Val Ala Glu Arg Thr Ile Ser Asp Asp
                740                 745                 750

Leu Glu Tyr Leu Ile Ser Lys Thr Val Asp Thr Asn Lys Ala Asp Tyr
                755                 760                 765

Ala Val Ile Thr Gly Val Gln Val His Asn Trp Ala Phe Asp Phe Glu
770                 775                 780

Asp Asp Ser Pro Asn Leu Glu Phe Val Phe Pro Thr Ser Ala Tyr Val
785                 790                 795                 800

Val Val Asp Gly Val Lys Thr His Val Asp Leu Ala Ala Met Pro Pro
                805                 810                 815

Leu Thr Pro Arg Gln Ile Arg Leu Val His Gly Gly Asp Gln Gly Val
                820                 825                 830

Val Cys Asn Thr Gly Gly Gln Ser Thr Leu Arg Ala Glu Asp Pro Pro
                835                 840                 845

Tyr Ala Tyr Asp Ser Lys Asp Ala Arg Lys Val Gln Arg Thr Arg Leu
850                 855                 860

Gln Asn Tyr Ile Ser Leu Ile Lys Asp Glu Gly Leu Glu Ser Val Ala
865                 870                 875                 880

Ala Ala Pro Ser Ser Pro Ala Trp Ala Lys Gln Ile Thr Lys Ser Val
                885                 890                 895

Ala Asp Arg Thr Asn Ser Thr Ala Leu Asp Met Lys Phe Ala Gln Asn
                900                 905                 910

Glu Asp Leu Lys Glu Met Gln Ala Gln Leu Glu Ala Lys Tyr Gln Ser
                915                 920                 925

Leu
```

<210> SEQ ID NO 67
<211> LENGTH: 250
<212> TYPE: PRT
<213> ORGANISM: Chlamydomonas reinhardtii

<400> SEQUENCE: 67

```
Met Thr Arg Trp Arg Pro Arg Pro Trp Pro Ala Gly Leu Val Ala
1               5                   10                  15

Phe Ala Arg Ala Leu Arg Ile His Phe Gln Pro Glu Val Thr Ile Glu
                20                  25                  30

Ser Glu Leu Lys Asn Ile Leu Thr Pro Ala Glu Leu Gln Met Leu Ala
            35                  40                  45

Lys Ser Gln His Arg Pro Val Arg Ala Ile His Ala Ile Ser Gln Ile
```

```
            50                  55                  60
Ile Gln Ser Val Pro Met Ser Ser Ile His Gln Gln Met Ser Asn
 65                  70                  75                  80

Asn Leu Thr Phe Phe His Asp Val Leu Gly Gly Cys Glu Arg Leu Leu
                     85                  90                  95

Arg Ala Pro Ile Pro Val Ser Tyr Thr Arg His Thr Ala Arg Phe Leu
                100                 105                 110

Phe Ala Trp Leu Thr Leu Leu Pro Phe Ala Leu Tyr Gly Ser Cys Gly
            115                 120                 125

Val Ser Val Ile Pro Val Cys Ser Gly Ile Ala Ala Val Leu Cys Gly
        130                 135                 140

Ile Glu Glu Ile Gly Val Gln Cys Glu Glu Pro Phe Gly Ile Leu Pro
145                 150                 155                 160

Leu Asp Val Ile Cys Asn Arg Ile Gln Ala Asp Val Met Ala Thr Leu
                165                 170                 175

Lys Asp Asp Ala Asp Thr Lys Thr Ile Leu Ala Glu Ala Gly Leu Ile
                180                 185                 190

Ser Leu Arg Ala Asn Ser Ala Met Ala Val Glu Asn Ala Leu Pro Asp
            195                 200                 205

Leu Asp Ser Ile Asn Ala Ala Pro Asn Gly Asn Gly Ser His Asn
        210                 215                 220

Gly Asn Gly Ala Ala Val Pro Val Ser Val Ser Ala Gly Ala Ser Gly
225                 230                 235                 240

Asn Gly Met Asn Val Arg Ile Ser Pro Arg
                245                 250

<210> SEQ ID NO 68
<211> LENGTH: 883
<212> TYPE: PRT
<213> ORGANISM: Micractinium conductrix

<400> SEQUENCE: 68

Met Arg Arg Arg Ala Leu Ala Ala Ala Ala Gly Ser Thr Ala
 1               5                  10                  15

Pro Pro Pro His Arg Leu Gly Asp Asp Gly Ala Gly Asn Ala Ala Pro
                20                  25                  30

Pro Pro Leu Asp Pro Ser Met Pro Leu Pro Leu Pro Trp Gln Ala Tyr
             35                  40                  45

Phe Asp Gly Arg His Ala Ala Ser Cys Pro Gly Arg Gly Ala Thr Phe
         50                  55                  60

Asn Val Tyr Thr Ala Gly Ser Ala Gly Pro Val Val Leu Cys Leu His
 65                  70                  75                  80

Gly Gly Gly Tyr Thr Gly Leu Ser Trp Ser Leu Ile Ala Arg Ala Leu
                 85                  90                  95

Lys Asp Lys His Arg Val Val Ala Pro Asp Leu Arg Cys His Gly Leu
                100                 105                 110

Thr Val Ala Glu Asp Glu Ala Asp Phe Ser Ala Asp Thr Leu Ala Gly
             115                 120                 125

Asp Val Val Ala Leu Trp Arg Ala Leu Phe Ala Gly Gly Ala Ala
         130                 135                 140

Gly Ser Asp Gly Ser Thr Gly Ser Gly Gly Gly Gly Ser Ser
145                 150                 155                 160

Glu Ala Asp Val Gln Gln His Leu Gln Arg Leu Arg Gln Gly Pro Pro
                165                 170                 175
```

-continued

```
Pro Pro Thr Val Leu Val Gly His Ser Met Gly Ala Ile Ala Val
            180                 185                 190

His Ala Ala Ala Leu Gly Gly Ile Thr Ser Leu Ala Gly Ile Val Val
        195                 200                 205

Ile Asp Val Val Glu Gly Thr Ala Leu Ala Ser Leu Pro Tyr Met Ala
    210                 215                 220

Gly Val Leu Glu Lys Arg Pro Arg Arg Phe Ala Ser Leu Gln Gln Ala
225                 230                 235                 240

Val Asp Trp Ala Val Asp Ser Gly Met Cys Lys Arg Gln Glu Ala Ala
                245                 250                 255

His Val Ser Leu Pro Ala Met Leu Arg Arg Glu Pro Pro Gly Gly Pro
            260                 265                 270

Thr Gly Gly Gly Ala Glu Ala Ala Gly Gly Val Val Arg Leu Val Pro
        275                 280                 285

Gly Gly Leu Ala Pro Leu Ala Glu Gly Glu Glu Glu Glu Asp Gly
    290                 295                 300

Ala Glu Ala Ala Ala Ala Gln Gln Gln Gln Gln Gln Gln Gln Gln Gln
305                 310                 315                 320

Gln Gln Gln Gln Val Gln Gln Pro Ala Ala Gly Thr Gln Gln Ala Ala
                325                 330                 335

Pro Ser Gly Gly Gly Gly Gly Gly Gly Trp Val Trp Arg Thr Pro
            340                 345                 350

Leu Glu Arg Ser Ala Pro Phe Trp Glu Gly Trp Tyr Gln Gly Leu Ser
        355                 360                 365

Asp Met Phe Leu Lys Leu Ser Val Pro Lys Val Leu Val Leu Val Gly
    370                 375                 380

Thr Asp Arg Leu Asp Arg Pro Leu Thr Ile Gly Gln Met Gln Gly Arg
385                 390                 395                 400

Phe Gln Pro Val Leu Leu Pro Gln Ala Gly His Ala Val His Glu Asp
                405                 410                 415

Glu Pro Glu Ala Thr Ala Asp Ala Ile Ala Ala Phe Ile Lys Arg Phe
            420                 425                 430

Arg Asn Gly Glu Pro Pro Leu Gln Ile Pro Arg Pro Thr Pro Gly Leu
        435                 440                 445

Arg Pro Val Leu Pro Val Ala Met Gly Pro Ala Asp Ser Leu Arg Val
450                 455                 460

Gln Ser Lys Pro Asp Arg Ser Ile Asp Arg Ala Ser Ser Ser Asp Lys
465                 470                 475                 480

Val Val Ser Phe Pro Ala Leu Asp Ser Ile Glu Arg Tyr Tyr Glu Pro
                485                 490                 495

Val Lys Glu Asp Ala Arg Gln Tyr Arg Arg Thr Val Phe Asp Phe Glu
            500                 505                 510

Lys Trp Arg Glu His Arg Ser Thr Lys Arg Tyr Ala Arg His Ile Lys
        515                 520                 525

Ser Ile Lys Gly Ser Arg Met Val Arg Gly Leu Ala Ala Pro Leu Leu
    530                 535                 540

Trp Leu Thr Ala Val Ala Ala Val Ala Thr Phe Asn Thr Leu Val
545                 550                 555                 560

Glu Ala Gly Leu Ala Pro Asp Val Leu Pro Glu Leu Lys Phe Ser Asn
                565                 570                 575

Asn Gly Pro Phe Gly Leu Thr Ser Phe Ala Leu Ser Leu Leu Leu Val
            580                 585                 590

Phe Arg Thr Asn Ala Ser Tyr Ala Arg Trp Leu Asp Ala Arg Lys Asn
```

595                 600                 605
Trp Gly Thr Leu Thr Asn Arg Ser Arg Asp Leu Thr Arg Gln Ala Leu
    610                 615                 620

Thr Phe Phe Pro Ala Glu Asp Pro Ala Leu Phe His Leu Leu Cys Arg
625                 630                 635                 640

Trp Val Gln Ala Tyr Ser Arg Ser Leu Met Cys His Leu Arg Asp Asp
                645                 650                 655

Val Ser Ile Glu Glu Leu Pro Lys Ala Leu Leu Pro Tyr Glu Val
            660                 665                 670

Glu Ala Val Leu Ala Ser Arg His Arg Pro Leu Tyr Cys Leu Gln Met
        675                 680                 685

Leu Ser Glu Ile Val Arg Ala His Val Pro Pro Ala Gly Gln Pro
690                 695                 700

Pro Ala Gly Ala Ala Ala Ala Val Ala Ala Ala Asp Pro Phe
705                 710                 715                 720

Ala Gly Ala Ala Leu Ala Ala Ala Leu Arg Ala Ala Ala Gln Arg
                725                 730                 735

Met Asp Glu Asn Leu Ser Ile Phe Glu Asp Val Cys Gly Thr Cys Glu
            740                 745                 750

Arg Ile Leu Arg Ala Pro Ile Pro Leu Ser Tyr Thr Arg His Thr Ser
        755                 760                 765

Arg Phe Met Thr Ile Tyr Leu Ser Leu Leu Pro Phe Thr Leu Trp Asp
770                 775                 780

Ser Ala Gly Trp Ala Met Val Pro Leu Ile Ala Ile Val Ala Phe Leu
785                 790                 795                 800

Leu Leu Gly Ile Glu Glu Ile Gly Val Ser Ile Glu Glu Pro Phe Ser
                805                 810                 815

Ile Leu Pro Leu Glu Gln Met Cys Asp Thr Ile Gln Ala Ser Val Val
            820                 825                 830

Glu Leu Arg Ala Ile Asn Ser Gln Gln His Glu Gly Ser Ser Gly Asp
        835                 840                 845

Gly Gly Asn Gly Asn Gly Val Ala Ala Ala Pro Arg Gln Pro Pro Ser
850                 855                 860

Ala Arg Ala Leu Leu Arg Arg Gly Val Ala Glu Ala Ala Ala Asp
865                 870                 875                 880

Ala Leu Ala

<210> SEQ ID NO 69
<211> LENGTH: 2445
<212> TYPE: PRT
<213> ORGANISM: Chlorella sorokiniana

<400> SEQUENCE: 69

Met Gly Gly His Gly Phe Ile Glu Gly Phe Leu Lys Ser Trp Gly Val
1               5                   10                  15

Ile Leu Ala Ser Glu Ile Gly Asp Lys Thr Phe Phe Ile Ala Ala Ile
            20                  25                  30

Met Ala Met Arg His Ala Arg Leu Thr Val Phe Ala Gly Ala Met Ala
        35                  40                  45

Ala Leu Ala Ala Met Thr Val Leu Ser Ala Ala Leu Gly Trp Ala Ala
    50                  55                  60

Pro Asn Leu Ile Ser Lys Thr Tyr Thr His Tyr Ala Ala Thr Ala Leu
65                  70                  75                  80

Phe Phe Phe Phe Gly Gly Arg Met Leu Tyr Glu Ala Val Thr Asn Ala

```
                    85                  90                  95
His Ala Gly Glu Asn Glu Leu Asp Glu Val Glu Lys Glu Leu Glu Ala
                100                 105                 110

Val Asp Lys Ser Pro Lys Thr Gly Pro Ala Ala Asn Gly Lys Asn
            115                 120                 125

Pro Leu Leu Gly Thr Leu Arg Arg Phe Val Ser Pro Val Leu Leu Glu
    130                 135                 140

Ala Phe Thr Leu Thr Phe Leu Ala Glu Trp Gly Asp Arg Ser Gln Ile
145                 150                 155                 160

Ala Thr Ile Gly Leu Ala Ala Ala Asp Val Phe Gly Val Thr Val
                165                 170                 175

Gly Gly Ile Leu Gly His Ala Met Cys Thr Gly Ala Ala Val Leu Gly
                180                 185                 190

Gly Lys His Leu Ala Glu His Ile Asp Glu Arg Lys Val Ala Tyr Phe
            195                 200                 205

Gly Gly Val Leu Phe Leu Leu Phe Gly Ala His Ser Leu Tyr Thr Gly
    210                 215                 220

Val Pro Glu Cys Gly Gly Glu Ala Lys Met Pro Ser Leu Ala Ala Thr
225                 230                 235                 240

Glu Pro Val Asp Tyr Ala Val Leu Gly Ala Ala Gly Ala Ala Ala Leu
                245                 250                 255

Ala Gly Leu Ala Ala Cys Leu Tyr Thr Val Pro Trp Arg Leu Cys Arg
                260                 265                 270

Ala Ala Ala Pro Pro Ser Ala Pro Lys Ala Thr Arg Ser Phe Asn Val
            275                 280                 285

Leu Trp His Gly Arg Ser Leu Leu Ala Leu Leu Leu Thr Ala Trp Ala
    290                 295                 300

Leu Ser Pro Leu Leu Arg Val Ser Arg Leu Trp Gly Ala Asn Ser Phe
305                 310                 315                 320

Val Phe Ser Asp Gly Val Thr Ser Trp Thr Gly Ser Gly Trp Met Cys
                325                 330                 335

Arg Ile Tyr Leu Thr Ala Ala Leu Gly Val Leu Gln Pro Leu Cys Ala
                340                 345                 350

Phe Leu Ala Leu Leu Met Leu Thr Ala Gly Leu Ser Arg Arg His Arg
            355                 360                 365

Pro Glu Ala Leu Arg His Pro Asn Ala Arg Leu Leu Gly Leu Ala Ala
    370                 375                 380

Leu Cys Thr Leu Pro Val Ala Ala Val Gln Val Val Ala Trp Leu
385                 390                 395                 400

Ser Leu Ala Val Gln Tyr Gln Gly Gln Pro Leu Glu Gln Ala Pro Arg
                405                 410                 415

Ser Val Leu Gly Tyr Phe Phe Ala Thr Tyr Trp Glu Ser Pro Glu
                420                 425                 430

Gln Cys Gly Thr Gln Ala Ala Ala Ala Ala Val Val Pro Ala Ala
            435                 440                 445

Ala Asn Asp Ala Ala Ala Leu Gln Thr Pro Gly Gly Ser Gly Ser Leu
    450                 455                 460

Ser Leu Ser Ala Ala Gly Ser Pro Gly Asp Ala Ala Ala Gly Ala
465                 470                 475                 480

Ala Val Ala Pro Asp Gly Gly Cys Thr Leu Cys Cys Phe Pro Ala Ala
                485                 490                 495

Ala Val Ala Val His Ala Ile Phe Thr Val Ala Phe Leu Ala Ala Leu
                500                 505                 510
```

```
Trp Val Thr Cys Ser Arg Leu Ala Asp Ala Val Leu Asn Ser Arg Leu
        515                 520                 525

Lys Arg Arg Met Arg Leu Phe Gln Leu Ala His Ser Leu Leu Ala Val
530                 535                 540

Gly Gly Val Ala Ala Leu Gly Val Ser Ile Val Gln Gly Pro Phe Thr
545                 550                 555                 560

Trp Leu Asn Gln Ala Cys Trp Ala Ala Tyr Val Gly Thr Ala Val Ala
                565                 570                 575

Thr Val Ala Leu Val Leu Trp Glu Val Val Ser Pro Val Arg Asp
                580                 585                 590

Leu Arg Ser Val Asp Lys Arg Leu Ala Leu Trp Ala Asp Ala Thr Thr
        595                 600                 605

Ala Ala Phe Ala Ala Ala Gly Ala Asp Glu Pro Pro Met Ser Thr Gln
610                 615                 620

Ser Ser Gly Gly Ser Ser Val Leu Ile Lys Ala His Asn Arg Ser Ala
625                 630                 635                 640

Glu Ala Glu Ala Tyr Val Gln Ala Ala Ala Ala Arg Thr Leu Ser
                645                 650                 655

Ala Ser Pro Ala Gln Gly Gln Glu Lys Gly Gln Pro Ala Pro Pro Arg
                660                 665                 670

Pro Ser Leu Gln Leu Ala Pro Leu Ala Leu Pro Pro Leu Pro Gln Gly
        675                 680                 685

Thr Pro Arg Arg Ser Pro Ala Lys Gln Pro Thr Pro Leu Trp Arg Gln
        690                 695                 700

Gln Ala Gln Pro Ser Leu Leu Arg Gln Gln Tyr Gly Thr Ala Pro Ser
705                 710                 715                 720

Pro Leu Val Ser Pro Pro Arg Gln Pro Ala Arg Val Thr Val Ala Gly
                725                 730                 735

Ala Ala Ala Asp Leu Pro Pro Gly Pro Val Thr Ala Gly Leu Lys
                740                 745                 750

Ala Ala Gln Arg Arg Gln Pro Gly Ser Leu Arg Gly Lys Gln Glu Asp
        755                 760                 765

Val Trp Ser Leu Glu Asp Ala Ala Glu Met Gly Ala Ala Cys Ser Asn
        770                 775                 780

Ser Glu Lys Glu Leu Gly Arg Arg Tyr Met Arg Ser Leu Ser Thr Phe
785                 790                 795                 800

Asn Phe Gln Arg Trp Ala Phe His Arg Ser Thr Asp Arg Tyr Ala Arg
                805                 810                 815

His Met Leu Gly Ile Phe Gln Ser Arg Ile Val Arg Gly Leu Ala Ala
                820                 825                 830

Pro Leu Leu Ser Ala Gly Ala Thr Ala Thr Leu Val Cys Leu Tyr Glu
        835                 840                 845

Gln Ala Leu Gln Gln Gly Ala Leu Pro Ala Gln Leu Pro Ser Leu Val
850                 855                 860

Ile Ser Pro Leu Pro Leu Asp Leu Thr Ser Ala Ala Leu Gly Leu Leu
865                 870                 875                 880

Leu Val Phe Arg Thr Asn Ser Ser Tyr Glu Arg Trp Gln Gln Ala Leu
                885                 890                 895

Ala Ala Trp Gly Ala Ile Thr Thr Arg Ser Arg Asp Thr Met Arg Gln
                900                 905                 910

Leu Leu Cys Tyr Thr Ala Ala Thr Pro Glu Ala Gly Pro Ala Ser Thr
        915                 920                 925
```

-continued

```
Lys Leu Leu Thr Val Ala Ala Thr Gly Arg Trp Leu Val Ala Phe Ala
    930             935                 940
Arg Ala Leu Lys Ala Gln Leu Thr Glu Asp Ser Asp Leu Arg Ala Glu
945             950                 955                 960
Leu Glu Gly Ile Leu Thr Pro Thr Glu Leu Asp Leu Leu Cys Thr Ser
                965                 970                 975
Tyr Gln Pro Ser Ser Phe Thr Leu Ser Val Leu Thr Glu Leu Val Ala
            980                 985                 990
Ala Ala Pro Leu Arg Asp Ser Gln Arg Ile Arg Val Asp Glu Asn Leu
        995                1000                1005
Thr Ala Cys Glu Asp Ala Met Ser Ala Cys Glu Arg Ile Leu Arg Thr
    1010                1015                1020
Pro Ile Pro Leu Ser Tyr Thr Arg His Thr Ser Arg Phe Met Val Ile
1025                1030                1035                1040
Trp Leu Ser Cys Leu Pro Leu Gly Leu Trp Pro Ala Val Gly Trp Gly
                1045                1050                1055
Thr Val Pro Leu Thr Val Ala Ile Ala Phe Leu Leu Gly Ile Glu
                1060                1065                1070
Glu Ile Gly Val Ala Val Glu Glu Pro Phe Ser Ile Leu Pro Leu Asp
        1075                1080                1085
Glu Leu Cys Arg Glu Ile Glu Ile Ser Leu Ser Asp Ile Val Glu Gln
    1090                1095                1100
Ala Ser Ser Ser Lys Arg Ala Ala Lys Glu Ala Val Ser Ala Ala Ala
1105                1110                1115                1120
Ala Ala Ala Val Thr Ala Ala Ala Glu Ala Ala Ala Ala Ala
                1125                1130                1135
Ala Ala Ala Ala Glu Ala Ala Asp Gly Ser Gly Ser Ser Thr Ser Ser
            1140                1145                1150
Gly Asp Ser Thr Pro Leu Tyr Ala Ala Ala Gln Ala Pro Ala Ala
        1155                1160                1165
Ala Asn Ala Val Ala Pro Leu Leu Pro Gly Ala Leu Gly Arg Ala Ser
    1170                1175                1180
Pro Leu Lys Met Ala Ala Lys Asp Leu Glu Ser Gly Asp Ala Ser Thr
1185                1190                1195                1200
Ser Ser Asp Gly Cys Arg Leu Glu Pro Ser Pro Lys Lys Gly Leu Lys
                1205                1210                1215
Gln Ser Leu Ser Arg Ala Phe Leu Ser Ser Gly Leu Gln Val Thr Phe
            1220                1225                1230
Lys Asp Ile Thr Tyr Thr Val Val Asn Ser Gln Asn Lys Lys Glu Lys
        1235                1240                1245
Leu Asp Leu Leu Lys Gly Val Gly Gly Tyr Leu Gln Ala Gly Glu Met
    1250                1255                1260
Ala Ala Leu Met Gly Pro Ser Gly Ser Gly Lys Ser Thr Leu Leu Asp
1265                1270                1275                1280
Val Leu Ser Gly Arg Lys Thr Val Gly Glu Leu Gln Gly Glu Val Ala
                1285                1290                1295
Phe Ala Gly Asn Arg Pro Thr Pro Gln Phe Leu Arg Arg Phe Thr Gly
            1300                1305                1310
Tyr Val Glu Gln Phe Asp Thr Leu Leu Asp Ile Leu Thr Val Glu Glu
        1315                1320                1325
Met Leu Met Tyr Thr Ala Glu Leu Lys Arg Pro Val Ser Gln Thr Leu
    1330                1335                1340
Glu Gln Lys Lys Gly Ala Val Asp Glu Leu Ile Glu Val Leu Gly Leu
```

-continued

```
            1345                1350                1355                1360
Asp Gly Cys Arg Thr Val Arg Ile Gly Asn Pro Met Ala Arg Gly Ile
            1365                1370                1375
Ser Gly Gly Gln Ala Lys Arg Val Asn Ile Gly Ile Ala Leu Val Thr
            1380                1385                1390
Asn Pro Arg Val Leu Phe Leu Asp Glu Pro Thr Ser Gly Leu Asp Ser
            1395                1400                1405
Tyr Thr Ala Asn Glu Val Met Ser Val Val Lys Ser Leu Ala Ser His
            1410                1415                1420
Gly Ile Thr Val Cys Ala Thr Ile His Ser Pro Thr Pro Tyr Thr Phe
1425                1430                1435                1440
Asn Leu Phe Asp Arg Leu Leu Leu Leu Lys Gly Arg Val Val Tyr
            1445                1450                1455
Phe Gly Pro Asn Gly Lys Leu Ala Leu Asn Tyr Phe His Thr Gln Cys
            1460                1465                1470
Pro Cys Leu Ala Gly Leu Lys Glu Gly Glu Asn Glu Ala Glu Trp Leu
            1475                1480                1485
Val Asp Leu Thr Thr Gln Ala Asp Arg Gln Gly Arg Ala Ala Asp Phe
            1490                1495                1500
Ala Asp Thr Tyr Glu Arg Ser Glu Phe Lys Ala Ala Ala Glu Lys Glu
1505                1510                1515                1520
Ile Ala Ala Gln Leu Ala Thr Ala Ser Asp Leu Asp Glu Ala Thr Lys
            1525                1530                1535
Arg Asp Leu Ala Val Arg Arg Asp Thr Val Thr Pro Phe Trp Trp Gly
            1540                1545                1550
Leu Arg Thr Leu Leu Lys Tyr Arg Thr Leu Lys Asn Tyr Arg Asn Pro
            1555                1560                1565
Glu Tyr Leu Gly Pro Arg Ile Gly Asp Lys Leu Ile Phe Ser Leu Leu
            1570                1575                1580
Ile Phe Thr Leu Phe Trp Lys Val Gly Asn Asn Leu Ala Gln Asp Asn
1585                1590                1595                1600
Leu Met Asn Ile Ala Ala Val Leu Phe Met Trp Thr Thr Leu Pro Ala
            1605                1610                1615
Phe Gly Ala Ala Ser Tyr Val Pro Ala Ile Val Leu Glu Arg Pro Leu
            1620                1625                1630
Phe Thr Arg Glu Arg Asn Asp Gly Leu Tyr Arg Val Ile Thr Tyr Leu
            1635                1640                1645
Val Ala Lys Ile Ile Glu Glu Leu Gly Leu Ala Leu Leu Cys Ser Ile
            1650                1655                1660
Val Phe Ala Asn Ile Val Trp Trp Ala Leu Gln Leu Gln Gly Ser Phe
1665                1670                1675                1680
Ala Leu Phe Trp Leu Ile Tyr Phe Leu Thr Leu Ser Thr Gly Ile Val
            1685                1690                1695
Leu Ala Tyr Thr Val Ala Ala Leu Ser Pro Asn Met Asp Val Ala Asn
            1700                1705                1710
Ala Ala Leu Pro Ala Tyr Val Val Thr Leu Leu Phe Phe Ala Gly Phe
            1715                1720                1725
Leu Ile Arg Phe Asp Lys Ile Pro Asn Tyr Trp Lys Trp Tyr Ser Tyr
            1730                1735                1740
Ile Asp Val Leu Arg Tyr Ala Trp Gly Ala Leu Met Lys Asn Gln Phe
1745                1750                1755                1760
Asn Gly Asp Arg Asn Val Glu Phe Val Ser Gly Gln Thr Ile Leu Asp
            1765                1770                1775
```

```
Tyr Tyr Ser Leu Ser Gly Ile Asn Ala Trp Gly Trp Leu Gly Ile Glu
            1780                1785                1790

Ala Ala Phe Val Ala Val Phe Phe Gly Phe Ala Tyr Leu Ala Leu Lys
            1795                1800                1805

Tyr Ile Ser His Pro Leu Lys Met Thr Thr Lys Asp Leu Glu Ala Gly
            1810                1815                1820

Asp Ala Ser Thr Gly Ser Asp Gly Cys His Leu Gly Leu Glu Ala Ser
1825                1830                1835                1840

Pro Lys Lys Gly Leu Lys Gln Ser Leu Ser Arg Ala Phe Leu Ser Ser
            1845                1850                1855

Gly Leu Gln Val Thr Phe Lys Asp Ile Thr Tyr Thr Val Val Asn Ser
            1860                1865                1870

Gln Asn Lys Lys Glu Lys Leu Asp Leu Leu Lys Gly Val Gly Gly Tyr
            1875                1880                1885

Leu Gln Ala Gly Glu Met Ala Ala Leu Met Gly Pro Ser Gly Ser Gly
            1890                1895                1900

Lys Ser Thr Leu Leu Asp Val Leu Ser Gly Arg Lys Thr Val Gly Glu
1905                1910                1915                1920

Leu Gln Gly Glu Val Ala Phe Ala Gly Asn Arg Pro Thr Pro Gln Phe
            1925                1930                1935

Leu Arg Arg Phe Thr Gly Tyr Val Glu Gln Phe Asp Thr Leu Leu Asp
            1940                1945                1950

Ile Leu Thr Val Glu Glu Met Leu Met Tyr Thr Ala Glu Leu Lys Arg
            1955                1960                1965

Pro Val Glu Gln Ser Leu Glu His Lys Arg Ala Ala Val Asp Glu Leu
            1970                1975                1980

Ile Glu Val Leu Ala Leu Glu Gly Cys Arg Thr Val Arg Ile Gly Asn
1985                1990                1995                2000

Pro Met Ala Arg Gly Ile Ser Gly Gly Gln Ala Lys Arg Val Asn Ile
            2005                2010                2015

Gly Ile Ala Leu Val Thr Asn Pro Arg Val Leu Phe Leu Asp Glu Pro
            2020                2025                2030

Thr Ser Gly Leu Asp Ser Tyr Thr Ala Asn Glu Val Met Ser Val Val
            2035                2040                2045

Lys Ser Leu Ala Ser His Gly Ile Thr Val Cys Ala Thr Ile His Ser
            2050                2055                2060

Pro Thr Pro Tyr Thr Phe Asn Leu Phe Asp Arg Leu Leu Leu Leu Leu
2065                2070                2075                2080

Lys Gly Arg Val Val Tyr Phe Gly Pro Asn Gly Lys Leu Ala Leu Asp
            2085                2090                2095

Tyr Phe His Thr Gln Cys Pro Cys Leu Ala Gly Leu Lys Glu Gly Glu
            2100                2105                2110

Asn Glu Ala Glu Trp Leu Val Asp Leu Thr Thr Gln Ala Asp Arg Gln
            2115                2120                2125

Gly Arg Ala Ala Asp Phe Ala Asp Thr Tyr Glu Arg Ser Glu Phe Lys
            2130                2135                2140

Ala Ala Ala Asp Lys Glu Val Ala Ala Gln Leu Ala Thr Ala Ser Asn
2145                2150                2155                2160

Leu Asp Glu Ala Thr Lys Arg Asp Leu Ala Val Arg Arg Asp Thr Val
            2165                2170                2175

Thr Pro Phe Trp Trp Gly Leu Arg Thr Leu Leu Lys Tyr Arg Thr Leu
            2180                2185                2190
```

```
Lys Asn Tyr Arg Asn Pro Glu Tyr Leu Gly Pro Arg Ile Gly Asp Lys
         2195                2200                2205

Leu Ile Phe Ser Leu Leu Ile Phe Thr Leu Phe Trp Lys Val Gly Asn
         2210                2215                2220

Asn Leu Ala Gln Asp Asn Leu Met Asn Ile Thr Ser Met Leu Phe Met
2225                2230                2235                2240

Trp Thr Val Leu Pro Ala Phe Gly Ala Ala Ser Tyr Val Pro Ala Ile
         2245                2250                2255

Val Leu Glu Arg Pro Leu Phe Thr Arg Glu Arg Asn Asp Gly Leu Tyr
         2260                2265                2270

Arg Val Ile Thr Tyr Leu Val Ala Lys Ile Val Glu Glu Leu Gly Leu
         2275                2280                2285

Ala Leu Leu Cys Ser Ile Val Phe Ala Asn Ile Val Trp Trp Ala Leu
         2290                2295                2300

Gln Leu Gln Gly Ser Phe Ala Leu Phe Trp Leu Ile Tyr Tyr Leu Thr
2305                2310                2315                2320

Leu Ser Thr Gly Ile Val Leu Ala Tyr Thr Val Ala Ala Leu Ser Pro
         2325                2330                2335

Asn Met Asp Val Ala Asn Ala Ala Leu Pro Ala Tyr Val Val Thr Leu
         2340                2345                2350

Leu Phe Phe Ala Gly Cys Leu Ile Arg Phe Val Asp Ile Pro Asn Tyr
         2355                2360                2365

Trp Lys Trp Tyr Ala Tyr Ile Asp Val Leu Arg Tyr Ala Trp Gly Ala
         2370                2375                2380

Leu Met Lys Asn Gln Phe Asp Gly Asp Arg Asn Val Glu Phe Val Gly
2385                2390                2395                2400

Gly Gln Thr Ile Leu Asp Tyr Tyr Ser Leu Ser Gly Ile Asn Ala Trp
         2405                2410                2415

Gly Trp Leu Gly Ile Glu Ala Ala Phe Val Ala Val Phe Phe Cys Phe
         2420                2425                2430

Ala Tyr Leu Ala Leu Lys Tyr Ile Ser His Val Arg Arg
         2435                2440                2445

<210> SEQ ID NO 70
<211> LENGTH: 282
<212> TYPE: PRT
<213> ORGANISM: Chlamydomonas reinhardtii

<400> SEQUENCE: 70

Met Ala Thr Leu Lys Asp Asp Ala Asp Thr Lys Thr Val Leu Ala Glu
1               5                   10                  15

Ala Gly Leu Ile Ser Leu Ile Pro Gly His Trp Arg Asn Ala Asp Thr
            20                  25                  30

Asn Leu Ser Leu Ser Arg Arg Tyr Gly Gly Tyr Glu Val Val Tyr
            35                  40                  45

Cys Ala Pro Pro Arg Ser Ser Gln Ala Gly Pro Val Ser Trp Ala Ala
            50                  55                  60

Asn Lys Asp Pro Asn Ala Pro Ile Gln Ser Asn Pro Leu Gly Ser Phe
65                  70                  75                  80

Ser Ser Gln Leu Gln Asn Gln Pro Thr Leu Pro Arg Ser Glu Glu Ala
            85                  90                  95

Arg Lys Tyr Phe Arg Thr Val Tyr Asp Phe Pro Gln Trp Gln Thr His
            100                 105                 110

Arg Asn Gln Tyr Arg Leu Met Lys Arg Leu Phe Ser Ile Pro Gln Ser
            115                 120                 125
```

His Val Ile Gln Asn Ala Leu Pro Ser Ile Met Trp Val Ala Phe Thr
    130                 135                 140

Ser Thr Cys Val Ala Ala Tyr Met Tyr Gly Tyr Asp Gln His Met Leu
145                 150                 155                 160

Pro Glu Gly Phe Pro Thr Leu Ala Pro Asn Ala Ala Cys Ser Ala Phe
                165                 170                 175

Ile Ser Asn Thr Ser Val Ala Leu Ser Leu Leu Val Phe Arg Thr
            180                 185                 190

Asn Ser Ser Tyr Gly Arg Trp Asp Glu Ala Arg Lys Met Trp Gly Gly
            195                 200                 205

Leu Leu Asn Arg Ser Arg Asp Ile Met Arg Gln Gly Ala Thr Cys Phe
    210                 215                 220

Pro Asp Asp Gln Val Glu Ala Lys Lys Ala Leu Ala Arg Trp Val Val
225                 230                 235                 240

Ala Phe Ser Arg Ala Leu Arg Ile His Phe Gln Pro Glu Ser Gly Tyr
                245                 250                 255

Trp Gln Ser Ala Arg Ala Leu Leu Ala Gly Arg Ala Ser Val Ile
            260                 265                 270

Gln Gly Ser Ala Cys Val Val Ala Thr Gln
            275                 280

<210> SEQ ID NO 71
<211> LENGTH: 302
<212> TYPE: PRT
<213> ORGANISM: Chlamydomonas reinhardtii

<400> SEQUENCE: 71

Val Tyr Asp Phe Pro Gln Trp Gln Lys His Arg Ser Ser Tyr Arg Phe
1               5                   10                  15

Ala Glu Arg Leu Phe Gln Leu Ser Gln Ser His Ile Leu Gln Asn Ala
            20                  25                  30

Leu Pro Ala Ile Ser Trp Val Thr Leu Val Ala Thr Leu Val Ala Ser
        35                  40                  45

Tyr Gly Tyr Ser Tyr Asp Gln His Met Leu Pro Asp Val Phe Pro Ser
50                  55                  60

Ile Ser Pro Asn Ala Ser Cys Thr Ala Phe Ile Ser Asn Thr Ser Val
65                  70                  75                  80

Ala Leu Ser Leu Leu Leu Val Phe Arg Thr Asn Ser Ser Tyr Gly Arg
                85                  90                  95

Trp Asp Glu Ala Arg Lys Met Trp Gly Gly Leu Leu Asn Arg Ser Arg
            100                 105                 110

Asp Ile Met Arg Gln Gly Ala Thr Cys Phe Pro Asp Asp Gln Val Glu
        115                 120                 125

Ala Lys Lys Ala Leu Ala Arg Trp Thr Val Ala Phe Ser Arg Ala Leu
    130                 135                 140

Arg Ile His Phe Gln Pro Glu Val Thr Ile Glu Ser Glu Leu Gln Asn
145                 150                 155                 160

Ile Leu Thr Pro Ala Glu Leu Gln Met Leu Ala Lys Ser Gln His Arg
                165                 170                 175

Pro Val Arg Ala Ile His Ala Ile Ser Gln Ile Ile Gln Ser Val Pro
            180                 185                 190

Met Ser Ser Ile His Gln Gln Gln Met Ser Asn Asn Leu Thr Phe Phe
        195                 200                 205

His Asp Val Leu Gly Gly Cys Glu Arg Leu Leu Arg Ala Pro Ile Pro

```
                210                 215                 220
Val Ser Tyr Thr Arg His Thr Ala Arg Phe Leu Phe Ala Trp Leu Thr
225                 230                 235                 240

Leu Leu Pro Phe Ala Leu Tyr Pro Thr Thr Gly Trp Gly Val Val Pro
                245                 250                 255

Val Cys Thr Gly Ile Ala Ala Val Leu Cys Gly Ile Glu Glu Ile Gly
                260                 265                 270

Val Gln Cys Glu Glu Pro Phe Gly Ile Leu Pro Leu Asp Val Ile Cys
                275                 280                 285

Asn Arg Ile Gln Ala Asp Val Met Ala Thr Leu Lys Asp Asp
                290                 295                 300

<210> SEQ ID NO 72
<211> LENGTH: 414
<212> TYPE: PRT
<213> ORGANISM: Chlamydomonas reinhardtii

<400> SEQUENCE: 72

Met Ser Val Ala Arg Ser Ala Ala Pro Glu Ile Phe Ile Leu Ala
1               5                   10                  15

Ala Ala Arg Ala Leu His Leu Cys Ser Leu Lys Lys Asn Ala Leu Ser
                20                  25                  30

Asn Met Val Ile Arg Phe Met Ser Ile Asn Pro Arg Ser Leu Ser Trp
                35                  40                  45

Leu Gln Ser Phe Cys Gln Lys Asn Ala Lys Ser Ala Ala Arg Asp Gln
50                  55                  60

Arg Gln Leu Tyr Glu Val Glu Gly Arg Gly Thr Val Pro Phe Asp His
65                  70                  75                  80

Tyr Lys Glu Gly Ser Arg His Ala Arg Arg Met Thr Phe Thr Phe Asp
                85                  90                  95

Asp Trp Lys Arg His Arg Ser Ser Asn Arg Tyr Leu Tyr His Leu Lys
                100                 105                 110

Thr Leu Thr Glu Ser Gly Ile Val Arg Gly Ile Trp Ala Pro Val Ala
                115                 120                 125

Trp Val Thr Leu Phe Thr Ala Val Val Ala Thr Leu Asn Val Ala His
                130                 135                 140

Gly Ala Ala Met Leu Pro Pro Trp Val Pro Ala Met Pro Gln Ile Ala
145                 150                 155                 160

Ile Glu Pro Val Gln Leu Thr Ser Ile Ala Leu Ser Leu Leu Leu Val
                165                 170                 175

Phe Arg Thr Asn Ala Ser Tyr Ser Arg Trp Asp Glu Gly Arg Arg Ser
                180                 185                 190

Phe Gly Ser Ile Thr Thr Val Ser Arg Asp Ile Ala Arg Gln Ala Phe
                195                 200                 205

Ala Trp Phe Arg Pro Asp Asp Tyr Glu Ser Arg Val Arg Val Gly Arg
                210                 215                 220

Trp Leu Val Ala Leu Gly Arg Ser Thr Met Val His Leu Arg Glu Glu
225                 230                 235                 240

His Asp Met Glu Asp Glu Leu Arg Glu Val Leu Lys Pro Ala Glu Val
                245                 250                 255

Gln Ala Val Val Ser Ala Val His Ala Pro Ser Phe Cys Leu Gln Met
                260                 265                 270

Ile Thr Leu Ile Ile Arg Thr Ala Gly Leu Pro Gln Glu Leu Val Ile
                275                 280                 285
```

```
Arg Met Asp Glu Asn Val Ser Arg Leu Thr Asp Ala Val Ser Ala Cys
    290                 295                 300

Glu Arg Ile Leu Asn Thr Pro Ile Pro Leu Ser Tyr Thr Arg His Thr
305                 310                 315                 320

Ala Arg Phe Leu Met Ala Trp Leu Ala Cys Leu Pro Phe Cys Leu Trp
                325                 330                 335

Thr Tyr Cys Gly Pro Ala Met Val Pro Ile Ala Ala Leu Val Ala Phe
                340                 345                 350

Val Leu Leu Gly Ile Glu Glu Ile Gly Val Tyr Ile Glu Glu Leu Asp
                355                 360                 365

Arg Leu Val Lys Val Gly Ser Pro Thr Ala Ser Pro Arg Pro Glu Pro
370                 375                 380

Ala Ser Thr Asn Ser Asn Asn Ala Val Thr Asp Thr Ala Phe Gly Leu
385                 390                 395                 400

Gly Ala Ala Gly Gly Phe Ser Pro Ala Val Ala Gly Ala Met
                405                 410

<210> SEQ ID NO 73
<211> LENGTH: 374
<212> TYPE: PRT
<213> ORGANISM: Phaeodactylum tricornutum CCAP 1055/1

<400> SEQUENCE: 73

Met Leu Ser Ser Ser Arg Trp Gly Ser Ala Phe Val Cys Phe Leu Ala
1               5                   10                  15

Leu Ala Cys Ser Ser Ser Tyr Arg Thr Gln Ala Phe Ile Val Pro Ser
                20                  25                  30

Gly Thr Ser Ser Arg Val Ser Val Ala Val Arg Ser Leu Pro Pro Pro
            35                  40                  45

Arg Asp Ile Ala Tyr Gly Glu Ser Arg Lys Tyr Arg Arg Thr Val
    50                  55                  60

Tyr Thr His Asp Asp Trp Val Asn His Arg Ser Pro Asp Arg Phe Trp
65                  70                  75                  80

Arg Asn Ile Ile Ala Met Pro Thr Ser Gly Val Tyr Lys Asn Leu Ala
                85                  90                  95

Lys Glu Cys Ile Ala Thr Thr Ala Val Ala Thr Ala Ile Val Val Tyr
                100                 105                 110

Asn Ala Leu Val Gly Gly Tyr Thr Asp Phe Gly Gly Val Gln His Ala
            115                 120                 125

Ala Val Leu Gln Asn Glu Leu Leu Pro Lys Ile Gly Met Pro Val Ser
    130                 135                 140

Pro Phe Thr Val Ser Gly Ser Phe Leu Gly Phe Leu Leu Ile Phe Arg
145                 150                 155                 160

Thr Asn Ser Ser Tyr Lys Arg Trp Asp Glu Ala Arg Lys Asn Trp Gly
                165                 170                 175

Met Asn Ile Asn His Thr Arg Asp Leu Val Arg Met Gly Thr Ala Phe
                180                 185                 190

Tyr Asp Lys Thr Gly Val Thr Asp Glu Gln Arg Lys Lys Asp Leu Gln
            195                 200                 205

Ala Leu Ser Leu Ala Thr Trp Ser Phe Val Arg Ala Met Lys Arg His
    210                 215                 220

Leu Ser Pro Glu Gln Glu Asp Glu Gln Asp Phe Arg Arg Glu Leu His
225                 230                 235                 240

Glu Arg Leu Pro Pro Arg Gln Ala Gln Ala Ile Ile Asp Ala Ala His
                245                 250                 255
```

```
Arg Pro Asn Arg Ala Leu Phe Asp Leu Ser Val Ala Ile Glu Asn Leu
        260                 265                 270

Pro Met His Phe Met Arg Lys Asn Glu Ile His Asn Ala Ala Thr Ile
        275                 280                 285

Phe Glu Asp Asn Leu Gly Ser Ser Glu Arg Leu Leu Thr Ser Pro Ile
        290                 295                 300

Pro Leu Phe Tyr Ala Arg His Thr Ala Arg Phe Leu Gly Val Trp Leu
305                 310                 315                 320

Leu Leu Met Pro Phe Cys Leu Tyr Asp Pro Phe Ala Gly Ser Trp Asn
                325                 330                 335

His Val Gly Met Ile Pro Ala Thr Ala Leu Ile Ser Ile Phe Leu Phe
            340                 345                 350

Gly Ile Glu Glu Leu Ala Thr Ser Met Glu Glu Pro Phe Thr Ile Leu
                355                 360                 365

Pro Met Gln Ala Phe Cys
        370

<210> SEQ ID NO 74
<211> LENGTH: 455
<212> TYPE: PRT
<213> ORGANISM: Phaeodactylum tricornutum CCAP 1055/1

<400> SEQUENCE: 74

Met Met Arg Asn Phe Ala Ser Val Leu Leu Leu Ser Ser Gly Ala
1               5                   10                  15

Ala Ala Phe Ala Pro Val Gln His Asn Gly Val Arg Thr Ile Ala Thr
            20                  25                  30

Pro Ser Thr Pro Leu Tyr Gly Asn Thr Lys Gln Pro Pro Ala Leu Pro
        35                  40                  45

Pro Ile Lys Asp Ile Ser Tyr Gly Glu Glu Ser Arg Lys Tyr Arg Arg
50                  55                  60

Thr Val Tyr Ser His Asp Asp Trp Val Lys His Arg Ser Ser Asp Arg
65                  70                  75                  80

Phe Leu Arg Asn Leu Leu Ala Ile Gly Ser Ser Gly Val Tyr Lys Ser
                85                  90                  95

Leu Ala Lys Glu Val Leu Ala Thr Thr Gly Val Ala Thr Phe Ile Val
            100                 105                 110

Leu Tyr Asn Cys Leu Val Gly Gly Tyr Thr Asp Leu Glu Gly Ile Lys
        115                 120                 125

His Ser Ala Leu Ile Glu Ser Val Trp Ala Pro Leu Met Ala Leu Pro
130                 135                 140

Leu Ala Pro Phe Thr Leu Ser Ser Pro Ser Leu Gly Leu Leu Leu Val
145                 150                 155                 160

Phe Arg Thr Asn Thr Ser Tyr Gln Arg Trp Asp Glu Ala Arg Lys Asn
                165                 170                 175

Trp Gly Met Asn Ile Asn His Thr Arg Asp Leu Val Arg Met Gly Thr
            180                 185                 190

Ser Phe Tyr Asp Asn Ala Ala Val Ser Ser Glu Gln Arg Ala Lys Asp
        195                 200                 205

Leu Lys Ala Leu Ser Leu Ala Thr Trp Ser Phe Val Arg Ala Met Lys
210                 215                 220

Arg His Leu Ser Pro Glu Ser Glu Asp Glu Gln Asp Phe Arg Arg Glu
225                 230                 235                 240

Leu Phe Glu Arg Leu Pro Ala Pro Gln Ala Gln Ala Ile Ile Asp Ala
```

```
                    245             250             255
Ala His Arg Pro Asn Arg Ala Leu Phe Asp Leu Ser Val Ala Ile Glu
            260             265             270

Asn Leu Pro Met His Phe Leu Arg Lys Asn Gln Val His Gln Ala Val
            275             280             285

Thr Ile Phe Glu Asp Asn Leu Gly Ser Ser Glu Arg Leu Leu Thr Ser
    290             295             300

Pro Val Pro Leu Phe Tyr Ser Arg His Thr Ala Arg Phe Leu Ser Phe
305             310             315             320

Trp Leu Leu Leu Pro Phe Ala Leu Trp Asp Pro Phe Ala Gly Thr
            325             330             335

Trp Asn His Val Gly Met Ile Pro Ala Thr Ala Val Ile Ser Ile Phe
            340             345             350

Leu Phe Gly Ile Glu Glu Leu Ala Thr Gln Met Glu Glu Pro Phe Thr
            355             360             365

Ile Leu Pro Met Gln Ala Phe Cys Asp Lys Ile Gly Asn Trp Cys Asn
370             375             380

Glu Ile Val Ser Trp Gln Ala Gly Asp Asn Gly Met Ala Val Asn Met
385             390             395             400

Pro Ser Met Ile Ser Pro Glu Gly Leu Pro Glu Leu Lys Glu Pro Ala
                405             410             415

Pro Val Pro Ala Met Ala Val Ala Ser Val Ala Ala Met Pro Val
            420             425             430

Met Ala Asn Gly Asp Ile Asn Gly Asp Thr Thr Gly Ile Thr Met Asp
            435             440             445

Gln Pro His Asn Ala Ile Pro
450             455

<210> SEQ ID NO 75
<211> LENGTH: 408
<212> TYPE: PRT
<213> ORGANISM: Thalassiosira pseudonana CCMP1335

<400> SEQUENCE: 75

Met Pro Ser Phe Thr Ser Leu Ser Thr Leu Leu Leu Ala Leu Ser
1               5               10              15

Ser Pro Gln Ile Ser Ala Phe Ala Pro Leu Ser Ser Thr Ser Thr Pro
            20              25              30

Ile Asn Val Ala Pro Ser Thr Thr Ser Thr Thr Asn Leu Gln Met
        35              40              45

Gly Pro Pro Lys Thr Asp Ile Val Leu Ser Glu Thr Tyr Gly Glu Gly
    50              55              60

Ser Arg Lys Tyr Arg Arg Thr Val Tyr Thr His Asn Glu Trp Val Lys
65              70              75              80

His Arg Ser Ser Asp Arg Phe Ala Lys Asn Leu Phe Ser Met Val Asn
            85              90              95

Ser Gly Val Tyr Lys Ser Leu Ala Lys Glu Val Phe Ala Thr Thr Ala
            100             105             110

Val Ala Ser Ala Ile Val Ala Trp Asn Gly Ile Ala Gly Gly Tyr Thr
            115             120             125

Asp Phe Asn Gly Val Glu His Gly Ala Ile Met Ser Phe Leu Pro Gln
    130             135             140

Leu Val Leu Pro Leu Thr Pro Phe Thr Leu Leu Ser Pro Ser Leu Gly
145             150             155             160
```

```
Leu Leu Leu Val Phe Arg Thr Asn Ser Ser Tyr Gly Arg Trp Asp Glu
            165                 170                 175

Ala Arg Lys Met Trp Gly Leu Asn Ile Asn His Thr Arg Asp Leu Asn
        180                 185                 190

Arg Met Ala Thr Ala Trp Tyr Gly His Asp Asn Gln Ile Ile Asp Pro
        195                 200                 205

Ala Lys Arg Ala Glu Asp Leu Arg Gln Val Ser Leu Tyr Thr Trp Ala
210                 215                 220

Phe Val Arg Ser Met Lys Arg His Leu Ser Pro Pro Ser Glu Asp Glu
225                 230                 235                 240

Glu Ala Phe Val Glu Glu Leu Tyr Ala Arg Met Ala Pro Glu Gln Ala
                245                 250                 255

Glu Ala Ile Ile Ser Ala Ala His Arg Pro Asn Arg Ala Leu Tyr Asp
                260                 265                 270

Leu Ser Val Val Ile Asp Lys Leu Pro Met His Phe Met Arg Lys Asn
            275                 280                 285

Glu Ile Asn Lys Asn Leu Ser Ile Phe Glu Asp Thr Leu Gly Gly Cys
        290                 295                 300

Glu Arg Leu Leu Ser Ser Pro Val Pro Leu Phe Tyr Thr Arg His Thr
305                 310                 315                 320

Ala Arg Phe Leu Ser Thr Trp Leu Leu Leu Pro Leu Ala Met Tyr
                325                 330                 335

Gln Pro Phe Ser Gly Ser Trp Asn His Val Ala Met Ile Pro Ala Thr
                340                 345                 350

Ala Leu Thr Ser Val Phe Leu Phe Gly Ile Asp Glu Leu Ser Thr Gln
            355                 360                 365

Leu Glu Glu Pro Phe Thr Ile Leu Pro Met Gln Gly Phe Cys Asp Lys
        370                 375                 380

Ile Gly Gly Trp Cys Asp Glu Ile Val Ser Trp Arg Gly Gln Gly Leu
385                 390                 395                 400

Asp Lys Glu Glu Gln Gln Tyr Tyr
                405

<210> SEQ ID NO 76
<211> LENGTH: 390
<212> TYPE: PRT
<213> ORGANISM: Thalassiosira pseudonana CCMP1335

<400> SEQUENCE: 76

Met Gly Pro Pro Ile Asp Pro Ser Val Pro Val Thr Asp Gln Val Gly
1               5                   10                  15

Glu Gly Ser Arg Lys Tyr Arg Arg Thr Val Tyr Thr His Asp Asp Trp
            20                  25                  30

Val Arg His Arg Ser Pro Asp Arg Phe Gly Asn Asn Leu Ser Thr Leu
        35                  40                  45

Phe Asn Ser Gly Ile Tyr Lys Gln Val Ala Asn Glu Val Phe Ala Thr
    50                  55                  60

Thr Ala Val Ala Thr Phe Val Phe Leu Trp Asn Met Ile Ala Gly Gly
65                  70                  75                  80

Tyr Thr Asp Leu Ala Gly Val Gln His Gly Pro Ile Ile Asp Ser Pro
                85                  90                  95

Leu Ala Gln Met Val Gly Leu Pro Met Thr Ala Phe Thr Ile Leu Thr
            100                 105                 110

Pro Ser Leu Gly Leu Leu Val Phe Arg Thr Asn Thr Ser Tyr Gly
        115                 120                 125
```

Arg Trp Asp Glu Ala Arg Lys Met Trp Gly Leu Asn Ile Asn His Thr
130                 135                 140

Arg Asp Leu Asn Arg Met Ala Thr Ala Trp Tyr Gly Asn Glu Gly Asn
145                 150                 155                 160

Met Asp Ser Val Ala Phe Met Gly Gly Asp Ile Pro Tyr Ser Gln Pro
                165                 170                 175

Ile Asp Pro Val Gln Arg Ala Tyr Asp Leu Gly Gln Val Ser Leu Phe
                180                 185                 190

Thr Trp Ala Phe Val Arg Ser Met Lys Arg His Leu Ser Pro Pro Glu
            195                 200                 205

Glu Asp Glu Glu Asp Phe Lys Ala Glu Leu Arg Ala Arg Leu Thr Pro
210                 215                 220

Glu Gln Ala Glu Asn Ile Ile Asn Ala Ala His Arg Pro Asn Arg Ala
225                 230                 235                 240

Leu Phe Asp Leu Ser Val Ala Ile Glu Asn Leu Pro Met His Phe Leu
                245                 250                 255

Arg Lys Asn Ala Ile Asn Thr Asn Leu Ser Ile Phe Glu Asp Thr Leu
                260                 265                 270

Gly Gly Cys Glu Arg Leu Leu Ser Ser Pro Val Pro Leu Phe Tyr Ser
            275                 280                 285

Arg His Thr Ala Arg Phe Leu Ser Thr Trp Leu Leu Leu Leu Pro Phe
290                 295                 300

Gly Leu Tyr Glu Gln Phe Lys Asp Ser Trp Asn His Ile Ala Met Ile
305                 310                 315                 320

Pro Ala Thr Ala Phe Ile Ser Val Cys Leu Phe Gly Ile Glu Glu Leu
                325                 330                 335

Ala Thr Gln Leu Glu Glu Pro Phe Thr Ile Leu Pro Met Gln Gly Phe
            340                 345                 350

Cys Asp Lys Ile Gly Gly Trp Cys Asp Glu Ile Val Ser Trp Ala Gly
            355                 360                 365

Gln Gly Gln Gln Glu Tyr Thr Glu Glu Asn Ala Met Ser Asn Glu Gln
            370                 375                 380

Glu Met Thr Tyr Trp Arg
385                 390

<210> SEQ ID NO 77
<211> LENGTH: 426
<212> TYPE: PRT
<213> ORGANISM: Erythranthe guttata

<400> SEQUENCE: 77

Met Thr Asn Pro Ile His His Ser Ala Thr Lys Leu Ser Pro Ser Ser
1               5                   10                  15

Ser Ser Ser Ser Leu Ser Ser His Phe Thr Pro Lys Thr Leu Lys Lys
                20                  25                  30

Phe His Leu Tyr Pro Ser Asn Asn His Arg Ser Asn His His Leu
            35                  40                  45

Arg Phe Ser Cys Cys Gln Ser Ser Lys Asp Ser Asn Phe Ser Leu Asn
50                  55                  60

Gln Asp Ser Thr Phe Phe Ser Ile Leu Leu Ala Leu Pro Asn Trp Val
65                  70                  75                  80

Asp Ser Ile Gln Glu Lys Gly Leu Glu Lys Lys Arg Ser Leu Tyr Asp
                85                  90                  95

His Gly Asp Trp Val Gln His Arg Ser Ser Ser Arg His Val Arg His

```
                100                 105                 110
Phe Leu Ser Ser Leu Gly Ser Arg Val Ile Ser Leu Leu Pro Pro
            115                 120                 125
Val Ile Val Phe Thr Ser Val Ala Val Val Ser Thr Tyr Asn Thr
        130                 135                 140
Ala Val Ala Leu Ala Trp Leu Pro Glu Phe Phe Pro Ile Leu Arg Ala
145                 150                 155                 160
Ser Ser Leu Pro Tyr Gln Leu Thr Ala Pro Ala Leu Ala Leu Leu Leu
                165                 170                 175
Val Phe Arg Thr Glu Ala Ser Tyr Ser Arg Phe Asp Glu Gly Lys Lys
            180                 185                 190
Ala Trp Thr Lys Val Val Ser Gly Thr Asn Asp Phe Ala Arg Gln Val
        195                 200                 205
Ile Ala Ser Ala Val Gly Pro Asp Asp Ser Val Leu Lys Thr Ala Ile
210                 215                 220
Leu Gln Tyr Val Val Ala Phe Pro Val Ala Leu Lys Cys His Val Ile
225                 230                 235                 240
His Asp Ser Asp Ile Glu Gln Asp Leu Lys Asn Ile Leu Glu Thr Asp
                245                 250                 255
Asp Leu Ala Val Val Leu Thr Ser Asn His Arg Pro Arg Cys Ile Ile
            260                 265                 270
Glu Phe Ile Ser Gln Ser Leu Arg Ser Leu Asp Val Asp Pro Thr Lys
        275                 280                 285
Leu Gln Val Leu Glu Ser Lys Leu Ser Cys Phe His Glu Gly Ile Gly
    290                 295                 300
Val Cys Glu Gln Leu Leu Gly Ile Pro Ile Pro Leu Ser Tyr Thr Arg
305                 310                 315                 320
Leu Thr Ser Arg Phe Leu Val Leu Trp His Phe Thr Leu Pro Ile Ile
                325                 330                 335
Leu Trp Asp Asp Cys His Trp Ile Val Val Pro Ala Thr Phe Ile Ser
            340                 345                 350
Ala Ala Ser Leu Phe Cys Ile Glu Glu Val Gly Val Leu Ile Glu Glu
        355                 360                 365
Pro Phe Pro Met Leu Ala Leu Asp Glu Leu Cys Glu Lys Val Arg Ser
    370                 375                 380
Asn Ile Glu Asp Val Met Arg Asn Glu Lys Leu Ile Gln Ala Arg Val
385                 390                 395                 400
Asn Ala Lys Arg Lys Thr His Tyr Lys Arg Asp Ser Pro Asn Gly Trp
                405                 410                 415
Thr Ala Ser Leu Glu Asn Arg Lys Pro Asp
            420                 425

<210> SEQ ID NO 78
<211> LENGTH: 412
<212> TYPE: PRT
<213> ORGANISM: Solanum lycopersicum

<400> SEQUENCE: 78

Met Thr Asn Pro Arg Thr Leu Phe Thr Ile Gln Ser Pro Thr Asn Ala
1               5                   10                  15

Ser Phe Ser Ser His Phe Thr Leu Lys Asn Pro Ser Lys Ser Gln Gln
            20                  25                  30

Gln Pro Pro Val Tyr Lys Lys Leu Asn Phe Arg Val Leu Cys Ser Ser
        35                  40                  45
```

Gln Pro Ser Arg Thr Pro Gln Asn Ser Asn Leu Ile Ser Thr Leu Val
        50                  55                  60

Lys Ile Leu Arg Val Val Pro Asp Trp Ala Asp Lys Ile Gln Glu Gly
 65                  70                  75                  80

Gly Met Arg Lys Lys Arg Ser Leu Tyr Lys His Glu Thr Trp Val Gln
                 85                  90                  95

His Arg Ser Ser Leu Arg His Val Arg His Leu Phe Ser Ser Phe Asn
                100                 105                 110

Ser Arg Val Val Leu Ser Leu Ile Pro Pro Val Ile Ala Phe Thr Ser
                115                 120                 125

Phe Ala Phe Val Ile Ala Ser Tyr Asn Ser Ala Val Ser Phe His Trp
130                 135                 140

Leu Pro Glu Phe Phe Pro Ile Leu Arg Ala Ser Pro Gln Pro Tyr Gln
145                 150                 155                 160

Leu Thr Ala Pro Ala Leu Ala Leu Leu Val Phe Arg Thr Glu Ala
                165                 170                 175

Ser Tyr Ser Arg Phe Glu Ala Gly Lys Lys Ala Trp Thr Lys Val Ile
                180                 185                 190

Ala Gly Thr Asn Asp Phe Ala Arg Gln Val Ile Ala Cys Val Asp Lys
                195                 200                 205

Arg Asp Asp Val Leu Lys Glu Ala Leu Leu Gln Tyr Ile Met Ala Phe
210                 215                 220

Pro Val Ala Leu Lys Cys His Ile Val Tyr Asp Ser Asp Ile Ala Ser
225                 230                 235                 240

Asp Leu Lys Asn Leu Leu Glu Ala Asp Leu Ala Val Val Leu Ser
                245                 250                 255

Ser Lys His Arg Pro Arg Cys Ile Ile Gly Phe Ile Ala Gln Ser Leu
                260                 265                 270

Gln Ser Leu Asn Leu Glu Gly Thr Ile Leu Ser Gln Leu Glu Ser Lys
                275                 280                 285

Ile Ser Cys Phe His Glu Gly Ile Gly Val Cys Glu Gln Leu Leu Gly
                290                 295                 300

Ile Pro Ile Pro Leu Ser Tyr Thr Arg Leu Thr Ser Arg Phe Leu Val
305                 310                 315                 320

Leu Trp His Leu Thr Leu Pro Ile Ile Leu Trp Asp Cys His Trp
                325                 330                 335

Ile Val Val Pro Ala Thr Phe Ile Ser Ala Ala Ser Leu Phe Cys Ile
                340                 345                 350

Glu Glu Val Gly Val Leu Ile Glu Glu Pro Phe Pro Met Leu Ala Leu
                355                 360                 365

Asp Glu Leu Cys Gln Arg Val His Asp Asn Ile His Glu Ala Met Ala
370                 375                 380

Asn Glu Lys Gln Ile Gln Glu Ile Val Asn Ser Lys Arg Lys Arg Ser
385                 390                 395                 400

Phe Ser Glu His Ser Pro Asn Gly Trp Pro Thr Ser
                405                 410

<210> SEQ ID NO 79
<211> LENGTH: 414
<212> TYPE: PRT
<213> ORGANISM: Fragaria vesca subsp. vesca

<400> SEQUENCE: 79

Met Leu Thr Gln Pro Thr Asn Cys Ile Lys Pro Thr Ser Asn Ile Leu
 1                   5                  10                  15

```
Phe Ser Phe Asn Ser Ile Pro Lys Ser Phe Lys Leu His Pro Pro
                20                  25                  30

Leu Asn Pro Arg Thr Leu Ser Leu Lys His His Cys Ser Gln Tyr Pro
            35                  40                  45

Asn Pro Thr Pro Ser Ser Ser Ser Ser Ser Pro Phe Gln Pro Leu
 50                  55                  60

Ser Ser Ile Leu Arg Ile Ile Pro Asp Trp Ala Asp Glu Ile Lys Glu
 65                  70                  75                  80

Arg Gly Phe Arg Gln Asp Arg Thr Leu Tyr Asp His Glu Lys Trp Val
                85                  90                  95

His His Arg Ser Ser Tyr Arg His Leu Arg His Phe Leu Thr Ser Leu
                100                 105                 110

Ser Ser Arg Val Ile Leu Ser Leu Ile Pro Pro Val Ile Ala Phe Thr
            115                 120                 125

Leu Val Ala Val Val Ile Ala Ser Tyr Asn Thr Ala Val Ala Leu Glu
        130                 135                 140

Trp Leu Pro Glu Val Phe Pro Met Leu Arg Ser Ser Thr Leu Pro Tyr
145                 150                 155                 160

Gln Leu Thr Ala Pro Ala Leu Ala Leu Leu Val Phe Arg Thr Glu
                165                 170                 175

Ala Ser Tyr Ser Arg Phe Glu Glu Gly Arg Lys Ala Trp Thr Lys Val
                180                 185                 190

Ile Ala Gly Thr Asn Asp Phe Ala Arg Gln Ile Ile Ser Gly Val Glu
            195                 200                 205

Asn Ser Gly Asp Ala Glu Leu Lys Lys Ala Leu Leu Gln Tyr Val Val
        210                 215                 220

Ala Phe Pro Val Ala Leu Lys Cys His Val Ile Tyr Gly Ser Asn Met
225                 230                 235                 240

Gly Arg Asp Leu Gln Asn Leu Leu Glu Val Asp Asp Leu Leu Val Val
                245                 250                 255

Leu Ser Ser Lys His Gly Pro Gly Cys Ile Ile Glu Phe Ile Ser Gln
                260                 265                 270

Asn Ile Arg Met Leu Lys Leu Glu Glu Ser Arg Arg Asn Met Leu Glu
            275                 280                 285

Ser Asn Met Ser Cys Phe His Glu Gly Ile Ser Val Cys Glu Asn Leu
        290                 295                 300

Ile Gly Thr Pro Ile Pro Leu Ser Tyr Thr Arg Leu Thr Ser Arg Phe
305                 310                 315                 320

Leu Val Leu Trp His Leu Thr Leu Pro Ile Leu Trp Asp Asp Cys
                325                 330                 335

His Trp Ile Val Val Pro Ala Thr Phe Ile Ser Ala Ser Leu Phe
            340                 345                 350

Cys Ile Glu Glu Val Gly Val Leu Ile Glu Glu Pro Phe Pro Met Leu
        355                 360                 365

Ala Leu Asp Asp Leu Cys Arg Ser Val Gln Glu Asn Val Gln Glu Ala
        370                 375                 380

Leu Ser Arg Glu Lys Leu Ile Gln Ala Arg Leu Thr Ala Lys Gly Arg
385                 390                 395                 400

Ile Gln Lys Gln Gln His Cys Pro Asn Gly Gln Pro Lys Ser
                405                 410
```

<210> SEQ ID NO 80
<211> LENGTH: 416

```
<212> TYPE: PRT
<213> ORGANISM: Gossypium arboreum

<400> SEQUENCE: 80

Met Ala Gln Ser Pro Asn Ser Pro Lys Leu Ser Leu Ser Pro Ser Phe
1               5                   10                  15

Thr Ser Lys Pro Phe Leu His Phe His Phe Asn Ser Ser Leu Pro Ala
            20                  25                  30

Lys Phe Lys Arg Pro Pro Ser Phe Lys Ile Leu Phe Ser Ala Ser Gln
        35                  40                  45

Pro Pro Pro Pro Ser Ser Lys Pro Thr Thr Ala Pro Lys Thr Phe Asn
    50                  55                  60

Leu Ile Thr Leu Leu Arg Ala Ile Pro Asp Trp Ala Asp Arg Ile Gln
65                  70                  75                  80

Glu Arg Gly Met Gln Gln Asn Arg Ala Leu Tyr Asn His Glu Lys Trp
                85                  90                  95

Val His His Arg Ser Ser Leu Arg His Leu Arg His Leu Leu Ser Ser
            100                 105                 110

Leu Gln Ser Arg Val Ile Leu Ser Leu Val Pro Pro Val Leu Ala Phe
        115                 120                 125

Thr Ser Val Ala Thr Val Val Ala Leu Tyr Asn Thr Ala Val Asp Leu
    130                 135                 140

His Trp Phe Pro Gly Phe Phe Pro Val Leu Arg Ala Ser Ser Leu Pro
145                 150                 155                 160

Tyr Gln Leu Thr Ala Pro Ala Leu Ala Leu Leu Val Phe Arg Thr
                165                 170                 175

Glu Ala Ser Tyr Ser Arg Tyr Glu Glu Gly Arg Lys Ala Trp Thr Lys
            180                 185                 190

Val Ile Ala Gly Thr Asn Asp Phe Ala Arg Gln Val Ile Ala Gly Val
        195                 200                 205

Asp Asn Ser Ala Asp Asp Gln Ser Ile Lys Ala Ala Leu Leu Gln Tyr
    210                 215                 220

Ile Met Ala Phe Pro Val Ala Leu Lys Cys His Val Met Tyr Gly Ser
225                 230                 235                 240

Asp Ile Gly Arg Asp Leu Gln Asn Leu Leu Glu Val Asp Asp Leu Ala
                245                 250                 255

Val Ile Leu Asn Ser Lys His Arg Pro Arg Cys Ile Ile Glu Phe Ile
            260                 265                 270

Ser Gln Ser Leu His Leu Leu Asn Leu Glu Glu Ser Lys Arg Thr Thr
        275                 280                 285

Leu Glu Ser Lys Ile Ser Cys Phe His Glu Gly Ile Gly Val Cys Glu
    290                 295                 300

Gln Leu Met Gly Ile Pro Ile Pro Leu Ser Tyr Thr Arg Leu Thr Ser
305                 310                 315                 320

Arg Phe Leu Val Leu Trp His Leu Thr Leu Pro Ile Ile Leu Trp Asp
                325                 330                 335

Asp Cys His Trp Ile Val Val Pro Ala Thr Phe Ile Ser Ala Ala Ser
            340                 345                 350

Leu Phe Cys Ile Glu Glu Val Gly Val Leu Ile Glu Glu Pro Phe Pro
        355                 360                 365

Met Leu Ala Leu Asp Glu Leu Cys Ile Val Thr Gln Asn Asn Ile Arg
    370                 375                 380

Glu Ala Ile Ala Thr Glu Lys Asp Ile Gln Ala Met Leu Lys Gly Lys
385                 390                 395                 400
```

Arg Lys Arg His Ser Tyr Lys Arg Ser Pro Asn Gly Cys Pro Asn Thr
            405                 410                 415

<210> SEQ ID NO 81
<211> LENGTH: 416
<212> TYPE: PRT
<213> ORGANISM: Gossypium hirsutum

<400> SEQUENCE: 81

Met Ala Gln Ser Pro Asn Ser Pro Lys Leu Ser Leu Ser Ser Ser Phe
1               5                   10                  15

Thr Ser Lys Pro Phe Leu His Phe His Ser Asn Ser Ser Leu Pro Ala
            20                  25                  30

Lys Phe Lys Arg Pro Pro Ser Phe Lys Ile Leu Phe Ser Ala Ser Gln
        35                  40                  45

Pro Pro Pro Pro Ser Ser Lys Pro Thr Thr Ala Pro Lys Thr Phe Asn
    50                  55                  60

Leu Ile Thr Leu Leu Arg Ala Ile Pro Asp Trp Ala Asp Arg Ile Gln
65                  70                  75                  80

Glu Arg Gly Met Gln Gln Asn Arg Ala Leu Tyr Asn His Glu Lys Trp
                85                  90                  95

Val His Arg Ser Ser Leu Arg His Leu Arg His Leu Leu Ser Ser
            100                 105                 110

Leu Gln Ser Arg Val Ile Leu Ser Leu Val Pro Pro Val Leu Ala Phe
            115                 120                 125

Thr Ser Val Ala Ile Val Ile Ala Leu Tyr Asn Thr Ala Val Asp Leu
    130                 135                 140

His Trp Phe Pro Gly Phe Phe Pro Val Leu Arg Ala Ser Ser Leu Pro
145                 150                 155                 160

Tyr Gln Leu Thr Ala Pro Ala Leu Ala Leu Leu Val Phe Arg Thr
                165                 170                 175

Glu Ala Ser Tyr Ser Arg Tyr Glu Glu Gly Arg Lys Ala Trp Thr Lys
            180                 185                 190

Val Ile Ala Gly Thr Asn Asp Phe Ala Arg Gln Val Ile Ala Gly Val
        195                 200                 205

Asp Asn Ser Ala Asp Asp Gln Ser Ile Lys Ala Ala Leu Leu Gln Tyr
    210                 215                 220

Ile Met Ala Phe Pro Val Ala Leu Lys Cys His Val Met Tyr Gly Ser
225                 230                 235                 240

Asp Ile Gly Arg Asp Leu Gln Asn Leu Glu Val Asp Asp Leu Ala
                245                 250                 255

Leu Ile Leu Asn Ser Lys His Arg Pro Arg Cys Ile Ile Glu Phe Ile
            260                 265                 270

Ser Gln Ser Leu Gln Leu Leu Asn Leu Glu Glu Ser Lys Arg Thr Met
        275                 280                 285

Leu Glu Ser Lys Ile Ser Cys Phe His Glu Gly Ile Gly Val Cys Glu
    290                 295                 300

Gln Leu Met Gly Ile Pro Ile Pro Leu Ser Tyr Thr Arg Leu Thr Ser
305                 310                 315                 320

Arg Phe Leu Val Leu Trp His Leu Thr Leu Pro Ile Ile Leu Trp Asp
                325                 330                 335

Asp Cys His Trp Ile Val Val Pro Ala Thr Phe Ile Ser Ala Ala Ser
            340                 345                 350

Leu Phe Cys Ile Glu Glu Val Gly Val Leu Ile Glu Glu Pro Phe Pro

```
            355                 360                 365
Met Leu Ala Leu Asp Glu Leu Cys Ile Val Thr Gln Asn Asn Ile Lys
        370                 375                 380

Glu Ala Ile Ala Thr Glu Lys Asp Ile Gln Ala Met Leu Lys Gly Lys
385                 390                 395                 400

Arg Lys Arg His Ser Tyr Lys His Ser Pro Asn Gly Cys Pro Asn Thr
                405                 410                 415

<210> SEQ ID NO 82
<211> LENGTH: 416
<212> TYPE: PRT
<213> ORGANISM: Gossypium raimondii

<400> SEQUENCE: 82

Met Ala Gln Ser Pro Asn Ser Pro Lys Leu Ser Leu Ser Ser Ser Phe
1               5                   10                  15

Thr Ser Lys Pro Phe Leu His Phe His Ser Asn Ser Ser Leu Pro Ala
            20                  25                  30

Lys Phe Lys Arg Pro Pro Ser Phe Lys Ile Leu Phe Ser Ala Ser Gln
        35                  40                  45

Pro Pro Pro Pro Ser Ser Lys Pro Thr Thr Ala Pro Lys Thr Phe Asn
    50                  55                  60

Leu Ile Thr Leu Leu Arg Ala Ile Pro Asp Trp Ala Asp Arg Ile Gln
65                  70                  75                  80

Glu Arg Gly Met Gln Gln Asn Arg Ala Leu Tyr Asn His Glu Lys Trp
                85                  90                  95

Val His His Arg Ser Ser Leu Arg His Leu Arg His Leu Leu Ser Ser
            100                 105                 110

Leu Gln Ser Arg Val Ile Leu Ser Leu Val Pro Pro Val Leu Ala Phe
        115                 120                 125

Thr Ser Val Ala Ile Val Val Ala Leu Tyr Asn Thr Ala Val Asp Leu
    130                 135                 140

His Trp Phe Pro Gly Phe Phe Pro Val Leu Arg Ala Ser Ser Leu Pro
145                 150                 155                 160

Tyr Gln Leu Thr Ala Pro Ala Leu Ala Leu Leu Leu Val Phe Arg Thr
                165                 170                 175

Glu Ala Ser Tyr Ser Arg Tyr Glu Glu Gly Arg Lys Ala Trp Thr Lys
            180                 185                 190

Val Ile Ala Gly Thr Asn Asp Phe Ala Arg Gln Val Ile Ala Gly Val
        195                 200                 205

Asp Asn Ser Ala Asp Asp Gln Ser Ile Lys Ala Ala Leu Leu Gln Tyr
    210                 215                 220

Ile Met Ala Phe Pro Val Ala Leu Lys Cys His Val Met Tyr Gly Ser
225                 230                 235                 240

Asp Ile Gly Arg Asp Leu Gln Asn Leu Leu Glu Val Asp Asp Leu Ala
                245                 250                 255

Leu Ile Leu Asn Ser Lys His Arg Pro Arg Cys Ile Ile Glu Phe Ile
            260                 265                 270

Ser Gln Ser Leu Gln Leu Leu Asn Leu Glu Glu Ser Lys Arg Thr Met
        275                 280                 285

Leu Glu Ser Lys Ile Ser Cys Phe His Glu Gly Ile Gly Val Cys Glu
    290                 295                 300

Gln Leu Met Gly Ile Pro Ile Pro Leu Ser Tyr Thr Arg Leu Thr Ser
305                 310                 315                 320
```

```
Arg Phe Leu Val Leu Trp His Leu Thr Leu Pro Ile Ile Leu Trp Asp
                325                 330                 335

Asp Cys His Trp Ile Val Val Pro Ala Thr Phe Ile Ser Ala Ala Ser
            340                 345                 350

Leu Phe Cys Ile Glu Glu Val Gly Val Leu Ile Glu Glu Pro Phe Pro
        355                 360                 365

Met Leu Ala Leu Asp Glu Leu Cys Ile Val Thr Gln Asn Asn Ile Lys
    370                 375                 380

Glu Ala Ile Ala Thr Glu Lys Asp Ile Gln Ala Met Leu Lys Gly Lys
385                 390                 395                 400

Arg Lys Arg His Ser Tyr Lys His Ser Pro Asn Gly Cys Pro Asn Thr
                405                 410                 415
```

<210> SEQ ID NO 83
<211> LENGTH: 417
<212> TYPE: PRT
<213> ORGANISM: Nicotiana attenuata

<400> SEQUENCE: 83

```
Met Thr Asn Ser Arg Thr Leu Phe Ser Ile Gln Ser Pro Thr Asn Ala
1               5                   10                  15

Ser Phe Ser Ser His Phe Thr Leu Lys Leu Pro Ser Lys Leu Gln Gln
                20                  25                  30

Gln Ser Phe Pro Ser Lys Leu Ser Cys Lys Lys Phe Ser Phe Thr Thr
            35                  40                  45

Phe Lys Val Arg Cys Cys Pro Gln Gln Thr Pro Gln Asn Gln Asn Ser
    50                  55                  60

Thr Ser Ala Leu Ile Ser Ile Leu Arg Ile Ile Pro Asp Trp Ala Asp
65                  70                  75                  80

Arg Ile Gln Glu Gly Gly Met Lys Lys Lys Arg Ser Leu Tyr Lys His
                85                  90                  95

Glu Ser Trp Val Gln His Arg Ser Ser Leu Arg His Val Arg His Leu
            100                 105                 110

Phe Ser Ser Leu Asn Ser Arg Val Ile Leu Ser Leu Val Pro Pro Val
    115                 120                 125

Ile Ala Phe Thr Ser Val Ala Val Val Ile Ala Ser Tyr Asn Ser Ala
130                 135                 140

Val Leu Met His Trp Leu Pro Glu Phe Phe Pro Val Leu Arg Ala Ser
145                 150                 155                 160

Pro Leu Pro Tyr Gln Leu Thr Ala Pro Ala Leu Ala Leu Leu Leu Val
                165                 170                 175

Phe Arg Thr Glu Ala Ser Tyr Ser Arg Phe Glu Thr Gly Lys Lys Ala
            180                 185                 190

Trp Thr Lys Val Ile Ala Gly Thr Asn Asp Phe Ala Arg Gln Val Ile
    195                 200                 205

Ala Cys Val Asp Lys Ser Asp Ala Val Leu Lys Glu Ala Leu Leu Gln
210                 215                 220

Tyr Ile Met Ala Phe Pro Val Ala Leu Lys Cys His Ile Thr Tyr Gly
225                 230                 235                 240

Ser Asp Ile Ala Ser Asp Leu Lys Asn Leu Glu Ala Asp Asp Leu
                245                 250                 255

Ala Leu Val Leu Ser Ser Lys His Arg Pro Arg Cys Val Ile Gly Phe
            260                 265                 270

Ile Ser Gln Cys Leu Gln Ser Leu Asn Leu Glu Gly Thr Lys Leu Thr
    275                 280                 285
```

Gln Leu Glu Ser Lys Ile Ser Cys Phe His Glu Gly Ile Gly Val Cys
            290                 295                 300

Glu Gln Leu Ala Gly Ile Pro Ile Pro Leu Ser Tyr Thr Arg Leu Thr
305                 310                 315                 320

Ser Arg Phe Leu Val Leu Trp His Leu Thr Leu Pro Ile Ile Leu Trp
                325                 330                 335

Asp Asp Cys His Trp Ile Val Val Pro Ala Thr Phe Ile Ser Ala Ala
                340                 345                 350

Ser Leu Phe Cys Ile Glu Glu Val Gly Val Leu Ile Glu Glu Pro Phe
                355                 360                 365

Pro Met Leu Ala Leu Asp Glu Leu Cys Gln Leu Val Arg Asp Asn Ile
            370                 375                 380

Gln Glu Ala Met Ala Asn Glu Lys Gln Ile Gln Glu Arg Leu Asn Ala
385                 390                 395                 400

Lys Arg Lys Arg Arg Phe Ser Glu His Ser Gln Asn Gly Trp Pro Thr
                405                 410                 415

Ser

<210> SEQ ID NO 84
<211> LENGTH: 417
<212> TYPE: PRT
<213> ORGANISM: Nicotiana sylvestris

<400> SEQUENCE: 84

Met Thr Asn Ser Arg Thr Leu Phe Ser Ile Gln Ser Pro Thr Asn Ala
1               5                   10                  15

Ser Phe Ser Ser His Phe Thr Leu Lys Leu Pro Ser Lys Leu Gln Gln
                20                  25                  30

Gln Ser Phe Pro Ser Lys Leu Ser Tyr Lys Lys Phe Ser Phe Ser Thr
            35                  40                  45

Phe Lys Val Arg Cys Cys Pro Gln Gln Thr Pro Glu Asn Gln Asn Ser
50                  55                  60

Thr Ser Ala Leu Ile Ser Ile Leu Arg Ile Ile Pro Asp Trp Ala Asp
65                  70                  75                  80

Arg Ile Gln Glu Glu Gly Met Lys Lys Lys Arg Ser Leu Tyr Lys His
                85                  90                  95

Glu Ser Trp Val Gln His Arg Ser Ser Leu Arg His Val Arg His Leu
            100                 105                 110

Phe Ser Ser Leu Asn Ser Arg Val Ile Leu Ser Leu Val Pro Pro Val
            115                 120                 125

Ile Ala Phe Thr Ser Val Ala Val Val Ile Ala Ser Tyr Asn Ser Ala
        130                 135                 140

Val Ser Met His Trp Leu Pro Glu Phe Pro Val Leu Arg Ala Ser
145                 150                 155                 160

Pro Leu Pro Tyr Gln Leu Thr Ala Pro Ala Leu Ala Leu Leu Leu Val
                165                 170                 175

Phe Arg Thr Glu Ala Ser Tyr Ser Arg Phe Glu Thr Gly Lys Lys Ala
            180                 185                 190

Trp Thr Lys Val Ile Ala Gly Thr Asn Asp Phe Ala Arg Gln Val Ile
        195                 200                 205

Ala Cys Val Asp Lys Ser Asp Ala Val Leu Lys Glu Ala Leu Leu Gln
    210                 215                 220

Tyr Ile Met Ala Phe Pro Val Ala Leu Lys Cys His Ile Thr Tyr Gly
225                 230                 235                 240

```
Ser Asp Ile Ala Ser Asp Leu Lys Asn Leu Leu Glu Ala Asp Asp Leu
            245                 250                 255

Ala Leu Val Leu Ser Ser Lys His Arg Pro Arg Cys Val Ile Gly Phe
        260                 265                 270

Ile Ser Gln Cys Leu Gln Ser Leu Asn Leu Glu Gly Thr Lys Leu Thr
    275                 280                 285

Gln Leu Glu Ser Lys Ile Ser Cys Phe His Glu Gly Ile Gly Val Cys
290                 295                 300

Glu Gln Leu Ala Gly Ile Pro Ile Pro Leu Ser Tyr Thr Arg Leu Thr
305                 310                 315                 320

Ser Arg Phe Leu Val Leu Trp His Leu Thr Leu Pro Ile Ile Leu Trp
                325                 330                 335

Asp Asp Cys His Trp Ile Val Val Pro Ala Thr Phe Ile Ser Ala Ala
            340                 345                 350

Ser Leu Phe Cys Ile Glu Glu Val Gly Val Leu Ile Glu Glu Pro Phe
        355                 360                 365

Pro Met Leu Ala Leu Asp Glu Leu Cys Gln Leu Val Arg Asp Asn Ile
    370                 375                 380

Gln Glu Ala Met Ala Asn Glu Lys Gln Ile Gln Glu Arg Leu Asn Ala
385                 390                 395                 400

Lys Arg Lys Lys Cys Phe Ser Glu His Ser Pro Asn Gly Trp Pro Thr
                405                 410                 415

Ser

<210> SEQ ID NO 85
<211> LENGTH: 417
<212> TYPE: PRT
<213> ORGANISM: Nicotiana tabacum

<400> SEQUENCE: 85

Met Thr Asn Ser Arg Thr Leu Phe Ser Ile Gln Ser Pro Thr Asn Ala
1               5                   10                  15

Ser Phe Ser Ser His Phe Thr Leu Lys Leu Pro Ser Lys Leu Gln Gln
            20                  25                  30

Gln Ser Phe Pro Ser Lys Leu Ser Tyr Lys Lys Phe Ser Phe Ser Thr
        35                  40                  45

Phe Lys Val Arg Cys Cys Pro Gln Gln Thr Pro Glu Asn Gln Asn Ser
    50                  55                  60

Thr Ser Ala Leu Ile Ser Ile Leu Arg Ile Ile Pro Asp Trp Ala Asp
65                  70                  75                  80

Arg Ile Gln Glu Glu Gly Met Lys Lys Arg Ser Leu Tyr Lys His
                85                  90                  95

Glu Ser Trp Val Gln His Arg Ser Ser Leu Arg His Val Arg His Leu
            100                 105                 110

Phe Ser Ser Leu Asn Ser Arg Val Ile Leu Ser Leu Val Thr Pro Val
        115                 120                 125

Ile Ala Phe Thr Ser Val Ala Val Val Ile Ala Ser Tyr Asn Ser Ala
    130                 135                 140

Val Ser Met His Trp Leu Pro Glu Phe Pro Val Leu Arg Ala Ser
145                 150                 155                 160

Pro Leu Pro Tyr Gln Leu Thr Ala Pro Ala Leu Ala Leu Leu Leu Val
                165                 170                 175

Phe Arg Thr Glu Ala Ser Tyr Ser Arg Phe Glu Thr Gly Lys Lys Ala
            180                 185                 190
```

Trp Thr Lys Val Ile Ala Gly Thr Asn Asp Phe Ala Arg Gln Val Ile
              195                 200                 205

Ala Cys Val Asp Lys Ser Asp Ala Val Leu Lys Glu Ala Leu Leu Gln
210                 215                 220

Tyr Ile Met Ala Phe Pro Val Ala Leu Lys Cys His Ile Thr Tyr Gly
225                 230                 235                 240

Ser Asp Ile Ala Ser Asp Leu Lys Asn Leu Leu Glu Ala Asp Asp Leu
              245                 250                 255

Ala Leu Val Leu Ser Ser Lys His Arg Pro Arg Cys Val Ile Gly Phe
              260                 265                 270

Ile Ser Gln Cys Leu Gln Ser Leu Asn Leu Glu Gly Thr Lys Leu Thr
              275                 280                 285

Gln Leu Glu Ser Lys Ile Ser Cys Phe His Glu Gly Ile Gly Val Cys
290                 295                 300

Glu Gln Leu Ala Gly Ile Pro Ile Pro Leu Ser Tyr Thr Arg Leu Thr
305                 310                 315                 320

Ser Arg Phe Leu Val Leu Trp His Leu Thr Leu Pro Ile Ile Leu Trp
              325                 330                 335

Asp Asp Cys His Trp Ile Val Val Pro Ala Thr Phe Ile Ser Ala Ala
              340                 345                 350

Ser Leu Phe Cys Ile Glu Glu Val Gly Val Leu Ile Glu Glu Pro Phe
              355                 360                 365

Pro Met Leu Ala Leu Asp Glu Leu Cys Gln Leu Val Arg Asp Asn Ile
370                 375                 380

Gln Glu Ala Met Ala Asn Glu Lys Gln Ile Gln Glu Arg Leu Asn Ala
385                 390                 395                 400

Lys Arg Lys Lys Cys Phe Ser Glu His Ser Pro Asn Gly Trp Pro Thr
              405                 410                 415

Ser

<210> SEQ ID NO 86
<211> LENGTH: 417
<212> TYPE: PRT
<213> ORGANISM: Nicotiana tomentosiformis

<400> SEQUENCE: 86

Met Thr Asn Ser Arg Thr Leu Phe Ser Ile Gln Ser Pro Thr Asn Ala
1               5                   10                  15

Ser Phe Ser Ser His Phe Thr Leu Lys Thr Pro Ser Lys Leu Gln Gln
              20                  25                  30

Gln Ser Phe Pro Ser Lys Leu Asn Phe Lys Lys Leu Arg Phe Ser Thr
              35                  40                  45

Phe Lys Val Arg Cys Cys Pro Gln Gln Thr Pro Gln Asn Gln Asn Pro
50                  55                  60

Thr Ser Ala Leu Ile Ser Ile Leu Arg Ile Ile Pro Asp Trp Ala Asp
65                  70                  75                  80

Arg Ile Gln Glu Glu Gly Met Lys Lys Lys Arg Ser Leu Tyr Thr His
              85                  90                  95

Glu Ser Trp Met Gln His Arg Ser Ser Leu Arg His Val Arg His Leu
              100                 105                 110

Phe Ser Ser Leu Asn Ser Arg Val Ile Leu Ser Leu Val Pro Pro Val
              115                 120                 125

Ile Ala Phe Thr Ser Val Ala Val Val Ile Ala Ser Tyr Asn Ser Ala
              130                 135                 140

```
Val Ser Met His Trp Leu Pro Glu Leu Phe Pro Val Leu Arg Ala Ser
145                 150                 155                 160

Pro Leu Pro Tyr Gln Leu Thr Ala Pro Ala Leu Ala Leu Leu Leu Val
                165                 170                 175

Phe Arg Thr Glu Ala Ser Tyr Ser Arg Phe Glu Thr Gly Lys Lys Ala
            180                 185                 190

Trp Thr Lys Val Ile Ala Gly Thr Asn Asp Phe Ala Arg Gln Val Ile
        195                 200                 205

Ala Cys Val Asp Lys Ser Asp Ala Val Leu Lys Ala Ala Leu Leu Gln
210                 215                 220

Tyr Ile Met Ala Phe Pro Val Ala Leu Lys Cys His Ile Thr Tyr Gly
225                 230                 235                 240

Ser Asp Ile Ala Ser Asp Leu Lys Asn Leu Leu Glu Ala Asp Asp Leu
                245                 250                 255

Ala Val Val Leu Ser Ser Lys His Arg Pro Arg Cys Ile Ile Gly Phe
            260                 265                 270

Ile Ser Gln Cys Leu Gln Ser Leu His Leu Glu Gly Thr Lys Leu Thr
        275                 280                 285

Gln Leu Glu Ser Lys Ile Ser Cys Phe His Gly Ile Gly Val Cys
290                 295                 300

Glu Gln Leu Ala Gly Ile Pro Ile Pro Leu Ser Tyr Thr Arg Leu Thr
305                 310                 315                 320

Ser Arg Phe Leu Val Leu Trp His Leu Thr Leu Pro Ile Ile Leu Trp
                325                 330                 335

Asp Asp Cys His Trp Ile Val Val Pro Ala Thr Phe Ile Ser Ala Ala
            340                 345                 350

Ser Leu Phe Cys Ile Glu Glu Val Gly Val Leu Ile Glu Glu Pro Phe
        355                 360                 365

Pro Met Leu Ala Leu Asp Glu Leu Cys Gln Leu Val His Asp Asn Ile
370                 375                 380

Gln Glu Ser Met Ala Asn Glu Lys Lys Ile Gln Glu Arg Leu Ser Ala
385                 390                 395                 400

Lys Arg Lys Arg Arg Phe Ser Glu His Ser Gln Asn Gly Trp Pro Thr
                405                 410                 415

Ser

<210> SEQ ID NO 87
<211> LENGTH: 412
<212> TYPE: PRT
<213> ORGANISM: Solanum pennellii

<400> SEQUENCE: 87

Met Thr Asn Pro Arg Thr Leu Phe Thr Ile Gln Ser Pro Thr Asn Ala
1               5                   10                  15

Ser Phe Ser Ser His Phe Thr Leu Lys Asn Pro Ser Lys Ser Gln Gln
            20                  25                  30

Gln Gln Pro Val Tyr Lys Lys Leu Asn Phe Arg Val Leu Cys Ser Ser
        35                  40                  45

Gln Pro Ser Arg Thr Pro Gln Asn Ser Asn Leu Ile Ser Thr Leu Val
    50                  55                  60

Lys Ile Leu Arg Val Val Pro Asp Trp Ala Asp Lys Ile Gln Glu Gly
65                  70                  75                  80

Gly Met Arg Lys Lys Arg Ser Leu Tyr Lys His Glu Thr Trp Val Gln
                85                  90                  95
```

His Arg Ser Ser Leu Arg His Val Arg His Leu Phe Ser Ser Phe Asn
            100                 105                 110
Ser Arg Val Val Leu Ser Leu Ile Pro Val Ile Ala Phe Thr Ser
            115                 120                 125
Phe Ala Phe Val Ile Ala Ser Tyr Asn Ser Ala Val Ser Phe His Trp
130                 135                 140
Leu Pro Glu Phe Phe Pro Ile Leu Arg Ala Ser Pro Gln Pro Tyr Gln
145                 150                 155                 160
Leu Thr Ala Pro Ala Leu Ala Leu Leu Val Phe Arg Thr Glu Ala
            165                 170                 175
Ser Tyr Ser Arg Phe Glu Ala Gly Lys Lys Ala Trp Thr Lys Val Ile
            180                 185                 190
Ala Gly Thr Asn Asp Phe Ala Arg Gln Val Ile Ala Cys Val Asp Lys
            195                 200                 205
Arg Asp Asp Val Leu Lys Glu Ala Leu Leu Gln Tyr Ile Met Ala Phe
            210                 215                 220
Pro Val Ala Leu Lys Cys His Ile Val Tyr Asp Ser Asp Ile Ala Ser
225                 230                 235                 240
Asp Leu Lys Asn Leu Leu Glu Ala Asp Leu Ala Val Val Leu Ser
            245                 250                 255
Ser Lys His Arg Pro Arg Cys Ile Ile Gly Phe Ile Ala Gln Ser Leu
            260                 265                 270
Gln Ser Leu Asn Leu Glu Gly Thr Ile Leu Ser Gln Leu Glu Ser Lys
            275                 280                 285
Ile Ser Cys Phe His Glu Gly Ile Gly Val Cys Glu Gln Leu Leu Gly
            290                 295                 300
Ile Pro Ile Pro Leu Ser Tyr Thr Arg Leu Thr Ser Arg Phe Leu Val
305                 310                 315                 320
Leu Trp His Leu Thr Leu Pro Ile Ile Leu Trp Asp Asp Cys His Trp
            325                 330                 335
Ile Val Val Pro Ala Thr Phe Ile Ser Ala Ala Ser Leu Phe Cys Ile
            340                 345                 350
Glu Glu Val Gly Val Leu Ile Glu Glu Pro Phe Pro Met Leu Ala Leu
            355                 360                 365
Asp Glu Leu Cys Gln Arg Val His Asp Asn Ile His Glu Ala Met Ala
            370                 375                 380
Asn Glu Lys Gln Ile Gln Glu Ile Val Asn Ser Lys Arg Lys Arg Ser
385                 390                 395                 400
Phe Ser Glu His Ser Pro Asn Gly Trp Pro Thr Ser
            405                 410

<210> SEQ ID NO 88
<211> LENGTH: 412
<212> TYPE: PRT
<213> ORGANISM: Solanum tuberosum

<400> SEQUENCE: 88

Met Thr Asn Pro Arg Thr Phe Phe Thr Ile Gln Ser Pro Thr Asn Ala
1               5                   10                  15
Ser Phe Ser Ser His Phe Thr Leu Lys Lys Pro Ser Asn Ser Gln Gln
            20                  25                  30
Gln Pro Pro Val Tyr Lys Lys Phe Thr Phe Arg Val Leu Cys Ser Ser
            35                  40                  45
Gln Pro Ser Arg Thr Pro Gln Asn Ser Asn Leu Ile Ser Thr Leu Val

```
            50                  55                  60
Lys Ile Leu Arg Val Val Pro Asp Trp Ala Asp Lys Ile Gln Glu Gly
 65                  70                  75                  80

Gly Met Arg Lys Lys Arg Ser Leu Tyr Lys His Glu Thr Trp Val Gln
                 85                  90                  95

His Arg Ser Ser Leu Arg His Leu Arg His Leu Phe Ser Ser Phe Asn
                100                 105                 110

Ser Arg Val Val Leu Ser Leu Ile Pro Pro Val Ile Ala Phe Thr Ser
                115                 120                 125

Phe Ala Phe Val Ile Ala Cys Tyr Asn Ser Ala Val Ser Leu His Trp
            130                 135                 140

Leu Pro Glu Phe Phe Pro Ile Leu Arg Ala Ser Pro Gln Pro Tyr Gln
145                 150                 155                 160

Leu Thr Ala Pro Ala Leu Ala Leu Leu Val Phe Arg Thr Glu Ala
                165                 170                 175

Ser Tyr Ser Arg Phe Glu Ala Gly Lys Lys Ala Trp Thr Lys Val Ile
                180                 185                 190

Ala Gly Thr Asn Asp Phe Ala Arg Gln Val Ile Ala Cys Val Asp Lys
                195                 200                 205

Arg Asp Asp Val Leu Lys Glu Ala Leu Leu Gln Tyr Ile Met Ala Phe
210                 215                 220

Pro Val Ala Leu Lys Cys His Ile Val Tyr Asp Ser Asp Ile Ala Ser
225                 230                 235                 240

Asp Leu Lys Asn Leu Leu Glu Ala Asp Leu Ala Leu Val Val Ser
                245                 250                 255

Ser Lys His Arg Pro Arg Cys Ile Ile Gly Phe Ile Ser Gln Ser Leu
                260                 265                 270

Gln Ser Leu Asn Leu Asp Gly Thr Ile Leu Ser Gln Leu Glu Ser Lys
                275                 280                 285

Ile Thr Cys Phe His Glu Gly Ile Gly Val Cys Glu Gln Leu Leu Gly
            290                 295                 300

Ile Pro Ile Pro Leu Ser Tyr Thr Arg Leu Thr Ser Arg Phe Leu Val
305                 310                 315                 320

Leu Trp His Leu Thr Leu Pro Ile Ile Leu Trp Asp Asp Cys His Trp
                325                 330                 335

Ile Val Val Pro Ala Thr Phe Ile Ser Ala Ala Ser Leu Phe Cys Ile
                340                 345                 350

Glu Glu Val Gly Val Leu Ile Glu Gly Pro Phe Pro Met Leu Ala Leu
                355                 360                 365

Asp Glu Leu Cys Gln Arg Val His Asp Asn Ile His Glu Ala Met Ala
370                 375                 380

Asn Glu Lys Gln Ile Gln Glu Ile Val Asn Ser Lys Arg Lys Arg Ser
385                 390                 395                 400

Phe Ser Glu His Ser Pro Asn Gly Trp Pro Thr Ser
                405                 410

<210> SEQ ID NO 89
<211> LENGTH: 481
<212> TYPE: PRT
<213> ORGANISM: Chlorella sorokiniana

<400> SEQUENCE: 89

Met Val Val Ala Ala Cys Arg Gly His Ala Met Leu Ser Asp Ala Ala
1               5                   10                  15
```

-continued

```
Gln Arg Arg Gly Pro Ala Ala Gly Gln Gly Pro Ala Ala Ala Ala
                 20                  25                  30
Ile Arg Gly Leu Ser Pro Cys Arg Arg Ser Ala Ser Thr Trp Arg Leu
             35                  40                  45
Val Pro Ala Ala Gln Arg Arg Pro Arg Pro Met Met Asp Ser Ile
 50                  55                  60
Leu Asp Asp Leu Gly Ser Asn Gly Asp Ser Ala Ala Glu Ser Ser Thr
 65                  70                  75                  80
Asp Leu Ala Ala Ala Glu Pro Pro Ala Val Phe Pro Pro Leu Leu Ser
                 85                  90                  95
Val Asp Leu Ala Ser Asp Pro Val Lys Glu Gly Ser Arg Arg Tyr Arg
                 100                 105                 110
Arg Thr Val Phe Asp Phe Asn Glu Trp Arg Lys His Arg Ser Thr Glu
             115                 120                 125
Arg Tyr Val Arg His Met Gln Ser Met Thr Ser Ser Arg Met Val Arg
     130                 135                 140
Gly Leu Ala Ala Pro Leu Ala Tyr Ile Phe Ala Val Thr Ala Val
145                 150                 155                 160
Ser Val Tyr Asn Ala Ser Val Glu Ala Gly Leu Leu Pro Ser Leu Leu
                 165                 170                 175
Pro Glu Val Lys Met Ala Ser Asn Gly Pro Phe Gly Ser Val Ser Phe
                 180                 185                 190
Ala Ile Ser Leu Leu Leu Val Phe Arg Thr Asn Ala Ser Tyr Ala Arg
             195                 200                 205
Trp Leu Asp Ala Arg Lys Ala Trp Gly Lys Leu Ile Asn Arg Ser Arg
210                 215                 220
Asp Leu Thr Arg Gln Ala Leu Thr Tyr Phe Pro Pro Glu Asp Lys Pro
225                 230                 235                 240
Leu Leu Asp Leu Leu Cys Arg Trp Thr Val Ala Phe Ser Arg Thr Leu
                 245                 250                 255
Lys Cys His Leu Cys Glu Asp Tyr Pro Leu Ala Glu Glu Leu Ala Arg
                 260                 265                 270
Val Leu Arg Pro His Glu Ala Glu Ala Leu Leu Leu Ala Lys His Arg
             275                 280                 285
Pro Thr Tyr Cys Leu Gln Ile Leu Ser Glu Thr Leu Lys Ser Ala His
     290                 295                 300
Leu Pro Pro Pro Leu Pro Val Ala Gln Pro His Asn Gly Ala Thr Ala
305                 310                 315                 320
Gly His Ala Ala Ala Gln Ala Val Ala Val Pro Ala Ala Ala
                 325                 330                 335
Ala Tyr Arg Met Asp Glu Asn Leu Thr Glu Phe Glu Asp Ile Val Gly
                 340                 345                 350
Thr Cys Glu Arg Ile Leu Arg Ala Pro Ile Pro Leu Ser Tyr Thr Arg
             355                 360                 365
His Thr Ser Arg Phe Met Ile Ile Trp Leu Thr Leu Leu Pro Phe Ala
     370                 375                 380
Leu Trp Asp Ser Val Gly Trp Ala Thr Val Pro Leu Ala Val Ile Val
385                 390                 395                 400
Ala Phe Leu Leu Leu Gly Ile Glu Glu Ile Gly Val Ser Ile Glu Glu
                 405                 410                 415
Pro Phe Ser Ile Leu Pro Leu Asp Ala Leu Cys Asp Thr Ile Glu Ala
                 420                 425                 430
Asn Val Lys Glu Leu Gln Arg Thr His Ser Gln Gln Gly Gly Gly Gly
```

```
                435                 440                 445
Gly Glu Glu Gly Ser His Lys Ala Arg Pro Pro Ala Arg Asp Ile
450                 455                 460

Val Gly Met Ala Ala Ala Glu Ala Glu Ala Glu Ala Ala Val Ala
465                 470                 475                 480

Lys

<210> SEQ ID NO 90
<211> LENGTH: 590
<212> TYPE: PRT
<213> ORGANISM: Chlorella sorokiniana

<400> SEQUENCE: 90

Met Ser Ala Leu Leu Arg Ala Arg Val Ser Ala Phe Leu Ala Gly Val
1               5                   10                  15

Ala Val Ala Gly Val Phe Gly Val Tyr Gln Leu Arg Gly Asp Val Ala
                20                  25                  30

Glu Gly Gln Gln Arg Leu Leu Asp Gln Thr Lys Lys Tyr Thr Ala Gly
            35                  40                  45

Leu Glu Gly Arg Val Ala Glu Leu Glu Ala Ala Val Ala Arg Leu Ser
50                  55                  60

Ser Asn Arg Ala Leu Lys Pro Asn Ser Ala Ala Pro Pro Ala Pro
65                  70                  75                  80

Ala Met Pro Ala Gly Leu Met Thr Gln Gln Ser Thr Ala Cys Ser Ala
                85                  90                  95

Ala Ala Ala Ser Gly Arg Leu Gln Gly Ala Ala Arg Ser Leu Pro Arg
            100                 105                 110

Arg His Ala Leu Ser Gly Ala Ala Val Gly Arg Pro Ala Pro Ala Gly
        115                 120                 125

Leu Gly Arg Gly Leu Ser Ser Ala Ser Arg Ala Gln Gly Arg Arg Ala
130                 135                 140

Gly Ala Val Arg Val Gln Ala Ala Thr Pro Gly Val Pro Gly Ala
145                 150                 155                 160

Asn Ser Ala Ser Glu Gly Pro Phe Asp Trp Met Thr Asp Glu Trp Lys
                165                 170                 175

Glu Ala Asp Arg Lys Asn Leu Arg Thr Val Phe Asp Phe Asp Ala Trp
            180                 185                 190

Lys Arg His Arg Ser Ser Ser Arg Tyr Trp Arg His Leu Gly His Leu
        195                 200                 205

Pro Asn Ser Arg Ile Leu Lys Trp Val Ala Gly Pro Leu Ser Tyr Val
210                 215                 220

Thr Ala Val Ala Ile Gly Val Cys Ala Tyr His Thr Ala Ala Glu Ala
225                 230                 235                 240

Gly Ile Val Pro Glu Val Leu Pro Glu Leu Ala Lys Gly Ala Ala Ala
                245                 250                 255

Pro Phe Gly Leu Thr Ser Phe Ala Leu Ser Thr Leu Val Leu Arg
            260                 265                 270

Thr Asn Thr Ser Tyr Gln Arg Trp Asp Glu Ala Arg Lys Met Trp Gly
        275                 280                 285

Leu Ile Val Asn Arg Ser Arg Asp Val Ala Arg Gln Ala Leu Gly Tyr
290                 295                 300

Ile Pro Ala Ser Gln Pro Glu Leu Gln Asp Met Phe Cys Arg Trp Leu
305                 310                 315                 320

Val Ala Tyr Cys Arg Ser Leu Met Cys His Leu Arg Pro Gly Glu Asp
```

```
                    325                 330                 335
Leu Arg Ala Glu Leu Glu Gly Lys Leu Lys Pro Glu Glu Leu Glu Ala
                340                 345                 350
Leu Leu Ser Ser Ala His Arg Pro Asn Tyr Thr Cys Gln Val Leu Thr
                355                 360                 365
Ala Val Ile Lys Arg Ala Gln Leu Pro Gly Asp Asp Ile Asp Asn Arg
                370                 375             380
Asp Ser Phe Ala Asn Val Lys Ala Ser Ala Phe Arg Met Asp Glu
385                 390                 395                 400
Asn Leu Thr Gln Phe Ala Asp Val Thr Gly Gly Cys Glu Arg Ile Leu
                405                 410                 415
Arg Thr Pro Val Pro Leu Met Tyr Thr Arg His Asn Ser Arg Phe Leu
                420                 425                 430
Met Ile Trp Leu Ser Leu Leu Pro Phe Thr Leu Trp Asp Thr Cys His
                435                 440                 445
Trp Ala Thr Val Pro Val Thr Ala Leu Val Ala Phe Leu Leu Leu Gly
450                 455                 460
Ile Lys Glu Val Gly Val Ala Ile Glu Pro Phe Thr Ile Leu Pro
465                 470                 475                 480
Leu Glu Val Ile Cys Asn Thr Ile Glu Gly Asn Val Trp Glu Leu His
                485                 490                 495
Arg Met His Ser Ala Asn Gly Val Glu Gln Gln His Ala Ala Gly Asn
                500                 505                 510
Ala Val Val Thr Ala Glu Ala Leu Val Asp Ile Met Ala Pro Gln Thr
                515                 520                 525
Ile Gly Gly Leu Ala Leu Asn Gly Ala Gly Ser Ala Ala Tyr Val Asn
                530                 535                 540
Gly Asn Gly Asn Gly Ala Tyr Thr Asn Gly Ala Ala Asn Gly Asn Gly
545                 550                 555                 560
Ala Glu Ser Gly Thr Ile Lys Val Pro Pro Glu Glu Leu Ile Arg Ala
                565                 570                 575
Ala Gln Gly Leu Arg Gln Arg Val Ser Ser Ser Leu Arg Gln
                580                 585                 590

<210> SEQ ID NO 91
<211> LENGTH: 450
<212> TYPE: PRT
<213> ORGANISM: Chlorella sorokiniana

<400> SEQUENCE: 91

Met Ala Thr Pro Ala Ala Ala Ala Pro Arg Arg Leu Gly Ala Ala Ala
1               5                   10                  15
Ala Pro Lys Gly Leu Pro Arg Leu Ala Gly Val Ser Arg Pro Arg
                20                  25                  30
Arg Ala Ala Gln Thr Ala Gly Ser Phe His Ser Ala Ala Leu Pro Val
                35                  40                  45
Asp Gln Ala Val Asn Gly Asn Gly Thr Val Pro Pro Asp Pro Glu Pro
            50                  55                  60
Glu Pro Thr Tyr Ser Trp Phe Ser Gln Glu Trp Lys Glu Glu Arg Arg
65              70                  75                  80
Lys Lys Lys Gly Arg Thr Val Phe Asp Phe Glu Arg Trp Gln Lys His
                85                  90                  95
Arg Ser Ser Ala Arg Tyr Leu Arg His Met Ala Gly Met Phe Ser Ser
                100                 105                 110
```

Ser Val Ile Gln Gly Leu Ala Val Pro Leu Ala Tyr Val Thr Val
        115                 120                 125

Ser Val Gly Val Ala Thr Tyr Tyr Thr Ala Ala Lys Gly Met Val
        130                 135                 140

Pro Leu Phe Pro Ala Leu Lys Val Leu Ala Ser Ala Pro Phe Ser Leu
145                 150                 155                 160

Thr Ser Phe Ala Leu Ser Leu Leu Val Phe Arg Thr Asn Ser Ser
                165                 170                 175

Tyr Gly Arg Trp Asp Glu Ala Arg Lys Met Trp Gly Gln Val Val Asn
                180                 185                 190

Arg Ser Arg Asp Ile Ala Arg Gln Ala Leu Ala Tyr Ile Pro Ala Ala
                195                 200                 205

Gln Val His Leu Gln Asp Val Ile Cys Arg Trp Thr Ile Ala Tyr Thr
        210                 215                 220

Arg Ala Leu Met Cys His Leu Arg Gln Gly Glu Asp Leu Gly Ser Glu
225                 230                 235                 240

Leu Ala Gly Ile Leu Ser Pro Ser Glu Leu Ala Leu Leu Ala Ala
                245                 250                 255

Lys His Arg Pro Asn Phe Cys Thr Gln Val Leu Ser Ala Ala Val Arg
                260                 265                 270

Asp Ala Gln Leu Pro Gly Thr Gly Pro Thr Ser Arg Glu Pro Thr Ala
        275                 280                 285

Ala Val Pro Ala Gly Ala Ala Tyr Arg Met Asp Glu Asn Ile Thr Val
        290                 295                 300

Phe Val Glu Val Ser Gly Gly Cys Glu Arg Ile Leu Arg Thr Pro Ile
305                 310                 315                 320

Pro Leu Gly Tyr Thr Arg His Thr Ser Arg Phe Leu Met Leu Trp Leu
                325                 330                 335

Thr Leu Leu Pro Phe Ser Leu Trp Glu Ser Cys Gly Leu Ala Met Ile
                340                 345                 350

Pro Val Ala Ala Leu Val Ala Phe Leu Leu Gly Val Glu Glu Ile
        355                 360                 365

Gly Val Gln Ile Glu Glu Pro Phe Ser Ile Leu Pro Leu Glu Val Ile
        370                 375                 380

Ser Ser Thr Ile Glu Gly Asn Ile Arg Glu Leu Gln Ala Thr His Gly
385                 390                 395                 400

Ala Ala Ala Ala Val Pro Ser Pro Ile His Asp Ile Arg Pro Pro
                405                 410                 415

Gln Leu Gln Ser Pro Glu Gly Asn Ser Ser Asn Val Val Gly Ala Pro
                420                 425                 430

Ser Leu Ala Thr Asn Gly Ala Pro Ala Gly Arg Pro Ser Gly Gly Gly
                435                 440                 445

Ala Arg
    450

<210> SEQ ID NO 92
<211> LENGTH: 408
<212> TYPE: PRT
<213> ORGANISM: Chlorella sorokiniana

<400> SEQUENCE: 92

Met Gln Lys Arg Thr Arg Pro Arg Ser Arg Leu Pro Pro Val Thr Leu
1               5                   10                  15

Cys Cys Arg Leu Pro Pro Ala Ala Gln Pro Pro Arg Gly Val His Ala
            20                  25                  30

```
Ala Gln Ala Leu Leu Arg Pro Ala Gly Cys Ser Gly Ser Gln Gln Gln
            35                  40                  45

Arg Arg Arg Arg Arg Pro Pro Ser Thr Ala Ala Ser Leu Leu Pro Leu
 50                  55                  60

Gly Asp Arg Asp Glu Asp Lys Glu Glu Arg Leu Arg Arg Phe Arg Val
 65                  70                  75                  80

Met Tyr Asp Phe Asp Ala Trp Ala Ala His Arg Ser Val Lys Arg Tyr
                 85                  90                  95

Trp Arg His Phe Ile Gly Leu Phe Arg Ser Arg Ile Val Ala Gly Ile
            100                 105                 110

Ala Leu Pro Ile Leu Leu Val Phe Leu Glu Ala Thr Gly Val Cys Trp
            115                 120                 125

Tyr Glu Thr Ala Leu Arg Ser Gly Leu Leu Pro Ala Thr Trp Arg Ser
            130                 135                 140

Ile Gln Val Arg Ala Pro Met Leu Phe Ser Leu Ser Ser Phe Ala Leu
145                 150                 155                 160

Ser Leu Leu Leu Gly Phe Arg Thr Asn Gln Ser Ile Ala Arg Phe Asp
                165                 170                 175

Glu Ala Arg Arg Leu Trp Asn Thr Met Ile Asn Arg Cys Arg Asp Ala
            180                 185                 190

Met Arg Gln Ala Val Ser Tyr Leu Gly Pro Gln Leu Pro Gln Gln Ala
            195                 200                 205

Ala Leu Leu Gly Ala Leu Ser Arg Trp Leu Gln Ala Phe Pro Trp Val
            210                 215                 220

Leu Lys Asn His Val Arg Glu His Lys His Trp Gln Ala Glu Leu Gly
225                 230                 235                 240

Asp Ile Leu Glu Pro Ser Glu Leu Glu Ala Val Val Ala Ser Lys His
                245                 250                 255

Pro Pro Leu Leu Ala Leu Gln Val Ile Thr Glu Leu Leu Asp Arg Ala
            260                 265                 270

Pro Ile Ser Ala Lys Gln Arg Leu Arg Ile Asp Gly Cys Val Thr Asp
            275                 280                 285

Leu Ser Asp Val Val Gly Gly Cys Gln Arg Ile Leu Asn Thr Pro Ile
            290                 295                 300

Pro Val Ser Tyr Thr Arg His Thr Cys Arg Tyr Leu Thr Val Trp Leu
305                 310                 315                 320

Phe Leu Leu Pro Leu Ser Ile Phe Asn Gln Cys Gly Trp Val Thr Val
                325                 330                 335

Phe Ser Ser Val Val Leu Ala Phe Phe Leu Leu Thr Ile Glu Glu Ile
            340                 345                 350

Gly Val Thr Ile Glu Glu Pro Phe Asn Ile Leu Pro Leu Ala Glu Leu
            355                 360                 365

Asn Arg Gly Ala Asp Val Ala Gln Asn Leu Asp Arg Ile Asp Glu Val
            370                 375                 380

Val Ala Leu Val Asp Ala Ala Thr Gly Ser Arg Arg Thr Ala Met Gln
385                 390                 395                 400

Leu Ala Pro Ala Tyr Pro Ile Glu
                405
```

<210> SEQ ID NO 93
<211> LENGTH: 456
<212> TYPE: PRT
<213> ORGANISM: Chlorella sorokiniana

```
<400> SEQUENCE: 93

Met Ser Thr Ala Met Leu Ala Gly Ser Arg Ile Gln Leu Gln Gln Pro
1               5                   10                  15

Ala Gly Leu Gly Gly Ser Arg Leu Gln Arg Ala Ala Pro Val Ala
            20                  25                  30

Ala Ala Ala Arg Leu Gly Ser Val Arg Pro Ala Gly Leu Gln Ala Arg
        35                  40                  45

Ser Thr Ala Ala Arg Arg Ala Asp Arg Ser Ala Leu Arg Val Ser Ala
    50                  55                  60

Thr Ala Ser Pro Glu Ala Ala Pro Val Lys Leu Ser Gly Asp Asp Leu
65                  70                  75                  80

Lys Glu Ala Asn Arg Lys His Met Arg Ser Val Phe Asp Phe Asp Leu
                85                  90                  95

Trp Lys Lys His Arg Ser Ser Arg Tyr Leu Arg His Ile Val Gly
            100                 105                 110

Leu Gly Glu Ser Arg Ile Val Ser Gly Leu Met Ala Pro Leu Thr Tyr
            115                 120                 125

Val Met Thr Leu Ser Leu Ala Val Ala Cys Tyr Asn Ala Ala Ala Glu
    130                 135                 140

Ala Gly Tyr Leu Pro Val Phe Pro Glu Leu Lys Leu Ala Thr Asn Ala
145                 150                 155                 160

Pro Phe Gly Leu Thr Ser Phe Ala Leu Ser Leu Leu Val Phe Arg
                165                 170                 175

Thr Asn Ser Ser Tyr Gly Arg Trp Asp Glu Ala Arg Lys Met Trp Gly
                180                 185                 190

Leu Ile Val Asn Arg Ser Arg Asp Phe Ile Arg Gln Gly Leu Gly Tyr
            195                 200                 205

Ile Pro Pro Glu Gln Glu Leu Gln Lys Met Leu Val Arg Trp Thr
210                 215                 220

Val Ala Tyr Ser Arg Ser Leu Met Cys His Leu Arg Pro Gly Glu Asp
225                 230                 235                 240

Leu Arg Val Glu Leu Lys Asp Thr Leu Lys Pro Glu Glu Leu Glu Ala
            245                 250                 255

Leu Leu Ala Ser Thr His Arg Pro Asn Tyr Val Val Gln Val Leu Thr
            260                 265                 270

Ala Ile Ile Lys Thr Ala Gln Leu Pro Ala Ala Val Thr Asn Asn Arg
        275                 280                 285

Asp Ser Thr Gly Cys Val Pro Ala Gly Ala Ala Tyr Arg Met Asp Glu
    290                 295                 300

Asn Leu Thr Val Phe Ala Asp Val Thr Gly Gly Cys Glu Arg Ile Leu
305                 310                 315                 320

Arg Thr Pro Ile Pro Leu Ser Tyr Thr Arg His Thr Ser Arg Phe Met
                325                 330                 335

Met Ile Trp Leu Thr Leu Leu Pro Phe Thr Leu Trp Asp Ser Cys His
            340                 345                 350

Trp Ala Met Leu Pro Ile Ala Gly Ile Val Ser Phe Leu Leu Leu Gly
        355                 360                 365

Ile Glu Glu Ile Gly Val Gln Ile Glu Pro Phe Thr Ile Leu Pro
    370                 375                 380

Leu Glu Val Ile Ser Arg Thr Ile Gly Asn Val Trp Glu Leu Tyr
385                 390                 395                 400

Arg Met His Ser Gly Glu Ala Leu Glu Lys Gln Ala Glu Leu Ala
            405                 410                 415
```

Asn Gly Gln Asp Val Gln Val Leu Asn Ala Gln Asp Leu Val Ala Leu
            420                 425                 430

Met Ala Pro Ser Ala Val Gly Asn Thr Ala Asn Gly Thr Ser Arg Lys
            435                 440                 445

Ser Leu Val Val Asn Tyr Gly Leu
            450                 455

<210> SEQ ID NO 94
<211> LENGTH: 589
<212> TYPE: PRT
<213> ORGANISM: Chlorella sorokiniana

<400> SEQUENCE: 94

Met Gly Leu Met Pro Asn Met Glu Asn Thr Tyr Ser His Val Pro Arg
1               5                   10                  15

Ser Ala Met Ala Ala Met Ala Ala Ser Ala Pro Ala Asp Ala Ser Thr
            20                  25                  30

Asn Ala Gly Gly Ser Pro Gly Val Gly Arg Leu Ala Ala Arg Thr Ser
            35                  40                  45

Ser Glu Pro Pro Ser Gly Val His Ser Arg Ser Ser Leu Thr Asn
    50                  55                  60

Leu Ala Arg Leu Pro Gly Lys Ala Arg Ala Lys Leu Gln Asn Leu Thr
65                  70                  75                  80

His Ser Gln Phe Val Arg Phe Ile Glu Asp Asn Ala Gln Asp Lys
                85                  90                  95

Glu Glu Asn Asp Ile Tyr Arg Gly Ala Ala Ala Arg Gln Asn Pro
            100                 105                 110

Ala Asp Gln Val Phe Thr Phe Glu Arg Trp Asn Lys His Arg Asn Pro
            115                 120                 125

Met Arg Tyr Ala Lys His Leu Leu His Met Phe Thr Ser Arg Val Phe
            130                 135                 140

Lys Gln Leu Leu Gly Pro Val Leu Ala Val Met Ala Leu Ala Leu Ser
145                 150                 155                 160

Val Gly Ile Tyr Glu Thr Leu Val Ser Ala Gly Ala Leu Pro Gly His
                165                 170                 175

Trp Pro His Val Thr Leu Ala Leu Gly Gln Gly Phe Asn Leu Thr Ala
            180                 185                 190

Phe Ala Leu Ser Leu Leu Val Phe Arg Thr Asn Ser Ser Tyr Asp
            195                 200                 205

Arg Trp Trp Glu Gly Arg Lys Leu Trp Gly Gly Val Val Asn Arg Thr
            210                 215                 220

Arg Asn Ile Val Arg Gln Ser Leu Val Phe Phe Arg Glu Asp Val His
225                 230                 235                 240

Leu Lys Glu Leu Leu Ala Arg Trp Thr Met Ala Phe Pro Lys Val Leu
                245                 250                 255

Met Val His Leu Arg Glu Gly Met Asp Leu Gln Ala Glu Val Ala His
            260                 265                 270

Ile Leu Thr Ala Asn Glu Val Ala Ala Leu Val Ala Ala His Arg
            275                 280                 285

Pro Asn Phe Val Leu Gln Val Met Ala Glu Ala Ile Arg Ala Ala Arg
            290                 295                 300

Pro His Glu Leu Ala Arg Met Arg Met Asp Asp Asn Leu Thr Phe Phe
305                 310                 315                 320

Glu Asp Ala Met Gly Ser Cys Glu Arg Ile Leu Arg Thr Pro Ile Pro

```
                    325                 330                 335
Leu Ser Tyr Thr Arg His Thr Ser Arg Phe Leu Leu Val Trp Leu Ile
            340                 345                 350

Leu Leu Pro Phe Thr Leu Trp Ala Ala Tyr Ser Trp Phe Ala Val Ile
            355                 360                 365

Leu Ser Gly Ile Phe Ala Phe Leu Met Phe Gly Ile Asp Glu Ile Gly
            370                 375                 380

Val Gln Ile Glu Glu Pro Phe Gly Ile Leu Pro Leu Glu Ala Ala Gly
385                 390                 395                 400

Ala Thr Ile Glu Arg Asn Ile Arg Glu Leu Leu Ala Arg Asn Tyr Glu
                405                 410                 415

Val Ala Ser Leu Val His Gln Gln Asn Leu Pro Val Gly Leu Gly Asp
                420                 425                 430

Ser Arg Gly Lys Gln Pro Ala Gly Ser Ser Pro Ala Pro Ala Gly Gly
                435                 440                 445

Leu Gly Gly Thr Gly Gly Ser Ala Val Ser Leu Ile Gly Leu Ala Ala
            450                 455                 460

Glu Gly Glu Thr Glu Asp Phe Gly Glu Met Thr Gly Ala Ser Pro Ala
465                 470                 475                 480

Asp Ala Ala Val Asp Ala Glu Gly Lys Leu Gly Gly Ala Arg
                485                 490                 495

Pro Ser Ile Ile Arg Leu Ser Ala Thr Ala Gly Gly Ala Ala Pro Ala
                500                 505                 510

Ala Ser Pro Arg Arg Val Gln Phe Ala Asp Asp Ser Thr Val Ile Asp
            515                 520                 525

Val Arg Ser Ser Asp Gly Gly Ala Val Gly Ala Arg Pro Val Val Ile
530                 535                 540

Ser Ala Ala Ala Pro Gly Gly Leu Asp Tyr Arg Arg Gln Pro Leu Leu
545                 550                 555                 560

Leu Glu Val Glu Leu Ala Ser Gly Ala Ser Pro Leu Ile Ser Pro Arg
                565                 570                 575

Asp Ser Pro Ser Ser Ser Tyr Ser Ser Trp Leu His Asp
                580                 585

<210> SEQ ID NO 95
<211> LENGTH: 490
<212> TYPE: PRT
<213> ORGANISM: Micractinium conductrix

<400> SEQUENCE: 95

Met Pro Ala Ala Leu Cys Thr Gly Ser Ala Met Gln Leu Gln Arg Arg
1               5                   10                  15

Ser Pro Val Thr Ala Ala Pro Ala Ala Ala Gln Arg Leu Val
            20                  25                  30

Ala Pro Ala Ala Ala Ala Pro Gln His Ala Ala Ser Leu Arg Cys
            35                  40                  45

Ser Leu Arg Ser Thr Phe Pro Gly Gly Ala Ser Ile Ser Ser Val Ala
            50                  55                  60

Ala Leu Arg Thr Ser Ala Gly Arg Arg Ser Leu His Val Ala Gly Ala
65                  70                  75                  80

Val Gly Pro Asn Glu Lys Arg Ala Gln Ile Gln Gln Arg Leu Asp
                85                  90                  95

Ser Leu Ser Lys Ile Asp Val Leu Phe Asp Glu Glu Leu Lys Ala Leu
                100                 105                 110
```

Asp Thr Asn Leu Val Lys Glu Leu Val Ala Asp Asp Phe Lys Glu Gln
            115                 120                 125

Asp Arg Lys Lys Leu Arg Val Val Phe Asp Phe Asp Arg Trp Gln Arg
        130                 135                 140

His Arg Ser Ser Arg Tyr Leu Arg His Met Thr Gly Leu Phe Thr
145                 150                 155                 160

Ser Arg Thr Leu Lys Trp Met Gly Ala Pro Leu Val Cys Thr Leu Ser
                165                 170                 175

Val Ala Thr Ala Val Gly Ile Tyr Tyr Thr Ala Ala Glu Met Gly Met
            180                 185                 190

Val Pro Asp Ile Pro Asp Ile Lys Thr Asn Ala Val Phe Gly Leu Thr
        195                 200                 205

Ser Phe Ala Leu Ala Asn Leu Leu Val Leu Thr Thr Asn Thr Ala Tyr
    210                 215                 220

Gln Arg Phe Asp Glu Ala Arg Lys Met Trp Gly Leu Ile Val Asn Arg
225                 230                 235                 240

Ser Arg Asp Met Thr Arg Gln Gly Leu Ala Tyr Ile Pro Glu Asp Gln
                245                 250                 255

Pro Glu Leu Gln Glu Met Phe Cys Arg Trp Val Val Ala Tyr Ser Arg
            260                 265                 270

Ser Leu Met Cys His Leu Arg Ala Gly Glu Asn Leu Glu Arg Glu Leu
        275                 280                 285

Leu Gly Lys Leu Pro Glu Ser Glu Leu Arg Ala Leu Leu Thr Ala Thr
    290                 295                 300

His Arg Pro Asn Phe Thr Asn Gln Val Ile Ala Gln Ile Leu Lys Arg
305                 310                 315                 320

Ala Asp Leu Pro Gly Ala Glu Val Lys Pro Trp Asp Ser Thr Ala Asn
                325                 330                 335

Val Lys Ala Ser Ala Phe Val Arg Met Asp Glu His Leu Thr Val Phe
            340                 345                 350

Ala Asp Val Thr Gly Gly Cys Glu Arg Ile Leu Arg Thr Pro Val Pro
        355                 360                 365

Leu Met Tyr Ser Arg His Thr Ser Arg Met Leu Thr Ile Trp Leu Ser
    370                 375                 380

Phe Leu Pro Phe Ser Leu Trp Asp Ala Cys His Trp Trp Thr Val Pro
385                 390                 395                 400

Val Thr Gly Leu Val Ala Tyr Leu Leu Leu Gly Ile Lys Glu Ile Gly
                405                 410                 415

Leu Thr Val Glu Glu Pro Phe Ser Ile Leu Pro Leu Lys Ile Cys
            420                 425                 430

Asp Thr Ile Glu Ser Asn Val Trp Glu Leu His Ser Thr His Ser Ala
        435                 440                 445

Gln Gly Ala Ala Ala Ser Arg Arg Ser Ala Thr Arg Asp Ala
    450                 455                 460

Thr Gln Ser Met Asp Ala Glu Asp Leu Val Ser Ile Ala Ala Ala Val
465                 470                 475                 480

Asp Ala Gly Ala Met Pro Ala Pro Ala Gln
                485                 490

<210> SEQ ID NO 96
<211> LENGTH: 460
<212> TYPE: PRT
<213> ORGANISM: Micractinium conductrix

<400> SEQUENCE: 96

```
Met Arg Leu Leu Pro Gly Cys Arg Arg Pro Gly Ala Ala His Gly Thr
1               5                   10                  15
Ala Ala Ser Leu Gly Cys Arg Pro Gln Arg Gln Arg Leu Arg Arg Ala
                20                  25                  30
Pro Leu Ala Thr Ala Gln Pro Ser Asp Gly Asp Ser Ser Ser Ser Ser
            35                  40                  45
Asn Gly Thr Gly Leu Leu Ser Lys Val Pro Ala Val Leu Lys Ser Val
        50                  55                  60
Asp Glu Asp Ala Val Tyr Val Tyr Asp Ser Gly Ser Asp Asp Val Pro
65                  70                  75                  80
Leu Asp Ile Leu Leu Leu Pro Leu Asp Arg Asp Asp Tyr Lys Glu Asp
                85                  90                  95
Ser Arg Arg His Phe Arg Thr Val Phe Asp His Asn Arg Trp Ala Ala
                100                 105                 110
His Arg Ser Thr Arg Arg Tyr Val Arg His Val Leu Gly Met Thr Ser
            115                 120                 125
Ser Arg Met Val Arg Gly Leu Ala Ala Pro Leu Phe Phe Val Ala Gly
        130                 135                 140
Ile Ser Ala Ala Val Cys Ala Gly His Gln Ala Ala Glu Ala Gly Leu
145                 150                 155                 160
Leu Pro Leu Pro Glu Val Ala His Gln Leu Gln Met Arg Ser Thr Glu
                165                 170                 175
Pro Phe Ala Leu Thr Ser Phe Ala Leu Ser Leu Leu Leu Val Phe Arg
            180                 185                 190
Thr Asn Ser Ser Tyr Ser Arg Trp Leu Asp Ala Arg Lys Asn Trp Gly
        195                 200                 205
Leu Val Val Thr Arg Ser Arg Asp Leu Val Arg Gln Gly Ile Thr His
        210                 215                 220
Ile Pro His Ser Glu Arg Ala Leu Ile Asp Leu Leu Cys Arg Trp Thr
225                 230                 235                 240
Ala Ala Phe Ser Arg Ser Leu Met Ala His Leu Arg Ala Asp Val Asp
                245                 250                 255
Ala Glu Ala Glu Leu Arg Arg Val Leu Arg Pro Ala Glu Ala Glu Ala
                260                 265                 270
Ala Leu Ala Ala Glu His Arg Pro Gly Tyr Cys Leu Gln Val Leu Ser
            275                 280                 285
Glu Ile Ile Lys Asp Ala Gln Leu Glu Arg Pro His Ala Ala Ala Thr
        290                 295                 300
Ala Ala Ala Ala Thr Ala Arg Pro Gly Gln Ala Ala Lys Pro Thr Arg
305                 310                 315                 320
Leu Asp Gly Gly Ala Ala Cys Arg Met Asp Glu Asn Leu Thr Ala Leu
                325                 330                 335
Glu Asp Met Val Gly Gly Cys Glu Arg Ile Leu Arg Thr Pro Ile Pro
                340                 345                 350
Leu Ser Tyr Thr Arg His Thr Ser Arg Phe Met Met Ile Phe Leu Ser
            355                 360                 365
Leu Leu Pro Phe Ala Leu Trp Glu Ser Cys Arg Trp Ala Thr Val Pro
        370                 375                 380
Ala Val Thr Ile Ile Ser Phe Leu Leu Gly Ile Glu Glu Ile Gly
385                 390                 395                 400
Val Thr Ile Glu Glu Pro Phe Ser Ile Leu Pro Leu Gly Gln Leu Cys
                405                 410                 415
```

```
Asp Val Ile Glu Lys Asn Val Trp Glu Leu His Arg Cys His Val Gln
            420                 425                 430

Pro Ala Ser Ala Ala Ile Asp Gly Ser Gly Ser Arg Pro Leu Thr Ala
            435                 440                 445

Ala Gly Val Val Ala Ala Arg Leu Ala Glu Asp
    450                 455                 460

<210> SEQ ID NO 97
<211> LENGTH: 511
<212> TYPE: PRT
<213> ORGANISM: Micractinium conductrix

<400> SEQUENCE: 97

Met Arg Thr Glu Pro Gln Thr Arg Leu Ala Thr Gly Gly Ala Ala Thr
1               5                   10                  15

Gln Arg Arg Arg Ser Ala Pro Val Val Ala Gly Ser Ala Ala Gly Leu
            20                  25                  30

Pro Pro Pro Ser Pro Phe Ala Ser Ser Arg Ser Gly Ala Arg Thr Gln
            35                  40                  45

Arg Gly Ala Ala Ser Pro Glu Gln Arg Glu Val Thr Trp Ser Leu Glu
    50                  55                  60

Asp Ala Gly Ala Asp Met Thr Ile Asn Pro Asp Arg Glu Ala Gly Arg
65                  70                  75                  80

Arg Leu Met Arg Asp Leu Ser Asn Phe Ser His Arg Arg Trp Ala Phe
                85                  90                  95

His Arg Ser Thr Asp Arg Tyr Trp Arg His Leu Ala Gly Ile Phe Gln
            100                 105                 110

Ser Arg Ile Gly Arg Gln Leu Phe Val Pro Leu Ser Cys Ala Gly Gly
            115                 120                 125

Thr Ala Ala Ala Ile Cys Ala Tyr Glu Thr Leu Leu Arg Asp Gly Ala
    130                 135                 140

Leu Pro Ala Tyr Phe Pro Ser Phe Val Leu Pro Ser Leu Pro Phe Asp
145                 150                 155                 160

Phe Thr Ala Phe Ala Leu Ser Leu Leu Val Phe Arg Thr Asn Thr
                165                 170                 175

Ser Tyr Asp Arg Trp Gln Ala Ala Ile Asn Ala Trp Gly Asp Ile Ser
            180                 185                 190

Thr Arg Ser Arg Asp Thr Leu Arg Gln Leu Leu Ala Tyr Thr Ser Ala
            195                 200                 205

Thr Pro Ala Ala Ala Val Ala Arg Asp Thr Ser Ala Ala Pro Leu
    210                 215                 220

His Gly Ala Gly Gly Ser Gly Ala Ala Ala Ser Ala Ala Gln Thr
225                 230                 235                 240

Thr Ala Ala Ala Gly Lys Trp Leu Val Ala Phe Ser Arg Ser Leu Lys
                245                 250                 255

Ala Gln Leu Thr Glu Asp Ser Asp Leu Gln Ala Glu Leu Lys Gly Val
            260                 265                 270

Leu Thr Ala Gly Glu Leu Glu Leu Leu Thr Ala Ala Tyr His Arg Pro
    275                 280                 285

Ser Phe Ala Leu Ala Val Leu Ser Glu Leu Val Ala Ala Pro Val
    290                 295                 300

Arg Asp Ser Gln Arg Ala Arg Leu Asp Glu Asn Leu Thr Thr Leu Glu
305                 310                 315                 320

Asp Met Val Gly Gly Cys Glu Arg Leu Leu Arg Thr Pro Ile Pro Leu
                325                 330                 335
```

```
Ser Tyr Thr Arg His Thr Ser Arg Phe Met Val Ile Trp Leu Ser Cys
            340                 345                 350

Leu Pro Leu Cys Leu Trp Asn Ser Cys Gly Trp Gly Thr Val Pro Leu
            355                 360                 365

Thr Val Val Ile Ser Phe Leu Leu Gly Ile Glu Glu Ile Gly Val
    370                 375                 380

Ala Ile Glu Glu Pro Phe Ser Ile Met Pro Leu His Glu Met Cys Ala
385                 390                 395                 400

Glu Met Glu Cys Gly Leu Ala Asp Ile Leu Glu Gln Ala Ala Pro Ser
                405                 410                 415

Lys Arg Ala Ala Ala Gln Ala Ala Ala Ala Ala Leu Thr Ala Ala
            420                 425                 430

Ser Ala Ala Val Gly Gly Ser Ala Asp Ala Pro Ala Asp Ala Ser Gly
            435                 440                 445

Gly Gly Gly Gly Gly Ser Thr Ala Gly Ala Ala Pro Ala Pro Ala
450                 455                 460

Leu Gly Val Pro Ala Ala Ala Asn Ser Val Ala Pro Phe Val Leu
465                 470                 475                 480

Gly Met Thr Ala Gln Arg Leu Arg Arg Pro Leu Ser Ala Thr Pro Arg
            485                 490                 495

Pro Met Asp Ala Ile Phe Cys Ser Met Asp Pro Asp Ala Arg
            500                 505                 510
```

<210> SEQ ID NO 98
<211> LENGTH: 523
<212> TYPE: PRT
<213> ORGANISM: Micractinium conductrix

<400> SEQUENCE: 98

```
Met Pro Arg Thr Glu Asn Ser Tyr Thr His Gly Ala Arg Gly Ser Pro
1               5                   10                  15

Ser Leu Asp Pro Glu Gly Ser Pro Leu Thr Gln His Ala Arg Asn Ser
            20                  25                  30

Ser Leu Gln Asn Leu Ala Arg Leu Pro Gly Val Ala Arg Ala Lys Leu
        35                  40                  45

Gln Asn Leu Ser Gln Thr Lys Phe Val Arg Tyr Ile Glu Asp Asn Asp
    50                  55                  60

Asp Gly Ser Arg Asp Glu Asn Asp Ile Tyr Arg Gln His Pro Gly Asp
65                  70                  75                  80

Gln Val Phe Thr Phe Glu Arg Trp Asn Lys His Arg Asp Ser Phe Arg
                85                  90                  95

Tyr Ala Lys His Leu Ala His Met Phe Ser Ser Arg Val Phe Lys Gln
            100                 105                 110

Leu Leu Gly Pro Val Leu Cys Val Ser Ala Leu Ala Leu Ala Val Gly
        115                 120                 125

Val Tyr Glu Thr Leu Val Ala Ala Gly Lys Leu Pro Gly His Trp Pro
    130                 135                 140

His Val Thr Leu Ala Leu Gly Gln Gly Phe Asn Leu Thr Ala Phe Ala
145                 150                 155                 160

Leu Ser Leu Leu Leu Val Phe Arg Thr Asn Ser Ser Tyr Asp Arg Trp
                165                 170                 175

Trp Glu Ala Arg Lys Leu Trp Gly Gly Val Val Asn Arg Thr Arg Asp
            180                 185                 190

Phe Val Arg Gln Ser Leu Val Phe Phe Arg Asp Glu Asp Ala His Leu
```

```
                 195                 200                 205
Arg Glu Leu Leu Ala Lys Trp Thr Ile Ala Phe Pro His Val Leu Met
    210                 215                 220

Cys His Leu Arg Glu His Gly Asp Val Ala Lys Ala Val Ala Met Met
225                 230                 235                 240

Ala Glu Ile Val Arg Thr Ala Arg Pro Pro Glu Leu Cys Arg Met Arg
                245                 250                 255

Met Asp Glu Asn Leu Ser Phe Phe Glu Asp Ala Met Gly Ser Met Glu
            260                 265                 270

Arg Ile Leu Arg Thr Pro Ile Pro Leu Ser Leu Val Trp Leu Ile Leu
        275                 280                 285

Leu Pro Phe Thr Leu Trp Ala Ala Tyr Ser Trp Phe Ser Val Leu Leu
    290                 295                 300

Ser Gly Ile Phe Ala Phe Leu Met Phe Gly Ile Asp Glu Ile Gly Val
305                 310                 315                 320

Gln Ile Glu Glu Pro Phe Gly Ile Leu Pro Leu Glu Ala Ile Ser Ser
                325                 330                 335

Thr Ile Glu Arg Asn Ile Arg Glu Leu Leu Ala Arg Asn Asp Glu Val
            340                 345                 350

Val Gly Leu Val Ala Gln Ala Ala Gln Ala Gly Ala Val Ala Ala Ala
        355                 360                 365

Ala Ala Ala Ala Ala Asp Val Ala Val Ala Ala Leu Pro Gln Gly Gly
    370                 375                 380

Gln His Asp Ala Asp Ala Ala Thr Val Leu Ala Val Pro Gly Asp Glu
385                 390                 395                 400

Phe Gly Glu Met Val Ala Ala Gly Ser Pro Val Gly Lys Glu Pro Ser
                405                 410                 415

Ala Gly Asn Leu Ile Thr Leu Thr Ala Ser Ser Gly Glu Ala Ala Ala
            420                 425                 430

Ala Ala Ala Ala Ala His His His Leu His Ala Ala Arg Arg Val
        435                 440                 445

Gln Phe Gly Gly Ala Thr Val Ile Glu Val Gly Gly Ser Asp Glu Glu
    450                 455                 460

Ala Ala Gly Gly Gly Gly Ser Pro Leu Gly Ser Pro Ser His Ala
465                 470                 475                 480

His Ser Pro His Arg Ala Leu Asn Arg Gln Ala Ser Met Val Glu Val
                485                 490                 495

Glu Leu Ala Ser Gly Ala Ser Pro Leu Leu Ser Pro Thr Asp Gly Ser
            500                 505                 510

Ser Ala Pro Val Tyr Ser Asn Trp Leu Arg Asp
        515                 520

<210> SEQ ID NO 99
<211> LENGTH: 425
<212> TYPE: PRT
<213> ORGANISM: Micractinium conductrix

<400> SEQUENCE: 99

Met Thr Leu Leu Gln Gln Ala Val Pro Ser Arg Val Val Gly Gly
1               5                   10                  15

Arg Gln Pro Arg Gly Ile Gly Ser Val Leu Lys Pro Leu Arg Thr Ser
                20                  25                  30

Cys Arg Pro Ala Lys Ala Ala Arg Gly Arg Gln Ala Leu Pro Gln Ala
            35                  40                  45
```

-continued

```
Ser Leu Gln Pro Ala Val Ala Ala Gly Thr Ala Ala Pro Pro Pro
 50                  55                  60

Ser Tyr Val Ala Ser Ala Asn Asp Glu Arg Met Glu Ala Ser Arg Val
 65                  70                  75                  80

Glu Met Arg Ala Val Phe Asp Ala Asp Arg Trp Ile Met His Arg Ser
                 85                  90                  95

Thr Asp Arg Tyr Phe Arg His Leu Trp Gly Leu Pro Ser Ser Arg Val
                100                 105                 110

Leu Gln Gly Leu Phe Lys Pro Ile Gly Tyr Ile Leu Ala Ile Ser Ala
                115                 120                 125

Ala Val Cys Ala Tyr Gly Thr Ala Gln Ala Ala Gly Ala Leu Pro Ala
            130                 135                 140

Thr Leu Pro Leu Leu Ala Ser Ala Ile Lys Leu Lys Glu Leu Phe Gly
145                 150                 155                 160

Met Thr Ser Phe Ala Leu Ser Leu Leu Leu Val Phe Arg Thr Asn Ala
                165                 170                 175

Ser Tyr Ala Arg Trp Asp Glu Gly Arg Lys Met Trp Gly Met Val Leu
                180                 185                 190

Asn Arg Thr Arg Asn Ile Cys Arg Leu Gly Leu Ala Trp Ile Gly Asp
                195                 200                 205

Asp Lys Arg Glu Leu Arg Ser Met Leu Cys Arg Trp Ala Pro Ala Phe
210                 215                 220

Ser Lys Thr Leu Met Cys His Leu Arg Lys Gly Glu Asp Leu Arg Glu
225                 230                 235                 240

Glu Leu Glu Gly Ile Leu Leu Pro His Glu Ile Glu Gly Val Leu Arg
                245                 250                 255

Ala Ser His Arg Pro Asn Tyr Val Leu Gln Val Leu Ala Gln Ile Val
                260                 265                 270

Arg Thr Ala Gly Leu Pro Thr Ala Ala Thr Leu Arg Met Glu Asp Asp
            275                 280                 285

Leu Thr Asn Phe Gly Asp Ser Leu Gly Gly Cys Glu Arg Leu Leu Arg
290                 295                 300

Thr Pro Ile Pro Leu Phe Tyr Thr Arg His Thr Ser Arg Phe Leu Met
305                 310                 315                 320

Ile Trp Leu Thr Phe Leu Pro Ala Thr Leu Trp Pro Ala Cys Gly Leu
                325                 330                 335

Leu Thr Leu Pro Leu Val Phe Leu Ile Ser Phe Leu Leu Gly Val
                340                 345                 350

Asp Lys Ile Gly Val Ser Ile Glu Glu Pro Phe Ser Ile Leu Ala Leu
            355                 360                 365

Glu Val Ile Ala Gly Thr Ala Leu Ala Asn Val Arg Glu Leu Val Ala
370                 375                 380

Met His Glu Asp Thr Ala Ala Gly Val Ala Ala Ala Asn Gly Asn
385                 390                 395                 400

Gly Gly Ala Ala Gly Ala Pro Ala Glu Ala Asp Val Ser Ala Ala His
                405                 410                 415

Met Val Thr Leu Ala Gly Ala Ala Ala
            420                 425
```

<210> SEQ ID NO 100
<211> LENGTH: 490
<212> TYPE: PRT
<213> ORGANISM: Micractinium conductrix

<400> SEQUENCE: 100

```
Met Ser Ala Leu Leu Arg Ala Arg Val Ser Ser Phe Leu Ala Gly Val
1               5                   10                  15

Ala Val Ala Gly Val Phe Gly Val Tyr Gln Leu Arg Gly Asp Val Ala
            20                  25                  30

Glu Gly Gln Ala Gln Leu Leu Glu Gln Thr Lys Lys Tyr Thr Ser Gly
            35                  40                  45

Leu Glu Ala Arg Val Ala Glu Leu Glu Ala Ser Val Ala Arg Leu Gln
        50                  55                  60

Lys Ser Ser Leu Leu Leu Ala Ser Arg Pro Leu Gly Ala Gly Leu Val
65                  70                  75                  80

Gly Leu Arg Ser Ser Gln Gly Gly Leu Glu Arg Arg Arg Arg Ala Ser
                85                  90                  95

Ala Arg Val Ala Ala Val Ala Ser Pro Val Gly Asp Ile Glu Gly Arg
            100                 105                 110

Lys Pro Thr Val Asp Glu Arg Glu Ser Asp Leu Lys Glu Leu Arg
        115                 120                 125

Ser Val Phe Asp Phe Ala Ala Trp Lys Arg His Arg Ser Ser Asp Arg
        130                 135                 140

Tyr Trp Arg His Met Thr Gly Leu Trp Asp Ser Arg Thr Leu Asp Trp
145                 150                 155                 160

Val Gly Pro Pro Leu Thr Tyr Val Met Ser Val Ala Ala Leu Val Cys
                165                 170                 175

Leu Tyr His Ala Ala Asp Ala Gly Tyr Val Ala Glu Val Ile Pro
                180                 185                 190

Glu Leu Lys Pro Ala Ala Thr Ala Pro Phe Ser Leu Thr Ser Phe Ala
        195                 200                 205

Leu Ser Thr Leu Leu Val Leu Arg Thr Asn Thr Ser Tyr Gln Arg Trp
210                 215                 220

Asp Glu Ala Arg Lys Met Trp Gly Leu Ile Val Asn Arg Ser Arg Asp
225                 230                 235                 240

Ile Ser Arg Gln Ala Leu Gly Tyr Ile Pro Ala Thr Gln Pro Glu Leu
            245                 250                 255

Gln Asp Met Phe Ile Arg Trp Val Val Ala Tyr Ser Arg Ser Leu Met
            260                 265                 270

Cys His Leu Arg Ala Gly Glu Asp Leu Glu Lys Glu Leu Lys Asp Thr
        275                 280                 285

Leu Gly Pro Glu Glu Leu Lys Ala Leu Met Ala Ser Ala His Arg Pro
        290                 295                 300

Asn Tyr Thr Val Gln Val Leu Thr Ser Ile Ile Lys Ala Ala Gln Leu
305                 310                 315                 320

Pro Gly Glu Pro Ile Ser Asn Tyr Asn Ser Thr Ala Asn Val Lys Ala
            325                 330                 335

Ser Ala Ala Phe Arg Met Asp Glu Asn Leu Thr Cys Phe Ala Asp Val
            340                 345                 350

Thr Gly Gly Cys Glu Arg Ile Leu Arg Thr Pro Val Pro Leu Met Tyr
        355                 360                 365

Thr Arg His Asn Ser Arg Phe Leu Met Ile Trp Leu Thr Leu Pro
        370                 375                 380

Leu Thr Leu Trp Asp Ser Cys His Trp Phe Thr Met Pro Val Thr Gly
385                 390                 395                 400

Ile Val Ala Phe Leu Leu Leu Gly Ile Lys Glu Ile Gly Val Ile Val
                405                 410                 415
```

```
Glu Glu Pro Phe Ser Ile Leu Pro Leu Glu Lys Ile Cys Asp Thr Ile
                420                 425                 430

Glu Gly Asn Val Arg Glu Leu His Ala Thr His Ser Ala Asp Ala Ile
            435                 440                 445

Ser Ala Gln Leu Ala Val Ala Asn Ala Gln Asn Ser Gly Ala Ala Ser
    450                 455                 460

Gly Gly Val Asp Ala Asp Thr Leu Val Asn Thr Val Pro Ala Val
465                 470                 475                 480

Thr Leu Arg Lys Pro Ala Val Ala Ala Leu
                485                 490

<210> SEQ ID NO 101
<211> LENGTH: 1322
<212> TYPE: PRT
<213> ORGANISM: Micractinium conductrix

<400> SEQUENCE: 101

Met Gly Ala Ser Thr Asp Asp Ser Ala Ala Met Ala Asp His Pro Gly
1               5                   10                  15

Arg Thr Pro Gly Gly Arg Pro Pro Leu Ser Ser Ser Val Gly Gly
                20                  25                  30

Ser Ser Arg Ala Lys Ala Met Leu Ala Met Ala Thr Gly Gly Gly
            35                  40                  45

Lys Ala Lys Thr Arg Thr Pro Ser Gly Arg Pro Thr Pro Pro Ile
50                  55                  60

Thr Phe Glu Arg Arg Lys Lys Arg Pro Gln Ser Glu Pro Gly Asp Gly
65                  70                  75                  80

Gly Gly Gly Glu Ala Ala Ala Leu Gly Gly Glu Thr Thr Pro Lys Arg
                85                  90                  95

Gln Arg Thr Pro Ala Gly Ala Asp Cys Pro Ser Val Pro Val Ala Ala
            100                 105                 110

Pro Arg Pro Ala Ser Leu Leu Ala Ala Arg Pro Gly Ser Ala Ala Gly
        115                 120                 125

Ser Ala Gly Asp Ala Pro Arg Leu Thr Cys Tyr Ser Asn Ala Gln Arg
130                 135                 140

Leu Arg Glu Leu Ala Ala Glu Gly Gly Asp Ala Leu Ala Arg Arg Arg
145                 150                 155                 160

Ala Ala Leu Gly Gly Ser Gly Phe Ile His Arg Arg Pro Ser Ser Gly
                165                 170                 175

Gly Ser Leu Gly Arg Met Gln Gly Leu Ser Arg Leu Pro Ala Gly Met
            180                 185                 190

Met Asn Leu Gly Asn Thr Cys Tyr Leu Asn Ala Val Leu Gln Val Leu
        195                 200                 205

Leu Ser Leu Pro Ser Phe Val Ala Asp Leu Arg His Gly Arg Ala Ala
210                 215                 220

Leu Glu Ala Ala Gly Gln Pro Leu Ala Pro Ser Gly Val Tyr Ser Ala
225                 230                 235                 240

Leu Leu Glu Cys Ala Ala Ala Arg Glu Arg Gly Phe Glu Arg Tyr Leu
                245                 250                 255

Thr Pro Ala Ser Leu Lys Arg Ala Leu Asp Ala Ala Ser Ser Ala Phe
            260                 265                 270

His Gly Thr Leu Gln Gln Asp Ala His Glu Leu Phe Cys Ser Leu Leu
        275                 280                 285

Asp Ala Ala Gln Gly Glu Val Leu Ala Arg Glu Val Ala Arg Leu Gly
290                 295                 300
```

-continued

```
Arg Thr Arg Val Ala Val Ser Glu Thr Ala Asp Pro Gly Ala Arg Asn
305                 310                 315                 320

Phe Gly Phe Ala Met Gln His Glu Leu Val Cys Gly Ala Cys Gly His
                325                 330                 335

Thr Ser Gln Leu Val Glu Gln Tyr Thr His Leu Ser Leu Glu Leu Pro
                340                 345                 350

Pro Ala Gln Pro Gly Gly Thr Ala Ala Cys Ser Val Ala Ser Leu Leu
                355                 360                 365

Arg Asp Tyr Phe Lys Glu Glu Gln Val Glu Lys Ala Cys Glu Ala Cys
                370                 375                 380

Gly Gly Gly Gly Val Ala His Thr Leu Arg His Ala Val Lys Arg Leu
385                 390                 395                 400

Pro Arg Val Leu Val Leu His Leu Lys Arg Phe Lys Ile Ser Trp Ser
                405                 410                 415

Ala Glu Gln Gln Arg Val Val Cys Gln Lys Val His Thr Gly Val Gly
                420                 425                 430

Met Pro Glu Thr Val Gln Leu Gly Arg Leu Leu Ala Ala Gly Pro Ala
                435                 440                 445

Pro Pro Leu Leu Gly Gly Gln Gln Leu Gly Ala Gly Lys Glu Asn Glu
                450                 455                 460

Gln Leu Glu Ala Asn Ala Gly Val Val Gly Ser Ala Ala Gln Gln Gln
465                 470                 475                 480

Gln Gln Gln Gln Gln Arg Gly Asp Asp Ser Val Ala Lys Gly Leu Arg
                485                 490                 495

Met Arg Glu Gln Ala Gly Phe Ser Phe Tyr Ser Gly Gly Gly Gly Ala
                500                 505                 510

Thr Pro Val Ala Ala Ser Ala Leu Leu Ser Pro Gly Ala Leu His Ser
                515                 520                 525

Pro Thr Leu Arg Arg Arg Leu Gly Thr Pro Ala Ala Pro Lys Leu Ser
                530                 535                 540

Asn Ile Val Val Asp Asn Asp Asp Ala Val Leu Gln Arg Val Leu Ala
545                 550                 555                 560

Glu Ser Leu Arg Glu Gln Gln Pro Gly Gly Gly Gln Leu Pro Gly Gly
                565                 570                 575

Thr Ala Gln Gln Gln Gln Gln Gln Gln Gln Gln Gln Gln Gln Gln Gln
                580                 585                 590

Gln Gln Gln Asp Gly Pro Glu Leu Ser Leu Gly Pro Gly Gly Cys Leu
                595                 600                 605

Gln Arg His Ser Thr Glu Gly Ala Glu Cys Pro Leu Ile Arg Cys Gly
                610                 615                 620

Ser Pro Gly Leu Arg Gln Ala Glu Ala Pro Leu Leu Leu Pro Glu
625                 630                 635                 640

Val Ala Ala Ala Ala Ala Gly Ser Ala Pro Ala Gly Gly Cys His
                645                 650                 655

Lys Leu Glu Asp Gln Trp Phe Thr Gly Phe Arg Arg Gly Ser Pro Pro
                660                 665                 670

Ala Ala Pro Met Ala Ala Glu Gln Glu Ala Ala Glu Leu Gln Arg Val
                675                 680                 685

Leu Asp Met Ser Arg Arg Glu His Glu Arg Gln Ala Ala Ala Val Ala
                690                 695                 700

Val Arg Ser Ser Ser Ala Ala Gly Ser Ala Ala Gln Gln Glu Glu Ala
705                 710                 715                 720
```

```
Asp Leu Leu Arg Ala Ile Glu Leu Ser Met Gln Glu Gln Arg Gly Lys
                725                 730                 735

Gln Pro Thr Ser Thr Gln Pro Gln His Gly Gly Ser Gln Gly Thr
        740                 745                 750

Ala Gly Gly Asp Ser Ser Gly Gly Ala Gly Gly Ala Ala Gly Ala
        755                 760                 765

Ala Ala Pro Gly Ala Ser Ala Ala Ala Ala Ala Ala Ala Ala Val
        770                 775                 780

Thr Glu Gln Phe Asp Ala Gly Glu Ala Gly Lys Ala Glu Glu Ala Ala
785                 790                 795                 800

Ser Ala Val Gln Ser Val Ala Pro His Gly Asp Asp Gly Val Glu Leu
                805                 810                 815

Val Ala Asp Ala Gly Gly Ala Ala Pro Ala Pro Leu His Ala Gln Ile
                820                 825                 830

Val Glu Asp Asn Asp Ala Gln Leu Ala Ala Gln Arg Ala Gln Gln Ala
                835                 840                 845

Gln His Gly Ser Ser Gly Ala Ser Ala Asp Gln Ala Ala Ala Glu
        850                 855                 860

Val Thr Asp Ala Ala Glu Ala Ala Gly Ala Glu Glu Lys Ala Ala
865                 870                 875                 880

Ala Ala Ala Ala Val Arg Ser Gly Lys Pro Pro Ala Ala Glu Tyr Arg
                885                 890                 895

Leu His Ala Val Val Asn His Lys Gly Pro Ala Ala Ser Cys Gly His
                900                 905                 910

Phe Thr Ser Asp Ile Arg Asp Ala Ala Ser Gly Val Trp His Arg Phe
                915                 920                 925

Asp Asp Ser Leu Ala Ser Arg Ile Ala Gly Trp Glu Ala Arg Ser Ser
        930                 935                 940

Glu Lys Gln Arg Glu Cys Tyr Leu Leu Phe Tyr Thr Gly Thr Val Ala
945                 950                 955                 960

Gly Leu Ile Tyr Ser Asp Arg Asp Glu Gly Lys Glu Phe Arg Leu Ala
                965                 970                 975

Asp Phe Arg Thr Val Tyr Thr Phe Glu Ser Trp Ala Ala His Arg Ser
                980                 985                 990

Thr Met Arg Tyr Leu Arg His Phe Met Gly Met Phe Arg Ser Arg Val
        995                 1000                1005

Leu Cys Gly Leu Arg Val Pro Leu Leu Ile Ala Leu Glu Ala Thr
1010                1015                1020

Leu Val Cys Ser Tyr Glu His Ala Leu Lys Asn Gly Leu Leu Pro Ala
1025                1030                1035                1040

Phe Cys Arg Thr Ile Gln Ile Arg Ala Pro Met Leu Phe Ser Leu Ser
                1045                1050                1055

Ser Phe Ala Leu Ser Leu Leu Val Phe Arg Thr Asn Gln Ser Tyr
        1060                1065                1070

Ala Arg Phe Asp Glu Gly Arg Arg Leu Trp Ser Val Met Ala Asn Arg
                1075                1080                1085

Cys Arg Asp Val Met Arg Gln Ala Cys Ser Tyr Leu Ser Leu Gly Pro
                1090                1095                1100

Gln Asn Ala Ala Leu Leu Ala Thr Leu Ser Arg Trp Met Gln Ala Phe
1105                1110                1115                1120

Pro Trp Val Met Lys Asn Tyr Val Arg Glu Ser Lys Ser Trp His Ala
                1125                1130                1135

Asp Leu Gly Ser Leu Leu Arg Pro Ala Glu Leu Ala Ala Leu Leu Asp
```

```
                1140              1145              1150
Thr Arg Asn Pro Pro Leu Leu Thr Leu Gln Val Ile Thr Glu Ile Leu
            1155              1160              1165
Asp Arg Met Pro Ile Ser Thr Lys Gln Arg Leu Arg Leu Asp Ile Phe
        1170              1175              1180
Met Thr Glu Leu Ser Asp Met Val Gly Ala Ser Glu Arg Leu Ile Thr
1185              1190              1195              1200
Thr Pro Ile Pro Leu Ser Tyr Thr Arg His Thr Ala Arg Phe Leu Ile
            1205              1210              1215
Thr Trp Leu Val Leu Thr Pro Phe Thr Ile Phe Ser Ser Cys Gly Trp
        1220              1225              1230
Val Thr Ile Phe Ser Ser Val Leu Leu Ala Phe Phe Leu Leu Thr Ile
            1235              1240              1245
Glu Glu Ile Gly Val Thr Ile Glu Glu Pro Phe Asn Ile Leu Pro Leu
        1250              1255              1260
Glu Ala Ile Asn Thr Arg Val Cys Ala Asp Ile Ala Arg Tyr Pro Gln
1265              1270              1275              1280
Lys Ile Asp Thr Val Val Ser Leu Val Asp Asp Ala Thr Gly Thr Gln
            1285              1290              1295
Arg Pro Gln Gln Gln Pro Pro Phe Gln Pro Val Ala Glu Phe Val Ser
        1300              1305              1310
Thr Ala Ala Thr Ser Asp Asn Gly Asp Ser
            1315              1320

<210> SEQ ID NO 102
<211> LENGTH: 1327
<212> TYPE: PRT
<213> ORGANISM: Micractinium conductrix

<400> SEQUENCE: 102

Met Gly Ala Ser Thr Asp Asp Ser Ala Ala Met Ala Asp His Pro Gly
1               5                   10                  15
Arg Thr Pro Gly Gly Arg Pro Pro Leu Ser Ser Ser Val Gly Gly
            20                  25                  30
Ser Ser Arg Ala Lys Ala Met Leu Ala Met Ala Thr G

```
Met Asn Leu Gly Asn Thr Cys Tyr Leu Asn Ala Val Leu Gln Val Leu
            195                 200                 205

Leu Ser Leu Pro Ser Phe Val Ala Asp Leu Arg His Gly Arg Ala Ala
    210                 215                 220

Leu Glu Ala Ala Gly Gln Pro Leu Ala Pro Ser Gly Val Tyr Ser Ala
225                 230                 235                 240

Leu Leu Glu Cys Ala Ala Arg Glu Arg Gly Phe Glu Arg Tyr Leu
                245                 250                 255

Thr Pro Ala Ser Leu Lys Arg Ala Leu Asp Ala Ala Ser Ser Ala Phe
                260                 265                 270

His Gly Thr Leu Gln Gln Asp Ala His Glu Leu Phe Cys Ser Leu Leu
        275                 280                 285

Asp Ala Ala Gln Gly Glu Val Leu Ala Arg Glu Val Ala Arg Leu Gly
    290                 295                 300

Arg Thr Arg Val Ala Val Ser Glu Thr Ala Asp Pro Gly Ala Arg Asn
305                 310                 315                 320

Phe Gly Phe Ala Met Gln His Glu Leu Val Cys Gly Ala Cys Gly His
                325                 330                 335

Thr Ser Gln Leu Val Glu Gln Tyr Thr His Leu Ser Leu Glu Leu Pro
            340                 345                 350

Pro Ala Gln Pro Gly Gly Thr Ala Ala Cys Ser Val Ala Ser Leu Leu
        355                 360                 365

Arg Asp Tyr Phe Lys Glu Gln Val Glu Lys Ala Cys Glu Ala Cys
    370                 375                 380

Gly Gly Gly Gly Val Ala His Thr Leu Arg His Ala Val Lys Arg Leu
385                 390                 395                 400

Pro Arg Val Leu Val Leu His Leu Lys Arg Phe Lys Ile Ser Trp Ser
                405                 410                 415

Ala Glu Gln Gln Arg Val Val Cys Gln Lys Val His Thr Gly Val Gly
            420                 425                 430

Met Pro Glu Thr Val Gln Leu Gly Arg Leu Leu Ala Ala Gly Pro Ala
        435                 440                 445

Pro Pro Leu Leu Gly Gly Gln Gln Leu Gly Ala Gly Lys Glu Asn Glu
450                 455                 460

Gln Leu Glu Ala Asn Ala Gly Val Val Gly Ser Ala Ala Gln Gln
465                 470                 475                 480

Gln Gln Gln Gln Gln Arg Gly Asp Asp Ser Val Ala Lys Gly Leu Arg
                485                 490                 495

Met Arg Glu Gln Ala Gly Phe Ser Phe Tyr Ser Gly Gly Gly Ala
                500                 505                 510

Thr Pro Val Ala Ala Ser Ala Leu Leu Ser Pro Gly Ala Leu His Ser
        515                 520                 525

Pro Thr Leu Arg Arg Arg Leu Gly Thr Pro Ala Ala Pro Lys Leu Ser
    530                 535                 540

Asn Ile Val Val Asp Asn Asp Asp Ala Val Leu Gln Arg Val Leu Ala
545                 550                 555                 560

Glu Ser Leu Arg Glu Gln Gln Pro Gly Gly Gly Gln Leu Pro Gly Gly
                565                 570                 575

Thr Ala Gln Gln Gln Gln Gln Gln Gln Gln Gln Gln Gln Gln Gln
            580                 585                 590

Gln Gln Gln Asp Gly Pro Glu Leu Ser Leu Gly Pro Gly Gly Cys Leu
        595                 600                 605

Gln Arg His Ser Thr Glu Gly Ala Glu Cys Pro Leu Ile Arg Cys Gly
```

```
              610                 615                 620
Ser Pro Gly Leu Arg Gln Ala Glu Ala Ala Pro Leu Leu Pro Glu
625                 630                 635                 640

Val Ala Ala Ala Ala Ala Gly Ser Ala Pro Ala Gly Gly Cys His
                    645                 650                 655

Lys Leu Glu Asp Gln Trp Phe Thr Gly Phe Arg Arg Gly Ser Pro Pro
                660                 665                 670

Ala Ala Pro Met Ala Ala Glu Gln Glu Ala Ala Glu Leu Gln Arg Val
                675                 680                 685

Leu Asp Met Ser Arg Arg Glu His Glu Arg Gln Ala Ala Val Ala
690                 695                 700

Val Arg Ser Ser Ser Ala Ala Gly Ser Ala Ala Gln Gln Glu Glu Ala
705                 710                 715                 720

Asp Leu Leu Arg Ala Ile Glu Leu Ser Met Gln Glu Gln Arg Gly Lys
                    725                 730                 735

Gln Pro Thr Ser Thr Gln Pro Gln Gln His Gly Gly Ser Gln Gly Thr
                740                 745                 750

Ala Gly Gly Asp Ser Ser Gly Gly Ala Gly Gly Ala Ala Ala Gly Ala
                755                 760                 765

Ala Ala Pro Gly Ala Ser Ala Ala Ala Ala Ala Ala Ala Ala Val
770                 775                 780

Thr Glu Gln Phe Asp Ala Gly Glu Ala Gly Lys Ala Glu Glu Ala Ala
785                 790                 795                 800

Ser Ala Val Gln Ser Val Ala Pro His Gly Asp Asp Gly Val Glu Leu
                    805                 810                 815

Val Ala Asp Ala Gly Gly Ala Ala Pro Ala Pro Leu His Ala Gln Ile
                820                 825                 830

Val Glu Asp Asn Asp Ala Gln Leu Ala Ala Gln Arg Ala Gln Gln Ala
                835                 840                 845

Gln His Gly Ser Ser Gly Ala Ser Ala Asp Gln Gln Ala Ala Ala Glu
                850                 855                 860

Val Thr Asp Ala Ala Glu Ala Ala Ala Gly Ala Glu Glu Lys Ala Ala
865                 870                 875                 880

Ala Ala Ala Ala Val Arg Ser Gly Lys Pro Pro Ala Ala Glu Tyr Arg
                    885                 890                 895

Leu His Ala Val Val Asn His Lys Gly Pro Ala Ala Ser Cys Gly His
                900                 905                 910

Phe Thr Ser Asp Ile Arg Asp Ala Ala Ser Gly Val Trp His Arg Phe
                915                 920                 925

Asp Asp Ser Leu Ala Ser Arg Ile Ala Gly Trp Glu Ala Arg Ser Ser
930                 935                 940

Glu Lys Gln Arg Glu Cys Tyr Leu Leu Phe Tyr Thr Gly Thr Val Ala
945                 950                 955                 960

Gly Leu Ile Tyr Ser Asp Arg Asp Glu Gly Lys Glu Phe Arg Leu Ala
                965                 970                 975

Asp Phe Arg Thr Val Tyr Thr Phe Glu Ser Trp Ala Ala His Arg Ser
                980                 985                 990

Thr Met Arg Tyr Leu Arg His Phe Met Gly Met Phe Arg Ser Arg Val
                995                 1000                1005

Leu Cys Gly Leu Arg Val Pro Leu Leu Ile Ala Leu Glu Ala Thr
        1010                1015                1020

Leu Val Cys Ser Tyr Glu His Ala Leu Lys Asn Gly Leu Leu Pro Ala
1025                1030                1035                1040
```

-continued

Phe Cys Arg Thr Ile Gln Ile Arg Ala Pro Met Leu Phe Ser Leu Ser
                1045                1050                1055

Ser Phe Ala Leu Ser Leu Leu Val Phe Arg Thr Asn Gln Ser Tyr
                1060                1065                1070

Ala Arg Phe Asp Glu Gly Arg Arg Leu Trp Ser Val Met Ala Asn Arg
                1075                1080                1085

Cys Arg Asp Val Met Arg Gln Ala Cys Ser Tyr Leu Ser Leu Gly Pro
                1090                1095                1100

Gln Asn Ala Ala Leu Leu Ala Thr Leu Ser Arg Trp Met Gln Ala Phe
1105                1110                1115                1120

Pro Trp Val Met Lys Asn Tyr Val Arg Glu Ser Lys Ser Trp His Ala
                1125                1130                1135

Asp Leu Gly Ser Leu Leu Arg Pro Ala Glu Leu Ala Ala Leu Leu Asp
                1140                1145                1150

Thr Arg Asn Pro Pro Leu Leu Thr Leu Gln Val Ile Thr Glu Ile Leu
                1155                1160                1165

Asp Arg Met Pro Ile Ser Thr Lys Gln Arg Leu Arg Leu Asp Ile Phe
                1170                1175                1180

Met Thr Glu Leu Ser Asp Met Val Gly Ala Ser Glu Arg Leu Ile Thr
1185                1190                1195                1200

Thr Pro Ile Pro Leu Ser Tyr Thr Arg His Thr Ala Arg Phe Leu Ile
                1205                1210                1215

Thr Trp Leu Val Leu Thr Pro Phe Thr Ile Phe Ser Ser Cys Gly Trp
                1220                1225                1230

Val Thr Ile Phe Ser Ser Val Leu Leu Ala Phe Phe Leu Leu Thr Ile
                1235                1240                1245

Glu Glu Ile Gly Val Thr Ile Glu Gly Pro Phe Asn Ile Leu Pro Leu
                1250                1255                1260

Glu Ala Ile Asn Thr Arg Ala Ile Asn Thr Arg Val Cys Ala Asp Ile
1265                1270                1275                1280

Ala Arg Tyr Pro Gln Lys Ile Asp Thr Val Val Ser Leu Val Asp Asp
                1285                1290                1295

Ala Thr Gly Thr Gln Arg Pro Gln Gln Pro Pro Phe Gln Pro Val
                1300                1305                1310

Ala Glu Phe Val Ser Thr Ala Ala Thr Ser Asp Asn Gly Asp Ser
                1315                1320                1325

<210> SEQ ID NO 103
<211> LENGTH: 333
<212> TYPE: PRT
<213> ORGANISM: Physcomitrella patens

<400> SEQUENCE: 103

Met His Arg Asn Ser Val Tyr Gly His Gly Glu Trp Lys Lys His Lys
1               5                   10                  15

Ser Ser Trp Arg His Val Arg Val Cys Thr Ile Leu Ser Ser Gly
                20                  25                  30

Leu Ile Arg Ala Ile Gly Pro Pro Val Phe Leu Cys Thr Leu Val Ser
            35                  40                  45

Val Phe Val Ala Val Ile Asn His Cys Val Asp Asn Gly Val Leu Pro
        50                  55                  60

Ser Trp Phe Pro Val Leu Lys Val Ala Thr Leu Pro Phe Thr Leu Thr
65                  70                  75                  80

Ser Pro Val Leu Ala Leu Leu Leu Val Phe Arg Thr Asn Thr Ser Tyr

-continued

```
                85                  90                  95
Gln Arg Phe Asp Glu Ala Arg Lys Ala Trp Gly Ser Asn Val Asn Arg
            100                 105                 110

Ala Arg Asp Leu Ala Arg Gln Ala Leu Thr Trp Ile Arg Asn Pro Gly
        115                 120                 125

Asp Ser Lys Lys Leu Gln Cys Leu Leu Arg Tyr Thr Lys Ala Tyr Ser
130                 135                 140

Phe Cys Leu Met His His Leu Arg Glu Gly Cys Leu Arg Lys Glu
145                 150                 155                 160

Leu Glu Ala Thr Ile Val Asn Glu Glu Val Glu Cys Val Met Asn
                165                 170                 175

Ser Lys Asn Arg Pro Ile Trp Val Leu Gln Val Ile Ser Asp Ile Ile
            180                 185                 190

Asn Glu Cys Gln Ile Thr Pro Trp Glu Arg Ile Ala Met Asp Lys Asn
        195                 200                 205

Ile Thr Gln Phe His Asp Asn Val Gly Ala Cys Glu Arg Ile Phe Lys
    210                 215                 220

Thr Pro Ile Pro Val Ala Tyr Thr Arg Leu Thr Ser Arg Val Leu Thr
225                 230                 235                 240

Leu Trp His Leu Val Leu Pro Phe Ala Leu Trp Glu Thr Cys Gly Trp
                245                 250                 255

His Thr Ile Thr Val Ser Phe Val Ser Ser Ala Ala Leu Phe Tyr Ile
            260                 265                 270

Glu Glu Val Gly Val Met Ile Glu Glu Pro Phe Ser Ile Leu Ala Leu
        275                 280                 285

Ser Thr Ile Cys Thr Gly Ile Val Ala Ala Leu Glu Gly Leu Ser Asn
    290                 295                 300

Ala His Thr Asp Ala Leu Ile Leu Val Trp Gly Ile Val Glu Gln Gln
305                 310                 315                 320

Trp Ser Thr Lys Ala Asp His Leu Met Ile Asn Leu Lys
                325                 330
```

<210> SEQ ID NO 104
<211> LENGTH: 402
<212> TYPE: PRT
<213> ORGANISM: Physcomitrella patens

<400> SEQUENCE: 104

```
Met His Arg Asn Thr Val Tyr Gly His Asp Glu Trp Arg Arg His Lys
1               5                   10                  15

Ser Ser Trp Arg His Ala Arg His Val Ile Ser Ile Ala Ala Ser Gly
            20                  25                  30

Val Ile Ala Ala Leu Gly Pro Pro Val Leu Leu Ser Thr Ile Thr Ala
        35                  40                  45

Val Phe Val Thr Val Ile Asn His Gly Val Gln His Met Leu Val Ala
    50                  55                  60

Ser Trp Val Pro Tyr Leu Lys Val Ser Pro Ile Pro Phe Thr Phe Ile
65                  70                  75                  80

Ser Pro Val Leu Ala Phe Leu Leu Val Phe Arg Thr Asn Ser Ser Tyr
                85                  90                  95

Gln Arg Phe Asp Glu Ala Arg Lys Val Trp Gly Ser Asn Val Asn Arg
            100                 105                 110

Cys Arg Asp Leu Ala Arg Gln Ala Leu Ser Trp Ile Lys Asn Pro Glu
        115                 120                 125
```

Asp Ala Ala Arg Leu Glu Cys Leu Leu Arg Phe Leu Lys Ala Tyr Pro
130                 135                 140

Tyr Tyr Leu Lys Leu His Leu Thr Gln Glu Gly Pro Ser Ser Ser Thr
145                 150                 155                 160

Thr Ser Glu Ile Lys Asp Ile Leu Lys Asp Glu Glu Phe His Lys Val
            165                 170                 175

Ser Leu Val Gln Asn Gln Pro Ile Tyr Val Leu Gln Val Ile Ser Glu
            180                 185                 190

Ile Ile Ser Gln Cys His Ile Pro Asn Trp Glu Lys Ile Cys Met Asp
        195                 200                 205

Ala Asn Leu Thr Gln Phe His Asp Asn Val Gly Ala Cys Glu Arg Ile
210                 215                 220

Phe Lys Thr Pro Ile Pro Ile Ala Tyr Thr Arg Met Thr Ser Arg Met
225                 230                 235                 240

Leu Ile Met Trp His Leu Ala Leu Pro Tyr Gly Leu Trp Asn Asp Cys
                245                 250                 255

Arg Trp Leu Thr Ile Pro Ala Thr Phe Met Ser Ala Ala Leu Phe
            260                 265                 270

Tyr Ile Glu Gln Val Gly Val Val Ile Glu Glu Pro Phe Cys Ile Leu
        275                 280                 285

Ala Leu Asp Ser Ile Cys Gly Gly Ile Arg Ser Ala Ile Asp Met Phe
290                 295                 300

Arg Ala Thr Arg Glu Asp Val Phe Leu Leu Thr Glu Ser Ile Arg Ser
305                 310                 315                 320

Glu His Pro Lys Lys Thr Asp Thr Thr Lys Asn Leu Glu Gln Ile Ile
                325                 330                 335

Glu Met Glu Ser Met Asp Ser Asp Pro Leu Glu Glu Thr Ser Lys Glu
            340                 345                 350

Asp Glu Val Met Leu Gly Leu Gly Arg Ser Lys Ser Tyr Lys Ser Tyr
        355                 360                 365

Ser Gly Arg Lys Phe Phe Asp Lys Ser Arg Ser His Ser His Ser Thr
    370                 375                 380

Thr Ser Leu Tyr Gly Asp Leu Asn Val Gly Phe Ser Lys Leu Lys Ser
385                 390                 395                 400

Val Ser

<210> SEQ ID NO 105
<211> LENGTH: 353
<212> TYPE: PRT
<213> ORGANISM: Physcomitrella patens

<400> SEQUENCE: 105

Met His Arg Asn Thr Val Tyr Gly His Thr Glu Trp Arg Arg His Lys
1               5                   10                  15

Ser Cys Trp Arg His Ser Arg His Leu Ser Ser Ile Phe Ser Ser Gly
            20                  25                  30

Val Ile Phe Thr Leu Gly Pro Pro Val Ile Leu Cys Thr Leu Val Ala
        35                  40                  45

Thr Leu Val Ser Val Ile Asn His Leu Val Gln Asp Arg Arg Leu Pro
50                  55                  60

Lys Trp Met Pro Leu Leu His Val Ala Ser Leu Pro Phe Thr Leu Thr
65                  70                  75                  80

Ala Pro Val Leu Ala Leu Leu Leu Val Phe Arg Thr Asn Ala Ser Tyr
                85                  90                  95

Ser Arg Phe Asp Glu Ala Arg Lys Ala Trp Gly Ser Asn Val Asn Arg
                100                 105                 110

Thr Arg Asp Leu Ala Arg Gln Ala Leu Thr Trp Ile Arg Met Pro Cys
            115                 120                 125

Asp Ala Pro Lys Leu His Cys Leu Leu Arg His Ile Lys Ala Tyr Ser
        130                 135                 140

Leu Cys Leu Lys Asp His Met Thr Glu Asp Asn Thr Leu Arg Glu Glu
145                 150                 155                 160

Leu Thr Ala Val Leu Glu Pro Ser Glu Val Asp Cys Ala Met Ser Ser
                165                 170                 175

Gln His Arg Pro Asn Tyr Ile Leu Gln Val Met Ser Glu Leu Ile Ser
            180                 185                 190

Gln Cys Gln Ile Ser Gln Trp Glu Lys Ile Thr Met Asp Lys Asn Ile
        195                 200                 205

Thr Ala Phe His Asp Asn Val Gly Ala Cys Glu Arg Ile Phe Lys Thr
210                 215                 220

Pro Ile Pro Leu Ala Tyr Thr Arg Leu Thr Ser Arg Met Leu Met Phe
225                 230                 235                 240

Trp His Leu Ala Leu Pro Val Gly Leu Trp Asn Thr Cys Gly Trp Leu
                245                 250                 255

Thr Ile Pro Val Ser Phe Met Ser Ala Ala Leu Phe Tyr Ile Glu
            260                 265                 270

Glu Val Gly Val Leu Ile Glu Pro Phe Trp Ile Leu Pro Leu Leu
        275                 280                 285

Ser Ile Ser Gln Gly Ile Cys Ser Ala Val Asp Gly Leu Tyr Val Ala
290                 295                 300

His Lys Glu Ala Ser Met Leu Trp Ser Ile His Gln Pro Thr Asn Val
305                 310                 315                 320

Asn Asp His Val Ile Ile Ser Phe Asp Gly Ser Arg Ser Ala Gly Ile
                325                 330                 335

Tyr Gln His Asn Asn Ile Asp Val Lys Phe Ser Arg Val Asn Ser Val
            340                 345                 350

Gly

<210> SEQ ID NO 106
<211> LENGTH: 353
<212> TYPE: PRT
<213> ORGANISM: Physcomitrella patens

<400> SEQUENCE: 106

Met His Arg Asn Lys Val Tyr Gly His Ala Glu Trp Ala Lys His Lys
1               5                   10                  15

Ser Ser Trp Arg His Gly Arg His Leu Met Ser Ile Leu Ser Ser Gly
            20                  25                  30

Val Ile Ser Ala Val Gly Pro Pro Val Leu Ala Cys Thr Leu Leu Ala
        35                  40                  45

Thr Phe Val Thr Val Phe Asn Tyr Phe Val Lys Val Gly Arg Leu Pro
    50                  55                  60

Asn Trp Ile Pro Ile Leu Glu Val Ser Ser Leu Pro Phe Thr Leu Thr
65                  70                  75                  80

Ser Ser Val Leu Ser Leu Leu Val Phe Arg Thr Asn Ser Ser Tyr
                85                  90                  95

Asn Arg Phe Asp Glu Ala Arg Lys Ile Trp Gly Ser Asn Val Asn Arg
            100                 105                 110

```
Thr Arg Asp Leu Ala Arg Gln Ala Leu Ser Trp Ile Arg Ser Pro Ala
            115                 120                 125

Asp Ala Tyr Lys Leu Ser Cys Leu Leu Arg His Ile Lys Ala Tyr Pro
        130                 135                 140

Phe Ser Leu Lys Asp His Leu Thr Glu Asp Phe Ile Leu Lys Asp Glu
145                 150                 155                 160

Leu Asp Gln Ile Leu Glu Pro Gln Glu Leu Glu Ala Leu Met Ala Thr
                165                 170                 175

Lys His Arg Pro Asn Tyr Ile Leu Gln Val Leu Ser Glu Leu Val Asp
            180                 185                 190

Lys Cys Asn Leu Ser Glu Trp Glu Lys Met Ala Met Asp Glu Asn Ile
        195                 200                 205

Thr Thr Phe His Asp Asn Val Gly Ala Cys Glu Arg Ile Leu Lys Thr
210                 215                 220

Pro Ile Pro Leu Ala Tyr Thr Leu Val Thr Ser Arg Phe Leu Ile Leu
225                 230                 235                 240

Trp His Leu Val Leu Pro Phe Ala Leu Trp Ala Thr Cys His Trp Leu
            245                 250                 255

Thr Ile Pro Val Thr Phe Leu Thr Ala Thr Ala Leu Phe Tyr Ile Glu
        260                 265                 270

Glu Val Gly Val Leu Ile Glu Glu Pro Phe Trp Ile Leu Pro Leu Leu
    275                 280                 285

Ser Ile Ser Asp Gly Ile Val Ala Ala Leu Asp Gly Leu Ala Ala Ala
            290                 295                 300

His Lys Thr Ser Ser Leu Leu Trp Arg Leu His Gln Pro Asn Lys Asp
305                 310                 315                 320

His Val Val Gln Ile Thr Phe Glu Thr Ser Arg Ser Asp Gly Phe Arg
                325                 330                 335

Lys Ser Arg Asp Val Gly His Val Leu Leu Thr Arg Met Asn Ser Ile
            340                 345                 350

Ala

<210> SEQ ID NO 107
<211> LENGTH: 391
<212> TYPE: PRT
<213> ORGANISM: Physcomitrella patens

<400> SEQUENCE: 107

Met Phe Trp Lys His Pro Ser Gly Arg Thr Ala Ser Ser Glu Gly Phe
1               5                   10                  15

Val Ile Lys Pro Pro Asp Ser Val Gln Glu Gln Gln Ser Val Asp
            20                  25                  30

Thr Ala Gly Phe Ser Leu Leu Phe His Pro Asn Ala Leu Ser His Lys
        35                  40                  45

His Lys Val Ser Asp Glu Lys Val Ala Trp Gly Glu Thr Ser Lys Gly
    50                  55                  60

Gly Val Ser Gly Gly Gly Gly Gly Ser Val Thr Leu Glu Phe Phe
65                  70                  75                  80

Ser Phe Lys Asn Ala Ser Gln Arg Ser Val Trp Ala Arg Arg Met Gly
                85                  90                  95

Leu His Lys Ser Ser Trp Arg His Gly Arg His Ile Gln Thr Ala Phe
            100                 105                 110

Ser Thr Gly Val Ile Ser Ser Ile Ile Pro Arg Val Phe Phe Cys Thr
        115                 120                 125
```

```
Leu Ile Ser Val Leu Val Thr Ile Phe Asn His Ala Val Met Glu Gly
        130                 135                 140

Val Leu Pro His Trp Val Pro Ser Leu Arg Val Pro Thr Leu Pro Met
145                 150                 155                 160

Ser Leu Thr Ala Pro Val Leu Ser Leu Leu Val Phe Arg Thr Asn
                165                 170                 175

Ser Ser Tyr Asn Arg Leu Asp Glu Ala Arg Lys Ala Trp Gly Ser Asn
                180                 185                 190

Val Asn Arg Thr Arg Asp Val Ser Arg Gln Ala Leu Ser Trp Ile Cys
            195                 200                 205

Asp Pro Asp Asp Ala Asp Lys Leu Gln Ser Leu Leu Arg His Ile Lys
210                 215                 220

Ala Phe Ser Tyr Cys Leu Lys Asp His Leu Thr Gln Glu Asn Leu Leu
225                 230                 235                 240

Gln Glu Glu Leu Ala Arg Val Leu Glu Pro Arg Glu Val Glu Leu Val
                245                 250                 255

Leu Lys Ser Ser His Arg Pro Asn Tyr Val Leu His Val Met Ser Asp
                260                 265                 270

Thr Ile Lys His Cys Arg Ile Ser Lys Trp Glu Ser Lys Ser Met Asp
            275                 280                 285

Arg Asn Ile Thr Gln Phe His Asp Asn Val Gly Ala Cys Glu Arg Leu
290                 295                 300

Phe Lys Thr Pro Ile Pro Val Ala Tyr Thr Arg Met Ile Ser Arg Phe
305                 310                 315                 320

Leu Ser Ile Trp His Phe Leu Leu Pro Leu Ala Leu Trp Asn Ser Cys
                325                 330                 335

Arg Trp Leu Thr Ile Pro Val Thr Phe Val Ser Gly Val Gly Leu Phe
            340                 345                 350

Cys Ile Glu Glu Val Gly Val Leu Ile Glu Asp Pro Ser Thr Ser Leu
            355                 360                 365

Leu Cys Cys Gln Ser Ala Met Ala Phe Pro Gln Leu Trp Met Ala Ser
370                 375                 380

Ala Arg Leu Met Lys Glu Leu
385                 390

<210> SEQ ID NO 108
<211> LENGTH: 518
<212> TYPE: PRT
<213> ORGANISM: Auxenochlorella protothecoides

<400> SEQUENCE: 108

Met Pro Gly Ala Leu Ala Thr Ser Leu Asp Glu Pro Asp Arg Pro Gln
1               5                   10                  15

Arg Ser Val Ser Lys Thr Leu Lys Arg Ala Val Ser Ser Tyr Phe Val
            20                  25                  30

Pro Arg Gly Arg Phe Lys Lys Leu Leu Glu Ser Ala Glu Asn Asp Asn
        35                  40                  45

Glu Ala Asp Val Tyr Arg Arg Asn Ser Gly His Arg Val Phe Thr His
    50                  55                  60

Ala Asp Trp Ala Val His Arg Lys Pro Ser Arg Tyr Ala Arg His Leu
65                  70                  75                  80

Ala Leu Ile Phe Ala Ser Arg Ile Phe Arg Ser Leu Ile Pro Pro Ile
                85                  90                  95

Thr Ala Val Thr Leu Ile Ser Thr Leu Val Gly Val Tyr Glu Thr Leu
                100                 105                 110
```

```
Leu Lys Glu His Arg Leu Pro Ala Gln Trp Pro His Val Thr Leu Ala
        115                 120                 125

Leu Gly Gln Gly Phe Gln Leu Thr Ala Phe Ala Leu Ser Leu Leu Leu
        130                 135                 140

Val Phe Arg Thr Asn Ser Ala Tyr Gly Arg Trp Trp Glu Ala Arg Met
145                 150                 155                 160

Leu Trp Gly Ser Leu Thr Asn Arg Thr Arg Asp Phe Val Arg Gln Cys
                165                 170                 175

Leu Ala Phe Phe Pro Glu Asp Ala Lys Arg Leu Arg Glu Ala Ala Val
                180                 185                 190

Leu Trp Thr Ile Ala Leu Pro Tyr Val Val Lys Ala His Leu Arg Glu
                195                 200                 205

Gly Asn Arg Leu Glu Ser Glu Leu Glu Gly Ile Leu Thr Arg Asp Glu
        210                 215                 220

Val Asp Ala Leu Thr Gly Ala Thr His Arg Pro Cys Phe Val Leu Ala
225                 230                 235                 240

Ala Leu Ser Gln Val Val Ala Ala Gly Leu Asp Pro Gln Leu Arg
                245                 250                 255

Gln Arg Leu Asp Thr Asn Leu Thr Ala Phe Glu Asp Cys Ile Gly Gly
        260                 265                 270

Cys Glu Arg Ile Leu Arg Thr Pro Ile Pro Gln Ser Tyr Thr Arg His
        275                 280                 285

Thr Ser Arg Phe Leu Met Ile Trp Leu Ile Met Met Pro Phe Thr Leu
        290                 295                 300

Trp Ala Ala Tyr Ser Trp Val Ser Ile Leu Leu Ser Gly Leu Phe Ala
305                 310                 315                 320

Tyr Leu Met Leu Gly Ile Asp Glu Ile Gly Val Gln Ile Glu Glu Pro
                325                 330                 335

Phe Gly Val Leu Pro Leu Gly Ser Phe Cys Ala Thr Ile Glu Arg Asn
                340                 345                 350

Leu Arg Glu Leu His Tyr Ser Asn Pro Glu Ala Arg Phe Ala Ala Leu
        355                 360                 365

Pro Trp Leu Val Pro Ala Ser Pro Thr Cys Ser Arg Ala Ser Gly Ser
        370                 375                 380

Cys Asp Gly Ala Asp Met Ala Ala Gly Met Asp Asp Ile Asp Pro Val
385                 390                 395                 400

Ala Gly Lys Leu Pro His Leu Asn Gly Ala Pro Gln Ala Gly Gln Pro
                405                 410                 415

Arg Val Tyr Lys His Thr Ser Asp Ala Ala Glu Leu Ala Ala Gly His
                420                 425                 430

Val Arg Phe Ala His Arg Trp Leu Glu Pro His Pro His Leu Ile His
        435                 440                 445

Ser Pro Val His Pro His His Pro Asn His His Gly His Gly His
        450                 455                 460

Gly His Gly Ala Gln Glu His Gly Arg Gly Ala Phe His Gln Thr Ser
465                 470                 475                 480

Thr Leu His Ala Asp Val Glu Asp Gln Val Val His Pro Ala Ser Tyr
                485                 490                 495

Pro Thr Ala Ala Arg His Thr Pro Pro His Arg Ser Trp Phe Gly Gly
                500                 505                 510

Arg Trp Val Glu Glu Asp
        515
```

```
<210> SEQ ID NO 109
<211> LENGTH: 412
<212> TYPE: PRT
<213> ORGANISM: Capsicum baccatum

<400> SEQUENCE: 109

Met Thr Asn Pro Arg Ser Leu Phe Asn Ile Gln Ser Pro Thr Asn Ala
1               5                   10                  15

Ser Leu Ser Ser His Phe Thr Leu Lys Lys Pro Ser Lys Leu Leu Ser
            20                  25                  30

Tyr Lys Lys Leu Thr Phe Cys Ser Phe Lys Val Leu Cys Ser Ser Gln
        35                  40                  45

Pro Ser Lys Ala Pro Gln Asn Ser Asn Leu Thr Ser Thr Leu Val Ser
    50                  55                  60

Ile Leu Arg Val Ile Pro Asp Trp Ala Asp Lys Ile Gln Glu Gly Gly
65                  70                  75                  80

Met Arg Lys Lys Arg Ser Leu Tyr Lys His Glu Thr Trp Val Gln His
                85                  90                  95

Arg Ser Ser Leu Arg His Leu Arg His Leu Phe Ser Ser Phe Asn Ser
            100                 105                 110

Arg Val Val Leu Ser Leu Ile Pro Val Ile Ala Phe Thr Ser Phe
        115                 120                 125

Ala Phe Val Ile Ala Ser Tyr Asn Ser Ala Val Ser Leu His Trp Leu
    130                 135                 140

Pro Glu Phe Phe Pro Leu Leu Arg Ala Ser Pro Gln Pro Tyr Gln Leu
145                 150                 155                 160

Thr Ala Pro Ala Leu Ala Leu Leu Val Phe Arg Thr Glu Ala Ser
                165                 170                 175

Tyr Ala Arg Phe Glu Thr Gly Lys Lys Ala Trp Thr Asn Val Ile Ala
            180                 185                 190

Gly Thr Asn Asp Phe Ala Arg Gln Val Ile Thr Ala Cys Val Asp Lys
        195                 200                 205

Arg Asp Gly Val Leu Lys Glu Ala Leu Leu Gln Tyr Ile Met Ala Phe
    210                 215                 220

Pro Val Ala Leu Lys Cys His Ile Val Tyr Gly Ser Asp Leu Ala Ser
225                 230                 235                 240

Asp Leu Lys Asn Leu Leu Glu Ala Asp Leu Ala Val Val Leu Ser
                245                 250                 255

Ser Lys His Arg Pro Arg Cys Ile Ile Gly Phe Ile Ser Gln Ser Leu
            260                 265                 270

Gln Ser Leu Asn Leu Glu Gly Thr Lys Leu Ser Gln Leu Glu Ser Lys
        275                 280                 285

Ile Ser Cys Phe His Glu Gly Ile Gly Val Cys Glu Gln Leu Ile Gly
    290                 295                 300

Ile Pro Ile Pro Leu Ser Tyr Thr Arg Leu Thr Ser Arg Phe Leu Val
305                 310                 315                 320

Leu Trp His Leu Thr Leu Pro Ile Ile Leu Trp Asp Cys His Trp
                325                 330                 335

Leu Val Val Pro Ala Thr Phe Ile Ser Ala Ser Leu Phe Cys Ile
            340                 345                 350

Glu Glu Val Gly Val Leu Ile Glu Glu Pro Phe Pro Met Leu Ala Leu
        355                 360                 365

Asp Glu Leu Cys Gln Arg Val His Asp Asn Ile Gln Glu Ala Met Ala
    370                 375                 380
```

Ser Glu Lys Gln Ile Gln Glu Arg Leu Asn Thr Lys Arg Lys Arg His
385                 390                 395                 400

Phe Ser Glu Asn Ser Pro Asn Gly Trp Pro Thr Ser
                405                 410

<210> SEQ ID NO 110
<211> LENGTH: 435
<212> TYPE: PRT
<213> ORGANISM: Coccomyxa subellipsoidea C-169

<400> SEQUENCE: 110

Met Ile Ala Thr Ile His Thr Leu Tyr Tyr Gln Ala Gly Leu Gln Lys
1               5                   10                  15

Gly Phe Gln Thr Pro Arg Pro Arg Trp Arg Lys Leu His Tyr Ser Arg
                20                  25                  30

Ala Pro Gly Lys Leu Ser Arg Asn Leu Leu Val Arg Cys Gln Glu Thr
            35                  40                  45

Asp Ile Glu Trp Val Glu Arg Ala Ala Ile Gln Arg Glu Ala Trp Lys
    50                  55                  60

Glu Glu Ser Arg Lys Tyr Arg Arg Val Thr Phe Thr Tyr Asp Asp Trp
65                  70                  75                  80

Val Ala His Arg Ser Thr Thr Arg Tyr Ser Arg His Leu Ala Gly Ile
                85                  90                  95

Leu Asp Ser Arg Ile Phe Arg Gly Leu Leu Pro Thr Leu Thr Ala Val
                100                 105                 110

Met Met Val Ala Thr Phe Val Ser Val Tyr Glu Thr Leu Arg Glu Ala
            115                 120                 125

Gly Ile Leu Ile Pro His Asp Trp Val Gly Leu Thr Val Glu Ala Gly
130                 135                 140

Gln Ala Phe Asn Leu Thr Ser Phe Ala Leu Ser Leu Leu Leu Val Phe
145                 150                 155                 160

Arg Thr Asn Glu Ser Tyr Ser Arg Trp Leu Glu Ala Arg Lys Ala Trp
                165                 170                 175

Thr Asn Ile Val Thr Arg Ser Arg Asp Phe Ala Arg Gln Gly Leu Ser
            180                 185                 190

Trp Leu Ser Gly Asp Lys Gln Arg Glu Ser Met Leu Glu Arg Trp Thr
        195                 200                 205

Ile Ala Phe Ile Lys Cys Thr Met Ala His Val Arg Glu Glu Cys Asp
    210                 215                 220

Leu Gln Ser Leu Leu Glu Asp Val Leu Glu Ala His Glu Leu Glu Gln
225                 230                 235                 240

Leu Met Ala Ala Gln His Lys Pro Asn Phe Val Leu His Val Leu Ser
                245                 250                 255

Glu Leu Val Trp Gly Ala Asn Leu Met Glu Gly Gln Ala Met Arg Met
            260                 265                 270

Asp Glu Ala Leu Thr Val Phe Gly Glu Gln Val Gly Thr Cys Glu Arg
        275                 280                 285

Leu Leu Lys Thr Pro Ile Pro Leu Ser Tyr Thr Arg His Thr Ser Arg
    290                 295                 300

Phe Leu Val Met Trp Leu Ala Phe Leu Pro Phe Ser Leu Trp Asp Ala
305                 310                 315                 320

Cys His Trp Val Thr Ile Pro Ala Ser Gly Ile Ile Ala Phe Leu Leu
                325                 330                 335

Leu Gly Ile Glu Glu Ile Gly Val Gln Ile Glu Glu Pro Phe Gly Ile

```
                  340                 345                 350
Leu Pro Leu Gly Ala Trp Ile Leu Phe His Thr Ile Glu Ala Asp Ser
            355                 360                 365

Val Ile Asp Pro Gln Ser Phe Asp Cys Thr Ile Gln Gln Ser Val Lys
        370                 375                 380

Gly Ala Leu Ser Leu Ala Leu Leu Leu Arg Met Thr Gly Cys Ala Arg
385                 390                 395                 400

Arg Ala Ile Gln Arg Cys Cys Cys Gly Arg Asp Gln Thr Asp Gly Ala
            405                 410                 415

Arg His Glu Cys Ala Ser Ser Gly Gly Arg Pro Glu Arg Glu Arg
        420                 425                 430

Cys Lys Arg
        435

<210> SEQ ID NO 111
<211> LENGTH: 474
<212> TYPE: PRT
<213> ORGANISM: Coccomyxa subellipsoidea C-169

<400> SEQUENCE: 111

Met Ser Arg Leu Asn His His Ala Leu Phe Glu Asp His Val Val Thr
1               5                   10                  15

Ala Ala Asp Trp Tyr His Leu Arg Ser Trp Arg Arg His Leu Pro Asp
            20                  25                  30

Leu Thr Trp Val Thr Val Leu Ser Gly Phe Trp Leu Trp Val Val Tyr
        35                  40                  45

Phe Ala Leu Ile Ala Val Leu Ile Gly Leu Tyr His Thr Val Leu Val
    50                  55                  60

Pro Arg Gly Ala Pro Asp Trp Pro Pro Lys Asn Val Ala Ser Val Leu
65              70                  75                  80

Tyr Gln Pro Phe Ala Ile Thr Ser Phe Ala Leu Ala Leu Leu Met Val
            85                  90                  95

Phe Arg Thr Asn Ser Ser Tyr Ala Arg Trp Trp Glu Ala Arg Thr Val
        100                 105                 110

Trp Gly Gln Val Phe Asn Val Thr Arg Asn Leu Val Arg Gln Ala Asp
    115                 120                 125

Ala Trp Phe Gly Glu Glu Asp Val Ala Ala Phe Gln Met Leu Val Arg
130                 135                 140

Trp Cys Ala Ala Ala Gly Tyr Ile Leu Gln Ala His Leu Cys Thr Ala
145                 150                 155                 160

Lys Leu Gly Pro Glu Ala Glu Gly Leu Leu His Pro Glu Glu Leu Lys
            165                 170                 175

Leu Leu Ala Ser Trp Glu His Arg Pro Ile Cys Ala Gly Gln Val Leu
        180                 185                 190

Ser Ser Ile Val Ala Ser Ala Val Lys Asp Ser Gln Leu Arg Ala Ala
    195                 200                 205

Met Asp Asp Gln Ile Ala Thr Tyr Ile Asn Asp Ala Gly Ala Cys Glu
210                 215                 220

Arg Ile Gln Arg Thr Cys Ile Pro Phe Cys Tyr Thr Arg His Thr Ser
225                 230                 235                 240

Arg Phe Leu Ile Leu Trp Leu Thr Phe Leu Pro Phe Ala Leu Trp Glu
            245                 250                 255

Ile Cys Gly Trp Ala Ser Pro Val Ala Glu Ala Val Leu Ala Phe Leu
        260                 265                 270
```

```
Leu Met Gly Val Glu Asn Ile Gly Ile Gln Ile Glu Pro Phe His
            275                 280                 285

Val Leu Pro Met His Ser Tyr Cys Ala Val Ile Ala Lys Asn Ala Leu
290                 295                 300

Glu Val Ala Arg Glu Arg Lys Gly Leu Asp Leu Phe Val Glu Glu Ala
305                 310                 315                 320

Leu Arg Arg Glu Leu Cys Met Glu Pro Leu Gly Lys Leu Glu Asn Gly
            325                 330                 335

Gly Ala Gly Ala Asp Ser Asn Val Phe Val Arg Pro Ser Gly Ala Ala
            340                 345                 350

Gly Val Ser His Lys Ala Ser Pro Arg Pro Thr Asn Pro Ser Leu Arg
            355                 360                 365

Val Arg Cys Gln Ser His Arg His Asn Ala Asp Pro Ser Leu His Glu
370                 375                 380

Ala Arg Gly Val Phe Gln Met Val Pro Gln Arg Gly Glu Ala Thr Leu
385                 390                 395                 400

Leu Asp Ala Arg Asp Ala Leu Glu Thr Cys Ser Ala Leu Asn Asp Ala
            405                 410                 415

Ser Ser Lys Glu Ala Cys Tyr Ala Thr Phe Gly Cys Asp Gly Arg Arg
            420                 425                 430

Val Glu Lys Tyr Phe Gly Ala Val Glu Val Leu Glu Thr Ala Trp Glu
            435                 440                 445

Gln Val Lys Glu Glu Val Glu Asp Asp Glu Phe Val Glu Glu
            450                 455                 460

Asn Leu Ser Pro Trp Pro Trp Asp Gly Arg
465                 470
```

<210> SEQ ID NO 112
<211> LENGTH: 20
<212> TYPE: DNA
<213> ORGANISM: Artificial Sequence
<220> FEATURE:
<223> OTHER INFORMATION: Synthetic Construct

<400> SEQUENCE: 112
gacaccaaga ccatcctggc                                          20

<210> SEQ ID NO 113
<211> LENGTH: 21
<212> TYPE: DNA
<213> ORGANISM: Artificial Sequence
<220> FEATURE:
<223> OTHER INFORMATION: Synthetic Construct

<400> SEQUENCE: 113
aacagaactg cagaggtccc g                                        21

<210> SEQ ID NO 114
<211> LENGTH: 17
<212> TYPE: DNA
<213> ORGANISM: Artificial Sequence
<220> FEATURE:
<223> OTHER INFORMATION: Synthetic Construct

<400> SEQUENCE: 114
cggtgcccat gagctcc                                             17

<210> SEQ ID NO 115
<211> LENGTH: 17
<212> TYPE: DNA

```
<213> ORGANISM: Artificial Sequence
<220> FEATURE:
<223> OTHER INFORMATION: Synthetic Construct

<400> SEQUENCE: 115
gccactaacc ggcccaa                                                    17

<210> SEQ ID NO 116
<211> LENGTH: 18
<212> TYPE: DNA
<213> ORGANISM: Artificial Sequence
<220> FEATURE:
<223> OTHER INFORMATION: Synthetic Construct

<400> SEQUENCE: 116
aatcccgtcc atgtcgct                                                   18

<210> SEQ ID NO 117
<211> LENGTH: 18
<212> TYPE: DNA
<213> ORGANISM: Artificial Sequence
<220> FEATURE:
<223> OTHER INFORMATION: Synthetic Construct

<400> SEQUENCE: 117
cggcttgtga ggacctcg                                                   18

<210> SEQ ID NO 118
<211> LENGTH: 20
<212> TYPE: DNA
<213> ORGANISM: Artificial Sequence
<220> FEATURE:
<223> OTHER INFORMATION: Synthetic Construct

<400> SEQUENCE: 118
gccagaagga ctcgtacgtt                                                 20

<210> SEQ ID NO 119
<211> LENGTH: 20
<212> TYPE: DNA
<213> ORGANISM: Artificial Sequence
<220> FEATURE:
<223> OTHER INFORMATION: Synthetic Construct

<400> SEQUENCE: 119
cgccagagtc cagcacgata                                                 20

<210> SEQ ID NO 120
<211> LENGTH: 48
<212> TYPE: DNA
<213> ORGANISM: Artificial Sequence
<220> FEATURE:
<223> OTHER INFORMATION: Synthetic Construct

<400> SEQUENCE: 120
gctactcaca acaagcccag ttatgcagat gcaagcaaac cgttcgtc                  48

<210> SEQ ID NO 121
<211> LENGTH: 40
<212> TYPE: DNA
<213> ORGANISM: Artificial Sequence
<220> FEATURE:
<223> OTHER INFORMATION: Synthetic Construct

<400> SEQUENCE: 121
gagccaccca gatctccgtt cttgcgctcc ccacccatgg                           40
```

<210> SEQ ID NO 122
<211> LENGTH: 40
<212> TYPE: DNA
<213> ORGANISM: Artificial Sequence
<220> FEATURE:
<223> OTHER INFORMATION: Synthetic Construct

<400> SEQUENCE: 122
gctactcaca acaagcccag ttatggccac tggtcagacc                              40

<210> SEQ ID NO 123
<211> LENGTH: 37
<212> TYPE: DNA
<213> ORGANISM: Artificial Sequence
<220> FEATURE:
<223> OTHER INFORMATION: Synthetic Construct

<400> SEQUENCE: 123
gagccaccca gatctccgtt tctccttgtc tccgcac                                 37

<210> SEQ ID NO 124
<211> LENGTH: 46
<212> TYPE: DNA
<213> ORGANISM: Artificial Sequence
<220> FEATURE:
<223> OTHER INFORMATION: Synthetic Construct

<400> SEQUENCE: 124
gctactcaca acaagcccag ttatgcaagt cagcaaggtt ccctcg                       46

<210> SEQ ID NO 125
<211> LENGTH: 38
<212> TYPE: DNA
<213> ORGANISM: Artificial Sequence
<220> FEATURE:
<223> OTHER INFORMATION: Synthetic Construct

<400> SEQUENCE: 125
gagccaccca gatctccgtt ccggggcgag atgcgcac                                38

<210> SEQ ID NO 126
<211> LENGTH: 90
<212> TYPE: DNA
<213> ORGANISM: Artificial Sequence
<220> FEATURE:
<223> OTHER INFORMATION: Synthetic Construct

<400> SEQUENCE: 126
ctagtgggag cgagttgcaa ggcatatctc gctgatcggc accatggggg tggtggtgat       60
cagcgctata tgttttgcaa ctcgctcccg                                         90

<210> SEQ ID NO 127
<211> LENGTH: 90
<212> TYPE: DNA
<213> ORGANISM: Artificial Sequence
<220> FEATURE:
<223> OTHER INFORMATION: Synthetic Construct

<400> SEQUENCE: 127
ctagcgggag cgagttgcaa aacatatagc gctgatcacc accaccccca tggtgccgat       60
cagcgagata tgccttgcaa ctcgctccca                                         90

<210> SEQ ID NO 128

```
<211> LENGTH: 90
<212> TYPE: DNA
<213> ORGANISM: Artificial Sequence
<220> FEATURE:
<223> OTHER INFORMATION: Synthetic Construct

<400> SEQUENCE: 128
ctagtgagag cgtgttgcaa ggcatatctc gctgatcggc accatggggg tggtggtgat      60
cagcgctata tgttttgcaa cacgctctcg                                      90

<210> SEQ ID NO 129
<211> LENGTH: 90
<212> TYPE: DNA
<213> ORGANISM: Artificial Sequence
<220> FEATURE:
<223> OTHER INFORMATION: Synthetic Construct

<400> SEQUENCE: 129
ctagcgagag cgtgttgcaa aacatatagc gctgatcacc accaccccca tggtgccgat      60
cagcgagata tgccttgcaa cacgctctca                                      90

<210> SEQ ID NO 130
<211> LENGTH: 20
<212> TYPE: DNA
<213> ORGANISM: Artificial Sequence
<220> FEATURE:
<223> OTHER INFORMATION: Synthetic Construct

<400> SEQUENCE: 130
gctgtgtggc attgaggaga                                                 20

<210> SEQ ID NO 131
<211> LENGTH: 20
<212> TYPE: DNA
<213> ORGANISM: Artificial Sequence
<220> FEATURE:
<223> OTHER INFORMATION: Synthetic Construct

<400> SEQUENCE: 131
ggatgaggct gatgagtccg                                                 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Construct

<400> SEQUENCE: 132
acggtctacg acttccctca                                                 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Construct

<400> SEQUENCE: 133
ttggatcacg tgggattggg                                                 20

<210> SEQ ID NO 134
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 134
aagtcagcaa ggttccctcg                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Construct

<400> SEQUENCE: 135
tgaatgagcc tagcgggttg                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic Construct

<400> SEQUENCE: 136
atgtgctgtc cgtggctttc                                               20

<210> SEQ ID NO 137
<211> LENGTH: 22
<212> TYPE: DNA
<213> ORGANISM: Artificial Sequence
<220> FEATURE:
<223> OTHER INFORMATION: Synthetic Construct

<400> SEQUENCE: 137
cagaccttga ccatcttgtc cc                                            22

<210> SEQ ID NO 138
<211> LENGTH: 18
<212> TYPE: DNA
<213> ORGANISM: Artificial Sequence
<220> FEATURE:
<223> OTHER INFORMATION: Synthetic Construct

<400> SEQUENCE: 138
tgccccttct cagcacgt                                                 18

<210> SEQ ID NO 139
<211> LENGTH: 18
<212> TYPE: DNA
<213> ORGANISM: Artificial Sequence
<220> FEATURE:
<223> OTHER INFORMATION: Synthetic Construct

<400> SEQUENCE: 139
actgcctcac actcccct                                                 18

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct

<400> SEQUENCE: 140
gcaccaatca tgtcaagcct                                               20
```

```
<210> SEQ ID NO 141
<211> LENGTH: 20
<212> TYPE: DNA
<213> ORGANISM: Artificial Sequence
<220> FEATURE:
<223> OTHER INFORMATION: Synthetic Construct

<400> SEQUENCE: 141
gacgttacag cacacccttg                                                    20
```